United States Patent
Nara et al.

(10) Patent No.: US 7,915,267 B2
(45) Date of Patent: Mar. 29, 2011

(54) HETEROCYCLIC AMIDE COMPOUND AND USE THEREOF

(75) Inventors: Hiroshi Nara, Osaka (JP); Akira Kaieda, Osaka (JP); Kenjiro Sato, Osaka (JP); Jun Terauchi, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 12/091,773

(22) PCT Filed: Oct. 27, 2006

(86) PCT No.: PCT/JP2006/322043
§ 371 (c)(1),
(2), (4) Date: Apr. 28, 2008

(87) PCT Pub. No.: WO2007/049820
PCT Pub. Date: May 3, 2007

(65) Prior Publication Data
US 2009/0137603 A1 May 28, 2009

(30) Foreign Application Priority Data
Oct. 28, 2005 (JP) .................................. 2005-315267

(51) Int. Cl.
*A61K 31/519* (2006.01)
(52) U.S. Cl. ...................................... 514/260.1; 544/278
(58) Field of Classification Search .................... 544/278
See application file for complete search history.

(56) References Cited

U.S. PATENT DOCUMENTS

| 2003/0078276 A1 | 4/2003 | Andrianjara et al. |
| 2005/0176741 A1 | 8/2005 | Okano et al. |

FOREIGN PATENT DOCUMENTS

| JP | 2004-529874 | 9/2004 |
| WO | 98/39329 | 9/1998 |
| WO | WO-03/091224 A1 | 11/2003 |
| WO | WO-2005/105760 A1 | 11/2005 |

OTHER PUBLICATIONS

Joshi, Vidya, et al., "Synthesis of Some New 4-Quinazolinone-2-carboxy Esters, 2-Carboxamides, 2-Carboxyhydrazides & Their Tosyl Derivatives Having Potential Biological Activity," Indian Journal of Chemistry, vol. 26B, 1987, pp. 602.604.
Reddy, V. Gopal, et al., "Synthesis of some new 2-azaheteryl and 2,3-azahetero-annelated quinazolinones," Indian Journal of Chemistry, vol. 31B, 1992, pp. 764-767.
George, T., et al., "Synthesis of Substituted Quinazolines: Part II—Use of Diethyl Oxalate in Quinazoline Synthesis," Indian Journal of Chemistry, vol. 9, 1971, pp. 1077-1080.
Myakushkene, G., et al., "Synthesis and Antimonoamineoxidase Activity of 1-(2-Quinazolonecarbonyl)-2-Arylmethyl-And(1-Arylethyl)Hydrazines," Pharmaceutical Chemistry Journal, vol. 32, No. 10, 1998, pp. 521-523.
Reddy, P S N, et al., "Bisazaheterocycles: Part VIII—A new synthesis of 2, 2'-bisquinazolinones," Indian Journal of Chemistry, vol. 41B, 2002, pp. 1950-1952.
Kontogiorgis, et al., "Matrix Metalloproteinase Inhibitors: A Review on Pharmacophore Mapping and (Q)Sars Results", Current Medicinal Chemistry, 2005, 12, 339-355.

*Primary Examiner* — James O Wilson
*Assistant Examiner* — Brian McDowell
(74) *Attorney, Agent, or Firm* — Edwards Angell Palmer & Dodge LLP; Kongsik Kim, Esq.

(57) ABSTRACT

The present invention provides a novel amide compound represented by the following formula, which has a matrix metalloproteinase inhibitory activity and is useful as a pharmaceutical agent.

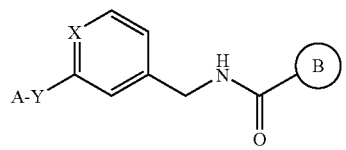

wherein each symbol is as defined in the specification.

5 Claims, No Drawings

HETEROCYCLIC AMIDE COMPOUND AND USE THEREOF

CROSS-REFERENCES TO RELATED APPLICATIONS

This application is a U.S. national phase application, pursuant to 35 U.S.C. §371, of PCT/JP2006/322043, filed Oct. 27, 2006 designating the United States and published on May 3, 2007 as WO 2007/049820 A1, which claims priority to Japanese application 2005-315267, filed Oct. 28, 2005. The entire contents of the aforementioned patent applications are incorporated herein by this reference.

TECHNICAL FIELD

The present invention relates to a heterocyclic amide compound having a superior matrix metalloproteinase inhibitory activity and useful as a drug for the prophylaxis or treatment of osteoarthritis, rheumatoid arthritis and the like, and the like.

BACKGROUND ART

Matrix metalloproteinase (MMP) is an endopeptidase that physiologically plays a key role in the tissue remodeling, wherein its protease activity is strictly controlled. In the diseased state, however, the control is disrupted, and the disruption induces excess degradation of extracellular matrix, which in turn is deeply involved in the etiology of many diseases including joint diseases such as osteoarthritis, rheumatoid arthritis and the like, bone diseases such as osteoporosis and the like, periodontal disease, infiltration and metastasis of tumor, corneal ulcer formation and the like (Expert Opinion on Therapeutic Patents, vol. 12, pp. 665-705 (2002)).

At present, MMP is known to include at least 26 different enzymes, which are divided into five groups based on the variation in the primary structure and substrate specificity: collagenase group (MMP-1, 8, 13, 18), gelatinase group (MMP-2, 9), stromelysin group (MMP-3, 10, 11), membrane MMP group (MMP-14, 15, 16, 17), and other group (MMP-7, 12). Of these, MMP-13 belonging to the collagenase group has been reported to almost always express in cartilage and bone tissue, and to show increased production amount in joint disease and the like.

Moreover, since MMP-13 shows a potent collagen degradation activity as compared to other collagenases, it is considered to be deeply involved in the bone and joint diseases.

There are many MMP inhibitors so far reported (see, for example, *Chemical Reviews*, vol. 99, pp. 2735-2776 (1999), *Current Medicinal Chemistry*, vol. 8, pp. 425-474 (2001)), and a number of reports have also been documented on the compounds showing MMP-13 inhibitory activity. They are largely divided into (i) hydroxamic acid derivatives (see, for example, *Journal of Medicinal Chemistry*, vol. 46, pp. 2361-2375 (2003), *Journal of Medicinal Chemistry*, vol. 46, pp. 2376-2396 (2003), WO2004/000811, WO03/091247, WO03/055851), (ii) carboxylic acid derivatives (see, for example, *Bioorganic & Medicinal Chemistry*, vol. 10, pp. 3529-3534 (2002), WO03/35610), (iii) thiol derivatives (see, for example, *Bioorganic & Medicinal Chemistry Letters*, vol. 9, pp. 1757-1760 (1999), WO03/091242), and (iv) others (see, for example, *Bioorganic & Medicinal Chemistry Letters*, vol. 11, pp. 969-972 (2001), WO98/17643, WO2004/014909), based on the contents thereof.

Meanwhile, as a compound having a heterocyclic amide skeleton, Bulletin of The Chemical Society of Japan, 1990, pp. 72-83 describes a compound represented by the formula

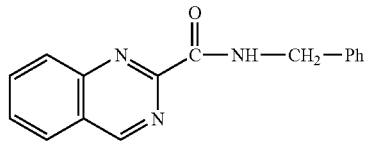

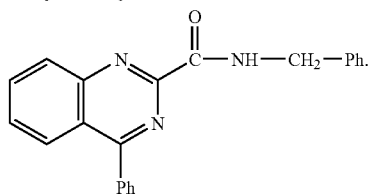

In addition, WO03/091224 describes a compound represented by

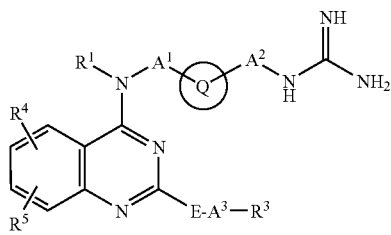

wherein $R^1$ is a hydrogen atom or alkyl; ring Q is a cyclohexylene group or a phenylene group; $A^1$ and $A^2$ are the same or different and each is a single bond or an alkylene group; E is —NHCO— or —CON($R^2$)— wherein $R^2$ is a hydrogen atom or alkyl; $A^3$ is $A^{31}$-$A^{32}$-$A^{33}$, $A^{31}$ and $A^{33}$ are the same or different and each is a single bond, or the same or different 1 or 2 saturated or unsaturated aliphatic hydrocarbon groups at substitutable position(s), which, when one carbon atom has two branched chains, may form a divalent cycloalkyl together with the carbon atom, $A^{32}$ is a single bond, an oxygen atom, a sulfur atom or —N($R^{32}$)— wherein $R^{32}$ is a hydrogen atom or alkyl; $R^3$ is an optionally substituted acyclic aliphatic hydrocarbon group having 1 to 8 carbon atoms, an optionally substituted mono- to tricyclic cyclic aliphatic hydrocarbon group having 3 to 10 carbon atoms, an optionally substituted mono- or bicyclic aromatic hydrocarbon group having 6 to 12 carbon atoms, or an optionally substituted mono- to tricyclic heterocyclic group; when B is —CON($R^2$)—, this —N($R^2$)— and -$A^3$-$R^3$ may form a cyclic amino group; and $R^4$ and $R^5$ are the same or different and each is a hydrogen atom, alkyl, alkoxy, or halogen.

DISCLOSURE OF THE INVENTION

There is a demand for the development of a novel compound superior in action effect, durability, safety, oral absorbability, selectivity and the like as compared to conventional MMP inhibitors and the like, and useful as a drug for the prophylaxis or treatment of joint diseases (osteoarthritis, rheumatoid arthritis and the like), osteoporosis, periodontal diseases, corneal ulcer and other MMP associated diseases.

The present inventors have conducted intensive studies and first succeeded in the creation of a novel compound represented by the formula

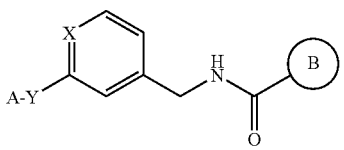

wherein
A is a zinc-binding group;
X is CZ wherein Z is a hydrogen atom or a halogen atom, or N;
Y is a spacer having 2 to 10 atoms and optionally having substituent(s); and
a group represented by the formula

is a group represented by the formula

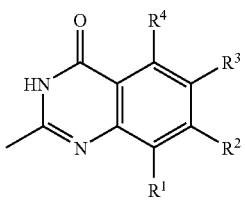

wherein
$R^1$, $R^2$, $R^3$ and $R^4$ are each
(i) a hydrogen atom,
(ii) a halogen atom,
(iii) a cyano group,
(iv) a hydroxy group,
(v) a nitro group,
(vi) a carboxyl group,
(vii) an alkoxycarbonyl group optionally having substituent(s),
(viii) an amino group optionally having substituent(s),
(ix) an alkyl group optionally having substituent(s),
(x) an alkenyl group optionally having substituent(s),
(xi) an alkynyl group optionally having substituent(s),
(xii) an aryl group optionally having substituent(s),
(xiii) an alkoxy group optionally having substituent(s),
(xiv) an aralkyloxy group optionally having substituent(s),
(xv) an aryloxy group optionally having substituent(s),
(xvi) a thiol group,
(xvii) an alkylthio group optionally having substituent(s),
(xviii) an aralkylthio group optionally having substituent(s),
(xix) a 5- to 8-membered aromatic heterocyclyl-thio group containing, besides carbon atoms, 1 to 4 heteroatoms selected from a nitrogen atom, an oxygen atom and a sulfur atom,
(xx) a mono- or di-alkylcarbamoyl-thio group,
(xxi) an alkylsulfonyl group optionally having substituent(s),
(xxii) an arylsulfonyl group optionally having substituent(s),
(xxiii) an aralkylsulfonyl group optionally having substituent(s),
(xxiv) a carbamoyl group optionally having substituent(s),
(xxv) a mono- or di-alkylamino-thiocarbonyloxy group,
(xxvi) a 5- to 8-membered non-aromatic heterocyclic group containing, besides carbon atoms, 1 to 4 heteroatoms selected from a nitrogen atom, a sulfur atom and an oxygen atom, or
(xxvii) a 5 to S-membered aromatic heterocyclic group containing, besides carbon atoms, 1 to 4 heteroatoms selected from a nitrogen atom, a sulfur atom and an oxygen atom,
a group represented by the formula

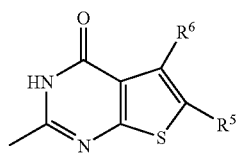

wherein
$R^5$ and $R^6$ are each
(i) a hydrogen atom,
(ii) a halogen atom,
(iii) a cyano group,
(iv) a hydroxy group,
(v) a nitro group,
(vi) a carboxyl group,
(vii) an alkoxycarbonyl group optionally having substituent(s),
(viii) an amino group optionally having substituent(s),
(ix) an alkyl group optionally having substituent(s),
(x) an alkenyl group optionally having substituent(s),
(xi) an alkynyl group optionally having substituent(s),
(xii) an aryl group optionally having substituent(s),
(xiii) an alkoxy group optionally having substituent(s),
(xv) an aralkyloxy group optionally having substituent(s),
(xv) an aryloxy group optionally having substituent(s),
(xvi) a thiol group,
(xvii) an alkylthio group optionally having substituent(s),
(xviii) an aralkylthio group optionally having substituent(s),
(xix) a 5- to 8-membered aromatic heterocyclyl-thio group containing, besides carbon atoms, 1 to 4 heteroatoms selected from a nitrogen atom, an oxygen atom and a sulfur atom,
(xx) a mono- or di-alkylcarbamoyl-thio group,
(xxi) an alkylsulfonyl group optionally having substituent (s)
(xxii) an arylsulfonyl group optionally having substituent (s),
(xxiii) an aralkylsulfonyl group optionally having substituent(s),
(xxiv) a carbamoyl group optionally having substituent(s),
(xxv) a mono- or di-alkylamino-thiocarbonyloxy group,
(xxvi) a 5- to 8-membered non-aromatic heterocyclic group containing, besides carbon atoms, 1 to 4 heteroatoms selected from a nitrogen atom, a sulfur atom and an oxygen atom, or
(xxvii) a 5- to 8-membered aromatic heterocyclic group containing, besides carbon atoms, 1 to 4 heteroatoms selected from a nitrogen atom, a sulfur atom and an oxygen atom, or
a group represented by the formula

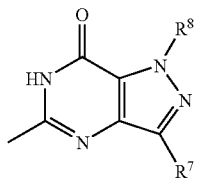

wherein
R⁷ and R⁸ are each
(i) a hydrogen atom,
(ii) a halogen atom,
(iii) a cyano group,
(iv) a hydroxy group,
(v) a nitro group,
(vi) a carboxyl group,
(vii) an alkoxycarbonyl group optionally having substituent(s),
(viii) an amino group optionally having substituent(s),
(ix) an alkyl group optionally having substituent(s),
(x) an alkenyl group optionally having substituent(s),
(xi) an alkynyl group optionally having substituent(s),
(xii) an aryl group optionally having substituent(s),
(xiii) an alkoxy group optionally having substituent(s),
(xiv) an aralkyloxy group optionally having substituent(s),
(xv) an aryloxy group optionally having substituent(s),
(xvi) a thiol group,
(xvii) an alkylthio group optionally having substituent (s),
(xviii) an aralkylthio group optionally having substituent(s),
(xix) a 5- to 8-membered aromatic heterocyclyl-thio group containing, besides carbon atoms, 1 to 4 heteroatoms selected from a nitrogen atom, an oxygen atom and a sulfur atom,
(xx) a mono- or di-alkylcarbamoyl-thio group,
(xxi) an alkylsulfonyl group optionally having substituent(s),
(xxii) an arylsulfonyl group optionally having substituent(s),
(xxiii) an aralkylsulfonyl group optionally having substituent(s),
(xxiv) a carbamoyl group optionally having substituent(s),
(xxv) a mono- or di-alkylamino-thiocarbonyloxy group,
(xxvi) a 5- to 8-membered non-aromatic heterocyclic group containing, besides carbon atoms, 1 to 4 heteroatoms selected from a nitrogen atom, a sulfur atom and an oxygen atom, or
(xxvii) a 5- to 8-membered aromatic heterocyclic group containing, besides carbon atoms, 1 to 4 heteroatoms selected from a nitrogen atom, a sulfur atom and an oxygen atom,
provided that
{[3-({[(4-oxo-3,4-dihydroquinazolin-2-yl)carbonyl]amino}methyl)phenyl]oxy}acetic acid,
5-{[3-({[(4-oxo-3,4-dihydroquinazolin-2-yl)carbonyl]amino}methyl)phenyl]oxy}pentanoic acid,
5-({3-[({[6-(methyloxy)-4-oxy-dihydroquinazolin-2-yl]carbonyl}amino)methyl]phenyl}oxy)pentanoic acid,
4-{[3-({[(4-oxo-3,4-dihydroquinazolin-2-yl)carbonyl]amino}methyl)phenyl]oxy}butanoic acid,
N-[(2-{[(5-methylisoxazol-3-yl)methyl]oxy}pyridin-4-yl)methyl]-4-oxo-3,4-dihydroquinazoline-2-carboxamide, and
N-[(2-{[(3,5-dimethylisoxazol-4-yl)methyl]oxy}pyridin-4-yl)methyl]-4-oxo-3,4-dihydroquinazoline-2-carboxamide
are excluded, or a salt thereof [hereinafter to be abbreviated as compound (I)], and found that this compound (I) unexpectedly has superior properties as an MMP inhibitor and is highly satisfactory as a pharmaceutical agent, which resulted in the completion of the present invention.

Accordingly, the present invention relates to

[1] a compound represented by the formula

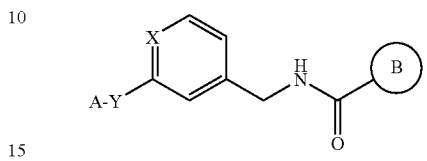

wherein
A is a zinc-binding group;
X is CZ wherein Z is a hydrogen atom or a halogen atom, or N;
Y is a spacer having 2 to 10 atoms and optionally having substituent(s); and
a group represented by the formula

is a group represented by the formula

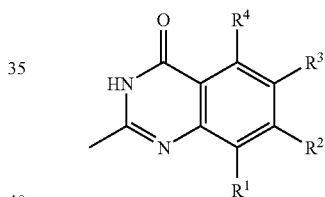

wherein
R¹, R², R³ and R⁴ are each
(i) a hydrogen atom,
(ii) a halogen atom,
(iii) a cyano group,
(iv) a hydroxy group,
(v) a nitro group,
(vi) a carboxyl group,
(vii) an alkoxycarbonyl group optionally having substituent(s),
(viii) an amino group optionally having substituent(s),
(ix) an alkyl group optionally having substituent(s),
(x) an alkenyl group optionally having substituent(s),
(xi) an alkynyl group optionally having substituent(s),
(xii) an aryl group optionally having substituent(s),
(xiii) an alkoxy group optionally having substituent(s),
(xiv) an aralkyloxy group optionally having substituent(s),
(xv) an aryloxy group optionally having substituent(s),
(xvi) a thiol group,
(xvii) an alkylthio group optionally having substituent(s),
(xviii) an aralkylthio group optionally having substituent(s),
(xix) a 5- to 8-membered aromatic heterocyclyl-thio group containing, besides carbon atoms, 1 to 4 heteroatoms selected from a nitrogen atom, an oxygen atom and a sulfur atom, (xx) a mono- or di-alkylcarbamoyl-thio group,
(xxi) an alkylsulfonyl group optionally having substituent(s),
(xxii) an arylsulfonyl group optionally having substituent(s),
(xxiii) an aralkylsulfonyl group optionally having substituent(s),
(xxiv) a carbamoyl group optionally having substituent(s),
(xxv) a mono- or di-alkylamino-thiocarbonyloxy group,
(xxvi) a 5- to 8-membered non-aromatic heterocyclic group containing, besides carbon atoms, 1 to 4 heteroatoms selected from a nitrogen atom, a sulfur atom and an oxygen atom, or
(xxvii) a 5- to 8-membered aromatic heterocyclic group containing, besides carbon atoms, 1 to 4 heteroatoms selected from a nitrogen atom, a sulfur atom and an oxygen atom,
a group represented by the formula

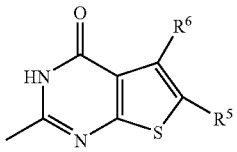

wherein
$R^5$ and $R^6$ are each
(i) a hydrogen atom,
(ii) a halogen atom,
(iii) a cyano group,
(iv) a hydroxy group,
(v) a nitro group,
(vi) a carboxyl group,
(vii) an alkoxycarbonyl group optionally having substituent(s),
(viii) an amino group optionally having substituent(s),
(ix) an alkyl group optionally having substituent(s),
(x) an alkenyl group optionally having substituent(s),
(xi) an alkynyl group optionally having substituent(s),
(xii) an aryl group optionally having substituent(s),
(xiii) an alkoxy group optionally having substituent(s),
(xiv) an aralkyloxy group optionally having substituent(s),
(xv) an aryloxy group optionally having substituent(s),
(xvi) a thiol group,
(xvii) an alkylthio group optionally having substituent(s),
(xviii) an aralkylthio group optionally having substituent(s),
(xix) a 5- to 8-membered aromatic heterocyclyl-thio group containing, besides carbon atoms, 1 to 4 heteroatoms selected from a nitrogen atom, an oxygen atom and a sulfur atom,
(xx) a mono- or di-alkylcarbamoyl-thio group,
(xxi) an alkylsulfonyl group optionally having substituent(s),
(xxii) an arylsulfonyl group optionally having substituent(s),
(xxiii) an aralkylsulfonyl group optionally having substituent(s),
(xxiv) a carbamoyl group optionally having substituent(s),
(xxv) a mono- or di-alkylamino-thiocarbonyloxy group,
(xxvi) a 5- to 8-membered non-aromatic heterocyclic group containing, besides carbon atoms, 1 to 4 heteroatoms selected from a nitrogen atom, a sulfur atom and an oxygen atom, or
(xxvii) a 5- to 8-membered aromatic heterocyclic group containing, besides carbon atoms, 1 to 4 heteroatoms selected from a nitrogen atom, a sulfur atom and an oxygen atom, or
a group represented by the formula

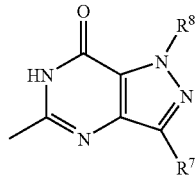

wherein
$R^7$ and $R^8$ are each
(i) a hydrogen atom,
(ii) a halogen atom,
(iii) a cyano group,
(iv) a hydroxy group,
(v) a nitro group,
(vi) a carboxyl group,
(vii) an alkoxycarbonyl group optionally having substituent (s),
(viii) an amino group optionally having substituent(s),
(ix) an alkyl group optionally having substituent(s),
(x) an alkenyl group optionally having substituent(s),
(xi) an alkynyl group optionally having substituent(s),
(xii) an aryl group optionally having substituent(s),
(xiii) an alkoxy group optionally having substituent(s),
(xiv) an aralkyloxy group optionally having substituent(s),
(xv) an aryloxy group optionally having substituent(s),
(xvi) a thiol group,
(xvii) an alkylthio group optionally having substituent(s),
(xviii) an aralkylthio group optionally having substituent(s)
(xix) a 5- to 8-membered aromatic heterocyclyl-thio group containing, besides carbon atoms, 1 to 4 heteroatoms selected from a nitrogen atom, an oxygen atom and a sulfur atom,
(xx) a mono- or di-alkylcarbamoyl-thio group,
(xxi) an alkylsulfonyl group optionally having substituent (s),
(xxii) an arylsulfonyl group optionally having substituent(s),
(xxiii) an aralkylsulfonyl group optionally having substituent(s),
(xxiv) a carbamoyl group optionally having substituent(s),
(xxv) a mono or di-alkylamino-thiocarbonyloxy group,
(xxvi) a 5- to 8-membered non-aromatic heterocyclic group containing, besides carbon atoms, 1 to 4 heteroatoms selected from a nitrogen atom, a sulfur atom and an oxygen atom, or
(xxvii) a 5- to 8-membered aromatic heterocyclic group containing, besides carbon atoms, 1 to 4 heteroatoms selected from a nitrogen atom, a sulfur atom and an oxygen atom,
provided that
{[3-({[(4-oxo-3,4-dihydroquinazolin-2-yl)carbonyl]amino}methyl)phenyl]oxy}acetic acid,
5-{[3-({[(4-oxo-3,4-dihydroquinazolin-2-yl)carbonyl]amino}methyl)phenyl]oxy}pentanoic acid,
5-({3-[({[6-(methyloxy)-4-oxy-dihydroquinazolin-2-yl]carbonyl}amino)methyl]phenyl}oxy)pentanoic acid, 4-{[3-({[(4-oxo-3,4-dihydroquinazolin-2-yl carbonyl]amino}methylphenyl]oxy}butanoic acid, N-[(2-{[(5-methylisoxazol-3-yl)methyl]oxy}pyridin-4-yl)methyl]-4-oxo-3,4-dihydroquinazoline-2-carboxamide, and N-[(2{-[(3,5-dimethylisoxazol-4-yl)methyl]oxy}pyridin-4-yl)methyl]-4-oxo-3,4-dihydroquinazoline-2-carboxamide are excluded, or a salt thereof,

[2] the compound of [1], wherein A is a pyrrolyl group optionally having substituent(s), an imidazolyl group optionally having substituent(s), a pyrazolyl group optionally having substituent(s), a triazolyl group optionally having substituent(s), a tetrazolyl group optionally having substituent(s) or a group represented by the formula —C(O)NHOH, or a salt thereof,

[3] the compound of [1], wherein Y is a spacer having 2 to 7 atoms and optionally having substituent(s), or a salt thereof,

[4] the compound of [1], wherein the group represented by the formula

is a group represented by the formula

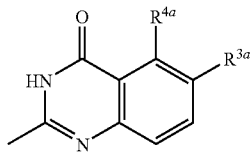

wherein
R$^{3a}$ and R$^{4a}$ are each
(i) a hydrogen atom,
(ii) a halogen atom,
(iii) a cyano group,
(iv) an amino group optionally having substituent(s),
(v) an alkyl group optionally having substituent(s), or
(vi) an alkoxy group optionally having substituent(s), a group represented by the formula

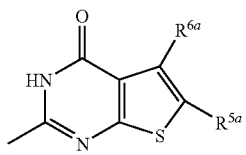

wherein
R$^{5a}$ and R$^{6a}$ are each
(i) a hydrogen atom,
(ii) an alkyl group optionally having substituent(s),
(iii) a cyano group,
(iv) a halogen atom,
(v) an aryl group optionally having substituent(s), or
(vi) a 5- to 8-membered aromatic heterocyclic group containing, besides carbon atoms, 1 to 4 heteroatoms selected from a nitrogen atom, a sulfur atom and an oxygen atom, or
a group represented by the formula

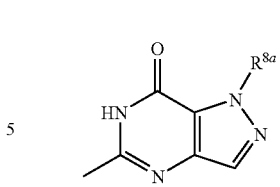

wherein
R$^{8a}$ is
(i) an alkyl group optionally having substituent(s), or
(ii) an aryl group optionally having substituent(s), or a salt thereof,

[5] a compound which is selected from the group consisting of the following, or a salt thereof:

4-oxo-5-phenyl-N-{3-[2-(1H-1,2,4-triazol-3-yloxy)ethoxy]benzyl}-3,4-dihydrothieno[2,3-d]pyrimidine-2-carboxamide, 5-(2-fluorophenyl)-4-oxo-N-{3-[2-(1H-1,2,4-triazol-3-yloxy)ethoxy]benzyl}-3,4-dihydrothieno[2,3-d]pyrimidine-2-carboxamide, 5-(2-chlorophenyl)-4-oxo-N-{3-[2-(1H-1,2,4-triazol-3-yloxy)ethoxy]benzyl}-3,4-dihydrothieno[2,3-d]pyrimidine-2-carboxamide, 5-(3-fluorophenyl)-4-oxo-N-{3-[2-(1H-1,2,4-triazol-3-yloxy)ethoxy]benzyl}-3,4-dihydrothieno[2,3-d]pyrimidine-2-carboxamide, 5-(3-methylphenyl)-4-oxo-N-{3-[2-(1H-1,2,4-triazol-3-yloxy)ethoxy]benzyl}-3,4-dihydrothieno[2,3-d]pyrimidine-2-carboxamide, 5-(3-fluorophenyl)-4-oxo-N-[(3-{[3-(1H-1,2,4-triazol-3-yloxy)propyl]oxy}phenyl)methyl]-3,4-dihydrothieno[2,3-d]pyrimidine-2-carboxamide, and 5-(2-fluorophenyl)-4-oxo-N-[(3-{[3-(1H-1,2,4-triazol-3-yloxy)propyl]oxy}phenyl)methyl]-3,4-dihydrothieno[2,3-d]pyrimidine-2-carboxamide,

[6] a prodrug of a compound represented by the formula

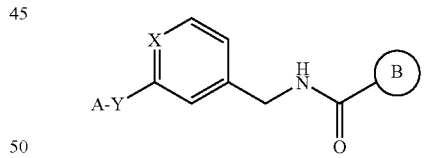

wherein
A is a zinc-binding group;
X is CZ wherein Z is a hydrogen atom or a halogen atom, or N;
Y is a spacer having 2 to 10 atoms and optionally having substituent(s); and
a group represented by the formula

is a group represented by the formula

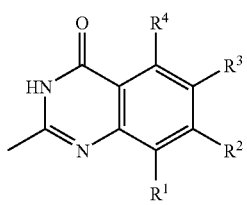

wherein
R¹, R², R³ and R⁴ are each
(i) a hydrogen atom,
(ii) a halogen atom,
(iii) a cyano group,
(iv) a hydroxy group,
(v) a nitro group,
(vi) a carboxyl group,
(vii) an alkoxycarbonyl group optionally having substituent(s),
(viii) an amino group optionally having substituent(s),
(ix) an alkyl group optionally having substituent(s),
(x) an alkenyl group optionally having substituent(s),
(xi) an alkynyl group optionally having substituent(s),
(xii) an aryl group optionally having substituent(s),
(xiii) an alkoxy group optionally having substituent(s),
(xiv) an aralkyloxy group optionally having substituent(s),
(xv) an aryloxy group optionally having substituent(s),
(xvi) a thiol group,
(xvii) an alkylthio group optionally having substituent(s),
(xviii) an aralkylthio group optionally having substituent(s),
(xix) a 5- to 8-membered aromatic heterocyclyl-thio group containing, besides carbon atoms, 1 to 4 heteroatoms selected from a nitrogen atom, an oxygen atom and a sulfur atom,
(xx) a mono- or di-alkylcarbamoyl-thio group,
(xxi) an alkylsulfonyl group optionally having substituent (s),
(xxii) an arylsulfonyl group optionally having substituent (s),
(xxiii) an aralkylsulfonyl group optionally having substituent(s),
(xxiv) a carbamoyl group optionally having substituent(s),
(xxv) a mono- or di-alkylamino-thiocarbonyloxy group,
(xxvi) a 5- to 8-membered non-aromatic heterocyclic group containing, besides carbon atoms, 1 to 4 heteroatoms selected from a nitrogen atom, a sulfur atom and an oxygen atom, or
(xxvii) a 5- to 8-membered aromatic heterocyclic group containing, besides carbon atoms, 1 to 4 heteroatoms selected from a nitrogen atom, a sulfur atom and an oxygen atom,
a group represented by the formula

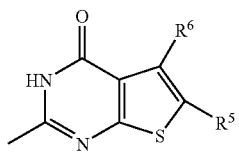

wherein
R⁵ and R⁶ are each
(i) a hydrogen atom,
(ii) a halogen atom,
(iii) a cyano group,
(iv) a hydroxy group,
(v) a nitro group,
(vi) a carboxyl group,
(vii) an alkoxycarbonyl group optionally having substituent(s),
(viii) an amino group optionally having substituent(s),
(ix) an alkyl group optionally having substituent(s),
(x) an alkenyl group optionally having substituent(s),
(xi) an alkynyl group optionally having substituent(s),
(xii) an aryl group optionally having substituent(s),
(xiii) an alkoxy group optionally having substituent(s),
(xiv) an aralkyloxy group optionally having substituent(s),
(xv) an aryloxy group optionally having substituent(s),
(xvi) a thiol group,
(xvii) an alkylthio group optionally having substituent(s),
(xviii) an aralkylthio group optionally having substituent(s),
(xix) a 5- to 8-membered aromatic heterocyclyl-thio group containing, besides carbon atoms, 1 to 4 heteroatoms selected from a nitrogen atom, an oxygen atom and a sulfur atom,
(xx) a mono- or di-alkylcarbamoyl-thio group,
(xxi) an alkylsulfonyl group optionally having substituent(s),
(xxii) an arylsulfonyl group optionally having substituent(s),
(xxiii) an aralkylsulfonyl group optionally having substituent(s),
(xxiv) a carbamoyl group optionally having substituent(s),
(xxv) a mono- or di-alkylamino-thiocarbonyloxy group,
(xxvi) a 5- to 8-membered non-aromatic heterocyclic group containing, besides carbon atoms, 1 to 4 heteroatoms selected from a nitrogen atom, a sulfur atom and an oxygen atom, or
(xxvii) a 5- to 8-membered aromatic heterocyclic group containing, besides carbon atoms, 1 to 4 heteroatoms selected from a nitrogen atom, a sulfur atom and an oxygen atom, or
a group represented by the formula

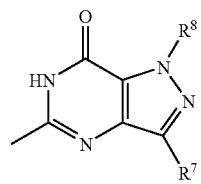

wherein
R⁷ and R⁸ are each
(i) a hydrogen atom,
(ii) a halogen atom,
(iii) a cyano group,
(iv) a hydroxy group,
(v) a nitro group,
(vi) a carboxyl group,
(vii) an alkoxycarbonyl group optionally having substituent(s),
(viii) an amino group optionally having substituent(s),
(ix) an alkyl group optionally having substituent(s),
(x) an alkenyl group optionally having substituent(s),
(xi) an alkynyl group optionally having substituent(s),
(xii) an aryl group optionally having substituent(s),
(xiii) an alkoxy group optionally having substituent(s), (xiv) an aralkyloxy group optionally having substituent(s),
(xv) an aryloxy group optionally having substituent(s),
(xvi) a thiol group,
(xvii) an alkylthio group optionally having substituent(s),
(xviii) an aralkylthio group optionally having substituent(s),
(xix) a 5- to 8-membered aromatic heterocyclyl-thio group containing, besides carbon atoms, 1 to 4 heteroatoms selected from a nitrogen atom, an oxygen atom and a sulfur atom,
(xx) a mono- or di-alkylcarbamoyl-thio group,
(xxi) an alkylsulfonyl group optionally having substituent(s),
(xxii) an arylsulfonyl group optionally having substituent(s),
(xxiii) an aralkylsulfonyl group optionally having substituent(s),
(xxiv) a carbamoyl group optionally having substituent(s),
(xxv) a mono- or di-alkylamino-thiocarbonyloxy group,
(xxvi) a 5- to 8-membered non-aromatic heterocyclic group containing, besides carbon atoms, 1 to 4 heteroatoms selected from a nitrogen atom, a sulfur atom and an oxygen atom, or
(xxvii) a 5- to 8-membered aromatic heterocyclic group containing, besides carbon atoms, 1 to 4 heteroatoms selected from a nitrogen atom, a sulfur atom and an oxygen atom,
provided that
{3-({[(4-oxo-3,4-dihydroquinazolin-2-yl)carbonyl]amino}methyl)phenyl]oxy}acetic acid,
5-{[3-({[(4-oxo-3,4-dihydroquinazolin-2-yl)carbonyl]amino}methyl)phenyl]oxy}pentanoic acid,
5-({3-[({[6-(methyloxy)-4-oxy-dihydroquinazolin-2-yl]carbonyl}amino)methyl]phenyl}oxy)pentanoic acid,
4-{[3-({[(4-oxo-3,4-dihydroquinazolin-2-yl)carbonyl]amino}methyl)phenyl]oxy}butanoic acid,
N-[(2-{[(5-methylisoxazol-3-yl)methyl]oxy}pyridin-4-yl)methyl]-4-oxo-3,4-dihydroquinazoline-2-carboxamide, and
N-[(2-{[(3,5-dimethylisoxazol-4-yl)methyl]oxy}pyridin-4-yl)methyl]-4-oxo-3,4-dihydroquinazoline-2-carboxamide are excluded,
or a salt thereof,
[7] a pharmaceutical agent comprising a compound represented by the formula

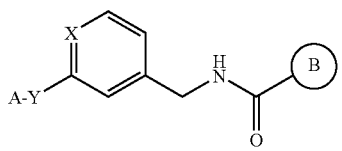

wherein
A is a zinc-binding group;
X is CZ wherein Z is a hydrogen atom or a halogen atom, or N;
Y is a spacer having 2 to 10 atoms and optionally having substituent(s); and
a group represented by the formula

is a group represented by the formula

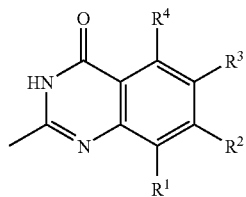

wherein
$R^1$, $R^2$, $R^3$ and $R^4$ are each
(i) a hydrogen atom,
(ii) a halogen atom,
(iii) a cyano group,
(iv) a hydroxy group,
(v) a nitro group,
(vi) a carboxyl group,
(vii) an alkoxycarbonyl group optionally having substituent(s),
(viii) an amino group optionally having substituent(s),
(ix) an alkyl group optionally having substituent(s),
(x) an alkenyl group optionally having substituent(s),
(xi) an alkynyl group optionally having substituent(s),
(xii) an aryl group optionally having substituent(s),
(xiii) an alkoxy group optionally having substituent(s),
(xiv) an aralkyloxy group optionally having substituent(s),
(xv) an aryloxy group optionally having substituent(s),
(xvi) a thiol group,
(xvii) an alkylthio group optionally having substituent(s),
(xviii) an aralkylthio group optionally having substituent (s)
(xix) a 5- to 8-membered aromatic heterocyclyl-thio group containing, besides carbon atoms, 1 to 4 heteroatoms selected from a nitrogen atom, an oxygen atom and a sulfur atom,
(xx) a mono- or di-alkylcarbamoyl-thio group,
(xxi) an alkylsulfonyl group optionally having substituent(s),
(xxii) an arylsulfonyl group optionally having substituent (s),
(xxiii) an aralkylsulfonyl group optionally having substituent(s),
(xxiv) a carbamoyl group optionally having substituent(s),
(xxv) a mono- or di-alkylamino-thiocarbonyloxy group,
(xxvi) a 5- to 8-membered non-aromatic heterocyclic group containing, besides carbon atoms, 1 to 4 heteroatoms selected from a nitrogen atom, a sulfur atom and an oxygen atom, or
(xxvii) a 5- to 8-membered aromatic heterocyclic group containing, besides carbon atoms, 1 to 4 heteroatoms selected from a nitrogen atom, a sulfur atom and an oxygen atom,
a group represented by the formula

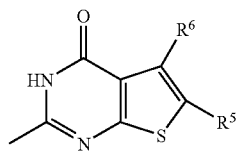

wherein
R⁵ and R⁶ are each
(i) a hydrogen atom,
(ii) a halogen atom,
(iii) a cyano group,
(iv) a hydroxy group,
(v) a nitro group,
(vi) a carboxyl group,
(vii) an alkoxycarbonyl group optionally having substituent(s),
(viii) an amino group optionally having substituent(s),
(ix) an alkyl group optionally having substituent(s),
(x) an alkenyl group optionally having substituent(s),
(xi) an alkynyl group optionally having substituent(s),
(xii) an aryl group optionally having substituent(s),
(xiii) an alkoxy group optionally having substituent(s),
(xiv) an aralkyloxy group optionally having substituent(s),
(xv) an aryloxy group optionally having substituent(s),
(xvi) a thiol group,
(xvii) an alkylthio group optionally having substituent(s),
(xviii) an aralkylthio group optionally having substituent(s),
(xix) a 5- to 8-membered aromatic heterocyclyl-thio group containing, besides carbon atoms, 1 to 4 heteroatoms selected from a nitrogen atom, an oxygen atom and a sulfur atom,
(xx) a mono- or di-alkylcarbamoyl-thio group,
(xxi) an alkylsulfonyl group optionally having substituent(s),
(xxii) an arylsulfonyl group optionally having substituent(s),
(xxiii) an aralkylsulfonyl group optionally having substituent(s),
(xxiv) a carbamoyl group optionally having substituent(s),
(xxv) a mono- or di-alkylamino-thiocarbonyloxy group,
(xxvi) a 5- to 8-membered non-aromatic heterocyclic group containing, besides carbon atoms, 1 to 4 heteroatoms selected from a nitrogen atom, a sulfur atom and an oxygen atom, or
(xxvii) a 5- to 8-membered aromatic heterocyclic group containing, besides carbon atoms, 1 to 4 heteroatoms selected from a nitrogen atom, a sulfur atom and an oxygen atom,
a group represented by the formula

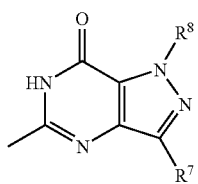

wherein
R⁷ and R⁸ are each
(i) a hydrogen atom,
(ii) a halogen atom,
(iii) a cyano group,
(iv) a hydroxy group,
(v) a nitro group,
(vi) a carboxyl group,
(vii) an alkoxycarbonyl group optionally having substituent (s),
(viii) an amino group optionally having substituent(s),
(ix) an alkyl group optionally having substituent(s),
(x) an alkenyl group optionally having substituent(s),
(xi) an alkynyl group optionally having substituent(s),
(xii) an aryl group optionally having substituent(s),
(xiii) an alkoxy group optionally having substituent(s),
(xiv) an aralkyloxy group optionally having substituent(s),
(xv) an aryloxy group optionally having substituent(s),
(xvi) a thiol group,
(xvii) an alkylthio group optionally having substituent(s),
(xviii) an aralkylthio group optionally having substituent(s),
(xix) a 5- to 8-membered aromatic heterocyclyl-thio group containing, besides carbon atoms, 1 to 4 heteroatoms selected from a nitrogen atom, an oxygen atom and a sulfur atom,
(xx) a mono- or di-alkylcarbamoyl-thio group,
(xxi) an alkylsulfonyl group optionally having substituent(s),
(xxii) an arylsulfonyl group optionally having substituent(s),
(xxiii) an aralkylsulfonyl group optionally having substituent (s),
(xxiv) a carbamoyl group optionally having substituent(s),
(xxv) a mono- or di-alkylamino-thiocarbonyloxy group,
(xxvi) a 5- to 8-membered non-aromatic heterocyclic group containing, besides carbon atoms, 1 to 4 heteroatoms selected from a nitrogen atom, a sulfur atom and an oxygen atom, or
(xxvii) a 5- to 8-membered aromatic heterocyclic group containing, besides carbon atoms, 1 to 4 heteroatoms selected from a nitrogen atom, a sulfur atom and an oxygen atom,
provided that
{[3-({[(4-oxo-3,4-dihydroquinazolin-2-yl)carbonyl]amino}methyl)phenyl]oxy}acetic acid,
5-{[3-({[(4-oxo-3,4-dihydroquinazolin-2-yl)carbonyl]amino}methyl)phenyl]oxy}pentanoic acid,
5-({3-[({[6-(methyloxy)-4-oxy-dihydroquinazolin-2-yl]carbonyl}amino)methyl]phenyl}oxy)pentanoic acid,
4-{[3-({[(4-oxo-3,4-dihydroquinazolin-2-yl)carbonyl]amino}methyl)phenyl]oxy}butanoic acid,
N-[(2-{[(5-methylisoxazol-3-yl)methyl]oxy}pyridin-4-yl)methyl]-4-oxo-3,4-dihydroquinazoline-2-carboxamide, and
N-[(2-([(3,5-dimethylisoxazol-4-yl)methyl]oxy}pyridin-4-yl)methyl]-4-oxo-3,4-dihydroquinazoline-2-carboxamide are excluded,
or a salt thereof, or a prodrug thereof,
[8] the pharmaceutical agent of [7], which is a matrix metalloproteinase inhibitor,
[9] the pharmaceutical agent of [8], wherein the matrix metalloproteinase is a matrix metalloproteinase-13 (MMP-13),
[10] the pharmaceutical agent of [7], which is an agent for the prophylaxis or treatment of osteoarthritis or rheumatoid arthritis,
[11] a method of inhibiting a matrix metalloproteinase, which comprises administering, to a mammal, an effective amount of a compound represented by the formula

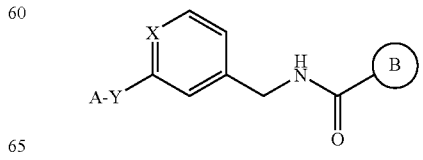

wherein

A is a zinc-binding group;

X is CZ wherein Z is a hydrogen atom or a halogen atom, or N;

Y is a spacer having 2 to 10 atoms and optionally having substituent(s); and a group represented by the formula is a group represented by the formula wherein $R^1$, $R^2$, $R^3$ and $R^4$ are each (i) a hydrogen atom,
(ii) a halogen atom,
(iii) a cyano group,
(iv) a hydroxy group,
(v) a nitro group,
(vi) a carboxyl group,
(vii) an alkoxycarbonyl group optionally having substituent(s)
(viii) an amino group optionally having substituent(s),
(ix) an alkyl group optionally having substituent(s),
(x) an alkenyl group optionally having substituent(s),
(xi) an alkynyl group optionally having substituent(s),
(xii) an aryl group optionally having substituent(s),
(xiii) an alkoxy group optionally having substituent(s),
(xiv) an aralkyloxy group optionally having substituent(s),
(xv) an aryloxy group optionally having substituent(s),
(xvi) a thiol group,
(xvii) an alkylthio group optionally having substituent(s),
(xviii) an aralkylthio group optionally having substituent(s),
(xix) a 5- to 8-membered aromatic heterocyclyl-thio group containing, besides carbon atoms, 1 to 4 heteroatoms selected from a nitrogen atom, an oxygen atom and a sulfur atom,
(xx) a mono- or di-alkylcarbamoyl-thio group,
(xxi) an alkylsulfonyl group optionally having substituent(s),
(xxii) an arylsulfonyl group optionally having substituent(s),
(xxiii) an aralkylsulfonyl group optionally having substituent(s),
(xxiv) a carbamoyl group optionally having substituent(s)
(xxv) a mono- or di-alkylamino-thiocarbonyloxy group,
(xxvi) a 5- to 8-membered non-aromatic heterocyclic group containing, besides carbon atoms, 1 to 4 heteroatoms selected from a nitrogen atom, a sulfur atom and an oxygen atom, or
(xxvii) a 5- to 8-membered aromatic heterocyclic group containing, besides carbon atoms, 1 to 4 heteroatoms selected from a nitrogen atom, a sulfur atom and an oxygen atom, a group represented by the formula wherein $R^5$ and $R^6$ are each (i) a hydrogen atom,
(ii) a halogen atom,
(iii) a cyano group,
(iv) a hydroxy group,
(v) a nitro group,
(vi) a carboxyl group,
(vii) an alkoxycarbonyl group optionally having substituent (s),
(viii) an amino group optionally having substituent(s),
(ix) an alkyl group optionally having substituent(s),
(x) an alkenyl group optionally having substituent(s),
(xi) an alkynyl group optionally having substituent(s),
(xii) an aryl group optionally having substituent(s),
(xiii) an alkoxy group optionally having substituent(s),
(xiv) an aralkyloxy group optionally having substituent(s),
(xv) an aryloxy group optionally having substituent(s),
(xvi) a thiol group,
(xvii) an alkylthio group optionally having substituent(s),
(xviii) an aralkylthio group optionally having substituent(s),
(xix) a 5- to 8-membered aromatic heterocyclyl-thio group containing, besides carbon atoms, 1 to 4 heteroatoms selected from a nitrogen atom, an oxygen atom and a sulfur atom,
(xx) a mono- or di-alkylcarbamoyl-thio group,
(xxi) an alkylsulfonyl group optionally having substituent (s),
(xxii) an arylsulfonyl group optionally having substituent(s),
(xxiii) an aralkylsulfonyl group optionally having substituent(s),
(xxiv) a carbamoyl group optionally having substituent(s),
(xxv) a mono- or di-alkylamino-thiocarbonyloxy group,
(xxvi) a 5- to 8-membered non-aromatic heterocyclic group containing, besides carbon atoms, 1 to 4 heteroatoms selected from a nitrogen atom, a sulfur atom and an oxygen atom, or
(xxvii) a 5- to 8-membered aromatic heterocyclic group containing, besides carbon atoms, 1 to 4 heteroatoms selected from a nitrogen atom, a sulfur atom and an oxygen atom, or a group represented by the formula wherein
R⁷ and R⁸ are each
(i) a hydrogen atom,
(ii) a halogen atom,
(iii) a cyano group,
(iv) a hydroxy group,
(v) a nitro group,
(vi) a carboxyl group,
(vii) an alkoxycarbonyl group optionally having substituent (s),
(viii) an amino group optionally having substituent(s),
(ix) an alkyl group optionally having substituent(s),
(x) an alkenyl group optionally having substituent(s),
(xi) an alkynyl group optionally having substituent(s),
(xii) an aryl group optionally having substituent(s),
(xiii) an alkoxy group optionally having substituent(s),
(xiv) an aralkyloxy group optionally having substituent (s),
(xv) an aryloxy group optionally having substituent(s),
(xvi) a thiol group,
(xvii) an alkylthio group optionally having substituent(s),
(xviii) an aralkylthio group optionally having substituent(s),
(xix) a 5- to 8-membered aromatic heterocyclyl-thio group containing, besides carbon atoms, 1 to 4 heteroatoms selected from a nitrogen atom, an oxygen atom and a sulfur atom,
(xx) a mono- or di-alkylcarbamoyl-thio group,
(xxi) an alkylsulfonyl group optionally having substituent(s),
(xxii) an arylsulfonyl group optionally having substituent(s),
(xxiii) an aralkylsulfonyl group optionally having substituent (s),
(xxiv) a carbamoyl group optionally having substituent (s),
(xxv) a mono- or di-alkylamino-thiocarbonyloxy group,
(xxvi) a 5- to 8-membered non-aromatic heterocyclic group containing, besides carbon atoms, 1 to 4 heteroatoms selected from a nitrogen atom, a sulfur atom and an oxygen atom, or
(xxvii) a 5- to 8-membered aromatic heterocyclic group containing, besides carbon atoms, 1 to 4 heteroatoms selected from a nitrogen atom, a sulfur atom and an oxygen atom,
provided that
{[3-({[(4-oxo-3,4-dihydroquinazolin-2-yl)carbonyl]amino}methyl)phenyl]oxy}acetic acid,
5-{[3-({[(4-oxo-3,4-dihydroquinazolin-2-yl)carbonyl]amino}methyl)phenyl]oxy}pentanoic acid,
5-({3-[({[6-(methyloxy)-4-oxy-dihydroquinazolin-2-yl]carbonyl}amino)methyl]phenyl}oxy)pentanoic acid,
4-{[3-({[(4-oxo-3,4-dihydroquinazolin-2-yl)carbonyl]amino}methyl)phenyl]oxy}butanoic acid,
N-[(2-{[(5-methylisoxazol-3-yl)methyl]oxy}pyridin-4-yl)methyl]-4-oxo-3,4-dihydroquinazoline-2-carboxamide, and
N-[(2-{[(3,5-dimethylisoxazol-4-yl)methyl]oxy}pyridin-4-yl)methyl]-4-oxo-3,4-dihydroquinazoline-2-carboxamide are excluded,
or a salt thereof, or a prodrug thereof,

[12] use of a compound represented by the formula

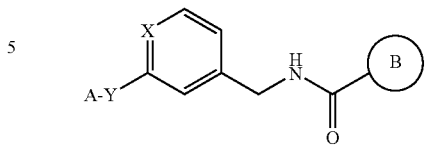

wherein
A is a zinc-binding group;
X is CZ wherein Z is a hydrogen atom or a halogen atom, or N;
Y is a spacer having 2 to 10 atoms and optionally having substituent(s); and
a group represented by the formula

is a group represented by the formula

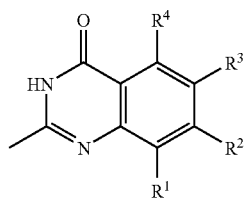

wherein
R¹, R², R³ and R⁴ are each
(i) a hydrogen atom,
(ii) a halogen atom,
(iii) a cyano group,
(iv) a hydroxy group,
(v) a nitro group,
(vi) a carboxyl group,
(vii) an alkoxycarbonyl group optionally having substituent(s),
(viii) an amino group optionally having substituent(s),
(ix) an alkyl group optionally having substituent(s),
(x) an alkenyl group optionally having substituent(s),
(xi) an alkynyl group optionally having substituent(s),
(xii) an aryl group optionally having substituent(s),
(xiii) an alkoxy group optionally having substituent(s),
(xiv) an aralkyloxy group optionally having substituent (s),
(xv) an aryloxy group optionally having substituent(s),
(xvi) a thiol group,
(xvii) an alkylthio group optionally having substituent (s)
(xviii) an aralkylthio group optionally having substituent(s),
(xix) a 5- to 8-membered aromatic heterocyclyl-thio group containing, besides carbon atoms, 1 to 4 heteroatoms selected from a nitrogen atom, an oxygen atom and a sulfur atom,
(xx) a mono- or di-alkylcarbamoyl-thio group,
(xxi) an alkylsulfonyl group optionally having substituent(s),
(xxii) an arylsulfonyl group optionally having substituent (s),
(xxiii) an aralkylsulfonyl group optionally having substituent(s),
(xxiv) a carbamoyl group optionally having substituent(s), (xxv) a mono- or di-alkylamino-thiocarbonyloxy group,
(xxvi) a 5- to 8-membered non-aromatic heterocyclic group containing, besides carbon atoms, 1 to 4 heteroatoms selected from a nitrogen atom, a sulfur atom and an oxygen atom, or
(xxvii) a 5- to 8-membered aromatic heterocyclic group containing, besides carbon atoms, 1 to 4 heteroatoms selected from a nitrogen atom, a sulfur atom and an oxygen atom,
a group represented by the formula

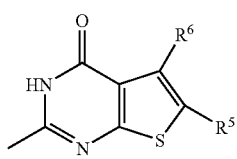

wherein
R⁵ and R⁶ are each
(i) a hydrogen atom,
(ii) a halogen atom,
(iii) a cyano group,
(iv) a hydroxy group,
(v) a nitro group,
(vi) a carboxyl group,
(vii) an alkoxycarbonyl group optionally having substituent(s),
(viii) an amino group optionally having substituent(s),
(ix) an alkyl group optionally having substituent(s),
(x) an alkenyl group optionally having substituent(s),
(xi) an alkynyl group optionally having substituent(s),
(xii) an aryl group optionally having substituent(s),
(xiii) an alkoxy group optionally having substituent(s),
(xiv) an aralkyloxy group optionally having substituent(s),
(xv) an aryloxy group optionally having substituent(s),
(xvi) a thiol group,
(xvii) an alkylthio group optionally having substituent(s),
(xviii) an aralkylthio group optionally having substituent(s),
(xix) a 5- to 8-membered aromatic heterocyclyl-thio group containing, besides carbon atoms, 1 to 4 heteroatoms selected from a nitrogen atom, an oxygen atom and a sulfur atom,
(xx) a mono- or di-alkylcarbamoyl-thio group,
(xxi) an alkylsulfonyl group optionally having substituent(s),
(xxii) an arylsulfonyl group optionally having substituent(s),
(xxiii) an aralkylsulfonyl group optionally having substituent(s),
(xxiv) a carbamoyl group optionally having substituent(s),
(xxv) a mono- or di-alkylamino-thiocarbonyloxy group,
(xxvi) a 5- to 8-membered non-aromatic heterocyclic group containing, besides carbon atoms, 1 to 4 heteroatoms selected from a nitrogen atom, a sulfur atom and an oxygen atom, or
(xxvii) a 5- to 8-membered aromatic heterocyclic group containing, besides carbon atoms, 1 to 4 heteroatoms selected from a nitrogen atom, a sulfur atom and an oxygen atom, or
a group represented by the formula

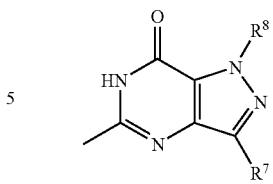

wherein
R⁷ and R⁸ are each
(i) a hydrogen atom,
(ii) a halogen atom,
(iii) a cyano group,
(iv) a hydroxy group,
(v) a nitro group,
(vi) a carboxyl group,
(vii) an alkoxycarbonyl group optionally having substituent(s),
(viii) an amino group optionally having substituent(s),
(ix) an alkyl group optionally having substituent(s),
(x) an alkenyl group optionally having substituent(s),
(xi) an alkynyl group optionally having substituent(s),
(xii) an aryl group optionally having substituent(s),
(xiii) an alkoxy group optionally having substituent(s),
(xiv) an aralkyloxy group optionally having substituent(s),
(xv) an aryloxy group optionally having substituent(s),
(xvi) a thiol group,
(xvii) an alkylthio group optionally having substituent(s),
(xviii) an aralkylthio group optionally having substituent(s),
(xix) a 5- to 8-membered aromatic heterocyclyl-thio group containing, besides carbon atoms, 1 to 4 heteroatoms selected from a nitrogen atom, an oxygen atom and a sulfur atom,
(xx) a mono- or di-alkylcarbamoyl-thio group,
(xxi) an alkylsulfonyl group optionally having substituent(s),
(xxii) an arylsulfonyl group optionally having substituent(s),
(xxiii) an aralkylsulfonyl group optionally having substituent(s),
(xxiv) a carbamoyl group optionally having substituent(s),
(xxv) a mono- or di-alkylamino-thiocarbonyloxy group,
(xxvi) a 5- to 8-membered non-aromatic heterocyclic group containing, besides carbon atoms, 1 to 4 heteroatoms selected from a nitrogen atom, a sulfur atom and an oxygen atom, or
(xxvii) a 5 to 8-membered aromatic heterocyclic group containing, besides carbon atoms, 1 to 4 heteroatoms selected from a nitrogen atom, a sulfur atom and an oxygen atom,
provided that
{[3-({[(4-oxo-3,4-dihydroquinazolin-2-yl)carbonyl]amino}methyl)phenyl]oxy}acetic acid,
5-{[3-({{[(4-oxo-3,4-dihydroquinazolin-2-yl)carbonyl]amino}methyl)phenyl]oxy}pentanoic acid,
5-({3-[({[6-(methyloxy)-4-oxy-dihydroquinazolin-2-yl]carbonyl}amino)methyl]phenyl}oxy)pentanoic acid,
4-{[3-({[(4-oxo-3,4-dihydroquinazolin-2-yl)carbonyl]amino}methyl)phenyl]oxy}butanoic acid,
N-[(2-{[(5-methylisoxazol-3-yl)methyl]oxy}pyridin-4-yl)methyl]-4-oxo-3,4-dihydroquinazoline-2-carboxamide, and
N-[(2-{[(3,5-dimethylisoxazol-4-yl)methyl]oxy}pyridin-4-yl)methyl]-4-oxo-3,4-dihydroquinazoline-2-carboxamide are excluded, or a salt thereof, or a prodrug thereof, for the production of a matrix metalloproteinase inhibitor, and the like.

Moreover, the present invention also relates to

[13] the compound of [1], wherein
A is a triazolyl group or a group represented by the formula —C(O)NHOH;
X is CH or N;
Y is —(CH$_2$)$_3$O—, —S(CH$_2$)$_2$O—, —S(CH$_2$)$_3$O—, —S(CH$_2$)$_4$O—, —O(CH$_2$)$_2$O—, —O(CH$_2$)$_3$O—, CH$_2$OCH$_2$—, —(CH$_2$)$_2$—C(O)—NH—, —C(O)—NH—CH$_2$—, —NH—C(O)—(CH$_2$)$_3$—O—, —CH$_2$—C(O)—NH—CH$_2$—, —C(O)—NH—,

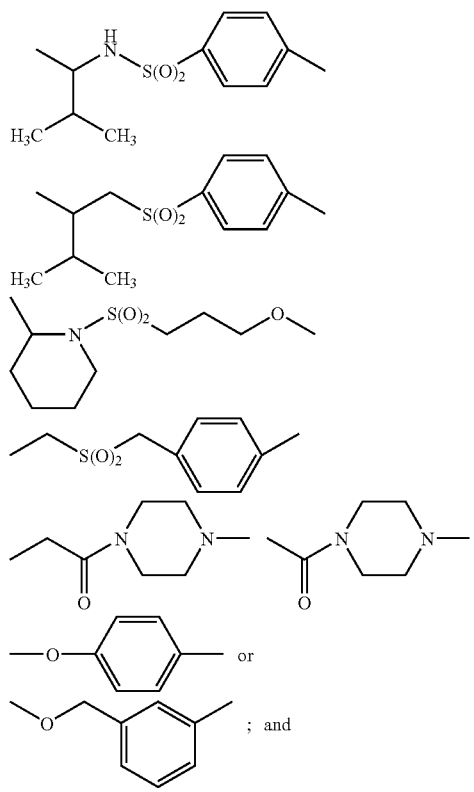

; and a group represented by the formula

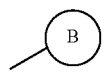

is a group represented by the formula

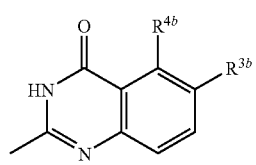

wherein
R$^{3b}$ is (i) a hydrogen atom, (ii) a halogen atom, (iii) a cyano group, (iv) an amino group, (v) a C$_{1-6}$ alkyl group, or (vi) a C$_{1-6}$ alkoxy group; and R$^{4b}$ is (i) a hydrogen atom, (ii) a halogen atom, (iii) a C$_{1-6}$ alkyl group optionally having a C$_{7-16}$ aralkyloxy group optionally having substituent(s) selected from (a) a C$_{1-6}$ alkoxy-carbonyl group and (b) a carboxyl group, (iv) a C$_{7-16}$ aralkylamino group optionally having a triazolyloxy-C$_{1-6}$ alkoxy group, or (v) a C$_{1-6}$ alkoxy group optionally having a C$_{6-14}$ aryl group optionally having substituent(s) selected from (a) a C$_{1-6}$ alkoxy-carbonyl group and (b) a carboxyl group, a group represented by the formula

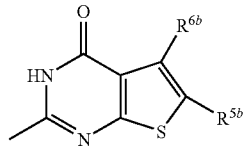

wherein
R$^{5b}$ is (i) a hydrogen atom, or (ii) a C$_{1-6}$ alkyl group; and
R$^{6b}$ is
(i) a hydrogen atom,
(ii) a cyano group,
(iii) a halogen atom,
(iv) a C$_{6-14}$ aryl group optionally having substituent(s) selected from a cyano group, a halogen atom, a C$_{1-6}$ alkyl group, a C$_{1-6}$ alkoxy group, a carboxyl group, a C$_{1-6}$ alkoxycarbonyl group and a C$_{6-14}$ aryl group,
(v) a C$_{1-6}$ alkyl group optionally having substituent(s) selected from (a) a C$_{7-14}$ aralkyloxy group optionally having a C$_{1-6}$ alkoxycarbonyl group or a carboxyl group and (b) a cyano group, or
(vi) a 5-membered aromatic heterocyclic group containing, besides carbon atoms, 1 to 4 heteroatoms selected from a nitrogen atom, a sulfur atom and an oxygen atom, or
a group represented by the formula

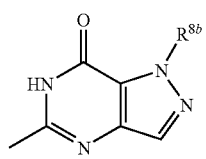

wherein
R$^{8b}$ is a C$_{1-6}$ alkyl group optionally having a C$_{6-14}$ aryloxy group optionally having substituent(s) selected from (a) a C$_{1-6}$ alkoxy-carbonyl group and (b) a carboxyl group, or a salt thereof, and

[14] the compound of [1], wherein
A is a triazolyl group;
X is CH or N;
Y is —(CH$_2$)$_3$O—, —S(CH$_2$)$_2$O—, —S(CH$_2$)$_3$O— or —O(CH$_2$)$_2$O—, O(CH$_2$)$_3$O—,

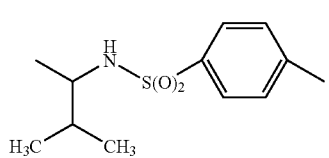

-continued

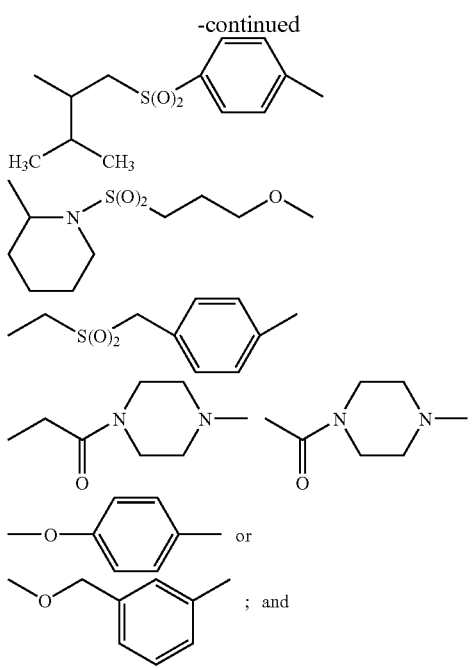

a group represented by the formula

is a group represented by the formula

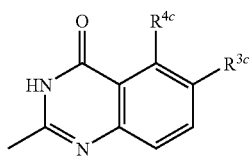

wherein
R$^{3c}$ is (i) a hydrogen atom, (ii) a halogen atom, (iii) a cyano group, (iv) an amino group, (v) a C$_{1-6}$ alkyl group, or (vi) a C$_{1-6}$ alkoxy group; and
R$^{4c}$ is (i) a hydrogen atom, (ii) a halogen atom, (iii) a C$_{7-16}$ aralkylamino group optionally having a Triazolyloxy-C$_{1-6}$ alkoxy group, or (iv) a C$_{1-6}$ alkoxy group optionally having a C$_{6-14}$ aryl group optionally having a carboxyl group, a group represented by the formula

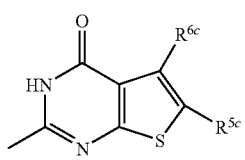

wherein
R$^{5c}$ is (i) a hydrogen atom, or (ii) a C$_{1-6}$ alkyl group; and
R$^{6c}$ is (i) a hydrogen atom,
(ii) a C$_{6-14}$ aryl group optionally having substituent(s) selected from a cyano group, a halogen atom, a C$_{1-6}$ alkyl group, a C$_{1-6}$ alkoxy group, a carboxyl group, a C$_{1-6}$ alkoxycarbonyl group and a C$_{6-14}$ aryl group,
(iii) a C$_{1-6}$ alkyl group optionally having substituent(s) selected from (a) a C$_{7-14}$ aralkyloxy group optionally having a C$_{1-6}$ alkoxycarbonyl group or a carboxyl group and (b) a cyano group, or
(iv) a 5-membered aromatic heterocyclic group containing, besides carbon atoms, 1 to 4 heteroatoms selected from a nitrogen atom, a sulfur atom and an oxygen atom, or a group represented by the formula

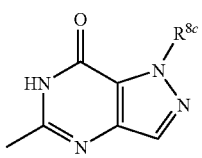

wherein
R$^{8c}$ is a C$_{1-6}$ alkyl group optionally having a C$_{6-14}$ aryloxy group optionally having substituent(s) selected from (a) a C$_{1-6}$ alkoxy-carbonyl group and (b) a carboxyl group,
or a salt thereof.

Furthermore, while compound (I) and a salt thereof produce tautomers, any tautomer is encompassed in the present invention, and compound (I) and a salt thereof may be any of solvates, hydrates, non-solvates and non-hydrates.

DETAILED DESCRIPTION OF THE INVENTION

The present invention is described in detail in the following.
(1) A
A is a zinc-binding group. The "zinc-binding group" means a functional group capable of bonding to a zinc (II) ion in the active site of MMP. As the "zinc-binding group", for example, groups shown below and tautomers thereof and the like can be mentioned.

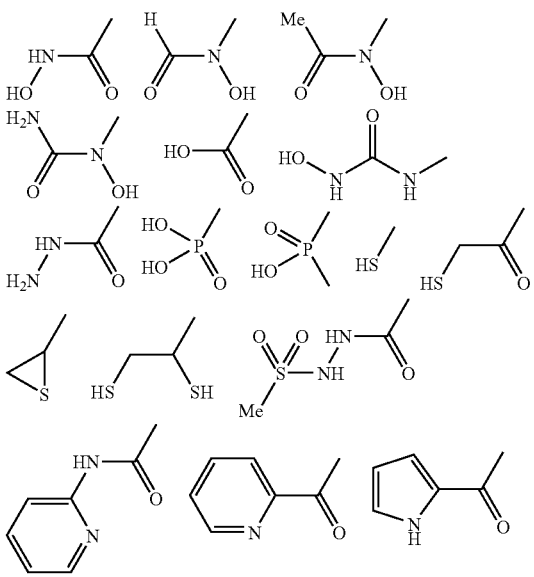

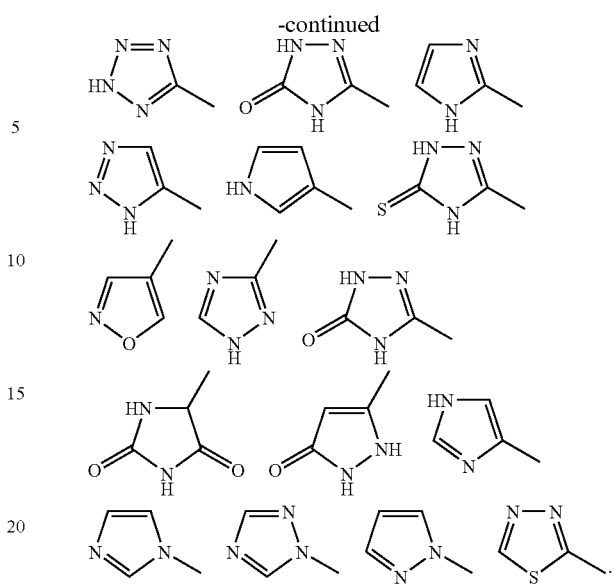
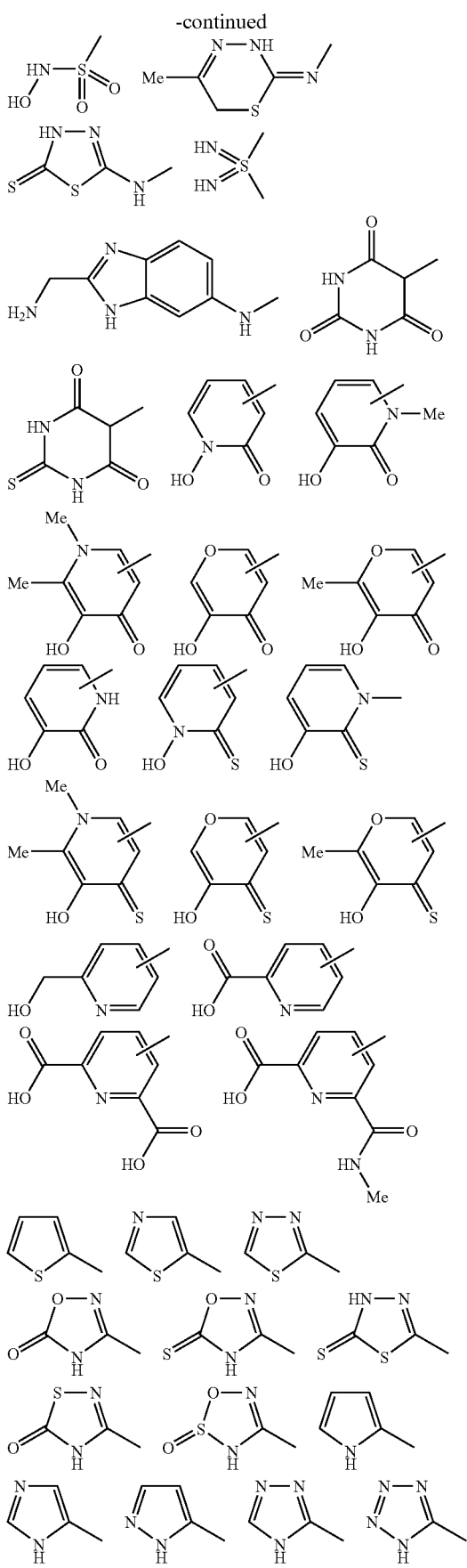

The above-mentioned "zinc-binding group" optionally has substituent(s) at substitutable position(s). As the "substituents", for example, (i) a halogen atom (e.g., a fluorine atom, chlorine atom, a bromine atom, an iodine atom),
(ii) a cyano group,
(iii) a hydroxy group,
(iv) a nitro group,
(v) a formyl group,
(vi) an amino group,
(vii) a mono- or di-$C_{1-6}$ alkylamino group (e.g., methylamino, ethylamino, propylamino, dimethylamino, diethylamino, dipropylamino etc.),
(viii) a $C_{1-6}$ alkyl-carbonylamino group (e.g., methylcarbonylamino, ethylcarbonylamino, propylcarbonylamino etc.),
(ix) a $C_{1-6}$ alkoxy-carbonylamino group (e.g., methoxycarbonylamino, ethoxycarbonylamino, propoxycarbonylamino etc.),
(x) a $C_{1-6}$ alkyl group (e.g., methyl, ethyl, propyl, isopropyl, butyl, isobutyl, sec-butyl, tert-butyl, pentyl, hexyl etc.),
(xi) a $C_{3-8}$ cycloalkyl group (e.g., cyclopropyl, cyclobutyl, cyclopentyl, cyclohexyl etc.),
(xii) a $C_{6-14}$ aryl group (e.g., phenyl, 1-naphthyl, 2-naphthyl etc.),
(xiii) a $C_{1-6}$ alkoxy group (e.g., methoxy, ethoxy, propoxy, isopropoxy, butoxy, isobutoxy, sec-butoxy, tert-butoxy etc.),
(xiv) a carboxyl group,
(xv) a $C_{1-6}$ alkoxy-carbonyl group (e.g., methoxycarbonyl, ethoxycarbonyl, propoxycarbonyl etc.),
(xvi) a $C_{7-16}$ aralkyloxy-carbonyl group (e.g., benzyloxycarbonyl etc.),
(xvii) a $C_{6-14}$ aryloxy-carbonyl group (e.g., phenyloxycarbonyl etc.),
(xviii) a $C_{3-8}$ cycloalkyl-carbonyl group (e.g., cyclopropylcarbonyl, cyclobutylcarbonyl, cyclopentylcarbonyl, cyclohexylcarbonyl etc.),
(xix) a $C_{7-16}$ aralkyl-carbonyl group (e.g., benzylcarbonyl etc.),
(xx) a carbamoyl group,
(xxi) a thiocarbamoyl group,
(xxii) a mono- or di-$C_{1-6}$ alkyl-carbamoyl group (e.g., methylcarbamoyl, ethylcarbamoyl, propylcarbamoyl, dimethylcarbamoyl, diethylcarbamoyl, dipropylcarbamoyl etc.), (xxiii) a mono- or di-$C_{7-16}$ aralkyl-carbamoyl group (e.g., benzylcarbamoyl, dibenzylcarbamoyl etc.), (xxiv) a thiol group, (xxv) a $C_{1-6}$ alkylthio group (e.g., methylthio, ethylthio, propylthio etc.), (xxvi) a $C_{7-16}$ aralkylthio group (e.g., benzylthio etc.), (xxvii) a $C_{1-6}$ alkylsulfonyl group (e.g., methylsulfonyl, ethylsulfonyl, propylsulfonyl etc.), (xxviii) a $C_{3-8}$ cycloalkylsulfonyl group (e.g., cyclopropylsulfonyl, cyclobutylsulfonyl, cyclopentylsulfonyl etc.), (xxix) a $C_{6-14}$ arylsulfonyl group (e.g., phenylsulfonyl, 1-naphthylsulfonyl, 2-naphthylsulfonyl etc.), (xxx) a $C_{7-15}$ aralkylsulfonyl group (e.g., benzylsulfonyl etc.), (xxxi) a 5- to 8-membered non-aromatic heterocyclic group containing, besides carbon atoms, 1 to 4 heteroatoms selected from a nitrogen atom, a sulfur atom and an oxygen atom (e.g., pyrrolidinyl, tetrahydrofuryl, tetrahydrothienyl, piperidyl, tetrahydropyranyl, morpholinyl, thiomorpholinyl, piperazinyl etc.), (xxxii) a 5- to 8-membered aromatic heterocyclic group containing, besides carbon atoms, 1 to 4 heteroatoms selected from a nitrogen atom, a sulfur atom and an oxygen atom (e.g., furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl etc.), (xxxiii) an ureido group, (xxxiv) a $C_{1-6}$ alkylureido group (e.g., methylureido, ethylureido, propylureido etc.)

(xxxv) a $C_{6-14}$ arylureido group (e.g., phenylureido, 1-naphthylureido, 2-naphthylureido etc.) and (xxxvi) a $C_{1-6}$ alkoxy-$C_{1-6}$ alkyl group (e.g., methoxymethyl, ethoxymethyl, propoxymethyl, methoxyethyl, ethoxyethyl, propoxyethyl, methoxypropyl, ethoxypropyl, propoxypropyl etc.), (xxxvii) a mono-, di- or tri-halogenated $C_{1-6}$ alkyl group (e.g., fluoromethyl, difluoromethyl, trifluoromethyl etc.) and the like can be mentioned. Any number of these substituents may be used at any substitutable positions).

A is preferably a pyrrolyl group optionally having substituent(s), an imidazolyl group optionally having substituent(s), a pyrazolyl group optionally having substituent(s), a triazolyl group optionally having substituent(s), a tetrazolyl group optionally having substituent(s), an unsubstituted tetrazolyl group, a thiadiazolyl group optionally having an amino group, a trioxohexahydropyrimidinyl group optionally having a $C_{1-6}$ alkoxy-$C_{1-6}$ alkyl group, a carboxyl group, a group represented by the formula —N(OH)C(O)H, a group represented by the formula —N(OH)C(O)CH$_3$, a group represented by the formula —N(OH)C(O)NH$_2$, a group represented by the formula C(O)NHOH, or a group represented by the following structure:

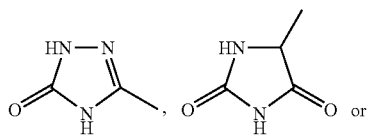

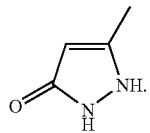

Of these, a triazolyl group optionally having substituent(s), a tetrazolyl group optionally having substituent(s) and a group represented by the formula —C(O)NHOH are preferable. Especially, an unsubstituted imidazolyl group, an unsubstituted pyrazolyl group, a triazolyl group optionally having a $C_{1-6}$ alkyl group, a $C_{6-14}$ aryl group or a mono-, die or tri-halogenated $C_{1-6}$ alkyl group, an unsubstituted tetrazolyl group, a thiadiazolyl group optionally having an amino group, a trioxohexahydropyrimidinyl group optionally having a $C_{1-6}$ alkoxy-$C_{1-6}$ alkyl group, a carboxyl group, a group represented by the formula —N(OH)C(O)H, a group represented by the formula —N(OH)C(O)CH$_3$, a group represented by the formula —N(OH)C(O)NH$_2$, a group represented by the formula —C(O)NHOH, and groups represented by the following structure:

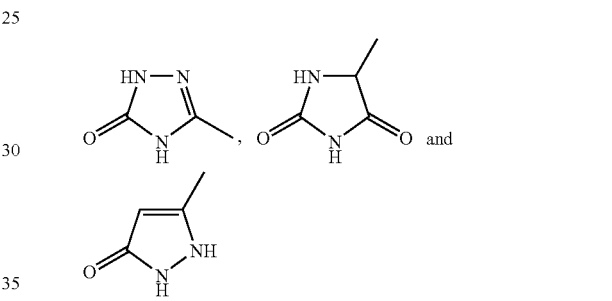

are preferable, and an unsubstituted triazolyl group is particularly preferable.

(2) X

X is CZ wherein Z is a hydrogen atom or a halogen atom, or N. As the halogen atom for Z, a fluorine atom, chlorine atom, a bromine atom and an iodine atom can be mentioned.

X is preferably CF, CH or N, more preferably CH or N.

(3) Y

Y is a spacer having 2 to 10 atoms and optionally having substituent(s). As the "spacer having 2 to 10 atoms", —(CH$_2$)$_{n1}$— (n1 is an integer of 2 to 10), —(CH$_2$)$_{n2}$—NH—(CH$_2$)$_{n3}$— (wherein n2 and n3 are each an integer of 0 to 9, and the sum of n2 and n3 is an integer of 1 to 9), —(CH$_2$)$_{n4}$—O—(CH$_2$)$_{n5}$— (wherein n4 and n5 are each an integer of 0 to 9, and the sum of n4 and n5 is an integer of 1 to 9), —(CH$_2$)$_{n6}$—S(O)$_{m1}$—(CH$_2$)$_{n7}$— (wherein n6 and n7 are each an integer of 0 to 9, the sum of n6 and n7 is an integer of 1 to 9, and m1 is 0 or 2), —(CH$_2$)$_{n8}$—NHC(O)—(CH$_2$)$_{n9}$— (wherein n8 and n9 are each an integer of 0 to 8, and the sum of n8 and n9 is an integer of 0 to 8), —(CH$_2$)$_{n10}$—C(O)NH—(CH$_2$)$_{n11}$— (wherein n10 and n11 are each an integer of 0 to 8, and the sum of n10 and n11 is an integer of 0 to 8), —(CH$_2$)$_{n12}$—NHS(O)$_2$—(CH$_2$)$_{n13}$— (wherein n12 and n13 are each an integer of 0 to 8, and the sum of n12 and n13 is an integer of 0 to 8), —$(CH_2)_{n14}$—$S(O)_2NH$—$(CH_2)_{n15}$— (wherein n14 and n15 are each an integer of 0 to 8, and the sum of n14 and n15 is an integer of 0 to 8), —$(CH_2)_{n16}$—NH—$(CH_2)_{n17}$—NH—$(CH_2)_{n18}$— (wherein n16 and n18 are each an integer of 0 to 7, n17 is an integer of 1 to 8, and the sum of n16, n17 and n18 is an integer of 1 to 8), —$(CH_2)_{n19}$—NH—$(CH_2)_{n20}$—O—$(CH_2)_{n21}$— (wherein n19 and n21 are each an integer of 0 to 7, n20 is an integer of 1 to 8, and the so sum of n19, n20 and n21 is an integer of 1 to 8), —$(CH_2)_{n22}$—NH—$(CH_2)_{n23}$—$S(O)_{m2}$—$(CH_2)_{n24}$— (wherein n22 and n24 are each an integer of 0 to 7, n23 is an integer of 1 to 8, the sum of n22, n23 and n24 is an integer of 1 to 8, and m2 is 0 or 2), —$(CH_2)_{n25}$—O—$(CH_2)_{n26}$—NH—$(CH_2)_{n27}$ (wherein n25 and n27 are each an integer of 0 to 7, n26 is an integer of 1 to 8, and the sum of n25, n26 and n27 is an integer of 1 to 8), —$(CH_2)_{n28}$—O—$(CH_2)_{n29}$—O—$(CH_2)_{n30}$— (wherein n28 and n30 are each an integer of 0 to 7, n29 is an integer of 1 to 8, and the sum of n28, n29 and n30 is an integer of 1 to 8), —$(CH_2)_{n31}$—O—$(CH_2)_{n32}$—$S(O)_{m3}$—$(CH_2)_{n33}$— (wherein n31 and n33 are each an integer of 0 to 7, n32 is an integer of 1 to 8, the sum of n31, n32 and n33 is an integer of 1 to 8, and m3 is 0 or 2), —$(CH_2)_{n34}$—$S(O)_{m4}$—$(CH_2)_{n35}$—NH—$(CH_2)_{n36}$— (wherein n34 and n36 are each an integer of 0 to 7, n35 is an integer of 1 to 8, the sum of n34, n35 and n36 is an integer of 1 to 8, and m4 is 0 or 2), —$(CH_2)_{n37}$—$S(O)_{m5}$—$(CH_2)_{n38}$—O—$(CH_2)_{n39}$— (wherein n37 and n39 are each an integer of 0 to 7, n38 is an integer of 1 to 8, the sum of n37, n38 and n39 is an integer of 1 to 8, and m5 is or 2), —$(CH_2)_{n40}$—$S(O)_{m6}$—$(CH_2)_{n41}$—$S(O)_{m7}$—$(CH_2)_{n42}$— (wherein n40 and n42 are each an integer of 0 to 7, n41 is an integer of 1 to 8, the sum of n40, n41 and n42 is an integer of 1 to 8, and m6 and m7 are each 0 or 2), —$(CH_2)_{n43}$—NH—$(CH_2)_{n44}$—NHC(O) $(CH_2)_{n45}$— (wherein n43 and n45 are each an integer of 0 to 6, n44 is an integer of 1 to 7, and the sum of n43, n44 and n45 is an integer of 1 to 7), —$(CH_2)_{n46}$—NH—$(CH_2)_{n47}$—C(O)NH—$(CH_2)_{n48}$— (wherein n46 and n48 are each an integer of 0 to 6, n47 is an integer of 1 to 7, and the sum of n46, n47 and n48 is an integer of 1 to 7), —$(CH_2)_{n49}$—NH—$(CH_2)_{n50}$—$NHS(O)_2$—$(CH_2)_{n51}$— (wherein n49 and n51 are each an integer of 0 to 6, n50 is an integer of 1 to 7, and the sum of n49, n50 and n51 is an integer of 1 to 7), —$(CH_2)_{n52}$—NH—$(CH_2)_{n53}$—$S(O)_2NH$—$(CH_2)_{n54}$— (wherein n52 and n54 are each an integer of 0 to 6, n53 is an integer of 1 to 7, and the sum of n52, n53 and n54 is an integer of 1 to 7), —$(CH_2)_{n55}$—O—$(CH_2)_{n56}$—NHC(O)—$(CH_2)_{n57}$— (wherein n55 and n57 are each an integer of 0 to 6, n56 is an integer of 1 to 7, and the sum of n55, n56 and n57 is an integer of 1 to 7), —$(CH_2)_{58}$—O—$(CH_2)_{n59}$—C(O)NH—$(CH_2)_{n60}$— (wherein n58 and n60 are each an integer of 0 to 6, n59 is an integer of 1 to 7, and the sum of n58, n59 and n60 is an integer of 1 to 7), —$(CH_2)_{n61}$—$O(CH_2)_{n62}$—$NHS(O)_2$ $(CH_2)_{n63}$— (wherein n61 and n63 are each an integer of 0 to 6, n62 is an integer of 1 to 7, and the sum of n61, n62 and n63 is an integer of 1 to 7), —$(CH_2)_{n64}$—O—$(CH_2)_{n65}$—$S(O)_2NH$—$(CH_2)_{n66}$— (wherein n64 and n66 are each an integer of 0 to 6, n65 is an integer of 1 to 7, and the sum of n64, n65 and n66 is an integer of 1 to 7), —$(CH_2)_{n67}$—$S(O)_{m8}$—$(CH_2)_{n68}$—NHC(O)—$(CH_2)_{n69}$— (wherein n67 and n69 are each an integer of 0 to 6, n68 is an integer of 1 to 7, the sum of n67, n68 and n69 is an integer of 1 to 7, and m8 is 0 or 2), —$(CH_2)_{n70}$—$S(O)_{m9}$—$(CH_2)_{n71}$—C(O)NH—$(CH_2)_{n72}$— (wherein n70 and n72 are each an integer of 0 to 6, n71 is an integer of 1 to 7, the sum of n70, n71 and n72 is an integer of 1 to 7, and m9 is 0 or 2), —$(CH_2)_{n73}$—$S(O)_{m10}$—$(CH_2)_{n74}$—$NHS(O)_2$—$(CH_2)_{n75}$— (wherein n73 and n75 are each an integer of 0 to 6, n74 is an integer of 1 to 7, the sum of n73, n74 and n75 is an integer of 1 to 7, and m10 is 0 or 2), —$(CH_2)_{n76}$—$S(O)_{m11}$—$(CH_2)_{n77}$—$S(O)_2NH$—$(CH_2)_{n78}$— (wherein n76 and n78 are each an integer of 0 to 6, n77 is an integer of 1 to 7, the sum of n76, n77 and n78 is an integer of 1 to 7, and m11 is 0 or 2), —$(CH_2)_{n79}$—NHC(O)—$(CH_2)_{n80}$—NH—$(CH_2)_{n81}$— (wherein n79 and n81 are so each an integer of 0 to 6, n80 is an integer of 1 to 7, and the sum of n79, n80 and n81 is an integer of 1 to 7), —$(CH_2)_{n82}$—C(O)NH—$(CH_2)_{n83}$—NH—$(CH_2)_{n84}$— (wherein n82 and n84 are each an integer of 0 to 6, n83 is an integer of 1 to 7, and the sum of n82, n83 and n84 is an integer of 1 to 7), —$(CH_2)_{n85}$—$NHS(O)_2$—$(CH_2)_{n86}$—NH—$(CH_2)_{n87}$— (wherein n85 and n87 are each an integer of 0 to 6, n86 is an integer of 1 to 7, and the sum of n85, n86 and n87 is an integer of 1 to 7), —$(CH_2)_{n88}$—$S(O)_2NH$—$(CH_2)_{n89}$—NH—$(CH_2)_{n90}$— (wherein n88 and n90 are each an integer of 0 to 6, n89 is an integer of 1 to 7, and the sum of n88, n89 and n90 is an integer of 1 to 7), —$(CH_2)_{n91}$—NHC(O)—$(CH_2)_{n92}$—$(CH_2)_{n93}$— (wherein n91 and n93 are each an integer of 0 to 6, n92 is an integer of 1 to 7, and the sum of n91, n92 and n93 is an integer of 1 to 7), —$(CH_2)_{n94}$—C(O)NH—$(CH_2)_{n95}$—O—$(CH_2)_{n96}$— (wherein n94 and n96 are each an integer of 0 to 6, n95 is an integer of 1 to 7, and the sum of n94, n95 and n96 is an integer of 1 to 7), —$(CH_2)_{97}$—$NHS(O)_2$—$(CH_2)_{n98}$—$O(CH_2)_{n99}$— (wherein n97 and n99 are each an integer of 0 to 6, n98 is an integer of 1 to 7, and the sum of n97, n98 and n99 is an integer of 1 to 7), —$(CH_2)_{n100}$—$S(O)_2NH$— $(CH_2)_{n101}$—$(CH_2)_{n102}$— (wherein n100 and n102 are each an integer of 0 to 6, n101 is an integer of 1 to 7, and the sum of n100, n101 and n102 is an integer of 1 to 7), —$(CH_2)_{n103}$—NHC(O)—$(CH_2)_{n104}$—$S(O)_{m12}$—$(CH_2)_{n105}$— (wherein n103 and n105 are each an integer of 0 to 6, n104 is an integer of 1 to 7, the sum of n103, n104 and n105 is an integer of 1 to 7, and m12 is 0 or 2), —$(CH_2)_{n106}$—C(O)NH—$(CH_2)_{n107}$—$S(O)_{m13}$—$(CH_2)_{n108}$— (wherein n106 and n108 are each an integer of 0 to 6, n107 is an integer of 1 to 7, the sum of n106, n107 and n108 is an integer of 1 to 7, and m13 is 0 or 2), —$(CH_2)_{n109}$—$NHS(O)_2$—$(CH_2)_{n110}$—$S(O)_{m14}$—$(CH_2)_{n111}$— (wherein n109 and n111 are each an integer of 0 to 6, n111 is an integer of 1 to 7, the sum of n109, n110 and n111 is an integer of 1 to 7, and m14 is 0 or 2), —$(CH_2)_{n112}$—$S(O)_2NH$—$(CH_2)_{n113}$—$S(O)_{m15}$—$(CH_2)_{n114}$— (wherein n112 and n114 are each an integer of 0 to 6, n113 is an integer of 1 to 7, the sum of n112, n113 and n114 is an integer of 1 to 7, and m15 is 0 or 2), —$(CH_2)_{n115}$—$S(O)_2NH$—$(CH_2)_{n116}$—NR—$(CH_2)_{n117}$— (wherein n115 and n117 are each an integer of 0 to 6, n116 is an integer of 1 to 7, and the sum of n115, n116 and n117 is an integer of 1 to 7), and the like can be mentioned.

The "spacer having 2 to 10 atoms" optionally has substituent(s) at substitutable positions), and as the substituents, (i) a halogen atom, (ii) a cyano group, (iii) a hydroxy group, (iv) an amino group, (v) a mono- or di-$C_{1-6}$ alkylamino group, (vi) a $C_{7-16}$ aralkylamino group, (vii) a $C_{1-6}$ alkyl-carbonylamino group, (viii) a $C_{1-6}$ alkylsulfonylamino group, (ix) a $C_{1-6}$ alkyl group optionally substituted by substituent(s) selected from a halogen atom, a $C_{1-6}$ alkoxy group and a 5- to 8-membered non-aromatic heterocyclic group containing, besides carbon atoms, 1 to 4 heteroatom selected from a nitrogen atom, an oxygen atom and a sulfur atom, and the like, (x) a $C_{7-16}$ aralkyloxy group, (xi) a $C_{6-14}$ aryl group, (xii) a $C_{1-6}$ alkoxy group, (xiii) a thiol group, (xiv) a $C_{1-6}$ alkylthio group, (xv) a $C_{7-16}$ aralkylthio group, (xvi) a 5- to 8-membered aromatic heterocyclyl-thio group containing, besides carbon atoms, 1 to 4 heteroatoms selected from a nitrogen atom, an oxygen atom and a sulfur atom, (xvii) a $C_{1-6}$ alkylsulfonyl group, (xviii) a carbamoyl group, (xix) a mono- or di-$C_{1-6}$ alkylamino-thiocarbonyloxy group, (xx) a mono- or di-$C_{1-6}$ alkylcarbamoyl-thio group, (xxi) a nitro group, (xxii) a carboxyl group, (xxiii) a $C_{1-6}$ alkoxy-carbonyl group, (xxiv) a $C_{1-6}$ alkyl-carbonyl group and the like can be mentioned.

In addition, when the partial structure of the "spacer having 2 to 10 atoms" contains —$CH_2$—$CH_2$—, the —$CH_2$—$CH_2$— may be replaced by a double bond or a triple bond.

Moreover, the substituents of the "spacer having 2 to 10 atoms" are optionally bonded to each other to form a ring (a $C_{3-7}$ cycloalkane (cyclopropane, cyclobutane, cyclopentane, cyclohexane, cycloheptane), a $C_{6-14}$ arene (benzene, naphthalene etc.), a 5- to 8-membered non-aromatic heterocycle containing, besides carbon atoms, 1 to 4 heteroatom selected from a nitrogen atom, an oxygen atom and a sulfur atom (pyrrolidine, tetrahydrofuran, tetrahydrothiophene, piperidine, tetrahydropyran, morpholine, thiomorpholine, piperazine etc.), a 5- to 8-membered aromatic heterocycle containing, besides carbon atoms, 1 to 4 heteroatom selected from a nitrogen atom, an oxygen atom and a sulfur atom (furan, thiophene, pyrrole, oxazole, isoxazole, thiazole, isothiazole, imidazole, pyrazole, 1,2,3-oxadiazole, 1,2,4-oxadiazole, 1,3,4-oxadiazole, furazan, 1,2,3-thiadiazole, 1,2,4-thiadiazole, 1,3,4-thiadiazole, 1,2,3-triazole, 1,2,4-triazole, tetrazole, pyridine, pyridazine, pyrimidine, pyrazine, triazine etc.) etc.). As a preferable spacer wherein the substituents are optionally bonded to each other to form a ring, those shown below can be mentioned.

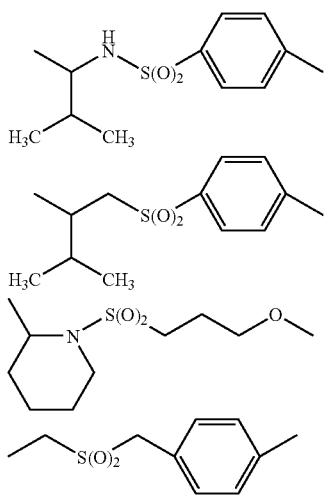

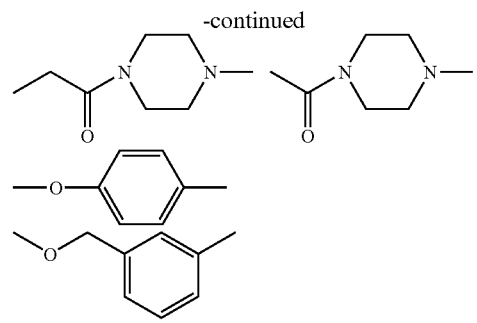

Y is preferably a spacer having 2 to 7 atoms and optionally having substituent(s), more preferably a spacer having 2 to 6 atoms and optionally having substituent(s).

Y is further more preferably the above-mentioned preferable spacer wherein the substituents are optionally bonded to each other to form a ring, or a spacer shown below.
—$(CH_2)_3$O—, —$S(CH_2)_2$O—, —$S(CH_2)_3$O—, —$S(CH_2)_4$O—, —$O(CH_2)_2$O—, —$O(CH_2)_3$O—, —$CH_2OCH_2$—, —$(CH_2)_2$—C(O)—NH—, —C(O)—NH—$CH_2$—, —NH—C(O)—$(CH_2)_3$O—, —$CH_2$—C(O)—NH—$CH_2$— or —C(O)—NH—

Y is particularly preferably a spacer shown below.
—$(CH_2)_3$O—, —$S(CH_2)_2$O—, —$S(CH_2)_3$O— or —$O(CH_2)_2$ O— the group represented by the formula

is a group represented by the formula

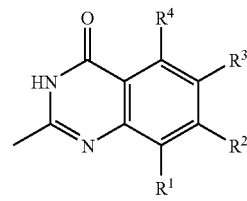

wherein
$R^1$, $R^2$, $R^3$ and $R^4$ are each
(i) a hydrogen atom,
(ii) a halogen atom,
(iii) a cyano group,
(iv) a hydroxy group,
(v) a nitro group,
(vi) a carboxyl group,
(vii) an alkoxycarbonyl group optionally having substituent(s),
(viii) an amino group optionally having substituent(s),
(ix) an alkyl group optionally having substituent(s),
(x) an alkenyl group optionally having substituent(s),
(xi) an alkynyl group optionally having substituent(s),
(xii) an aryl group optionally having substituent(s),
(xiii) an alkoxy group optionally having substituent(s),
(xiv) an aralkyloxy group optionally having substituent(s),
(xv) an aryloxy group optionally having substituent(s),
(xvi) a thiol group,
(xvii) an alkylthio group optionally having substituent(s), (xviii) an aralkylthio group optionally having substituent(s),
(xix) a 5- to 8-membered aromatic heterocyclyl-thio group containing, besides carbon atoms, 1 to 4 heteroatoms selected from a nitrogen atom, an oxygen atom and a sulfur atom,
(xx) a mono- or di-alkylcarbamoyl-thio group,
(xxi) an alkylsulfonyl group optionally having substituent(s),
(xxii) an arylsulfonyl group optionally having substituent(s),
(xxiii) an aralkylsulfonyl group optionally having substituent(s),
(xxiv) a carbamoyl group optionally having substituent(s),
(xxv) a mono- or di-alkylamino-thiocarbonyloxy group,
(xxvi) a 5- to 8-membered non-aromatic heterocyclic group containing, besides carbon atoms, 1 to 4 heteroatoms selected from a nitrogen atom, a sulfur atom and an oxygen atom, or
(xxvii) a 5- to 8-membered aromatic heterocyclic group containing, besides carbon atoms, 1 to 4 heteroatoms selected from a nitrogen atom, a sulfur atom and an oxygen atom,
a group represented by the formula

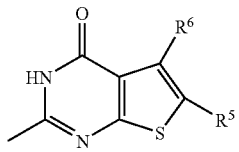

wherein
$R^5$ and $R^6$ are each
(i) a hydrogen atom,
(ii) a halogen atom,
(iii) a cyano group,
(iv) a hydroxy group,
(v) a nitro group,
(vi) a carboxyl group,
(vii) an alkoxycarbonyl group optionally having substituent(s),
(viii) an amino group optionally having substituent(s),
(ix) an alkyl group optionally having substituent(s),
(x) an alkenyl group optionally having substituent(s),
(xi) an alkynyl group optionally having substituent(s),
(xii) an aryl group optionally having substituent(s),
(xiii) an alkoxy group optionally having substituent(s),
(xiv) an aralkyloxy group optionally having substituent(s),
(xv) an aryloxy group optionally having substituent(s),
(xvi) a thiol group,
(xvii) an alkylthio group optionally having substituent(s),
(xviii) an aralkylthio group optionally having substituent(s),
(xix) a 5- to 8-membered aromatic heterocyclyl-thio group containing, besides carbon atoms, 1 to 4 heteroatoms selected from a nitrogen atom, an oxygen atom and a sulfur atom,
(xx) a mono- or di-alkylcarbamoyl-thio group,
(xxi) an alkylsulfonyl group optionally having substituent(s),
(xxii) an arylsulfonyl group optionally having substituent(s),
(xxiii) an aralkylsulfonyl group optionally having substituent(s)
(xxiv) a carbamoyl group optionally having substituent(s),
(xxv) a mono- or di-alkylamino-thiocarbonyloxy group,
(xxvi) a 5- to 8-membered non-aromatic heterocyclic group containing, besides carbon atoms, 1 to 4 heteroatoms selected from a nitrogen atom, a sulfur atom and an oxygen atom, or
(xxvii) a 5- to 8-membered aromatic heterocyclic group containing, besides carbon atoms, 1 to 4 heteroatoms selected from a nitrogen atom, a sulfur atom and an oxygen atom, or
a group represented by the formula

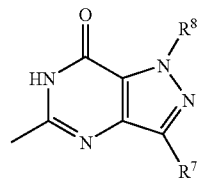

wherein
$R^7$ and $R^8$ are each
(i) a hydrogen atom,
(ii) a halogen atom,
(iii) a cyano group,
(iv) a hydroxy group,
(v) a nitro group,
(vi) a carboxyl group,
(vii) an alkoxycarbonyl group optionally having substituent(s),
(viii) an amino group optionally having substituent(s),
(ix) an alkyl group optionally having substituent(s),
(x) an alkenyl group optionally having substituent(s),
(xi) an alkynyl group optionally having substituent(s),
(xii) an aryl group optionally having substituent(s),
(xiii) an alkoxy group optionally having substituent(s),
(xiv) an aralkyloxy group optionally having substituent(s),
(xv) an aryloxy group optionally having substituent(s),
(xvi) a thiol group,
(xvii) an alkylthio group optionally having substituents(s),
(xviii) an aralkylthio group optionally having substituent(s),
(xix) a 5- to 8-membered aromatic heterocyclyl-thio group containing, besides carbon atoms, 1 to 4 heteroatoms selected from a nitrogen atom, an oxygen atom and a sulfur atom,
(xx) a mono- or di-alkylcarbamoyl-thio group,
(xxi) an alkylsulfonyl group optionally having substituent(s),
(xxii) an arylsulfonyl group optionally having substituent(s)
(xxiii) an aralkylsulfonyl group optionally having substituent(s),
(xxiv) a carbamoyl group optionally having substituent(s),
(xxv) a mono- or di-alkylamino-thiocarbonyloxy group,
(xxvi) a 5- to 8-membered non-aromatic heterocyclic group containing, besides carbon atoms, 1 to 4 heteroatoms selected from a nitrogen atom, a sulfur atom and an oxygen atom, or
(xxvii) a 5- to 8-membered aromatic heterocyclic group containing, besides carbon atoms, 1 to 4 heteroatoms selected from a nitrogen atom, a sulfur atom and an oxygen atom.

As the group represented by the formula

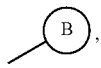

a group represented by the formula

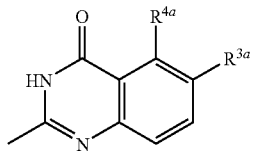

wherein
R$^{3a}$ and R$^{4a}$ are each
(i) a hydrogen atom,
(ii) a halogen atom,
(iii) a cyano group,
(iv) an amino group optionally having substituent(s),
(v) an alkyl group optionally having substituent(s), or
(vi) an alkoxy group optionally having substituent(s), a group represented by the formula

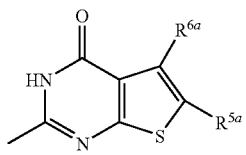

wherein
R$^{5a}$ and R$^{6a}$ are each
(i) a hydrogen atom, (ii) an alkyl group optionally having substituent(s),
(iii) a cyano group,
(iv) a halogen atom,
(v) an aryl group optionally having substituent(s), or
(vi) a 5- to 8-membered aromatic heterocyclic group containing, besides carbon atoms, 1 to 4 heteroatoms selected from a nitrogen atom, a sulfur atom and an oxygen atom, and
a group represented by the formula

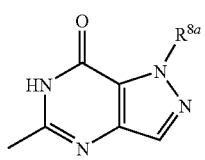

wherein
R$^{8a}$ is
(i) an alkyl group optionally having substituent(s), or
(ii) an aryl optionally having substituent(s),
are preferable. Of these, a group represented by the formula

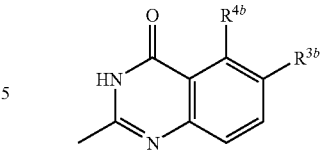

wherein
R$^{3b}$ is (i) a hydrogen atom, (ii) a halogen atom, (iii) a cyano group, (iv) an amino group, (v) a C$_{1-6}$ alkyl group, or (vi) a C$_{1-6}$ alkoxy group; and
R$^{4b}$ is (i) a hydrogen atom, (ii) a halogen atom, (iii) a C$_{1-6}$ alkyl group optionally having a C$_{7-16}$ aralkyloxy group optionally having substituent(s) selected from (a) a C$_{1-6}$ alkoxy-carbonyl group and (b) a carboxyl group, (iv) a C$_{7-16}$ aralkylamino group optionally having a triazolyloxy-C$_{1-6}$ alkoxy group, or (v) a C$_{1-6}$ alkoxy group optionally having a C$_{6-14}$ aryl group optionally having substituent(s) selected from (a) a C$_{1-6}$ alkoxy-carbonyl group and (b) a carboxyl group,
a group represented by the formula

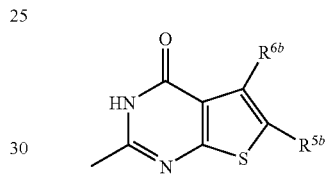

wherein
R$^{5b}$ is (i) a hydrogen atom, or (ii) a C$_{1-6}$ alkyl group; and
R$^{6b}$ is
(i) a hydrogen atom,
(ii) a cyano group,
(iii) a halogen atom,
(iv) a C$_{6-14}$ aryl group optionally having substituent(s) selected from a cyano group, a halogen atom, a C$_{1-6}$ alkyl group, a C$_{1-6}$ alkoxy group, a carboxyl group, a C$_{1-6}$ alkoxycarbonyl group and a C$_{6-14}$ aryl group,
(v) a C$_{1-6}$ alkyl group optionally having substituent(s) selected from (a) a C$_{7-14}$ aralkyloxy group optionally having a C$_{1-6}$ alkoxycarbonyl group or a carboxyl group and (b) a cyano group, or
(vi) a 5-membered aromatic heterocyclic group containing, besides carbon atoms, 1 to 4 heteroatoms selected from a nitrogen atom, a sulfur atom and an oxygen atom, and
a group represented by the formula

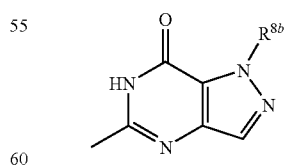

wherein
R$^{8b}$ is a C$_{1-6}$ alkyl group optionally having a C$_{6-14}$ aryloxy group optionally having substituent(s) selected from (a) a C$_{1-6}$ alkoxy-carbonyl group and (b) a carboxyl group,
are particularly preferable. Especially, a group represented by the formula

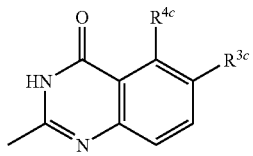

wherein
R$^{3c}$ is (i) a hydrogen atom, (ii) a halogen atom, (iii) a cyano group, (iv) an amino group, (v) a C$_{1-6}$ alkyl group, or (vi) a C$_{1-6}$ alkoxy group; and
R$^{4c}$ is (i) a hydrogen atom, (ii) a halogen atom, (iii) a C$_{7-16}$ aralkylamino group optionally having a triazolyloxy-C$_{1-6}$ alkoxy group, or (iv) a C$_{1-6}$ alkoxy group optionally having a C$_{6-14}$ aryl group optionally having a carboxyl group,
a group represented by the formula

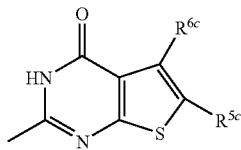

wherein
R$^{5c}$ is (i) a hydrogen atom, or (ii) a C$_{1-6}$ alkyl group; and
R$^{6c}$ is
(i) a hydrogen atom,
(ii) a C$_{6-14}$ aryl group optionally having substituent(s) selected from a cyano group, a halogen atom, a C$_{1-6}$ alkyl group, a C$_{1-6}$ alkoxy group, a carboxyl group, a C$_{1-6}$ alkoxycarbonyl group and a C$_{6-14}$ aryl group,
(iii) a C$_{1-6}$ alkyl group optionally having substituent(s) selected from (a) a C$_{7-14}$ aralkyloxy group optionally having a C$_{1-6}$ alkoxycarbonyl group or a carboxyl group and (b) a cyano group, or
(iv) a 5-membered aromatic heterocyclic group containing, besides carbon atoms, 1 to 4 heteroatoms selected from a nitrogen atom, a sulfur atom and an oxygen atom, and
a group represented by the formula

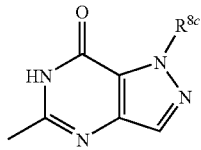

wherein
R$^{8c}$ is a C$_{1-6}$ alkyl group optionally having a C$_{6-14}$ aryloxy group optionally having substituent(s) selected from (a) a C$_{1-6}$ alkoxy-carbonyl group and (b) a carboxyl group,
are preferable.

As the "halogen atom" for R$^1$, R$^2$, R$^3$, R$^4$, R$^5$, R$^6$, R$^7$, R$^8$, R$^{3a}$, R$^{4a}$, R$^{5a}$, R$^{6a}$, R$^{3b}$, R$^{4b}$, R$^{6b}$, R$^{3c}$, R$^{4c}$, or R$^{6c}$, a fluorine atom, a chlorine atom, a bromine atom and an iodine atom can be mentioned.

As the "alkoxycarbonyl group optionally having substituent(s)" for R$^1$, R$^2$, R$^3$, R$^4$, R$^5$R$^6$, R$^7$, R$^8$, R$^{3a}$ or R$^{4a}$, a C$_{1-6}$ alkoxy-carbonyl group (e.g., methoxycarbonyl, ethoxycarbonyl, propoxycarbonyl, isopropoxycarbonyl, butoxycarbonyl, isobutoxycarbonyl, tert-butoxycarbonyl etc.) optionally having substituent(s) similar to the substituent(s) of the below-mentioned "alkyl group optionally having substituent(s)" for R$^1$, R$^2$, R$^3$, R$^4$, R$^5$, R$^6$, R$^7$, R$^8$, R$^{3a}$, R$^{4a}$, R$^{5a}$ or R$^{6a}$, can be mentioned.

As the "amino group optionally having substituent(s)" for R$^1$, R$^2$, R$^3$, R$^4$, R$^5$, R$^6$, R$^7$, R$^8$, R$^{3a}$ or R$^{4a}$, for example,
(i) an amino group,
(ii) a mono- or di-C$_{1-6}$ alkylamino group (e.g., methylamino, ethylamino, propylamino, dimethylamino, diethylamino, dipropylamino etc.),
(iii) a C$_{3-7}$ cycloalkylamino group (e.g., cyclopropylamino, cyclobutylamino, cyclopentylamino, cyclohexylamino, cycloheptylamino etc.),
(iv) a C$_{6-14}$ arylamino group (e.g., phenylamino, 1-naphthylamino, 2-naphthylamino etc.),
(v) a C$_{7-16}$ aralkyl-amino group (e.g., benzylamino etc.),
(vi) a C$_{1-6}$ alkyl-carbonylamino group (e.g., methylcarbonylamino, ethylcarbonylamino, propylcarbonylamino etc.),
(vii) a C$_{3-7}$ cycloalkyl-carbonylamino group (e.g., cyclopropylcarbonylamino, cyclobutylcarbonylamino, cyclopentylcarbonylamino, cyclohexylcarbonylamino etc.),
(viii) a C$_{6-14}$ aryl-carbonylamino group (e.g., phenylcarbonylamino etc.),
(ix) a C$_{7-16}$ aralkyl-carbonylamino group (e.g., benzylcarbonylamino etc.),
(x) a C$_{1-6}$ alkyl-sulfonylamino group (e.g., methylsulfonylamino, ethylsulfonylamino etc.)
(xi) a C$_{3-7}$ cycloalkyl-sulfonylamino group (e.g., cyclopropylsulfonylamino, cyclobutylsulfonylamino, cyclopentylsulfonylamino, cyclohexylsulfonylamino etc.),
(xii) a C$_{6-14}$ aryl-sulfonylamino group (e.g., phenylsulfonylamino etc.),
(xiii) a C$_{7-16}$ aralkyl-sulfonylamino group (e.g., benzylsulfonylamino etc.),
(xiv) a C$_{1-6}$ alkoxy-carbonylamino group (e.g., methoxycarbonylamino, ethoxycarbonylamino, propoxycarbonylamino etc.),
(xv) a C$_{3-7}$ cycloalkyloxy-carbonylamino group (e.g., cyclopropyloxycarbonylamino, cyclobutyloxycarbonylamino, cyclopentyloxycarbonylamino, cyclohexyloxycarbonylamino etc.),
(xvi) a C$_{6-14}$ aryloxy-carbonylamino group (e.g., phenyloxycarbonylamino etc.),
(xvii) a C$_{7-16}$ aralkyloxy-carbonylamino group (e.g., benzyloxycarbonylamino etc.),
(xviii) an ureido group,
(xix) a mono- or di-C$_{1-6}$ alkyl-ureido group (e.g., methylureido, ethylureido, dimethylureido, diethylureido etc.)
(xx) a C$_{3-7}$ cycloalkyl-ureido group (e.g., cyclopropylureido, cyclobutylureido etc.),
(xxi) a C$_{6-14}$ aryl-ureido group (e.g., phenylureido etc.),
(xxii) a C$_{7-16}$ aralkyl-ureido group (e.g., benzylureido etc.) and the like can be mentioned. The "C$_{7-16}$ aralkylamino group" optionally has substituent(s), and as the substituents, a triazolyloxy-C$_{1-6}$ alkoxy group and the like can be mentioned.

As the "alkyl group optionally having substituent(s)" for R$^1$, R$^2$, R$^3$, R$^4$, R$^5$, R$^6$, R$^7$, R$^8$, R$^{3a}$, R$^{4a}$, R$^{5a}$, R$^{6a}$ or R$^{8a}$, for example, a C$_{1-6}$ alkyl group (e.g., methyl, ethyl, propyl, isopropyl, butyl, isobutyl, sec-butyl, tert-butyl, pentyl, hexyl etc.) optionally having substituent(s) selected from
(1) a halogen atom (e.g., a fluorine atom, a chlorine atom, a bromine atom, an iodine atom),
(2) a cyano group,
(3) a hydroxy group,
(4) a nitro group,
(5) a formyl group, (6) an amino group,
(7) a mono- or di-$C_{1-6}$ alkylamino group (e.g., methylamino, ethylamino, propylamino, dimethylamino, diethylamino, dipropylamino etc.),
(8) a mono- or di-$C_{3-7}$ cycloalkyl-amino group (e.g., cyclopropylamino, cyclobutylamino, dicyclopropylamino, dicyclobutylamino etc.),
(9) a mono- or di-$C_{6-14}$ aryl-amino group (e.g., phenylamino, diphenylamino etc.),
(10) a mono- or di-$C_{7-16}$ aralkyl-amino group (e.g., benzylamino, dibenzylamino etc.),
(11) a $C_{1-6}$ alkoxy-carbonylamino group (e.g., methoxycarbonylamino, ethoxycarbonylamino, propoxycarbonylamino etc.),
(12) a $C_{1-6}$ alkyl group (e.g., methyl, ethyl, propyl, isopropyl, butyl, isobutyl, sec-butyl, tert-butyl, pentyl, hexyl etc.),
(13) a $C_{2-6}$ alkynyl group (e.g., ethynyl, propynyl etc.),
(14) a $C_{2-6}$ alkenyl group (e.g., ethenyl, propenyl etc.),
(15) a $C_{3-8}$ cycloalkyl group (e.g., cyclopropyl, cyclobutyl, cyclopentyl, cyclohexyl etc.),
(16) a $C_{6-14}$ aryl group (e.g., phenyl, 1-naphthyl, 2-naphthyl etc.) optionally having (a) a $C_{1-6}$ alkoxycarbonyl group (e.g., methoxycarbonyl, ethoxycarbonyl, propoxycarbonyl etc.) or (b) a carboxyl group,
(17) a $C_{7-16}$ aralkyl group (e.g., benzyl etc.) optionally having (a) a $C_{1-6}$ alkoxycarbonyl group (e.g., methoxycarbonyl, ethoxycarbonyl, propoxycarbonyl etc.) or (b) a carboxyl group,
(18) a $C_{1-6}$ alkoxy group (e.g., methoxy, ethoxy, propoxy, isopropoxy, butoxy, isobutoxy, sec-butoxy, tert-butoxy etc.),
(19) a $C_{3-7}$ cycloalkyloxy group (e.g., cyclopropyloxy, cyclobutyloxy etc.),
(20) a $C_{6-14}$ aryloxy group (e.g., phenyloxy etc.) optionally having (a) a C1-6 alkoxycarbonyl group (e.g., methoxycarbonyl, ethoxycarbonyl, propoxycarbonyl etc.) or (b) a carboxyl group,
(21) a $C_{7-16}$ aralkyloxy group (e.g., benzyloxy etc.) optionally having (a) a $C_{1-6}$ alkoxycarbonyl group (e.g., methoxycarbonyl, ethoxycarbonyl, propoxycarbonyl etc.) or (b) a carboxyl group,
(22) a carboxyl group,
(23) a $C_{1-6}$ alkoxy-carbonyl group (e.g., methoxycarbonyl, ethoxycarbonyl, propoxycarbonyl etc.),
(24) a $C_{3-7}$ cycloalkyloxy-carbonyl group (e.g., cyclopropyloxycarbonyl, cyclobutyloxycarbonyl etc.),
(25) a $C_{7-16}$ aralkyloxy-carbonyl group (e.g., benzyloxycarbonyl etc.),
(26) a $C_{6-14}$ aryloxy-carbonyl group (e.g., phenyloxycarbonyl etc.),
(27) a $C_{1-6}$ alkyl-carbonyl group (e.g., methylcarbonyl, ethylcarbonyl, propylcarbonyl etc.),
(28) a $C_{3-8}$ cycloalkyl-carbonyl group (e.g., cyclopropylcarbonyl, cyclobutylcarbonyl, cyclopentylcarbonyl, cyclohexylcarbonyl etc.),
(29) a $C_{6-14}$ aryl-carbonyl group (e.g., phenylcarbonyl etc.),
(30) a $C_{7-16}$ aralkyl-carbonyl group (e.g., benzylcarbonyl etc.),
(31) a carbamoyl group,
(32) a thiocarbamoyl group,
(33) a mono- or di-$C_{1-6}$ alkyl-carbamoyl group (e.g., methylcarbamoyl, ethylcarbamoyl, propylcarbamoyl, dimethylcarbamoyl, diethylcarbamoyl, dipropylcarbamoyl etc.),
(34) a $C_{3-7}$ cycloalkyl-carbamoyl group (e.g., cyclopropylcarbamoyl, cyclobutylcarbamoyl etc.),
(35) a $C_{6-14}$ aryl-carbamoyl group (e.g., phenylcarbamoyl etc.),
(36) a mono- or di-$C_{7-16}$ aralkyl-carbamoyl group (e.g., benzylcarbamoyl, dibenzylcarbamoyl etc.),
(37) a thiol group,
(38) a $C_{1-6}$ alkylthio group (e.g., methylthio, ethylthio, propylthio etc.),
(39) a $C_{3-7}$ cycloalkylthio group (e.g., cyclopropylthio, cyclobutylthio etc.),
(40) a $C_{6-14}$ arylthio group (e.g., phenylthio etc.),
(41) a $C_{7-6}$ aralkylthio group (e.g., benzylthio etc.),
(42) a $C_{1-6}$ alkylsulfonyl group (e.g., methylsulfonyl, ethylsulfonyl, propylsulfonyl etc.),
(43) a $C_{3-8}$ cycloalkylsulfonyl group (e.g., cyclopropylsulfonyl, cyclobutylsulfonyl, cyclopentylsulfonyl etc.),
(44) a $C_{6-14}$ arylsulfonyl group (e.g., phenylsulfonyl, 1-naphthylsulfonyl, 2-naphthylsulfonyl etc.),
(45) a $C_{7-15}$ aralkylsulfonyl group (e.g., benzylsulfonyl etc.),
(46) a 5- to 8-membered non-aromatic heterocyclic group containing, besides carbon atoms, 1 to 4 heteroatoms selected from a nitrogen atom, a sulfur atom and an oxygen atom (e.g., pyrrolidinyl, tetrahydrofuryl, tetrahydrothienyl, piperidyl, tetrahydropyranyl, morpholinyl, thiomorpholinyl, piperazinyl etc.),
(47) a 5- to 8-membered aromatic heterocyclic group containing, besides carbon atoms, 1 to 4 heteroatoms selected from a nitrogen atom, a sulfur atom and an oxygen atom (e.g., furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl etc.),
(48) an ureido group,
(49) a $C_{1-6}$ alkylureido group (e.g., methylureido, ethylureido, propylureido etc.) and
(50) a $C_{3-7}$ cycloalkyl-ureido group (e.g., cyclopropylureido, cyclobutylureido etc.),
(51) a 6-14 aryl-ureido group (e.g., phenylureido, 1-naphthylureido, 2-naphthylureido etc.),
(52) a $C_{7-16}$ aralkyl-ureido group (e.g., benzylureido etc.) and the like, can be mentioned.

As the "alkenyl group optionally having substituent(s)" for $R^1$, $R^2$, $R^3$, $R^4$, $R^5$, $R^6$, $R^7$ or $R^8$, a $C_{2-6}$ alkenyl group (e.g., vinyl, alkyl, isopropenyl, 2-methylallyl, 1-propenyl, 2-methyl-1-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl etc.) optionally having substituent(s) similar to the substituent(s) of the above-mentioned "alkyl group optionally having substituent(s)" for $R^1$, $R^2$, $R^3$, $R^4$, $R^5$, $R^6$, $R^7$, $R^8$, $R^{3a}$, $R^{4a}$, $R^{5a}$, or $R^{6a}$, can be mentioned.

As the "alkynyl group optionally having substituent(s)" for $R^1$, $R^2$, $R^3$, $R^4$, $R^5$, $R^6$, $R^7$ or $R^8$, a $C_{2-6}$ alkynyl group (e.g., ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl etc.) optionally having substituent(s) similar to the substituent(s) of the above-mentioned "alkyl group optionally having substituent(s)" for $R^1$, $R^2$, $R^3$, $R^4$, $R^5$, $R^6$, $R^7$, $R^8$, $R^{3a}$, $R^{4a}$, $R^{5a}$ or $R^{6a}$, can be mentioned.

As the "aryl group optionally having substituent(s)" for $R^1$, $R^2$, $R^3$, $R^4$, $R^5$, $R^6$, $R^7$, $R^8$, $R^{5a}$ or $R^{6a}$, a $C_{6-14}$ aryl group (e.g., phenyl, 1-naphthyl, 2-naphthyl etc.) optionally having substituent(s) similar to the substituent(s) of the above-mentioned "alkyl group optionally having substituent(s)" for $R^1$, $R^2$, $R^3$, $R^4 R^5$, $R^6 R^7$, $R^8$, $R^{3a}$, $R^{4a}$, $R^{5a}$ or $R^{6a}$, can be mentioned.

As the "alkoxy group optionally having substituent (s)" for $R^1, R^2, R^3, R^4, R^5, R^6, R^7, R^8, R^{3a}$ or $R^{4a}$, a $C_{1-6}$ alkoxy group (e.g., methoxy, ethoxy, propoxy, isopropoxy, butoxy, isobutoxy, sec-butoxy, tert-butoxy, pentoxy, hexyloxy etc.) optionally having substituent(s) similar to the substituent(s) of the above-mentioned "alkyl group optionally having substituent(s)" for $R^1, R^2, R^3, R^4R^5, R^6, R^7, R^8, R^{3a}, R^{4a}, R^{5a}$ or $R^{6a}$, and the like can be mentioned.

As the "aralkyloxy group optionally having substituent(s)" for $R^1, R^2, R^3, R^4, R^5, R^6, R^7$ or $R^8$, a $C_{7-16}$ aralkyloxy group (e.g., benzyloxy etc.) optionally having substituent(s) similar to the substituent(s) of the above-mentioned "alkyl group optionally having substituent(s)" for $R^1, R^2, R^3, R^4, R^5, R^6, R^7, R^8, R^{3a}, R^{4a}, R^{5a}$ or $R^{6a}$ and the like can be mentioned.

As the "aryloxy group optionally having substituent(s)" for $R^1, R^2, R^3, R^4, R^5, R^6, R^7$ or $R^8$, $C_{6-14}$ aryloxy group (e.g., phenoxy, 1-naphthyloxy, 2-naphthyloxy etc.) optionally having substituent(s) similar to the substituent(s) of the above-mentioned "alkyl group optionally having substituent(s)" for $R^1, R^2, R^3, R^4, R^5, R^6, R^7, R^8, R^{3a}, R^{4a}, R^{5a}$ or $R^{6a}$, and the like can be mentioned.

As the "alkylthio group optionally having substituent(s)" for $R^1, R^2, R^3, R^4, R^5, R^6, R^7$ or $R^8$, a $C_{1-6}$ alkylthio (e.g., methylthio, ethylthio, propylthio, isopropylthio, butylthio, isobutylthio, sec-butylthio, tert-butylthio, pentylthio, hexylthio etc.) optionally having substituent(s) similar to the substituent(s) of the above-mentioned "alkyl group optionally having substituent(s)" for $R^1, R^2, R^3, R^4, R^5, R^6, R^7, R^8, R^{3a}, R^{4a} R^{5a}$ or $R^{6a}$, and the like can be mentioned.

As the "aralkylthio group optionally having substituent(s)" for $R^1, R^2, R^3, R^4, R^5 R^6, R^7$ or $R^8$, a $C_{7-16}$ aralkylthio group (e.g., benzylthio etc.) optionally having substituent(s) similar to the substituent(s) of the above-mentioned "alkyl group optionally having substituent(s)" for $R^1, R^2, R^3, R^4, R^5, R^6, R^7, R^8, R^{3a}, R^{4a}, R^{5a}$ or $R^{6a}$, and the like can be mentioned.

As the "5- to 8-membered aromatic heterocyclyl-thio group containing, besides carbon atoms, 1 to 4 heteroatom selected from a nitrogen atom, an oxygen atom and a sulfur atom" for $R^1, R^2, R^3, R^4, R^5, R^6, R^7$ or $R^8$, for example, furylthio, thienylthio, pyrrolylthio, oxazolylthio, isoxazolylthio, thiazolylthio, isothiazolylthio, imidazolylthio, pyrazolylthio, 1,2,3-oxadiazolylthio, 1,2,4-oxadiazolylthio, 1,3,4-oxadiazolylthio, furazanylthio, 1,2,3-thiadiazolylthio, 1,2,4-thiadiazolylthio, 1,3,4-thiadiazolylthio, 1,2,3-triazolylthio, 1,2,4-triazolylthio, tetrazolylthio, pyridylthio, pyridazinylthio, pyrimidinylthio, pyrazinylthio, triazinylthio and the like can be mentioned.

As the "mono- or di-alkylcarbamoyl-thio group" for $R^1, R^2, R^3, R^4, R^5, R^6, R^7$ or $R^8$, a mono- or di-$C_{1-6}$ alkylcarbamoyl-thio group (e.g., methylcarbamoylthio, ethylcarbamoylthio, propylcarbamoylthio, butylcarbamoylthio, pentylcarbamoylthio, hexylcarbamoylthio, dimethylcarbamoylthio, diethylcarbamoylthio etc.) optionally having substituent(s) similar to the substituent(s) of the above-mentioned "alkyl group optionally having substituent(s)" for $R^1, R^2, R^3, R^4, R^5, R^6, R^7, R^8, R^{3a}, R^{4a}, R^{5a}$ or $R^{6a}$, and the like can be mentioned.

As the "alkylsulfonyl group optionally having substituent(s)" for $R^1, R^2, R^3, R^4, R^5, R^6 R^7$ or $R^8$, a $C_{1-6}$ alkylsulfonyl group (e.g., methylsulfonyl, ethylsulfonyl, propylsulfonyl etc.) optionally having substituent(s) similar to the substituent(s) of the above-mentioned "alkyl group optionally having substituent(s)" for $R^1, R^2, R^3, R^4, R^5, R^6, R^7, R^8, R^{3a}, R^{4a}, R^{5a}$ or $R^{6a}$, and the like can be mentioned.

As the "arylsulfonyl group optionally having substituent (s)" for $R^1, R^2, R^3, R^4, R^5, R^6, R^7$ or $R^8$, a $C_{6-14}$ arylsulfonyl group (e.g., phenylsulfonyl etc.) optionally having substituent(s) similar to the substituent(s) of the above-mentioned "alkyl group optionally having substituent(s)" for $R^1, R^2, R^3, R^4, R^5, R^6, R^7, R^8, R^{3a}, R^{4a}, R^{5a}$ or $R^{6a}$, and the like can be mentioned.

As the "aralkylsulfonyl group optionally having substituent(s)" for $R^1, R^2, R^3, R^4, R^5, R^6, R^7$ or $R^8$, a $C_{7-16}$ aralkylsulfonyl group (e.g., benzylsulfonyl etc.) optionally having substituent(s) similar to the substituent(s) of the above-mentioned "alkyl group optionally having substituent(s)" for $R^1, R^2, R^3, R^4, R^5, R^6, R^7, R^8, R^{3a}, R^{4a}, R^{5a}$ or $R^{6a}$, and the like can be mentioned.

As the "carbamoyl group optionally having substituent(s)" for $R^1, R^2, R^3, R^4, R^5, R^6, R^7$ or $R^8$, for example, a carbamoyl group, a mono- or di-$C_{1-6}$ alkyl-carbamoyl group (e.g., methylcarbamoyl, ethylcarbamoyl, propylcarbamoyl, dimethylcarbamoyl, diethylcarbamoyl, dipropylcarbamoyl etc.), a mono- or di-$C_{7-16}$ aralkyl-carbamoyl group (e.g., benzylcarbamoyl, dibenzylcarbamoyl etc.) and the like can be mentioned.

As the "mono- or di-alkylamino-thiocarbonyloxy group" for $R^1, R^2, R^3, R^4 R^5, R^6, R^7$ or $R^8$, for example, a mono- or di-$C_{1-6}$ alkylamino-thiocarbonyloxy group (e.g., methylaminothiocarbonyloxy, ethylaminothiocarbonyloxy, propylaminothiocarbonyloxy, butylaminothiocarbonyloxy, dimethylaminothiocarbonyloxy, diethylaminothiocarbonyloxy etc.) and the like can be mentioned.

As the "5- to 8-membered non-aromatic heterocyclic group containing, besides carbon atoms, 1 to 4 heteroatom selected from a nitrogen atom, a sulfur atom and an oxygen atom" for $R^1, R^2, R^3, R^4, R^5, R^6, R^7$ or $R^8$, for example, pyrrolidinyl, tetrahydrofuryl, tetrahydrothienyl, piperidyl, tetrahydropyranyl, morpholinyl, thiomorpholinyl, piperazinyl and the like can be mentioned.

As the "5- to 8-membered aromatic heterocyclic group containing, besides carbon atoms, 1 to 4 heteroatom selected from a nitrogen atom, a sulfur atom and an oxygen atom" for $R^1, R^2, R^3, R^4, R^5, R^6, R^7, R^8, R^{5a}, R^{6a}$ or $R^{6b}$ for example, furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl and the like can be mentioned.

Compound (I) is preferably a compound wherein

A is a triazolyl group;

X is CH or N;

Y is —(CH$_2$)$_3$O—, —S(CH$_2$)$_2$O—, —S(CH$_2$)$_3$O—, —S(CH$_2$)$_4$O—, —O(CH$_2$)$_2$O—, —CH$_2$OCH$_2$—, —(CH$_2$)$_2$—C(O)—NH—, —C(O)—NH—CH$_2$—, —NH—C(O)—(CH$_2$)$_3$—O—, —CH$_2$—C(O)—NH—CH$_2$— or —C(O)—NH—; and a group represented by the formula

is a group represented by the formula

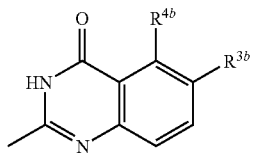

wherein
$R^{3b}$ is (i) a hydrogen atom, (ii) a halogen atom, (iii) a cyano group, (iv) an amino group, (v) a $C_{1-6}$ alkyl groups or (vi) a $C_{1-6}$ alkoxy group; and
$R^{4b}$ is (i) a hydrogen atom, (ii) a halogen atom, or (iii) a $C_{1-6}$ alkyl group, or
a group represented by the formula

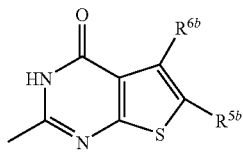

wherein
$R^{5b}$ is (i) a hydrogen atom, or (ii) a $C_{1-6}$ alkyl group; and
$R^{5b}$ is
(i) a hydrogen atom,
(ii) a $C_{1-6}$ alkyl group optionally having (a) a $C_{7-16}$ aralkyloxy group optionally having a $C_{1-6}$ alkoxycarbonyl group or a carboxyl group or (b) a cyano group, or
(iii) a 5-membered aromatic heterocyclic group containing, besides carbon atoms, 1 to 4 heteroatoms selected from a nitrogen atom, a sulfur atom and an oxygen atom,
particularly preferably a compound wherein
A is a triazolyl group;
X is CH or N;
Y is —(CH$_2$)$_3$O—, —S(CH$_2$)$_2$O—, —S(CH$_2$)$_3$O— or —O(CH$_2$)$_2$O—; and
a group represented by the formula

is a group represented by the formula

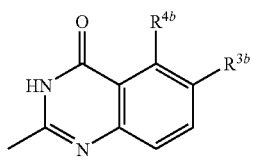

wherein
$R^{3b}$ is (i) a hydrogen atom, (ii) a halogen atom, (iii) a cyano group, (iv) an amino group, (v) a $C_{1-6}$ alkyl group, or (vi) a $C_{1-6}$ alkoxy group; and
$R^{4b}$ is (i) a hydrogen atom, (ii) a halogen atom, or (iii) a $C_{1-6}$ alkyl group, or a group represented by the formula

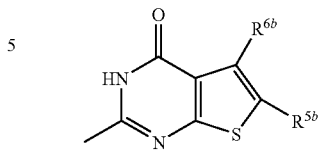

wherein
$R^{5b}$ is (i) a hydrogen atom, or (ii) a $C_{1-6}$ alkyl group; and
$R^{5b}$ is
(i) a hydrogen atom,
(ii) a $C_{1-6}$ alkyl group optionally having (a) a $C_{7-16}$ aralkyloxy group optionally having a $C_{1-6}$ alkoxycarbonyl group or a carboxyl group or (b) a cyano group,
(iii) a 5-membered aromatic heterocyclic group containing, besides carbon atoms, 1 to 4 heteroatoms selected from a nitrogen atom, a sulfur atom and an oxygen atom.

To be specific, compound (I) is particularly preferably
4-oxo-5-phenyl-N-{3-[2-(1H-1,2,4-triazol-3-yloxy)ethoxy]benzyl}-3,4-dihydrothieno[2,3-d]pyrimidine-2-carboxamide,
5-(2-fluorophenyl)-4-oxo-N-{3-[2-(1H-1,2,4-triazol-3-yloxy)ethoxy]benzyl}-3,4-dihydrothieno[2,3-d]pyrimidine-2-carboxamide,
5-(2-chlorophenyl)-4-oxo-N-{3-[2-(1H-1,2,4-triazol-3-yloxy)ethoxy]benzyl}-3,4-dihydrothieno[2,3-d]pyrimidine-2-carboxamide,
5-(3-fluorophenyl)-4-oxo-N-{3-[2-(1H-1,2,4-triazol-3-yloxy)ethoxy]benzyl}-3,4-dihydrothieno[2,3-d]pyrimidine-2-carboxamide,
5-(3-methylphenyl)-4-oxo-N-{3-[2-(1H-1,2,4-triazol-3-yloxy)ethoxy]benzyl}-3,4-dihydrothieno[2,3-d]pyrimidine-2-carboxamide,
5-(3-fluorophenyl)-4-oxo-N-[(3-{[3-(1H-1,2,4-triazol-3-yloxy)propyl]oxy}phenyl)methyl]-3,4-dihydrothieno[2,3-d]pyrimidine-2-carboxamide, or
5-(2-fluorophenyl)-4-oxo-N-[(3-{[3-(H-1,2,4-triazol-3-yloxy)propyl]oxy}phenyl)methyl]-3,4-dihydrothieno[2,3-d]pyrimidine-2-carboxamide,
or a salt thereof.

The production methods of the compound of the present invention are shown in the following.

Compound (I) or a salt thereof and a starting compound thereof can be produced by a method known per se, for example, a method shown in the following schemes and the like. In the following, "room temperature" generally means 0 to 30° C. and each symbol in the chemical structural formulas described in the schemes means as defined above unless otherwise specified. The compounds in the formulas include embodiments forming a salt, and as such salt, for example, those similar to the salt of compound (I) and the like can be mentioned.

The compounds obtained in respective steps can be used in the form of a reaction mixture or as a crude product for the next reaction. They can also be isolated from the reaction mixture by conventional methods, and can be easily purified by separation means such as recrystallization, distillation, chromatography and the like.

The reaction schemes are shown in the following. When a compound in the formulas is commercially available, the commercially available product may be used as it is.

[Scheme 1]

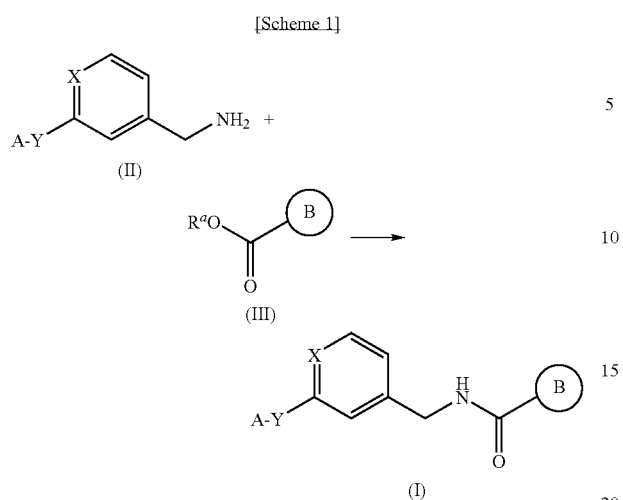

wherein $R^a$ is a $C_{1-6}$ alkyl group, and the other symbols are as defined above.

Compound (I) is obtained by reacting compound (II) or a salt thereof with compound (III) or a salt thereof.

As used herein, the $C_{1-6}$ alkyl group for $R^a$ means methyl, ethyl, propyl, isopropyl, butyl, isobutyl, sec-butyl, tert-butyl, pentyl, hexyl or the like.

In this reaction, the compound represented by the formula (III) or a salt thereof is used in an amount of 0.1 to 10 mol, preferably 0.2 to 5 mol, per 1 mol of the compound represented by the formula (II) or a salt thereof.

As the solvent for this reaction, for example, alcohols such as methanol, ethanol and the like, ethers such as dioxane, tetrahydrofuran and the like, aromatic hydrocarbons such as benzene, toluene, xylene and the like, esters such as ethyl acetate and the like, halogenated hydrocarbons such as chloroform, dichloromethane and the like, nitrites such as acetonitrile and the like, amides such as N,N-dimethylformamide, N,N-dimethylacetamide and the like, sulfoxides such as dimethyl sulfoxide and the like, and the like can be used alone or in combination of two or more.

In addition, this reaction can be advantageously carried out by adding a base. As such base, for example, inorganic bases (alkali metal hydroxides such as sodium hydroxide, potassium hydroxide and the like, alkali metal hydrogencarbonates such as sodium hydrogencarbonate, potassium hydrogencarbonate and the like, alkali metal carbonates such as sodium carbonate, potassium carbonate, cesium carbonate and the like, alkali metal hydrides such as sodium hydride, potassium hydride and the like, alkali metal amides such as sodium amide and the like, alkoxides such as sodium methoxide, sodium ethoxide and the like, and the like), organic bases (aliphatic amines such as trimethylamine, triethylamine, diisopropylethylamine and the like, aromatic bases such as pyridine and the like, and the like) and the like can be used. While the amount of the base to be used may vary depending on the kind of the compound and solvent to be used, and other reaction conditions, it is generally 0.1 to 10 mol, preferably 0.2 to 5 mol, per 1 mol of the compound represented by the formula (II) or a salt thereof. The reaction is carried out within a temperature range of generally from 50° C. to 200° C., preferably from −20° C. to 150° C. While the reaction time may vary depending on the kind of the compound, the reaction temperature and the like, it is about 1 hr to 96 hr, preferably about 1 hr to 48 hr.

Moreover, this reaction is advantageously carried out under microwave irradiation. The electric power for the microwave irradiation is 50 to 1200 watt, preferably 50 to 250 watt. The irradiation is performed using microwave having a frequency within the range of 850 to 25000 MHz, preferably within the range of 896±10 MHz, 915±25 MHz, 2375±50 MHz, 2450±50 MHz, 5800±75 MHz or 24125±125 MHz.

The compounds represented by the formula (II) and the formula (III) or salts thereof can be easily produced according to a method known per se or a method analogous thereto.

Compound (I') and compound (I"), in both of which Y is a linker containing an amide bond, can also be produced according to Scheme 2 and Scheme 3.

[Scheme 2]

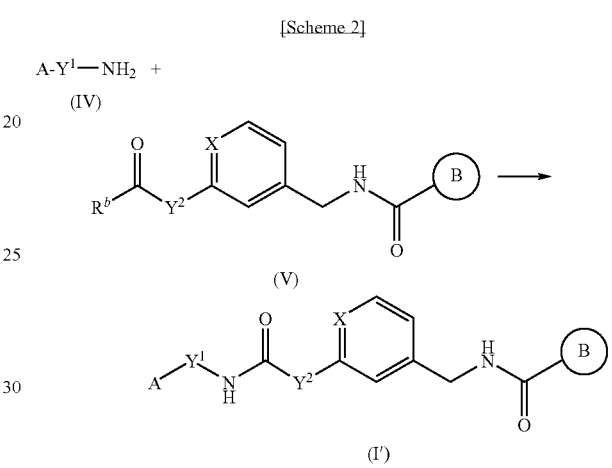

wherein $R^b$ is a hydroxy group, a halogen atom or a $C_{1-6}$ alkoxy group, $Y^1NHC(O)Y^2$ is a spacer represented by Y, which contains an amide structure, and the other symbols are as defined above.

Compound (I') is obtained by amidating compound (V) with compound (IV). As used herein, the halogen atom for $R^b$ means a fluorine atom, a chlorine atom, a bromine atom or an iodine atom, and the $C_{1-6}$ alkoxy group means methoxy, ethoxy, propoxy, isopropoxy, butoxy, sec-butoxy, tert-butoxy, pentoxy, hexoxy or the like.

In this reaction, the compound represented by the formula (V) or a salt thereof is used in an amount of 0.1 to 10 mol, preferably 0.2 to 5 mol, per 1 mol of the compound represented by the formula (IV) or a salt thereof.

As the solvent for this reaction, for example, alcohols such as methanol, ethanol and the like, ethers such as dioxane, tetrahydrofuran and the like, aromatic is hydrocarbons such as benzene, toluene, xylene and the like, esters such as ethyl acetate and the like, halogenated hydrocarbons such as chloroform, dichloromethane and the like, nitrites such as acetonitrile and the like, amides such as N,N-dimethylformamide, N,N-dimethylacetamide and the like, sulfoxides such as dimethyl sulfoxide and the like, and the like can be used alone or in combination of two or more.

This reaction can be advantageously carried out by adding a condensing agent (e.g., 1-ethyl-3-(3-dimethylaminopropyl) carbodiimide hydrochloride (WSC), dicyclohexylcarbodiimide (DCC) etc.).

In addition, this reaction can be advantageously carried out by adding a base. As such base, for example, inorganic bases (alkali metal hydroxides such as sodium hydroxide, potassium hydroxide and the like, alkali metal hydrogencarbonates such as sodium hydrogencarbonate, potassium hydrogencarbonate and the like, alkali metal carbonates such as sodium carbonate, potassium carbonate, cesium carbonate and the like, alkali metal hydrides such as sodium hydride, potassium hydride and the like, alkali metal amides such as sodium amide and the like, alkoxides such as sodium methoxide, sodium ethoxide and the like, and the like), organic bases (aliphatic amines such as trimethylamine, triethylamine, diisopropylethylamine and the like, aromatic bases such as pyridine and the like, and the like) and the like can be used. While the amount of the base to be used may vary depending on the kind of the compound and solvent to be used, and other reaction conditions, it is generally 0.1 to 10 mol, preferably 0.2 to 5 mol, per 1 mol of the compound represented by the formula (IV) or a salt thereof. The reaction is carried out within a temperature range of generally from −50° C. to 200° C., preferably from −20° C. to 150° C. While the reaction time may vary depending on the kind of the compound, the reaction temperature and the like, it is about 1 hr to 96 hr, preferably about 1 hr to 48 hr.

[Scheme 3]

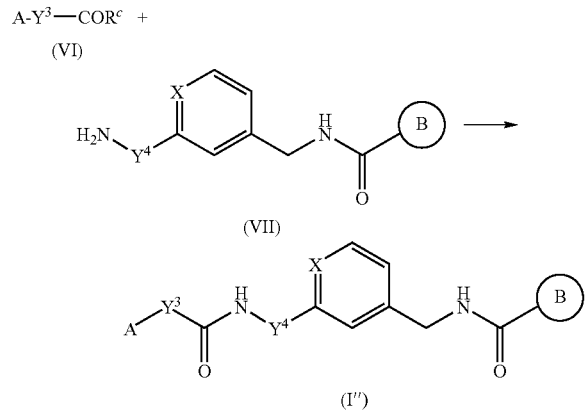

wherein $R^c$ is a hydroxy group, a halogen atom or a $C_{1-6}$ alkoxy group, $Y^3C(O)NHY^4$ is a spacer represented by Y, which contains an amide structure, and the other symbols are as defined above.

In this reaction, the compound represented by the formula (VII) or a salt thereof is used in an amount of 0.1 to 10 mol, preferably 0.2 to 5 mol, per 1 mol of the compound represented by the formula (VI) or a salt thereof.

As the solvent for this reaction, for example, alcohols such as methanol, ethanol and the like, ethers such as dioxane, tetrahydrofuran and the like, aromatic hydrocarbons such as benzene, toluene, xylene and the like, esters such as ethyl acetate and the like, halogenated hydrocarbons such as chloroform, dichloromethane and the like, nitriles such as acetonitrile and the like, amides such as N,N-dimethylformamide, N,N-dimethylacetamide and the like, sulfoxides such as dimethyl sulfoxide and the like, and the like can be used alone or in combination of two or more.

This reaction can be advantageously carried out by adding a condensing agent (e.g., 1-ethyl-3-(3-dimethylaminopropyl) carbodiimide hydrochloride (WSC), dicyclohexylcarbodiimide (DCC) etc.)

In addition, this reaction can be advantageously carried out by adding a base. As such base, for example, inorganic bases (alkali metal hydroxides such as sodium hydroxide, potassium hydroxide and the like, alkali metal hydrogencarbonates such as sodium hydrogencarbonate, potassium hydrogencarbonate and the like, alkali metal carbonates such as sodium carbonate, potassium carbonate, cesium carbonate and the like, alkali metal hydrides such as sodium hydride, potassium hydride and the like, alkali metal amides such as sodium amide and the like, alkoxides such as sodium methoxide, sodium ethoxide and the like, and the like), organic bases (aliphatic amines such as trimethylamine, triethylamine, diisopropylethylamine and the like, aromatic bases such as pyridine and the like, and the like) and the like can be used. While the amount of the base to be used may vary depending on the kind of the compound and solvent to be used, and other reaction conditions, it is generally 0-1 to 10 mol, preferably 0.2 to 5 mol, per 1 mol of the compound represented by the formula (VI) or a salt thereof. The reaction is carried out within a temperature range of generally from −50° C. to 200° C., preferably from −20° C. to 150° C. While the reaction time may vary depending on the kind of the compound, the reaction temperature and the like, it is about 1 hr to 96 hr, preferably about 1 hr to 48 hr.

In each of the reactions mentioned above, when the starting compounds have a reactive functional group (e.g., an amino group, a carboxyl group, a hydroxy group etc.) as a substituent, such groups may be protected with the protecting groups which are generally used in peptide chemistry and the like. In such case, if necessary, such protecting groups can be removed to obtain the objective compounds after the reactions. Such protecting groups can be introduced or removed by methods known per se, such as the method described in *Protective Groups in Organic Synthesis*, 3$^{rd}$ Ed. (1999), edited by Theodara W. Greene, Peter G. M. Wuts, published by Wiley-Interscience, or an analogous method thereto.

The above-mentioned reactions may be further combined with one or more of known hydrolysis reaction, deprotection reaction, acylation reaction, alkylation reaction, oxidization reaction, cyclization reaction, carbon chain elongation reaction and substituent exchange reaction on demand, whereby compound (I) can also be produced.

The compound (I) can be isolated and purified by a known means, such as phase transfer, concentration, solvent extraction, fractionation, liquid conversion, crystallization, recrystallization, chromatography and the like.

When compound (I) is obtained as a free compound, it can be converted to an objective salt by a method known per se or a method analogous thereto, and when it is conversely obtained as a salt, it can be converted to a free form or different objective salt by a method known per se or a method analogous thereto.

As the salt of compound (I), for example, metal salt, ammonium salt, salts with organic base, salts with inorganic acid, salts with organic acid, salts with basic or acidic amino acid and the like can be mentioned. As preferable examples of metal salt, for example, alkali metal salts such as sodium salt, potassium salt and the like, alkaline earth metal salts such as calcium salt, magnesium salt, barium salt and the like; aluminum salt and the like can be mentioned. As preferable examples of salts with organic base, for example, salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine, choline and the like can be mentioned. As preferable examples of salts with inorganic acid, for example, salts with hydrochloric acid, hydrobromic acid, nitric acid, sulfuric acid, phosphoric acid and the like can be mentioned. As preferable examples of salts with basic amino acid, for example, salts with arginine, lysin, ornithine and the like can be mentioned. As preferable examples of salts with acidic amino acid, for example, salts with aspartic acid, glutamic acid and the like can be mentioned. Of these, pharmaceutically acceptable salts are preferable. When, for example, the compound has an acidic functional group therein, inorganic salts such as alkali metal salts (e.g., sodium salt, potassium salt etc.), alkaline earth metal salts (e.g., calcium salt, magnesium salt, barium salt etc.) and the like, ammonium salt (e.g., choline etc.) and the like, and when the compound has a basic functional group therein, for example, salts with inorganic acid such as hydrochloric acid, hydrobromic acid, nitric acid, sulfuric acid, phosphoric acid and the like, and salts with organic acid such as acetic acid, phthalic acid, fumaric acid, oxalic acid, tartaric acid, maleic acid, citric acid, succinic acid, methanesulfonic acid, p-toluenesulfonic acid and the like can be mentioned.

The compound (I) of the present invention may be used as a prodrug, and such prodrug means a compound which is converted to compound (I) as a result of a reaction with an enzyme, gastric acid etc. under physiological conditions in vivo. Thus, the compound is converted into compound (I) by enzymatical oxidation, reduction, hydrolysis etc., or by hydrolysis due to gastric acid etc.

As a prodrug of compound (I), a compound obtained by subjecting an amino group of compound (I) to an acylation, alkylation or phosphorylation (e.g., a compound obtained by subjecting an amino group of compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation, etc.); a compound obtained by subjecting a hydroxy group in compound (I) to an acylation, alkylation, phosphorylation or boration (e.g., a compound obtained by subjecting a hydroxy group of compound (I) to an acetylation, palmitoylation, propanoylation, pivaloylation, succinylation, fumarylation, alanylation or dimethylaminomethylcarbonylation, etc.); a compound obtained by subjecting a carboxyl group of compound (I) to an esterification or amidation (e.g., a compound obtained by subjecting a carboxyl group of compound (I) to an ethyl-esterification, phenyl-esterification, carboxymethyl-esterification, dimethylaminomethyl-esterification, pivaloyloxymethyl-esterification, ethoxycarbonyloxyethyl-esterification, phthalidyl-esterification, (5-methyl-2-oxo-1,3-dioxolen-4-yl)methyl-esterification, cyclohexyloxycarbonylethyl-esterification or methylamidation, etc.) and the like. These compounds can be produced from compound (I) by a method known per se.

In addition, the prodrug of compound (I) may be a compound, which is converted to compound (I) under the physiological conditions, as described in *Pharmaceutical Research and Development*, Vol. 7 (Drug Design), pp. 163-198 (1990), published by Hirokawa Publishing Co.

The compound (I) or a salt thereof or a prodrug thereof of present invention has a superior MMP inhibitory activity, particularly an MMP-13 inhibitory activity.

Moreover, the compound (I) of the present invention shows low toxicity and is safe.

Accordingly, the compound (I) of the present invention having superior MMP inhibitory action, particularly MMP-13 inhibitory action, is useful as a safe drug for the prophylaxis or treatment of all MMP associated diseases, such as joint disease (e.g., osteoarthritis, spondyloarthropathy, rheumatoid arthritis (articular rheumatism) and the like), degenerated intervertebral discs, cartilage injury, tendonitis, arthritide, muscular pain, osteoporosis, cancer (e.g., tumor and the like such as primary, metastatic or recurrent tumors such as breast cancer, prostate cancer, pancreatic cancer, stomach cancer, lung cancer, colorectal cancer (colon cancer, rectal cancer, anal cancer), cancer of esophagus, duodenal cancer, head and neck cancer (lingual cancer, pharyngeal cancer, laryngeal cancer), cerebral tumor, schwannoma, non-small-cell lung cancer, lung small cell carcinoma, liver cancer, kidney cancer, biliary tract cancer, uterine cancer (endometrial cancer, cervical cancer), ovarian cancer, bladder cancer, skin cancer, angioma, malignant lymphoma, malignant melanoma, thyroid cancer, osteoncus, angiomatosis, angiofibroma, retina sarcoma, penile cancer, pediatric solid tumor, Kaposi's sarcoma, Kaposi's sarcoma caused by AIDS, tumor of the maxillary sinus, fibrosarcoma, fibrous histiocytoma, leiomyosarcoma, rhabdomyosarcoma, liposarcoma, hysteromyoma, osteoblastoma, osteosarcoma, chondrosarcoma, cancerous mesothelioma, leukemia and the like, and the like), periodontal disease, corneal ulcer, age-related macular degeneration, other ocularis disease, chronic ulcer, skin ulcer, abnormal wound healing, pathologic bone resorption (Paget's disease and the like), osteopenia, nephritis, angiogenesis, restenosis, atherosclerosis, aneurysm (abdominal aortic aneurysm etc), arteriosclerosis, myocardial infarction, cerebral infarction, asthma, emphysema, chronic obstructive pulmonary disease (COPD), liver cirrhosis, hepatitis, diabetes, central nervous system disease, multiple sclerosis, endometriosis, autoimmune disease (Crohn's disease, Sjogren's disease and the like), shock, inflammatory bowel disease (IBD), graft versus host reaction, infiltration or metastasis of cancer and the like, in mammals (e.g., mouse, rat, hamster, guinea pig, rabbit, cat, dog, bovine, horse, pig, sheep, monkey, humans, etc.), or as a contraceptive, particularly as a drug for the prophylaxis or treatment of osteoarthritis or rheumatoid arthritis.

The pharmaceutical preparations comprising compound (I) of the present invention may be in any solid preparations of powders, granules, tablets, capsules and the like, and in any liquid forms of syrups, emulsions, injections and the like.

The pharmaceutical preparations of the present invention can be produced by any conventional methods, for example, blending, kneading, granulation, tabletting, coating, sterilization, emulsification, etc., in accordance with the forms of the preparations to be produced. For the production of such pharmaceutical preparations, for example, each of the items in General Principles for pharmaceutical preparations in the Japanese Pharmacopoeia, can be made reference to. In addition, the pharmaceutical preparations of the present invention may be formulated into a sustained release preparation containing active ingredients and biodegradable polymer compounds. The sustained release preparation can be produced according to the method described in JP-A-9-263545.

In the pharmaceutical preparations of the present invention, the content of compound (I) varies depending on the form of the preparation, but is generally in about 0.01 to 100% by weight, preferably about 0.1 to 50% by weight, more preferably 0.5 to 20% by weight, of the total weight of the preparation.

When compound (I) of the present invention is used as the above-mentioned pharmaceutical preparations, it may be used alone, or in admixture with a suitable, pharmacologically acceptable carrier, such as excipients (e.g., starch, lactose, sucrose, calcium carbonate, calcium phosphate, etc.), binders (e.g., starch, gum arabic, carboxymethyl cellulose, hydroxypropyl cellulose, crystalline cellulose, alginic acid, gelatin, polyvinyl pyrrolidone, etc.), lubricants (e.g., stearic acid, magnesium stearate, calcium stearate, talc, etc.), disintegrants (e.g., calcium carboxymethylcellulose, talc, etc.), diluents (e.g., water for injection, physiological saline, etc.) and, if desired, with the additives (e.g., stabilizer, preservative, colorant, fragrance, dissolution aid, emulsifier, buffer, isotonic agent, etc.) and the like by conventional methods.

The compound can be formulated into solid preparations such as powder, fine granule, granule, tablet, capsule, etc., or into the liquid preparations such as injection, etc., and can be administered orally or parenterally. Further, compound (I) can be administered in the form of a formulation for local administration or directly on the diseased part having an articular disease. In the latter case, injection is preferred. The compound (I) can also be administered as a parenteral formulation for local administration (e.g., a formulation for injection for intramuscular, subcutaneous, intraorgan and on-site (in the vicinity of a joint) routes, a solid form such as implant, granule, powder, a liquid form such as suspension, an ointment, etc.).

For example, a practical formulation for injection can be obtained by mixing compound (I) with a dispersant (e.g., surfactant such as Tween 80, HCO-60, etc., carboxymethyl cellulose, sodium alginate, polysaccharide such as hyaluronic acid, polysorbate, etc.), a preservative (e.g., methylparaben, propylparaben, etc.), an isotonic agent (e.g., sodium chloride, mannitol, sorbitol, glucose, etc.), a buffer (e.g., calcium carbonate, etc.), a pH adjusting agent (e.g., sodium phosphate, potassium phosphate, etc.) and the like, into an aqueous suspension. Further, thus obtained formulation is made into a practically usable formulation for injection by dispersing it with an oil of plant origin such as sesame oil or corn oil, or with a mixture thereof with phospholipids such as lecithin, or with medium chain triglyceride (e.g., Miglyol 812, etc.) as in a suspension in oil.

In particular, when such formulation is administered directly into the joint cavity of a patient suffering from an articular disease for local administration, the formulation can be produced by dispersing compound (I) in a hyaluronic acid preparation for injection (for example, product by Kaken Pharmaceutical Co., Ltd.; ARTZ) as dispersing medium. The hyaluronic acid used in the dispersing medium may be a non-toxic salt thereof, and examples include an alkali metal salt such as sodium, potassium and the like, or an alkali earth metal salt such as magnesium, calcium and the like, a sodium salt being particularly preferred. The molecular weight of hyaluronic acid or a non-toxic salt thereof is about 200,000 to about 5,000,000 (measured by the viscosity method), preferably about 500,000 to about 3,000,000, and more preferably about 700,000 to 2,500,000.

The final concentration of hyaluronic acid or sodium hyaluronate in this dispersion is suitably less than 1% (W/V) for viscosity from the aspects of easiness of various handling and administration and the like, preferably from about 0.02 to less than 1%, and even more preferably from about 0.1 to 1% (W/V).

The dispersing medium may contain a pH adjusting agent, local anesthetic, antibiotics, a solubilizing agent, an isotonic agent, anti-adsorption agent, glycosaminoglycan, polysaccharides and the like by a method known per se. Preferred examples include mannitol, sorbitol, sodium chloride, glycine, ammonium acetate, or an aqueous protein that can be administered into body fluid without exhibiting any substantial pharmacological activity. The glycosaminoglycan include hyaluronic acid, chondroitin, chondroitin sulfate A, chondroitin sulfate C, dermatan sulfate, heparin, heparan sulfate, keratan sulfate and the like. The polysaccharide includes an acidic polysaccharide such as arginic acid.

The above-mentioned aqueous protein may be anything that is soluble in water, a physiological saline or a buffer, and examples include human serum albumin, human serum globulin, collagen, gelatin and the like. The pH adjusting agent includes, for example, glycine, ammonium acetate, citric acid, hydrochloric acid, sodium hydroxide and the like.

The local anesthetic includes, for example, chlorobutanol, xylocaine hydrochloride and the like. The antibiotic includes, for example, gentamicin and the like. The solubilizing agent includes, for example, glycerin, polyethylene glycol 400 and the like. The isotonic agent includes, for example, mannitol, sorbitol, sodium chloride and the like. The anti-adsorption agent includes, for example, polyoxyethylenesorbitan monooleate and the like.

Furthermore, when the dispersing medium contains an aqueous protein, the content of the aqueous protein in the preparation for a single dose is preferably 0.05 to 50 mg, more preferably 0.5 to 20 mg, and even more preferably 0.75 to 10 mg. Such preparation may contain phosphoric acid or a salt thereof (e.g., sodium phosphate, potassium phosphate, etc.).

When a preparation for injection contains phosphoric acid or a salt thereof, the concentration of sodium phosphate or potassium phosphate in the preparation for injection is about 0.1 mM to 500 mM, and preferably about 1 mM to 100 mM.

Sterilization of a preparation may be carried out by operating the entire production process under aseptic conditions, sterilizing with γ-rays, adding a preservative, and the like, without being particularly limited.

The prophylactic and therapeutic agent of the invention can be used in combination with other agents. For example, when compound (I) is used as a therapeutic agent for articular diseases, it can be used in combination with (i) a cyclooxygenase inhibitor (Cox-I or Cox-II inhibitor), (ii) a disease-modified anti-rheumatic drug and immune suppressant, (iii) a biologics, (iv) an analgesic and anti-inflammatory agent, (v) a therapeutic agent for bone diseases, (vi) p38 MAP kinase inhibitor and/or TNF-α production inhibitor, or (vii) c-JUN N-terminal kinase (JNK) inhibitor. Further, when compound (I) is used as an anticancer agent, it can be used in combination with (viii) other anticancer agents.

(i) A cyclooxygenase inhibitor (Cox-I or Cox-II inhibitor) includes, for example, Celecoxib, Rofecoxib, a salicylic acid derivative such as aspirin and the like, Diclofenac, Indomethacin, Loxoprofen and the like.

(ii) A disease-modified anti-rheumatic drug and immune suppressant includes, for example, methotrexate, Leflunomid, Prograf, sulfasalazine, D-penicillamine, oral gold agent, T-cell differentiation controlling agent and the like.

(iii) A biologics includes, for example, a monoclonal antibody (e.g., anti-TNF-α antibody, anti-IL-12 antibody, anti-IL-6 antibody, anti-ICAM-I antibody, anti-CD4 antibody, etc.), soluble receptor (e.g., soluble TNF-α receptor, etc.), proteinaceous ligand (IL-1 receptor antagonist, etc.) and the like.

(iv) An analgesic and anti-inflammatory agent includes, for example, centrally active analgesic (e.g., morphine, codeine, pentazocine, etc.), steroids (e.g., prednisolone, hydrocortisone, methylprednisolone, dexamethasone, betamethasone, etc.), anti-inflammatory enzymes (e.g., bromelain, lysozyme, proctase, etc.) and the like.

(v) A therapeutic agent for bone diseases (e.g., fracture, refracture, osteoporosis, osteomalacia, Paget's disease, spastic myelitis, chronic rheumatoid arthritis, destruction of articular tissues in osteoarthritis and its analogous diseases, etc.) includes, for example, a calcium preparation (e.g., calcium carbonate, etc.), a calcitonin preparation, a vitamin D preparation (e.g., alpha-calcidol, etc.), sex hormones (e.g., estrogen, estradiol, etc.), prostaglandin $A_1$, bisphosphonic acids, ipriflavones, fluorine compounds (e.g., sodium fluoride, etc.), vitamin $K_2$, bone morphogenic proteins (BMP), fibroblast growth factor (FGF), platelet-derived growth factor (PDGF), transforming growth factor (TGF-β), insulin-like growth factor-1 and -2 (IGF-1 and -2), parathyroid hormone (PTH) and the like.

(vi) A p38 MAP kinase inhibitor and/or TNF-α production inhibitor include compounds described in the publications of, for example, WO98/57966, WO98/56377, WO98/25619, WO98/07425, WO98/06715, U.S. Pat. No. 5,739,143, WO97/35855, WO97/33883, WO97/32583, WO97/25048, WO97/25046, WO96/10143, WO96/21654, WO95/07922, WO00/09525, WO99/17776, WO99/01131, WO98/28292, WO97/25047, WO97/25045, U.S. Pat. No. 5,658,903, WO96/21452, WO99/18942, U.S. Pat. No. 5,756,499, U.S. Pat. No. 5,864,036, U.S. Pat. No. 6,046,208, U.S. Pat. No. 5,716,955, U.S. Pat. No. 5,811,549, U.S. Pat. No. 5,670,527, U.S. Pat. No. 5,969,184, WO00/31072, WO00/31063, WO00/20402, WO00/18738, WO00/17175, WO00/12497, WO00/12074, WO00/07991, WO00/07980, WO00/02561, U.S. Pat. No. 6,096,711, WO99/64400, WO99/61440, WO99/59959, WO99/58523, WO99/58502, WO99/57101, WO99/32111, WO99/32110, WO99/26657, WO99/20624, WO99/18942, WO99/15164, WO99/00357, WO98/52940, WO98/52937, WO98/52558, WO98/06715, WO97/22256, WO96/21452, WO00/43366, WO00/42003, WO00/42002, WO00/41698, WO00/41505, WO00/40243, WO00/34303, WO00/25791, WO00/17204, WO00/10563, U.S. Pat. No. 6,080,546, WO99/61426, WO99/32463, WO99/32121, WO99/17776, WO98/28292, WO98/27098, WO98/25619, WO98/20868, WO97/35855, WO97/32583, WO97/25048, WO97/25047, WO97/25046, WO97/25045, U.S. Pat. No. 5,658,903, WO96/40143, WO96/21654, WO00/55153, WO00/55120, WO00/26209, U.S. Pat. No. 6,046,208, U.S. Pat. No. 5,756,499, U.S. Pat. No. 5,864,036, JP-A-2000-86657, WO99/59960, WO99/21859, WO99/03837, WO99/01449, WO99/01136, WO99/01130, U.S. Pat. No. 5,905,089, WO98/57966, WO98/52941, WO98/47899, WO98/07425, WO97/33883, WO00/42213, WO99/58128, WO00/04025, WO00/40235, WO00/31106, WO97/46228, WO00/59904, WO00/42003, WO00/42002, WO00/41698, WO00/10563, WO00/64894, WO99/61426, WO99/32463, U.S. Pat. No. 6,002,008, WO98/43960, WO98/27098, WO97/35856, WO97/35855, WO96/22985 and JP-A-61-145167.

(vii) A JNK inhibitor includes compounds described in the publications of, for example, WO00/35906, WO00/35909, WO00/35921, WO00/64872, WO00/75118 and WO02/62792.

(viii) An anticancer agent include, for example, 6-O—(N-chloroacetylcarbamoyl)fumagillol, bleomycin, methotrexate, actinomycin D, mitomycin C, daunorubicin, adriamycin, neocartinostatin, cytosine arabinoside, fluorouracil, tetrahydrofuryl-5-fluorouracil, picibanil, lentinan, levamisole, bestatin, azimexone, glytilitin, doxorubicin hydrochloride, acrarubicin hydrochloride, bleomycin hydrochloride, hepromycin sulfate, vincristine sulfate, vinblastine sulfate, irinotecan hydrochloride, cyclophosphamide, melphalan, busulphan, thiotepa, procarbazine hydrochloride, cisplatin, azathioprine, mercaptopurine, tegafur, carmofur, cytarabine, methyl testosterone, propionic acid testosterone, testosterone enanthate, mepitiostan, fosfestrol, chlormadinone acetate, leuprorelin acetate, buserelin acetate and the like.

When used in combination, the administration interval for compound (I) and the combination drug is not particularly limited. Compound (I) or a pharmaceutical composition thereof, and the drug for combination or a pharmaceutical composition thereof, may be administered to a subject of administration either simultaneously or with a time interval. The dose of the drug for combination may be determined to be in accordance with the clinically used dose, and can be suitably selected according to the subject of administration, administration route, type of disease, organization and the like.

The form of administration for combination is not particularly limited, and compound (I) and the drug for combination may be combined at the time of administration. Such form of administration include, for example, (1) administration of a single preparation which can be obtained by simultaneously formulating compound (I) or a pharmaceutical composition thereof with the drug for combination or a pharmaceutical composition thereof; (2) simultaneous administration by an identical route of administration, of two preparations which can be obtained by separately formulating compound (I) or a pharmaceutical composition thereof and the drug for combination or a pharmaceutical composition thereof; (3) administration with a time interval by an identical route of administration, of two preparations which can be obtained by separately formulating compound (I) or a pharmaceutical composition thereof with the drug for combination or a pharmaceutical composition thereof; (4) simultaneous administration by different routes of administration, of two preparations which can be obtained by separately formulating compound (I) or a pharmaceutical composition thereof with the drug for combination or a pharmaceutical composition thereof; (5) administration with a time interval by different routes of administration, of two preparations which can be obtained by separately formulating compound (I) or a pharmaceutical composition thereof with the drug for combination or a pharmaceutical composition thereof (for example, administration in the order of compound (I) or a pharmaceutical thereof and then the drug for combination or a pharmaceutical thereof, or administration in the reverse order), and the like.

The mixing ratio for compound (I) with the drug for combination in the combination of the present invention can be appropriately selected according to the subject of administration, the administration route, type of disease and the like.

For example, the content of compound (I) present in the combination of the present invention may vary depending on the type of preparation, but it is typically about 0.01 to 100% by weight, preferably about 0.1 to about 50% by weight, and more preferably about 0.5 to about 20% by weight, with respect to the whole preparation.

The content of the drug for combination present in the combination of the present invention may vary depending on the type of preparation, but it is typically about 0.01 to 100% by weight, preferably about 0.1 to about 50% by weight, and more preferably about 0.5 to about 20% by weight, with respect to the whole preparation.

The content of an additive such as carrier present in the combination of the present invention may vary depending on the type of preparation, but it is typically about 1 to 99.99% by weight, and preferably about 10 to 90% by weight, with respect to the whole preparation.

When compound (I) and the drug for combination are each separately formulated, the same contents may be used.

The dose may vary depending on the type of compound (I) or a pharmaceutically acceptable salt thereof, the administration route, symptoms, age of the patient, but in the case of administering orally to an adult patient having osteoarthritis, for example, the daily dose of compound (I) per kg body weight is about 0.005 to 50 mg, preferably about 0.05 to 10 mg, and more preferably about 0.2 to 4 mg, which can be administered in portions in 1 to 3 times.

When the pharmaceutical composition of the present invention is a sustained-release formulation, the dose may vary depending on the type and content of compound (I), type of formulation, the duration of drug release, the animal subject of administration (e.g., mammals such as mouse, rat, hamster, guinea pig, rabbit, cat, dog, bovine, horse, pig, sheep, monkey, human etc.) and purpose of administration, but in the case of parenteral administration, the release amount from the preparation is preferably from about 0.1 mg to about 100 mg of compound (I) per week.

For a drug for combination, the dose can be set to any level within the scope that side-effects do not occur. The daily dose for a drug for combination may vary depending on the extent of symptoms, the age, sex, body weight, and sensitivity of the subject of administration, the time and interval of administration, the properties, formulation, type of the pharmaceutical preparation, type of the active ingredient, and the like and may not be particularly limited. However, the dose of the drug, for example, in oral administration to a mammal is typically about 0.001 to 2000 mg, preferably about 0.01 to 500 mg, and more preferably about 0.1 to 100 mg per kg of body weight, which is typically administered in portions in 1 to 4 times.

When an agent for combination of the invention is administered, compound (I) and a drug for combination may be administered simultaneously; a drug for combination may be first administered, followed by compound (I); or compound (I) may be administered first, followed by a drug for combination. When the administration is carried out with a time interval, the time interval may vary depending on the effective component to be administered, formulation, route of administration and the like. For example, when a drug for combination is first administered, compound (I) can be administered within 1 minute to 3 days from the point of administration of the drug for combination, preferably within 10 minutes to 1 day, and more preferably within 15 minutes to 1 hour. When compound (I) is administered first, a drug for combination can be administered within 1 minute to 1 day from the point of administration of compound (I), preferably within 10 minutes to 6 hours, and more preferably within 15 minutes to 1 hour.

The pharmaceutical composition of the present invention is low in toxicity and thus can be used safely. In particular, the compounds of the Examples shown below exhibit excellent absorbability when administered orally, and thus can be used advantageously as an oral preparation.

EXAMPLE

The present invention is explained in detail in the following by referring to Examples and Reference Examples. The present invention is not limited in any way by the examples and may be changed without departing from the scope of the present invention.

An elution in column chromatography in each Example was performed under the observation by a TLC (Thin Layer Chromatography), unless otherwise specified. TLC was performed using a 60F$_{254}$ manufactured by Merck as a TLC plate. Detection was made by an UV detector or by means of a color development with a phosphomolybdic acid or a ninhydrin reagent. Silica gel 60 (70 to 230 mesh size) manufactured by Merck was employed as silica gel for column chromatography. A 60F$_{254}$ plate manufactured by Merck was employed as preparative TLC plate. A room temperature referred herein typically means a temperature from about 10° C. to 35° C.

NMR (Nuclear Magnetic Resonance) spectra were measured using a VARIAN model Gemini-200 spectrometer ($^1$H-NMR: 200 MHz or 300 MHz) or a BRUKER model DPX300 ($^1$H-NMR: 300 MHz). An internal standard was tetramethyl-silane and all δ values are represented in ppm. Abbreviations employed here are described below.

DMF: N,N-dimethylformamide, THF: tetrahydrofuran, EtOH: ethanol, DMA: N,N-dimethylacetamide, IPE: diisopropyl ether, CDCl$_3$: deuterated chloroform, DMSO-d$_6$: deuterated dimethyl sulfoxide, Hz: hertz, J: coupling constant, m: multiplet, q: quartet, t: triplet, d: doublet, s: singlet, br: broad, dd: double doublet, dq: double quartet.

Example 1

4-oxo-N-[(3-{[2-(1H-1,2,4-triazol-3-ylthio)ethyl]oxy}phenyl)methyl]-3,4-dihydroquinazoline-2-carboxamide

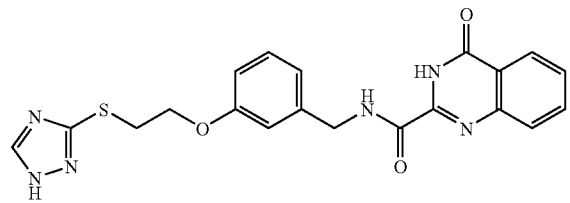

A suspension of ethyl 4-oxo-3,4-dihydro-2-quinazolinecarboxylate obtained according to the methods described in Journal of Organic Chemistry (1978), 43(23), 4485-7 and the like (200 mg, 0.917 mmol), 1-(3-{[2-(1H-1,2,4-triazol-3-ylthio)ethyl]oxy}phenyl)methanamine obtained in Reference Example 3 (298 mg, 1.19 mmol) and diisopropylethylamine (237 mg, 1.83 mmol) in ethanol (10 mL) was stirred at 90° C. for 15 hr. The reaction solvent was evaporated under reduced pressure, and the residue was extracted with ethyl acetate and water. The organic layer was washed with saturated brine, dried over sodium sulfate, and concentrated. The residue was purified by preparative HPLC (GILSON 215LIQUD HANDLER, 322PUMP, UV/VIS-156, SHISEIDO CAPCELL PACK C-18 UG120 S-5 (20 mmφ×50 mm), mobile phase: distilled water (containing 0.1% trifluoroacetic acid)/acetonitrile (containing 0.1% trifluoroacetic acid), gradient: distilled water/acetonitrile-90/10→0/100, time: 10 min, flow rate: 25 mL/min, detection wavelength: 220 nm), and the obtained crude crystals were recrystallized from ethanol to give the title compound as a white powder (29.2 mg, 8%).

melting point: 177-179° C.

Example 2

6-cyano-4-oxo-N-[(3-{[2-(1H-1,2,4-triazol-3-ylthio)ethyl]oxy}phenyl)methyl]-3,4-dihydroquinazoline-2-carboxamide

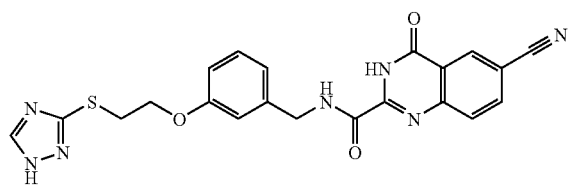

A suspension of 1-(3-{[2-(1H-1,2,4-triazol-3-ylthio)ethyl]oxy}phenyl)methanamine obtained in Reference Example 3

(300 mg, 0.999 mmol), ethyl 6-cyano-4-oxo-3,4-dihydroquinazoline-2-carboxylate obtained in Reference Example 51 (200 mg, 0.822 mmol) and diisopropylethylamine (0.180 mL, 1.05 mmol) in ethanol (2 mL) was stirred at 90° C. for 2 days. The reaction solvent was evaporated under reduced pressure, and the residue was purified by preparative HPLC (GILSON 215LIQUD HANDLER, 322PUMP, UV/VIS-156, SHISEIDO CAPCELL PACK C-18 UG120 S-5 (20 mmφ×50 mm), mobile phase: distilled water (containing 0.1% trifluoroacetic acid)/acetonitrile (containing 0.1% trifluoroacetic acid), gradient: distilled water/acetonitrile=90/100/100, time: 10 min, flow rate: 25 mL/min, detection wavelength: 220 nm), and the obtained crude crystals were recrystallized from ethanol to give the title compound as a white powder (97.4 mg, 26%).

melting point: 195-198° C.

Example 3

6-fluoro-4-oxo-N-[(3-{[2-(1H-1,2,4-triazol-3-ylthio)ethyl]oxy}phenyl)methyl]-3,4-dihydroquinazoline-2-carboxamide

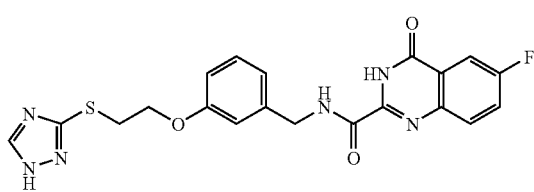

A suspension of 1-(3-{[2-(1H-1,2,4-triazol-3-ylthio)ethyl]oxy}phenyl)methanamine obtained in Reference Example 3 (318 mg, 1.27 mmol), ethyl 6-fluoro-4-oxo-3,4-dihydroquinazoline-2-carboxylate obtained in Reference Example 52 (100 mg, 0.423 mmol) and diisopropylethylamine (0.442 mL, 2.54 mmol) in THF (9 mL)-ethanol (3 mL) was stirred at 90° C. for 2 days. The reaction solvent was evaporated under reduced pressure, and the residue was extracted with 0.1N hydrochloric acid and THF-ethyl acetate. The organic layer was washed with saturated brine, dried over sodium sulfate, and concentrated. The residue was crystallized from toluene-ethanol, and the obtained crude crystals were recrystallized from THF-IPE to give the title compound as a white powder (45.7 mg, 25%).

melting point: 180-182° C.

Example 4

6-(methyloxy)-4-oxo-N-[(3-{[2-(1H-1,2,4-triazol-3-ylthio)ethyl]oxy}phenyl)methyl]-3,4-dihydroquinazoline-2-carboxamide

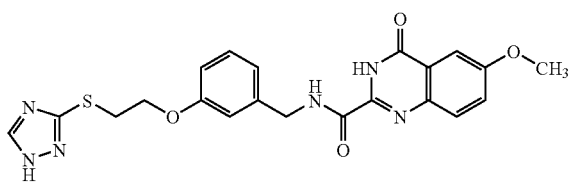

By a method similar to that in Example 3 and using, instead of ethyl 6-fluoro-4-oxo-3,4-dihydroquinazoline-2-carboxylate, ethyl 6-(methyloxy)-4-oxo-3,4-dihydroquinazoline-2-carboxylate obtained in Reference Example 53, the title compound was obtained as a yellow powder (85.6 mg, 47%).

melting point: 142-143° C.

Example 5

6-chloro-4-oxo-N-[(3-{[2-(1H-1,2,4-triazol-3-ylthio)ethyl]oxy}phenyl)methyl]-3,4-dihydroquinazoline-2-carboxamide

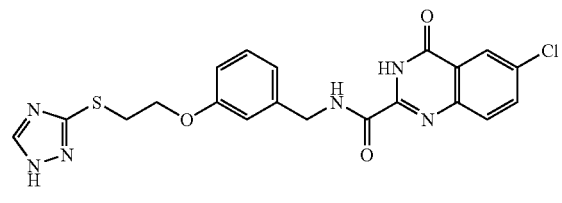

By a method similar to that in Example 3 and using, instead of ethyl 6-fluoro-4-oxo-3,4-dihydroquinazoline-2-carboxylate, ethyl 6-chloro-4-oxo-3,4-dihydro-2-quinazolinecarboxylate obtained in Reference Example 54, the title compound was obtained as a white powder (78.1 mg, 22%).

melting point: 168-171° C.

Example 6

6-methyl-4-oxo-N-[(3-{[2-(1H-1,2,4-triazol-3-ylthio)ethyl]oxy}phenyl)methyl]-3,4-dihydroquinazoline-2-carboxamide

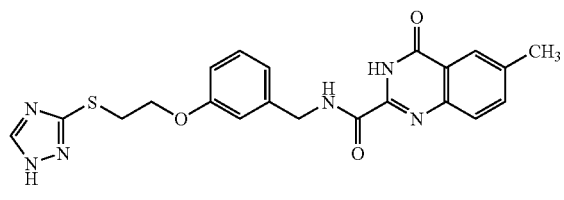

By a method similar to that in Example 3 and using, instead of ethyl 6-fluoro-4-oxo-3,4-dihydroquinazoline-2-carboxylate, ethyl 6-methyl-4-oxo-3,4-dihydroquinazoline-2-carboxylate obtained in Reference Example 55, the title compound was obtained as a yellow powder (51.6 mg, 27%).

melting point: 184-185° C.

Example 7

6-amino-4-oxo-N-[(3-{[2-(1H-1,2,4-triazol-3-ylthio)ethyl]oxy}phenyl)methyl]-3,4-dihydroquinazoline-2-carboxamide

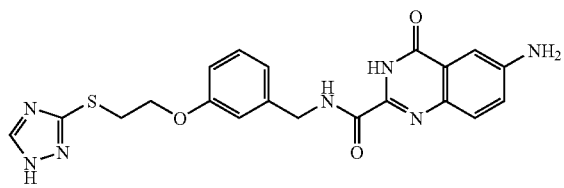

By a method similar to that in Example 3 and using, instead of ethyl 6-fluoro-4-oxo-3,4-dihydroquinazoline-2-carboxylate, ethyl 6-amino-4-oxo-3,4-dihydro-2-quinazolinecarboxylate obtained in Reference Example 56, the title compound was obtained as a yellow powder (180 mg, 48%).
melting point: 164-167° C.

Example 8

5,6-difluoro-4-oxo-N-[(3-{[2-(1H-1,2,4-triazol-3-ylthio)ethyl]oxy}phenyl)methyl]-3,4-dihydroquinazoline-2-carboxamide

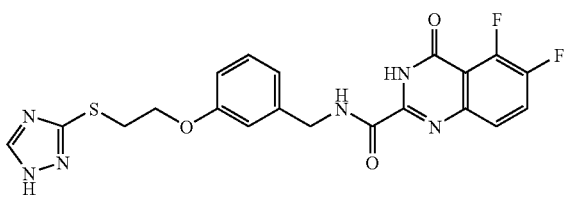

By a method similar to that in Example 3 and using, instead of ethyl 6-fluoro-4-oxo-3,4-dihydroquinazoline-2-carboxylate, ethyl 5,6-difluoro-4-oxo-3,4-dihydroquinazoline-2-carboxylate obtained in Reference Example 57, the title compound was obtained as a yellow powder (59.0 mg, 33%).
melting point: 165-168° C.

Example 9

5-methyl-4-oxo-N-[(3-{[2-(1H-1,2,4-triazol-3-ylthio)ethyl]oxy}phenyl)methyl]-3,4-dihydroquinazoline-2-carboxamide

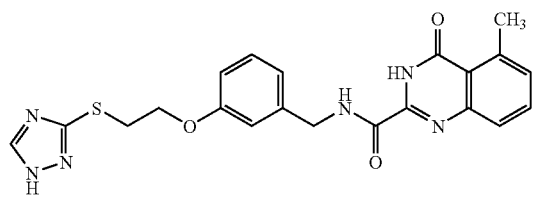

By a method similar to that in Example 3 and using, instead of ethyl 6-fluoro-4-oxo-3,4-dihydroquinazoline-2-carboxylate, ethyl 5-methyl-4-oxo-3,4-dihydroquinazoline-2-carboxylate obtained in Reference Example 58, the title compound was obtained as a yellow powder (75.0 mg, 40%).
melting point: 137-139° C.

Example 10

5-fluoro-4-oxo-N-[(3-{[2-(1H-1,2,4-triazol-3-ylthio)ethyl]oxy}phenyl)methyl]-3,4-dihydroquinazoline-2-carboxamide

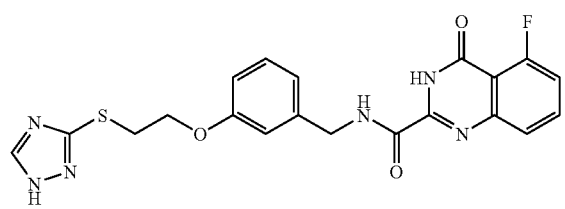

By a method similar to that in Example 3 and using, instead of ethyl 6-fluoro-4-oxo-3,4-dihydroquinazoline-2-carboxylate, ethyl 5-fluoro-4-oxo-3,4-dihydroquinazoline-2-carboxylate obtained in Reference Example 59, the title compound was obtained as a yellow powder (110 mg, 59%).
melting point: 164-167° C.

Example 11

4-oxo-N-[(3-{[2-(1H-1,2,4-triazol-3-ylthio)ethyl]oxy}phenyl)methyl]-3,4-dihydrothieno[2,3-d]pyrimidine-2-carboxamide

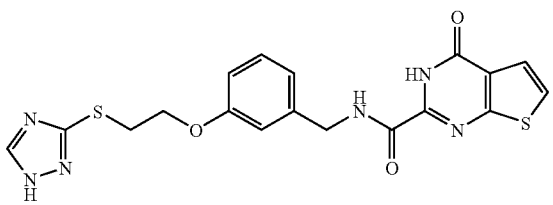

By a method similar to that in Example 3 and using, instead of ethyl 6-fluoro-4-oxo-3,4-dihydroquinazoline-2-carboxylate, ethyl 4-oxo-3,4-dihydrothieno[2,3-d]pyrimidine-2-carboxylate obtained in Reference Example 60, to the title compound was obtained as a white powder (102 mg, 27%).
melting point: 216-219° C.

Example 12

5-methyl-4-oxo-N-[(3-([2-(1H-1,2,4-triazol-3-ylthio) ethyl]oxy)phenyl)methyl]-3,4-dihydrothieno[2,3-d] pyrimidine-2-carboxamide

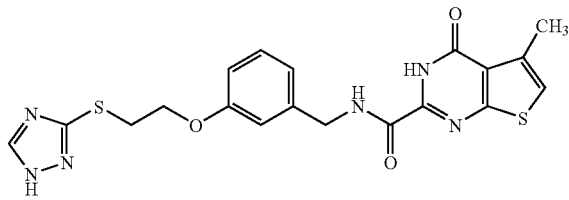

By a method similar to that in Example 3 and using, instead of ethyl 6-fluoro-4-oxo-3,4-dihydroquinazoline-2-carboxylate, ethyl 5-methyl-4-oxo-3,4-dihydrothieno[2,3-d]pyrimidine-2-carboxylate obtained according to the method described in U.S. Pat. No. 4,054,656, the title compound was obtained as a white powder (82.7 mg, 44%).
melting point: 178-179° C.

Example 13

6-methyl-4-oxo-N-[(3-{[2-(1H-1,2,4-triazol-3-ylthio)ethyl]oxy}phenyl)methyl]-3,4-dihydrothieno[2,3-d]pyrimidine-2-carboxamide

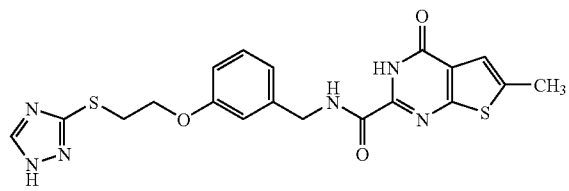

By a method similar to that in Example 3 and using, instead of ethyl 6-fluoro-4-oxo-3,4-dihydroquinazoline-2-carboxylate, ethyl 6-methyl-4-oxo-3,4-dihydrothieno[2,3-d]pyrimidine-2-carboxylate obtained according to the methods described in BE859818 and the like, the title compound was obtained as a white powder (225 mg, 61%).
melting point: 202-205° C.

Example 14

5,6-dimethyl-4-oxo-N-[(3-{[2-(1H-1,2,4-triazol-3-ylthio)ethyl]oxy}phenyl)methyl]-3,4-dihydrothieno[2,3-d]pyrimidine-2-carboxamide

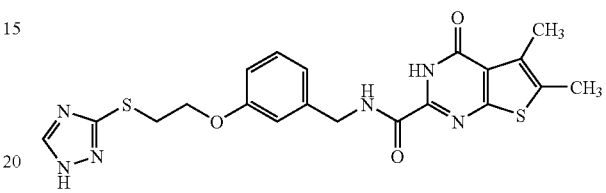

By a method similar to that in Example 3 and using, instead of ethyl 6-fluoro-4-oxo-3,4-dihydroquinazoline-2-carboxylate, ethyl 5,6-dimethyl-4-oxo-3,4-dihydrothieno[2,3-d]pyrimidine-2-carboxylate obtained according to the methods described in U.S. Pat. No. 4,054,656 and the like, the title compound was obtained as a white powder (30.3 mg, 8%).
melting point: 198-200° C.

Example 15

6-cyano-4-oxo-N-[(3-{[3-(1H-1,2,4-triazol-3-ylthio) propyl]oxy}phenyl)methyl]-3,4-dihydroquinazoline-2-carboxamide

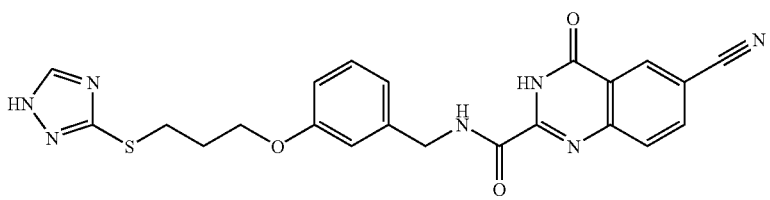

A solution of ethyl 6-cyano-4-oxo-3,4-dihydroquinazoline-2-carboxylate obtained in Reference Example 51 (200 mg, 0.822 mmol) and 1-{3-[(3-{[1-(triphenylmethyl)-1H-1,2,4-triazol-3-yl]thio}propyl)oxy]phenyl}methanamine obtained in Reference Example 7 (708 mg, 1.40 mmol) in DMA (10 mL) was stirred at 100° C. for 12 hr. The reaction mixture was concentrated under reduced pressure, and a solution of the residue in dichloromethane was treated with acidic resin (MP-TsOH: 100 mg) to give a brown oil (1.05 g). The oil was dissolved in dichloromethane (10 mL), and trifluoroacetic acid (3 mL) and triethylsilane (0.138 mL, 0.863 mmol) were added thereto at room temperature. The mixture was stirred for 1 hr, and concentrated under reduced pressure. The residue was purified by silica gel column chromatography (30%-100% ethyl acetate/hexane). The obtained powder was suspended in ethyl acetate, and the mixture was stirred under heating at 90° C. for 1 hr to give the title compound as a white powder (189 mg, 50%).
melting point: 196-197° C.

Example 16

5-methyl-4-oxo-N-[(3-{[3-(1H-1,2,4-triazol-3-ylthio)propyl]oxy}phenyl)methyl]-3,4-dihydrothieno[2,3-d]pyrimidine-2-carboxamide

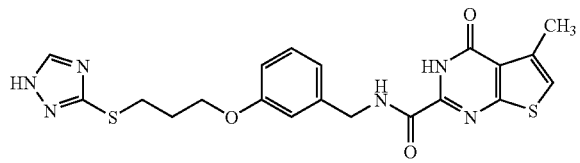

By a method similar to that in Example 15 and using, instead of ethyl 6-cyano-4-oxo-3,4-dihydroquinazoline-2-carboxylate, ethyl 5-methyl-4-oxo-3,4-dihydrothieno[2,3-d]pyrimidine-2-carboxylate obtained according to the method described in U.S. Pat. No. 4,054,656, the title compound was obtained as a white powder (171 mg, 45%).

melting point: 178-179° C.

Example 17

6-cyano-4-oxo-N-[(3-{[4-(1H-1,2,4-triazol-3-ylthio)butyl]oxy}phenyl)methyl]-3,4-dihydroquinazoline-2-carboxamide

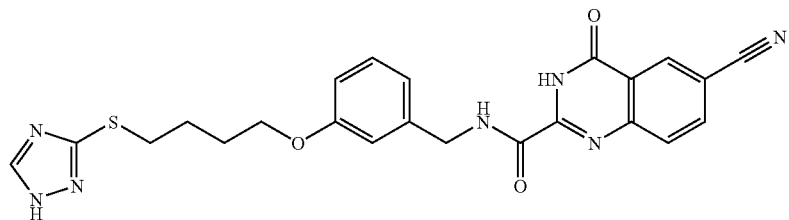

By a method similar to that in Example 15 and using, instead of 1-{3-[(3-{[1-(triphenylmethyl)-1H-1,2,4-triazol-3-yl]thio}propyl)oxy]phenyl}methaneamine, 1-{3-[(4-{([1-(triphenylmethyl)-1H-1,2,4-triazol-3-yl]thio}butyl)oxy]phenyl}methanamine obtained in Reference Example 11, the title compound was obtained as a pale-yellow powder (244 mg, 64%).

melting point: 173-177° C.

Example 18

5-methyl-4-oxo-N-[(3-{[4-(1H-1,2,4-triazol-3-ylthio)butyl]oxy}phenyl)methyl]-3,4-dihydrothieno[2,3-d]pyrimidine-2-carboxamide

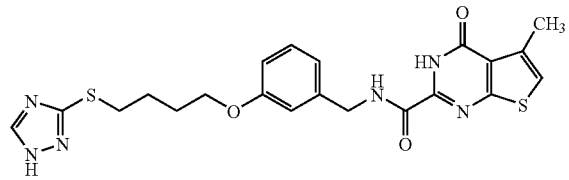

By a method similar to that in Example 15, and using, instead of ethyl 6-cyano-4-oxo-3,4-dihydroquinazoline-2-carboxylate, ethyl 5-methyl-4-oxo-3,4-dihydrothieno[2,3-d]pyrimidine-2-carboxylate obtained according to the method described in 034054656 and using, instead of 1-{3-[(3-{(1(triphenylmethyl)-1H-1,2,4-triazol-3-yl]thiopropyl)oxy}phenyl}methaneamine, 1-{3-[(4-{[1-(triphenylmethyl)-1H-1,2,4-triazol-3-yl]thio}butyl)oxy]phenyl}methanamine obtained in Reference Example 11, the title compound was obtained as a pales yellow powder (232 mg, 48%).

melting point: 161-163° C.

Example 19

4-oxo-N-[(2-{[2-(1H-1,2,4-triazol-3-ylthio)ethyl]oxy}pyridin-4-yl)methyl]-3,4-dihydroquinazoline-2-carboxamide

A suspension of ethyl 4-oxo-3,4-dihydro-2-quinazolinecarboxylate obtained according to the methods described in Journal of Organic Chemistry (1978), 43(23), 4485-7 and the like (200 mg, 0.917 mmol), 1-(2-{[2-(1H-1,2,4-triazol-3-ylthio)ethyl]oxy}pyridin-4-yl)methanamine hydrochloride obtained in Reference Example is (343 mg, 1.19 mmol) and diisopropylethylamine (462 mg, 3.57 mmol) in DMA (5 mL) was stirred at 90° C. for 15 hr. After cooling the mixture to room temperature, the resulting solid was collected by filtration, and washed with ethanol. The obtained crude powder was recrystallized from ethanol to give the title compound as a white powder (135 mg, 35%)

melting point: 187-119° C. .

Example 20

6-cyano-4-oxo-N-[(2-{[2-(1H-1,2,4-triazol-3-ylthio)ethyl]oxy}pyridin-4-yl)methyl]-3,4-dihydroquinazoline-2-carboxamide

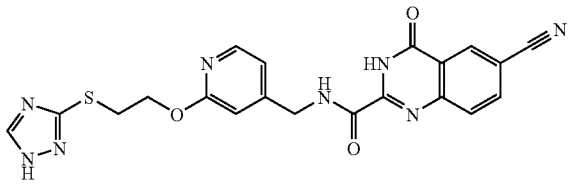

By a method similar to that in Example 19 and using, instead of ethyl 4-oxo-3,4-dihydro-2-quinazolinecarboxylate, ethyl 6-cyano-4-oxo-3,4-dihydroquinazoline-2-carboxylate obtained in Reference Example 51, the title compound was obtained as a white powder (21.9 mg, 6%).
melting point: 225-230° C.

Example 21

5-methyl-4-oxo-N-[(2-{[2-(1H-1,2,4-triazol-3-ylthio)ethyl]oxy}pyridin-4-yl)methyl]-3,4-dihydrothieno[2,3-d]pyrimidine-2-carboxamide

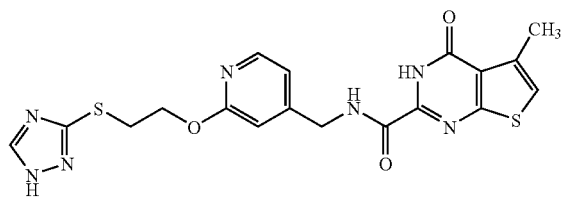

Step 1
By a method similar to that in Example 19, and using, instead of ethyl 4-oxo-3,4-dihydro-2-quinazolinecarboxylate, ethyl 5-methyl-4-oxo-3,4-dihydrothieno[2,3-d]pyrimidine-2-carboxylate obtained according to the method described in U.S. Pat. No. 4,054,656 and using, instead of 1-(2-{[2-(1H-1,2,4-triazol-3-ylthio)ethyl]oxy}pyridin-4-yl)methanamine hydrochloride, 1-{2-[(2-{[1-(triphenylmethyl)-1H-1,2,4-triazol-3-yl]thio}ethyl)oxy]pyridin-4-yl}methanamine obtained in Reference Example 20, 5-methyl-4-oxo-N-({2-[(2-{[1-(triphenylmethyl)-1H-1,2,4-triazol-3-yl]thio}ethyl)oxy]pyridin-4-yl}methyl)-3,4-dihydrothieno[2,3-d]pyrimidine-2-carboxamide was obtained as a white powder (85 mg, 20%).
Step 2
A solution of 5-methyl-4-oxo-N-({2-[(2-{[1-(triphenylmethyl)-1H-1,2,4-triazol-3-yl]thio}ethyl)oxy]pyridin-4-yl}methyl)-3,4-dihydrothieno[2,3-d]pyrimidine-2-carboxamide (395.0 mg, 0.576 mmol), triethylsilane (0.097 mL, 0.605 mmol) and trifluoroacetic acid (3.0 mL) in dichloromethane (10 mL) was stirred at room temperature for 2 hr. The reaction mixture was concentrated under reduced pressure, and the residue was crystallized from ethyl acetate-IPE to give the title compound as a white powder (53.6 mg, 21%).
melting point: 163-165° C.

Example 22

4-oxo-N-[(2-{[3-(1H-1,2,4-triazol-3-yl)propyl]oxy}pyridin-4-yl)methyl]-3,4-dihydroquinazoline-2-carboxamide

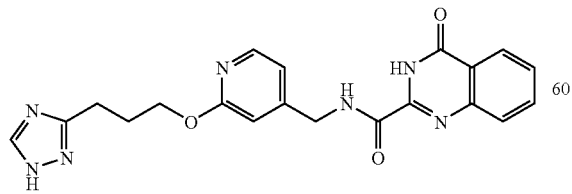

A suspension of ethyl 4-oxo-3,4-dihydro-2-quinazolinecarboxylate obtained according to the methods described in Journal of Organic Chemistry (1978), 43(23), 4485-7 and the like (25.0 mg, 0.11 mmol), 1-[2-({3-[1-(triphenylmethyl)-1H-1,2,4-triazol-3-yl]propyl}oxy)pyridin-4-yl]methanamine obtained in Reference Example 28 (28.0 mg, 0.069 mmol) and diisopropylethylamine (159 mg, 1.20 mmol) in ethanol (3 mL) was stirred at 80° C. for 15 hr. After cooling the mixture to room temperature, the resulting solid was collected by filtration, and washed with ethanol. 4N Hydrochloric acid and ethyl acetate were added to the crude crystals, and the mixture was stirred at room temperature for 2 hr. Water was added to the mixture, and the aqueous layer was weakly acidified with saturated aqueous sodium hydrogencarbonate, and extracted with ethyl acetate. The organic layer was washed with saturated brine, dried over sodium sulfate, and concentrated. The obtained crude crystals were recrystallized from ethanol to give the title compound as a white powder (28.0 mg, 60%).
melting point: 209-212° C.

Example 23

6-cyano-4-oxo-N-[(2-{[3-(1H-1,2,4-triazol-3-yl)propyl]oxy}pyridin-4-yl)methyl]-3,4-dihydroquinazoline-2-carboxamide

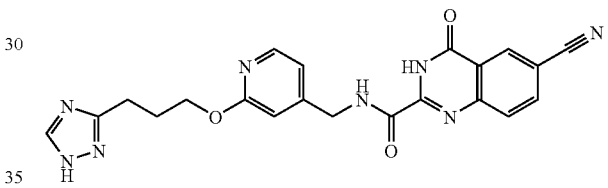

By a method similar to that in Example 22 and using, instead of ethyl 4-oxo-3,4-dihydro-2-quinazolinecarboxylate, ethyl 6-cyano-4-oxo-3,4-dihydroquinazoline-2-carboxylate obtained in Reference Example 51, the title compound was obtained as a white powder (87.0 mg, 32%).
melting point: 214-218° C.

Example 24

5-methyl-4-oxo-N-[(2-{[3-(1H-1,2,4-triazol-3-yl)propyl]oxy}pyridin-4-yl)methyl]-3,4-dihydrothieno[2,3-d]pyrimidine-2-carboxamide

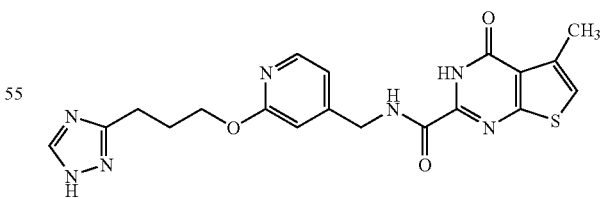

By a method similar to that in Example 22 and using, instead of ethyl 4-oxo-3,4-dihydro-2-quinazolinecarboxylate, ethyl 5-methyl-4-oxo-3,4-dihydrothieno[2,3-d]pyrimidine-2-carboxylate obtained according to the method described in U.S. Pat. No. 4,054,656, the title compound was obtained as a white powder (75.3 mg, 33%)
melting point: 200-203° C. .

Example 25

6-cyano-4-oxo-N-[(3-{[2-(1H-1,2,4-triazol-3-yloxy)ethyl]oxy}phenyl)methyl]-3,4-dihydroquinazoline-2-carboxamide

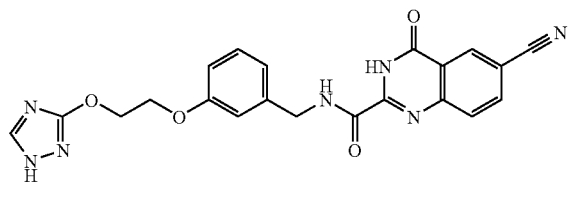

By a method similar to that in Example 22, and using, instead of ethyl 4-oxo-3,4-dihydro-2-quinazolinecarboxylate, ethyl 6-cyano-4-oxo-3,4-dihydroquinazoline-2-carboxylate obtained in Reference Example 51 and using, instead of 1-[2-({3-[1-(triphenylmethyl)-1H-1,2,4-triazol-3-yl]propyl}oxy)pyridin-4-yl]methaneamine, 1-{3-[(2-{[1-(triphenylmethyl)-1H-1,2,4-triazol-3-yl]oxy}ethyl)oxy]phenyl}methanamine obtained in Reference Example 32, the title compound was obtained as a yellow powder (31.7 mg, 12%).

melting point: 184-189° C.

Example 26

5-methyl-4-oxo-N-[(3-{[2-(1H-1,2,4-triazol-3-yloxy)ethyl]oxy}phenyl)methyl]-3,4-dihydrothieno[2,3-d]pyrimidine-2-carboxamide

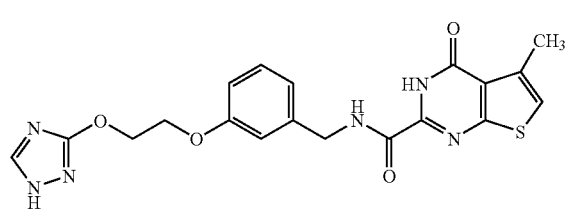

By a method similar to that in Example 22, and using, instead of ethyl 4-oxo-3,4-dihydro-2-quinazolinecarboxylate, ethyl 5-methyl-4-oxo-3,4-dihydrothieno[2,3-d]pyrimidine-2-carboxylate obtained according to the method described in U.S. Pat. No. 4,054,656 and using, instead of 1-[2-({3-[1-(triphenylmethyl)-1H-1,2,4-triazol-3-yl]propyl}oxy)pyridin-4-yl]methaneamine, 1-{3-[(2-{[1-(triphenylmethyl)-1H-1,2,4-triazol-3-yl]oxy}ethyl)oxy]phenyl}methanamine obtained in Reference Example 32, the title compound was obtained as a white powder (126 mg, 79%).

melting point: 225-227° C.

Example 27

4-oxo-5-(2-thienyl)-N-[(3-{[2-(1H-1,2,4-triazol-3-yloxy)ethyl]oxy}phenyl)methyl]-3,4-dihydrothieno[2,3-d]pyrimidine-2-carboxamide

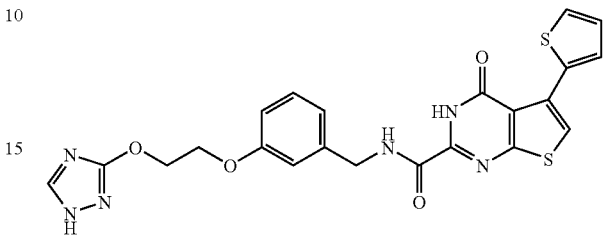

By a method similar to that in Example 22, and using, instead of ethyl 4-oxo-3,4-dihydro-2-quinazolinecarboxylate, ethyl 4-oxo-5-(2-thienyl)-3,4-dihydrothieno[2,3-d]pyrimidine-2-carboxylate obtained in Reference Example 39 and using, instead of 1-[2-({3-[1-(triphenylmethyl)-1H-1,2,4-triazol-3-yl]propyl}oxy)pyridin-4-yl]methaneamine, 1-{3-[(2-{[1-(triphenylmethyl)-1H-1,2,4-triazol-3-yl]oxy}ethyl)oxy]phenyl}methanamine obtained in Reference Example 32, the title compound was obtained as a white powder (149 mg, 46%).

melting point: 162-164° C.

Example 28

5-furan-2-yl-4-oxo-N-[(3-{[2-(1H-1,2,4-triazol-3-yloxy)ethyl]oxy}phenyl)methyl]-3,4-dihydrothieno[2,3-d]pyrimidine-2-carboxamide

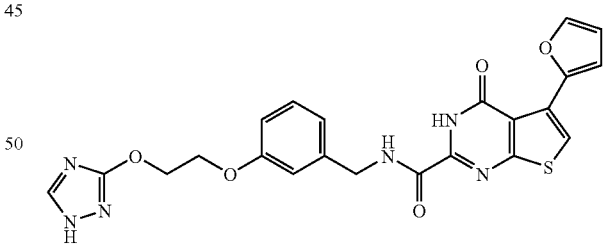

By a method similar to that in Example 22, and using, instead of ethyl 4-oxo-3,4-dihydro-2-quinazolinecarboxylate, ethyl 5-furan-2-yl-4-oxo-3,4-dihydrothieno[2,3-d]pyrimidine-2-carboxylate obtained in Reference Example 40 and using, instead of 1-[2-({3-[1-(triphenylmethyl)-1H-1,2,4-triazol-3-yl]propyl}oxy)pyridin-4-yl]methaneamine, 1-{3-[(2-{[1-(triphenylmethyl)-1H-1,2,4-triazol-3-yl]oxy}ethyl)oxy]phenyl}methanamine obtained in Reference Example 32, the title compound was obtained as a white powder (23.0 mg, 7%).

melting point: 142-143° C.

Example 29

5-(cyanomethyl)-4-oxo-N-[(3-{[2-(1H-1,2,4-triazol-3-yloxy)ethyl]oxy}phenyl)methyl]-3,4-dihydrothieno[2,3-d]pyrimidine-2-carboxamide

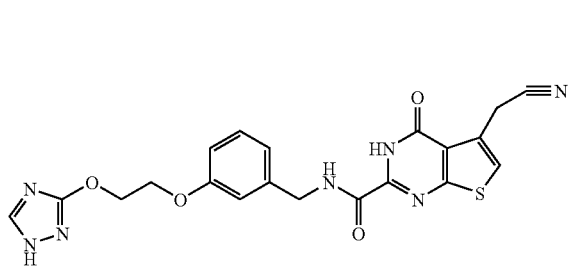

By a method similar to that in Example 22, and using, instead of ethyl 4-oxo-3,4-dihydro-2-quinazolinecarboxylate, ethyl 5-cyanomethyl-4-oxo-3,4-dihydrothieno[2,3-d]pyrimidine-2-carboxylate obtained in Reference Example 61 and using, instead of 1-[2-({3-[1-(triphenylmethyl)-1H-1,2,4-triazol-3-yl]propyl}oxy)pyridin-4-yl]methaneamine, 1-{3-[(2-{[1-(triphenylmethyl)-1H-1,2,4-triazol-3-yl]oxy}ethyl)oxy]phenyl}methanamine obtained in Reference Example 32, the title compound was obtained as a white powder (85.4 mg, 38%).

melting point: 262-263° C.

Example 30

4-oxo-N-[(3-{[(1H-1,2,4-triazol-3-ylmethyl)oxy]methyl}phenyl)methyl]-3,4-dihydroquinazoline-2-carboxamide

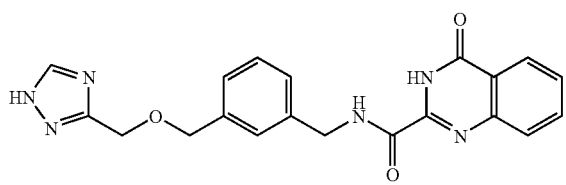

By a method similar to that in Example 22 and using, instead of 1-[2-({3-[1-(triphenylmethyl)-1H-1,2,4-triazol-3-yl]propyl}oxy)pyridin-4-yl]methaneamine, 1-{3-[({[1-(triphenylmethyl)-1H-1,2,4-triazol-3-yl]methyl}oxy)methyl]phenyl}methanamine obtained in Reference Example 38, the title compound was obtained as a white powder (66.0 mg, 18%).

melting point: 194-197° C.

Example 31

6-cyano-4-oxo-N-[(3-{[(1H-1,2,4-triazol-3-ylmethyl)oxy]methyl}phenyl)methyl]-3,4-dihydroquinazoline-2-carboxamide

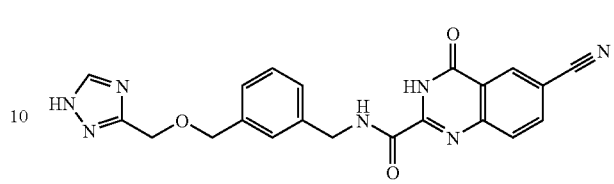

By a method similar to that in Example 22, and using, instead of ethyl 4-oxo-3,4-dihydro-2-quinazolinecarboxylate, ethyl 6-cyano-4-oxo-3,4-dihydroquinazoline-2-carboxylate obtained in Reference Example 51 and using, instead of 1-[2-({3-[1-(triphenylmethyl)-1H-1,2,4-triazol-3-yl]propyl}oxy)pyridin-4-yl]methaneamine, 1-{3-[({[1-(triphenylmethyl)-1H-1,2,4-triazol-3-yl]methyl}oxy)methyl]phenyl}methanamine obtained in Reference Example 38, the title compound was obtained as a white powder (20 mg, 6%).

melting point: 203-205° C.

Example 32

6-cyano-4-oxo-N-[(3-{[3-(1H-1,2,4-triazol-3-yl)propanoyl]amino}phenyl)methyl]-3,4-dihydroquinazoline-2-carboxamide

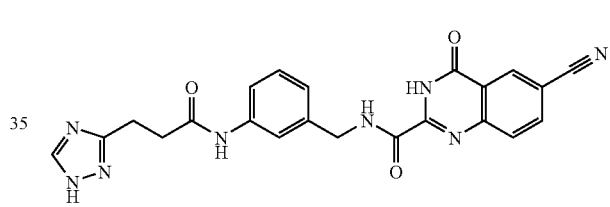

Step 1

A solution of N-[(3-aminophenyl)methyl]-6-cyano-4-oxo-3,4-dihydroquinazoline-2-carboxamide obtained in Reference Example 45 (120 mg, 0.376 mmol), 3-[1-(triphenylmethyl)-1H-1,2,4-triazol-3-yl]propanoic acid obtained in Reference Example 25 (152 mg, 0.396 mmol), 1-[3-(dimethylamino)propyl]-3-ethyl-carbodiimide hydrochloride (106 mg, 0.554 mmol) and 1-hydroxybenzotriazole (74.9 mg, 0.554 mmol) in DMF (5 mL) was stirred at 40° C. for 15 hr. The reaction mixture was concentrated under reduced pressure, and water was added to residue. The resulting solid was collected by filtration, washed with water and IPE, and dried to give 6-cyano-4-oxo-N-{[3-({3-[1-(triphenylmethyl)-1H-1,2,4-triazol-3-yl]propanoyl}amino)phenyl]methyl}-3,4-dihydroquinazoline-2-carboxamide as a white powder (232.0 mg, 86%).

Step 2

A solution of 6-cyano-4-oxo-N-{[3-({3-[1-(triphenylmethyl)-1H-1,2,4-triazol-3-yl]propanoyl}amino)phenyl]methyl}-3,4-dihydroquinazoline-2-carboxamide (215 mg, 0.314 mmol), triethylsilane (0.053 mL, 0.330 mmol) and trifluoroacetic acid (2 mL) in dichloromethane (3 mL) was stirred at room temperature for 2 hr. The reaction mixture was concentrated under reduced pressure, and the residue was crystallized from IPE. The resulting powder was recrystallized from ethanol to give is the title compound as a white powder (98.6 mg, 71%).

melting point: 298-301° C.

Example 33

5-methyl-4-oxo-N-[(3-{[3-(1H-1,2,4-triazol-3-yl)propanoyl]amino}phenyl)methyl]-3,4-dihydrothieno[2,3-d]pyrimidine-2-carboxamide

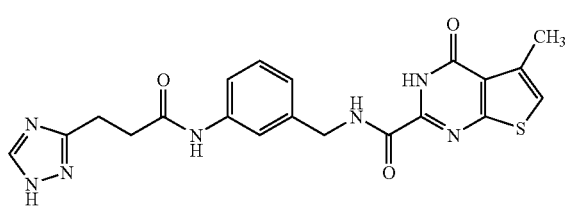

By a method similar to that in Example 32 and using, instead of N-[(3-aminophenyl)methyl]-6-cyano-4-oxo-3,4-dihydroquinazoline-2-carboxamide, N-[(3-aminophenyl)methyl]-5-methyl-4-oxo-3,4-dihydrothieno[2,3-d]pyrimidine-2-carboxamide obtained in Reference Example 48, the title compound was obtained as a white powder (63.0 mg, 43%).

melting point: 248-250° C.

Example 34

6-cyano-4-oxo-N-[(3-{[(1H-1,2,4-triazol-3-ylacetyl)amino]methyl}phenyl)methyl]-3,4-dihydroquinazoline-2-carboxamide

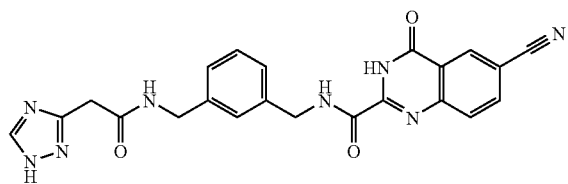

A solution of N-{[3-(aminomethyl)phenyl]methyl}-6-cyano-4-oxo-3,4-dihydroquinazoline-2-carboxamide hydrochloride obtained in Reference Example 47 (170 mg, 0.460 mmol), 1H-1,2,4-triazol-3-ylacetic acid obtained in Reference Example 15 (70.0 mg, 0.551 mmol), diisopropylethylamine (0.079 mL, 0.460 mmol), 1-[3-(dimethylamino)propyl]-3-ethyl-carbodiimide hydrochloride (106 mg, 0.550 mmol) and 1-hydroxybenzotriazole (74.0 mg, 0.550 mmol) in DMF (10 mL) was stirred at 40° C. for 15 hr. The reaction mixture was concentrated under reduced pressure, and water was added to the residue. The resulting solid was collected by filtration, washed with water and IPE, and dried. The obtained crude crystals were recrystallized from ethyl acetate-IPE to give the title compound as a white powder (49.4 mg, 24%).

melting point: 207-208° C.

Example 35

5-methyl-4-oxo-N-[(3-{[(1H-1,2,4-triazol-3-ylacetyl)amino]methyl}phenyl)methyl]-3,4-dihydrothieno[2,3-d]pyrimidine-2-carboxamide

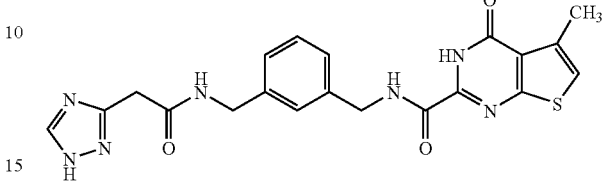

By a method similar to that in Example 34 and using, instead of N-{[3-(aminomethyl)phenyl]methyl}-6-cyano-4-oxo-3,4-dihydroquinazoline-2-carboxamide hydrochloride, N-{[3-(aminomethyl)phenyl]methyl}-5-methyl-4-oxo-3,4-dihydrothieno[2,3-d]pyrimidine-2-carboxamide hydrochloride obtained in Reference Example 50, the title compound was obtained as a white powder (151 mg, 53%).

melting point: 251-253° C.

Example 36

6-cyano-4-oxo-N-[(3-{[(1H-1,2,4-triazol-3-ylcarbonyl)amino]methyl}phenyl)methyl]-3,4-dihydroquinazoline-2-carboxamide

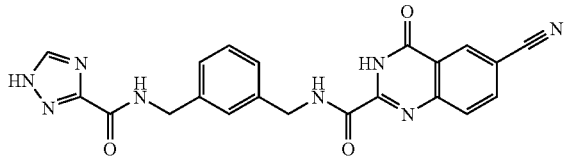

Step 1

By a method similar to that in Example 34 and using, instead of 1H-1,2,4-triazol-3-ylacetic acid, 1-(triphenylmethyl)-1H-1,2,4-triazole-3-carboxylic acid obtained in Reference Example 35, 6-cyano-4-oxo-N-({3-[({[1-(triphenylmethyl)-1H-1,2,4-triazol-3-yl]carbonyl}amino)methyl]phenyl}methyl)-3,4-dihydroquinazoline-2-carboxamide was obtained as a white powder (450 mg, 67%).

$^1$H-NMR (300 MHz, DMSO-$d_6$) δ: 4.40 (2H, d, J=6.2 Hz), 4.46 (2H, d, J=6.4 Hz), 7.02-7.12 (6H, m), 7.18-7.32 (4H, m), 7.36-7.44 (9H, m), 7.896 (1H, d, J=8.55 Hz), 8.21 (1H, d, J=8.5 Hz), 8.27 (1H, s) 8.53 (1H, s), 9.11 (1H, t, J=6.3 Hz), 9.64 (1H, t, J=6.1 Hz), 12.76 (1H, s).

Step 2

A solution of 6-cyano-4-oxo-N-({3-[({[1-(triphenylmethyl)-1H-1,2,4-triazol-3-yl]carbonyl}amino)methyl]phenyl}methyl)-3,4-dihydroquinazoline-2-carboxamide (420 mg, 0.626 mmol), triethylsilane (0.105 mL, 0.657 mmol) and trifluoroacetic acid (3 mL) in dichloromethane (10 mL) was stirred at room temperature for 30 min. The reaction mixture was concentrated under reduced pressure, and the residue was crystallized from IPE. The obtained powder was suspended in ethanol, and the suspension was stirred under heating for 2 hr to give the title compound as a white powder (113 mg, 42%).

melting point: 218-219° C.

Example 37

5-methyl-4-oxo-N-[(3-{[(1H-1,2,4-triazol-3-ylcarbonyl)amino]methyl}phenyl)methyl]-3,4-dihydrothieno[2,3-d]pyrimidine-2-carboxamide

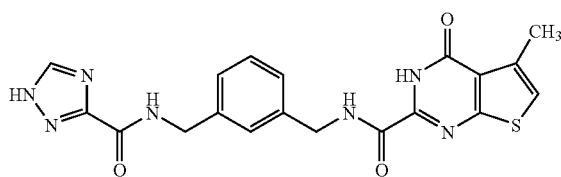

Step 1

By a method similar to that in Example 34, and using, instead of N-{[3-(aminomethyl)phenyl]methyl}-6-cyano-4-oxo-3,4-dihydroquinazoline-2-carboxamide hydrochloride, N-{[3-(aminomethyl)phenyl]methyl}-5-methyl-4-oxo-3,4-dihydrothieno[2,3-d]pyrimidine-2-carboxamide hydrochloride obtained in Reference Example 50 and using, instead of 1H-1,2,4-triazol-3-ylacetic acid, 1-(triphenylmethyl)-1H-1,2,4-triazole-3-carboxylic acid obtained in Reference Example 35, 5-methyl-4-oxo-N-({3-[({[1-(triphenylmethyl)-1H-1,2,4-triazol-3-yl]carbonyl}amino)methyl]phenyl}methyl)-3,4-dihydrothieno[2,3-d]pyrimidine-2-carboxamide was obtained as a white powder (597 mg, 90%).

$^1$H-NMR (300 MHz, DMSO-$d_6$) δ: 4.30-4.50 (4H, m), 7.03-7.12 (6H, m), 7.16-7.31 (5H, m), 7.35-7.45 (9H, m), 8.28 (1H, s), 9.11 (1H, t, J=6.2 Hz), 9.60 (1H, t, J=6.2 Hz), 12.26 (1H, s).

Step 2

A solution of 5-methyl-4-oxo-N-({3-[({[1-(triphenylmethyl)-1H-1,2,4-triazol-3-yl]carbonyl}amino)methyl]phenyl}methyl)-3,4-dihydrothieno[2,3-d]pyrimidine-2-carboxamide (565.0 mg, 0.849 mmol), triethylsilane (0.142 mL, 0.891 mmol) and trifluoroacetic acid (3 mL) in dichloromethane (10 mL) was stirred at room temperature for 30 min. The reaction mixture was concentrated under reduced pressure, and the residue was crystallized from IPE. The obtained powder was suspended in ethanol, and the suspension was stirred under heating for 2 hr to give the title compound as a white powder (359 mg, 99%).

melting point: 290-291° C.

Example 38

6-cyano-4-oxo-N-({3-[(1H-1,2,4-triazol-3-ylcarbonyl)amino]phenyl}methyl)-3,4-dihydroquinazoline-2-carboxamide

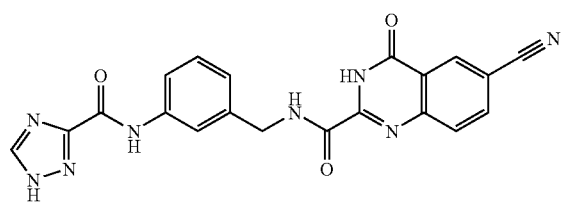

Step 1

By a method similar to that in Step 1 of Example 32 and using, instead of 3-[1-(triphenylmethyl)-1H-1,2,4-triazol-3-yl]propanoic acid, 1-(triphenylmethyl)-1H-1,2,4-triazole-3-carboxylic acid obtained in Reference Example 35, 6-cyano-4-oxo-N-{[3-({[1-(triphenylmethyl)-1H-1,2,4-triazol-3-yl]carbonyl}amino)phenyl]methyl}-3,4-dihydroquinazoline-2-carboxamide was obtained as a white powder (627 mg, 95%).

Step 2

By a method similar to that in Step 2 of Example 32 and using, instead of 6-cyano-4-oxo-N-{[3-({3-[1-(triphenylmethyl)-1H-1,2,4-triazol-3-yl]propanoyl}amino)phenyl]methyl}-3,4-dihydroquinazoline-2-carboxamide, 6-cyano-4-oxo-N-{[3-({[1-(triphenylmethyl)-1H-1,2,4-triazol-3-yl]carbonyl}amino)phenyl]methyl}-3,4-dihydroquinazoline-2-carboxamide, the title compound was obtained as a white powder (355 mg, 95%).

melting point: 321-322° C.

Example 39

5-methyl-4-oxo-N-({3-[(1H-1,2,4-triazol-3-ylcarbonyl)amino]phenyl}methyl)-3,4-dihydrothieno[2,3-d]pyrimidine-2-carboxamide

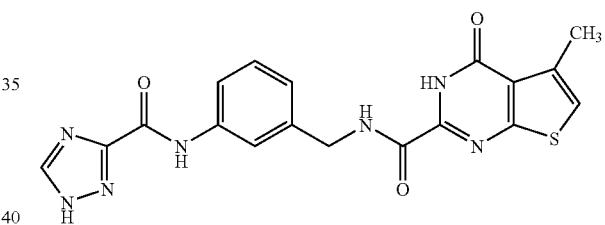

Step 1

By a method similar to that in Step 1 of Example 32, and using, instead of N-[(3-aminophenyl)methyl]-6-cyano-4-oxo-3,4-dihydroquinazoline-2-carboxamide, N-[(3-aminophenyl)methyl]-5-methyl-4-oxo-3,4-dihydrothieno[2,3-d]pyrimidine-2-carboxamide obtained in Reference Example 48 and using, instead of 3-[1-(triphenylmethyl)-1H-1,2,4-triazol-3-yl]propanoic acid, 1-(triphenylmethyl)-1H-1,2,4-triazole-3-carboxylic acid obtained in Reference Example 35, 5-methyl-4-oxo-N-{[3-({[1-(triphenylmethyl)-1H-1,2,4-triazol-3-yl]carbonyl}amino)phenyl]methyl}-3,4-dihydrothieno[2,3-d]pyrimidine-2-carboxamide was obtained as a white powder (575 mg, 88%).

Step 2

By a method similar to that in Step 2 of Example 32 and using, instead of 6-cyano-4-oxo-N-{[3-({3-[1-(triphenylmethyl)-1H-1,2,4-triazol-3-yl]propanoyl}amino)phenyl]methyl}-3,4-dihydroquinazoline-2-carboxamide, 5-methyl-4-oxo-N-{[3-({[1-(triphenylmethyl)-1H-1,2,4-triazol-3-yl]carbonyl}amino)phenyl]methyl}-3,4-dihydrothieno[2,3-d]pyrimidine-2-carboxamide, the title compound was obtained as a white powder (339 mg, 99%).

melting point: 301-302° C.

Example 40

4-oxo-N-[(3-{[4-oxo-4-(1H-1,2,4-triazol-3-ylamino)butyl]oxy}phenyl)methyl]-3,4-dihydroquinazoline-2-carboxamide

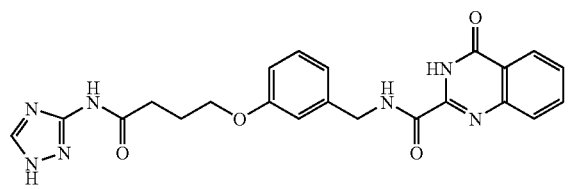

A solution of 4-{[3-({[(4-oxo-3,4-dihydroquinazolin-2-yl)carbonyl]amino}methyl)phenyl]oxy}butanoic acid obtained in Reference Example 44 (100 mg, 0.262 mmol), 1H-1,2,4-triazol-3-amine (26.4 mg, 0.314 mmol), 1-[3-(dimethylamino)propyl]-3-ethyl-carbodiimide hydrochloride (60.3 mg, 0.314 mmol) and 1-hydroxybenzotriazole (42.5 mg, 0.314 mmol) in DMF (5 mL) was stirred at 40° C. for 5 hr. Water was added to the reaction mixture, and the resulting solid was collected by filtration, washed with water and IPE, and dried to give the title compound as a white powder (95.0 mg, 73%).

melting point: 189-190° C.

Example 41 ethyl 4-[({[4-oxo-2-({[(2-{[3-(1H-1,2,4-triazol-3-yl)propyl]oxy}pyridin-4-yl)methyl]amino}carbonyl)-3,4-dihydrothieno[2,3-d]pyrimidin-5-yl]methyl}oxy)methyl]benzoate

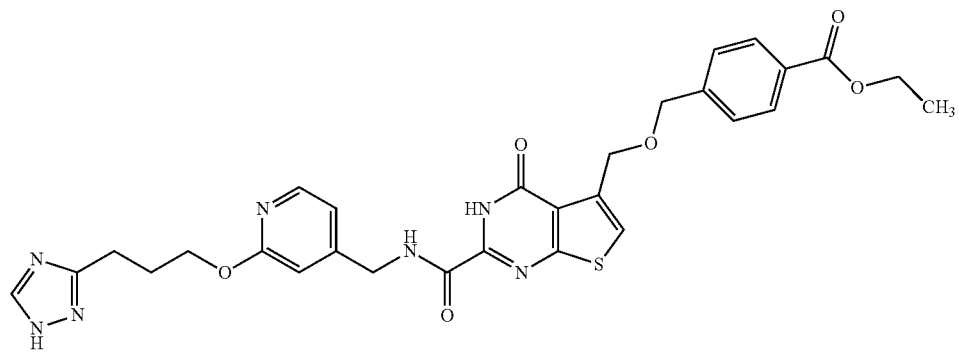

Step 1

By a method similar to that in Example 22 and using, instead of ethyl 4-oxo-3,4-dihydro-2-quinazolinecarboxylate, ethyl 5-{[({4-[(ethyloxy)carbonyl]phenyl}methyl)oxy]methyl}-4-oxo-3,4-dihydrothieno[2,3-d]pyrimidine-2-carboxylate obtained in Reference Example 62, ethyl 4-{[({4-oxo-2-[({[2-({3-[1-(triphenylmethyl)-1H-1,2,4-triazol-3-yl]propyl}oxy)pyridin-4-yl]methyl}amino)carbonyl]-3,4-dihydrothieno[2,3-d]pyrimidin-5-yl}methyl)oxy]methyl}benzoate was obtained as a white powder (701 mg, 86%).

$^1$H-NMR (300 MHz, DMSO-$d_6$) δ: 1.32 (3H, t, J=7.1 Hz), 2.05 (2H, tt, J=6.9, 6.9 Hz), 2.76 (2H, t, J=7.2 Hz), 4.22 (2H, t, J=6.4 Hz), 4.31 (2H, q, J=7.1 Hz), 4.41 (2H, d, J=6.0 Hz), 4.75 (2H, s), 4.90 (2H, s), 6.69 (1H, s), 6.92 (1H, dd, J=5.3, 1.3 Hz), 7.00-7.07 (6H, m), 7.32-7.38 (9H, m), 7.54 (2H, d, J=8.3 Hz), 7.63 (1H, s), 7.93-7.98 (3H, m), 8.07 (1H, dr J=5.5 Hz), 9.69 (1H, t, J=6.2 Hz), 12.43 (1H, s).

Step 2

By a method similar to that in Step 2 of Example 32 and using, instead of 6-cyano-4-oxo-N-{[3-({3-[1-(triphenylmethyl)-1H-1,2,4-triazol-3-yl]propanoyl}amino)phenyl]methyl}-3,4-dihydroquinazoline-2-carboxamide, ethyl 4-{[({4-oxo-2-[({[2-({3-[1-(triphenylmethyl)-1H-1,2,4-triazol-3-yl]propyl}oxy)pyridin-4-yl]methyl}amino)carbonyl]-3,4-dihydrothieno[2,3-d]pyrimidin-5-yl}methyl)oxy]methyl}benzoate, the title compound was obtained as a white powder (20.0 mg, 93%).

melting point: 235-238° C.

Example 42

4-[({[4-oxo-2-({[(2-{[3-(1H-1,2,4-triazol-3-yl)propyl]oxy}pyridin-4-yl)methyl]amino}carbonyl)-3,4-dihydrothieno[2,3-d]pyrimidin-5-yl]-methyl}oxy)methyl]benzoic acid

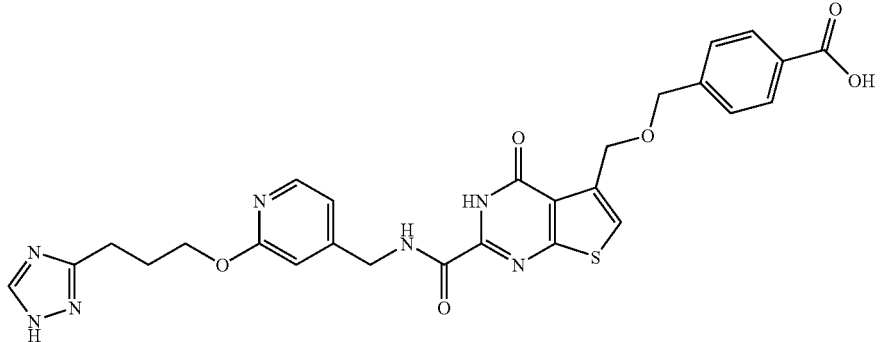

A mixture of ethyl 4-[({[4-oxo-2-({[(2-{[3-(1H-1,2,4-triazol-3-yl)propyl]oxy}pyridin-4-yl)methyl]amino}carbonyl)-3,4-dihydrothieno[2,3-d]pyrimidin-5-yl]methyl}oxy)methyl]benzoate obtained in Example 41 (309 mg, 0.512 mmol), 4N aqueous sodium hydroxide solution (0.64 mL, 2.6 mmol), THF (6 mL), methanol (6 mL) and water (6 mL) was stirred at 100° C. for 2 hr. The reaction mixture was concentrated under reduced pressure, and 1N hydrochloric acid and methanol were added to the residue. The resulting crystals were recrystallized from ethyl acetate to give the title compound as a white powder (221 mg, 75%).

melting point: 206-209° C.

Example 43

N-[(3-{[4-(hydroxyamino)-4-oxobutyl]oxy}phenyl)methyl]-4-oxo-3,4-dihydroquinazoline-2-carboxamide

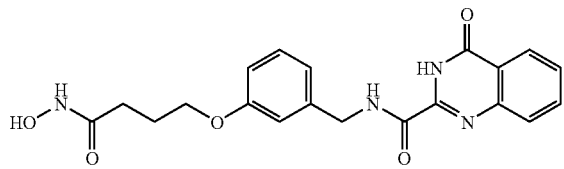

To a solution of 4-{3-({[(4-oxo-3,4-dihydroquinazolin-2-yl)carbonyl]amino}methyl)phenyl]oxy}butanoic acid obtained in Reference Example 44 (90.0 mg, 0.236 mmol) in THF (2 mL) were added DMF (0.02 mL) and oxalyl chloride (59.9 mg, 0.472 mmol) at 0° C., and the mixture was stirred at room temperature for 2 hr. To the reaction mixture was added a mixed solution of 50% aqueous hydroxylamine solution (0.5 mL), tert-butanol (0.5 mL) and THF (0.5 mL) at 0° C., and the mixture was stirred for 15 min. The mixture was concentrated under reduced pressure, and the residue was purified by preparative HPLC (GILSON 215LIQUD HANDLER, 322PUMP, UV/VIS-156, SHISEIDO CAPCELL PACK C-18 UG120 S-5 (20 mmφ×50 mm), mobile phase: distilled water (containing 0.1% trifluoroacetic acid)/acetonitrile (containing 0.1% trifluoroacetic acid), gradient: distilled water/acetonitrile=90/100/100, time: 10 min, flow rate: 25 mL/min, detection wavelength: 220 nm) to give a yellow powder. The obtained powder was recrystallized from ethyl acetate-hexane to give the title compound as a pale-yellow powder (8.0 mg, 9%).

melting point: 164-168° C.

Example 44

5,6-difluoro-4-oxo-N-[(3-{[2-(1H-1,2,4-triazol-3-yloxy)ethyl]oxy}phenyl)methyl]-3,4-dihydroquinazoline-2-carboxamide Step 1

A suspension of 1-{3-[(2-{[1-(triphenylmethyl)-1H-1,2,4-triazol-3-yl]oxy]ethyl)oxy}phenyl}methanamine obtained in Reference Example 32 (300 mg, 1.18 mmol) and ethyl 5,6-difluoro-4-oxo-3,4-dihydroquinazoline-2-carboxylate obtained in Reference Example 57 (562 mg, 1.18 mmol) in ethanol (10 mL) was stirred at 80° C. for 12 hr. The insoluble material was filtered off hot, and the filtrate was allowed to cool to room temperature. The precipitated solid was collected by filtration using glass filter, and the obtained solid was washed with diethyl ether to give 5,6-difluoro-4-oxo-N-({3-[(2-{[1-(triphenylmethyl)-1H-1,2,4-triazol-3-yl]oxy}ethyl)oxy]phenyl}methyl)-3,4-dihydroquinazoline-2-carboxamide as a pale-yellow powder (330 mg, 41%).

Step 2

To a solution of 5,6-difluoro-4-oxo-N-({3-[(2-{[1-(triphenylmethyl)-1H-1,2,4-triazol-3-yl]oxy}ethyl)oxy]phenyl}methyl)-3,4-dihydroquinazoline-2-carboxamide obtained in Step 1 (70 mg, 0.102 mmol) in dichloromethane (1 mL) were added trifluoroacetic acid (0.30 mL) and triethylsilane (0.020 mL, 0.123 mmol) at room temperature, and the mixture was stirred for 1 hr. The reaction mixture was concentrated under reduced pressure, and the residue was crystallized from diethyl ether to give the title compound as a pale-yellow powder (38 mg, 84%).

melting point: 205-207° C.

Example 45

6-fluoro-4-oxo-N-[(3-{[2-(1H-1,2,4-triazol-3-yloxy)ethyl]oxy}phenyl)methyl]-5-{[(3-{[2-(1H-1,2,4-triazol-3-yloxy)ethyl]oxy}phenyl)methyl]amino}-3,4-dihydroquinazoline-2-carboxamide

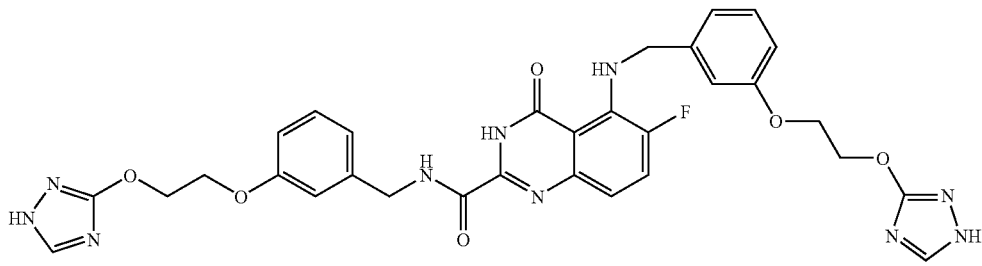

A suspension of 1-{3-[(2-{[1-(triphenylmethyl)-1H-1,2,4-triazol-3-yl]oxy}ethyl)oxy]phenyl}methanamine obtained in Reference Example 32 (300 mg, 1.18 mmol) and ethyl 5,6-difluoro-4-oxo-3,4-dihydroquinazoline-2-carboxylate obtained in Reference Example 57 (562 mg, 1.18 mmol) in ethanol (10 mL) was stirred at 80° C. for 12 hr. The precipitated solid was collected by filtering hot, and the obtained solid was dissolved in dichloromethane (2 mL). Trifluoroacetic acid (0.52 mL) and triethylsilane (0.042 mL, 0.263 mmol) were added to this solution at room temperature, and the mixture was stirred for 1 hr. The reaction mixture was concentrated under reduced pressure, and the residue was purified by preparative HPLC (GILSON 215LIQUD HANDLER, 322PUMP, UV/VIS-156, SHISEIDO CAPCELL PACK C-18 UG120 S-5 (20 mmφ×50 mm), mobile phase: distilled water (containing 0.1% trifluoroacetic acid)/acetonitrile (containing 0.1% trifluoroacetic acid), gradient: distilled water/acetonitrile=90/10→0/100, time: 10 min, flow rate: 25 mL/min, detection wavelength: 220 nm), and crystallized from ethanol-diethyl ether to give the title compound as a yellow powder (36 mg, 5% in two steps).

melting point: 195-197° C.

Example 46

4-(2-{[6-fluoro-4-oxo-2-({[(3-{[2-(1H-1,2,4-triazol-3-yloxy)ethyl]oxy}phenyl)methyl]amino}carbonyl)-3,4-dihydroquinazolin-5-yl]oxy}ethyl)benzoic acid A solution of 5,6-difluoro-4-oxo-N-({3-[(2-{[1-(triphenylmethyl)-1H-1,2,4-triazol-3-yl]oxy}ethyl)oxy]phenyl}methyl)-3,4-dihydroquinazoline-2-carboxamide obtained in Step 1 of Example 44 (150 mg, 0.219 mmol) and 4-(2-hydroxyethyl)benzoic acid (40 mg, 0.241 mmol) in DMA (4 mL) was added dropwise to a suspension of 60% sodium hydride (oil dispersion, 0.031 mg, 0.767 mmol) in DMA (2 mL) at room temperature, and the mixture was stirred at room temperature for 20 min, and then stirred at 80° C. under heating for 3 hr. After the reaction mixture was allowed to cool to room temperature, water (50 mL) was added thereto, and the mixture was washed with ethyl acetate (50 mL×2) The aqueous layer was neutralized with 0.1N hydrochloric acid, and the objective compound was extracted with ethyl acetate (80 mL). The organic layer was washed with saturated brine, dried over sodium sulfate, and concentrated under reduced pressure. To a solution of the residue in dichloromethane (2 mL) were added trifluoroacetic acid (0.47 mL) and triethylsilane (0.037 mL, 0.235 mmol) at room temperature, and the mixture was stirred for 1 hr. The reaction mixture was concentrated under reduced pressure, and the residue was purified by preparative HPLC (GILSON 215LIQUD HANDLER, 322PUMP, UV/VIS-156, SHISEIDO CAPCELL PACK C-18 UG120 S-5 (20 mm×50 mm), mobile phase: distilled water (containing 0.1% trifluoroacetic acid)/acetonitrile (containing 0.1% trifluoroacetic acid), gradient: distilled water/acetonitrile=90/100/100, time: 10 min, flow rate: 25 mL/min, detection wavelength: 220 nm), and crystallized from ethanol-diethyl ether to give the title compound as a yellow powder (36 mg, 28% in two steps).

melting point: 122-124° C.

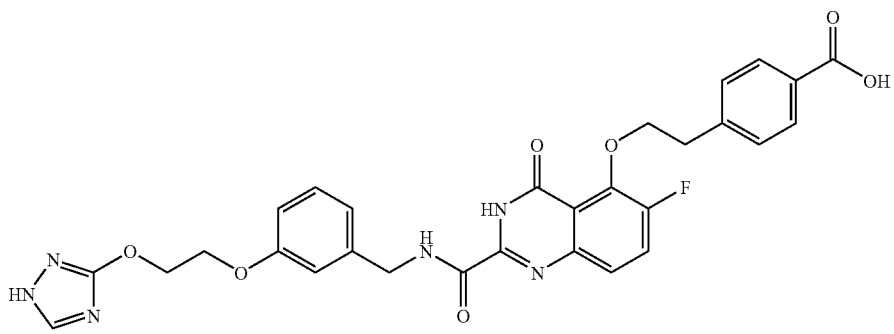

Example 47 methyl 4-({2-[7-oxo-5-({[(3-{[2-(1H-1,2,4-triazol-3-yloxy)ethyl]oxy}phenyl)methyl]amino}carbonyl}-6,7-dihydro-1H-pyrazolo[4,3-d]pyrimidin-1-yl]ethyl}oxy)benzoate

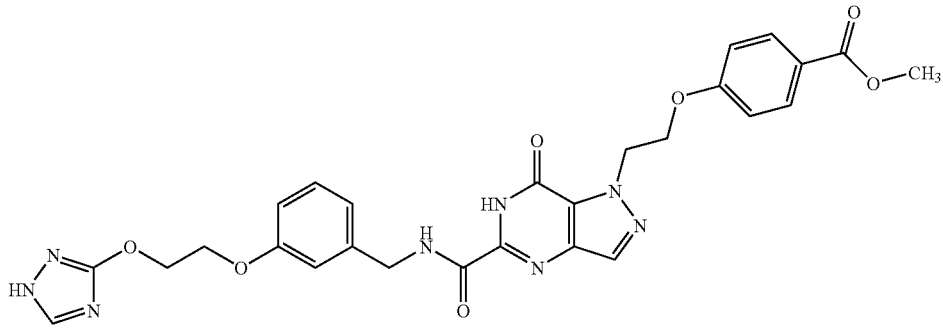

Step 1

By a method similar to that in Step 1 of Example 44 and using 1-{3-[(2-{[1-(triphenylmethyl)-1H-1,2,4-triazol-3-yl]oxy}ethyl)oxy]phenyl}methanamine obtained in Reference Example 32 and ethyl 1-[2-({4-[(methyloxy)carbonyl]phenyl}oxy)ethyl]-7-oxo-6,7-dihydro-1H-pyrazolo[4,3-d]pyrimidine-5-carboxylate obtained in Reference Example 63, methyl 4-([2-(7-oxo-5-([({3-[(2-{[1 (triphenylmethyl)-1H-1,2,4-triazol-3-yl]oxy}ethyl)oxy]phenylmethyl)amino]carbonyl)-6,7-dihydro 1-pyrazolo[4,3-d]pyrimidin-1-yl) ethyl]oxy}benzoate was obtained as a white powder (316 mg, 75%).

Step 2

By a method similar to that in Step 2 of Example 44 and using methyl 4-{[2-(7-oxo-5-{[({3-[(2-{[1-(triphenylmethyl)-1H-1,2,4-triazol-3-yl]oxy}ethyl)oxy]phenyl}methyl)amino]carbonyl}-6,7-dihydro-1H-pyrazolo[4,3-d]pyrimidin-1-yl)ethyl]oxy}benzoate obtained in Step 1, the title compound was obtained as a white powder (194 mg, 98%).

melting point: 180-182° C.

Example 48

4-({2-[7-oxo-5-({[(3-{[2-(1H-1,2,4-triazol-3-yloxy)ethyl]oxy}phenyl)methyl]amino}carbonyl)-6,7-dihydro-1H-pyrazolo[4,3-d]pyrimidin-1-yl]ethyl}oxy)benzoic acid

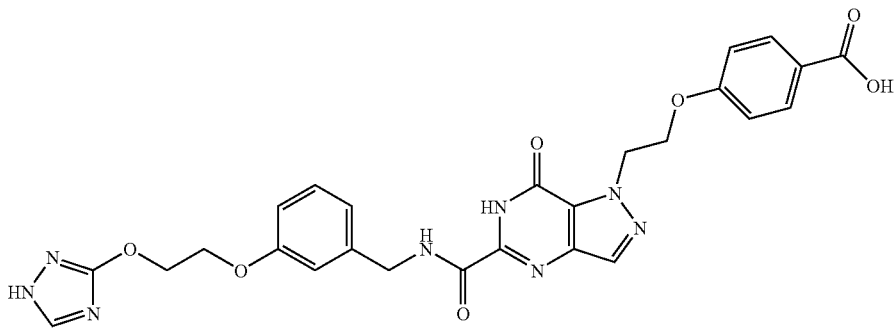

A mixture of methyl 4-({2-[7-oxo-5-({[(3-{[2-(1H-1,2,4-triazol-3-yloxy)ethyl]oxy}phenyl)methyl]amino}carbonyl)-6,7-dihydro-1H-pyrazolo[4,3-d]pyrimidin-1-yl]ethyl}oxy)benzoate obtained in Example 47 (164 mg, 0.285 mmol), 4N aqueous sodium hydroxide solution (0.250 mL), THF (2 mL), methanol (2 mL) and water (2 mL) was stirred at 90° C. for 2 hr. The solvent was evaporated under reduced pressure, and the residue was diluted with water (20 mL), and acidified with 1N hydrochloric acid (1.5 mL). The precipitated solid was collected by filtration, and washed with water (4 mL×2) and methanol (4 mL). The obtained solid was recrystallized from methanol to give the title compound as a white powder (120 mg, 75%).

melting point: 176-178° C.

Example 49 ethyl 4-({[4-oxo-2-({3-[2-(1H-1,2,4-triazol-3-yloxy)
ethoxy]benzyl}carbamoyl)-3,4-dihydrothieno[2,3-d]
pyrimidin-5-yl]methoxy}methyl)benzoate

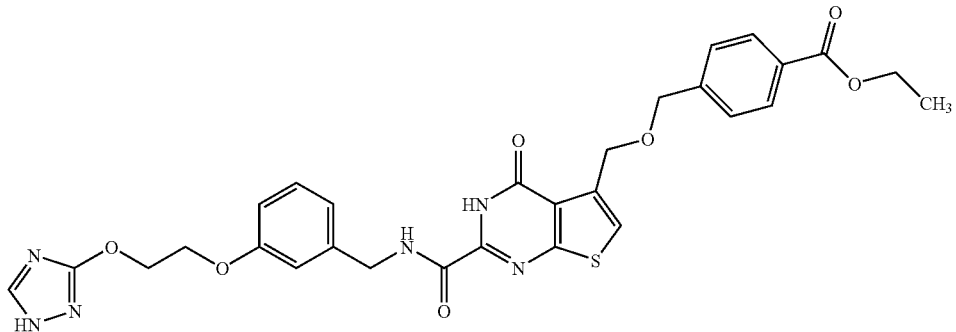

By a method similar to that in Example 22, and using, instead of ethyl 4-oxo-3,4-dihydro-2-quinazolinecarboxylate, ethyl 5-{[({4-[(ethyloxy)carbonyl]phenyl}methyl)oxy]methyl}-4-oxo-3,4-dihydrothieno[2,3-d]pyrimidine-2-carboxylate obtained in Reference Example 62 and using, instead of 1-[2-({3-[1-(triphenylmethyl)-1H-1,2,4-triazol-3-yl]propyl}oxy)pyridin-4-yl]methaneamine, 1-{3-[(2-{[1-(triphenylmethyl)-1H-1,2,4-triazol-3-yl]oxy}ethyl)oxy]phenyl}methanamine obtained in Reference Example 32, the title compound was obtained as a white powder (627.0 mg, 94%).

melting point: 230-231° C.

Example 50

4-({[4-oxo-2-({3-[2-(1H-1,2,4-triazol-3-yloxy)
ethoxy]benzyl}carbamoyl)-3,4-dihydrothieno[2,3-d]
pyrimidin-5-yl]methoxy}methyl)benzoic acid

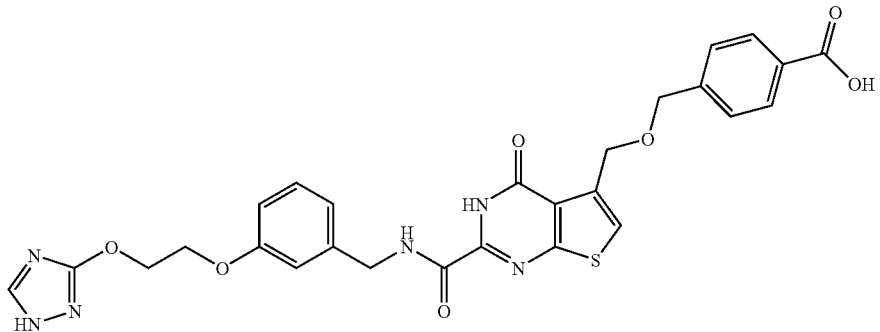

By a method similar to that in Example 42 and using, instead of ethyl 4-[({[4-oxo-2-({[(2-{[3-(1H-1,2,4-triazol-3-yl)propyl]oxy}pyridin-4-yl)methyl]amino}carbonyl)-3,4-dihydrothieno[2,3-d]pyrimidin-5-yl]methyl}oxy)methyl]benzoate, ethyl 4-({[4-oxo-2-({3-[2-(1H-1,2,4-triazol-3-yloxy)ethoxy]benzyl}carbamoyl)-3,4-dihydrothieno[2,3-d]pyrimidin-5-yl]methoxy}methyl)benzoate obtained in Example 49, the title compound was obtained as a white powder (419.2 mg, 80%).

melting point: 149-152° C.

Example 51

4-oxo-5-phenyl-N-{3-[2-(1H-1,2,4-triazol-3-yloxy)ethoxy]-3-benzyl}-3,4-dihydrothieno[2,3-d]pyrimidine-2-carboxamide

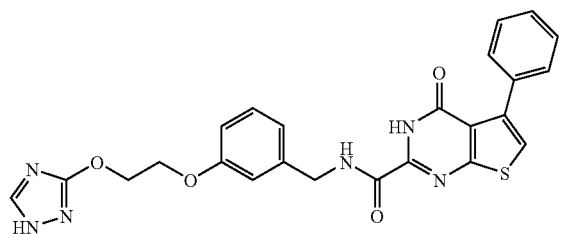

By a method similar to that in Example 22, and using, instead of ethyl 4-oxo-3,4-dihydro-2-quinazolinecarboxylate, ethyl 4-oxo-5-phenyl-3,4-dihydrothieno[2,3-d]pyrimidine-2-carboxylate obtained in Reference Example 64 and using, instead of 1-[2-({3-[1-(triphenylmethyl)-1H-1,2,4-triazol-3-yl]propyl}oxy)pyridin-4-yl]methaneamine, 1-{3-[(2-{[1-(triphenylmethyl)-1H-1,2,4-triazol-3-yl]oxy}ethyl)oxy]phenyl}methanamine obtained in Reference Example 32, the title compound was obtained as a white powder (208.4 mg, 72%).

melting point: 183-185° C.

Example 52

4-oxo-5-(3-thienyl)-N-{3-[2-(1H-1,2,4-triazol-3-yloxy)ethoxy]benzyl}-3,4-dihydrothieno[2,3-d]pyrimidine-2-carboxamide

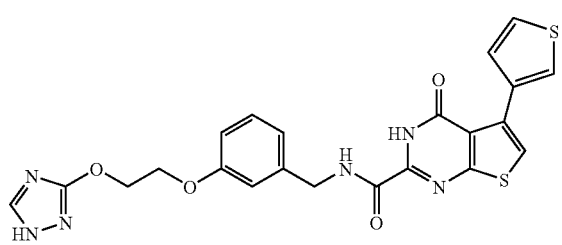

By a method similar to that in Example 22, and using, instead of ethyl 4-oxo-3,4-dihydro-2-quinazolinecarboxylate, ethyl 4-oxo-5-(3-thienyl)-3,4-dihydrothieno[2,3-d]pyrimidine-2-carboxylate obtained in Reference Example 65 and using, instead of 1-[2-({3-[1-(triphenylmethyl)-1H-1,2,4-triazol-3-yl]propyl}oxy)pyridin-4-yl]methaneamine, 1-{3-[(2-{[1-(triphenylmethyl)-1H-1,2,4-triazol-3-yl]oxy}ethyl)oxy]phenyl}methanamine obtained in Reference Example 32, the title compound was obtained as a white powder (48.0 mg, 34%).

melting point: 186-189° C.

Example 53

4-oxo-5-pyridin-4-yl-N-{3-[2-(1H-1,2,4-triazol-3-yloxy)ethoxy]benzyl}-3,4-dihydrothieno[2,3-d]pyrimidine-2-carboxamide

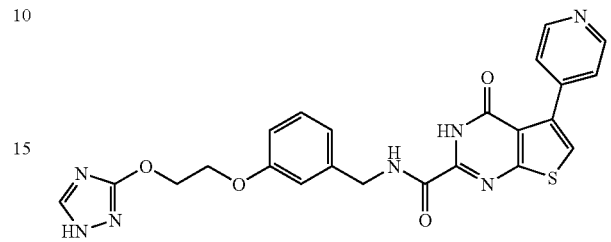

By a method similar to that in Example 22, and using, instead of ethyl 4-oxo-3,4-dihydro-2-quinazolinecarboxylate, ethyl 4-oxo-5-pyridin-4-yl-3,4-dihydrothieno[2,3-d]pyrimidine-2-carboxylate obtained in Reference Example 66 and using, instead of 1-[2-({3-[1-(triphenylmethyl)-1H-1,2,4-triazol-3-yl]propyl}oxy)pyridin-4-yl]methaneamine, 1-{3-[(2-{[1-(triphenylmethyl)-1H-1,2,4-triazol-3-yl]oxy}ethyl)oxy]phenyl}methanamine obtained in Reference Example 32, the title compound was obtained as a white powder (142.0 mg, 59%).

melting point: 233-236° C.

Example 54

4-oxo-5-pyridin-3-yl-N-{3-[2-(1H-1,2,4-triazol-3-yloxy)ethoxy]benzyl}-3,4-dihydrothieno[2,3-d]pyrimidine-2-carboxamide

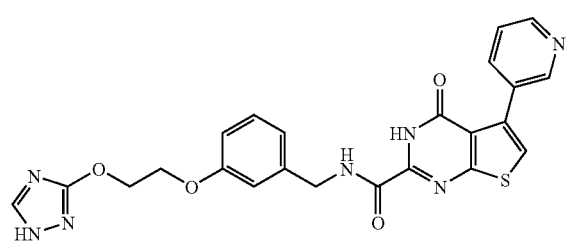

By a method similar to that in Example 22, and using, instead of ethyl 4-oxo-3,4-dihydro-2-quinazolinecarboxylate, ethyl 4-oxo-5-pyridin-3-yl-3,4-dihydrothieno[2,3-d]pyrimidine-2-carboxylate obtained in Reference Example 67 and using, instead of 1-[2-({3-[1-(triphenylmethyl)-1H-1,2,4-triazol-3-yl]propyl}oxy)pyridin-4-yl]methaneamine, 1-{3-[(2-{[1-(triphenylmethyl)-1H-1,2,4-triazol-3-yl]oxy}ethyl)oxy]phenyl}methanamine obtained in Reference Example 32, the title compound was obtained as a white powder (41.1 mg, 17%).

melting point: 191-195° C.

Example 55

5-isopropyl-4-oxo-N-{3-[2-(1H-1,2,4-triazol-3-yloxy)ethoxy]benzyl}-3,4-dihydrothieno[2,3-d]pyrimidine-2-carboxamide

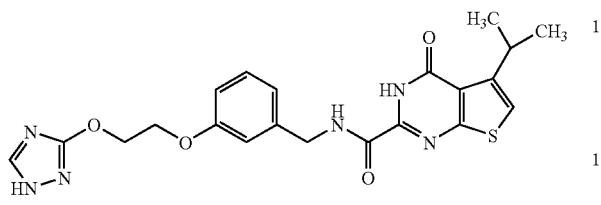

By a method similar to that in Example 22, and using, instead of ethyl 4-oxo-3,4-dihydro-2-quinazolinecarboxylate, ethyl 5-isopropyl-4-oxo-3,4-dihydrothieno[2,3-d]pyrimidine-2-carboxylate obtained in Reference Example 68 and using, instead of 1-[2-({3-[1-(triphenylmethyl)-1H-1,2,4-triazol-3-yl]propyl}oxy)pyridin-4-yl]methaneamine, 1-{3-[(2-{[1-(triphenylmethyl)-1H-1,2,4-triazol-3-yl]oxy}ethyl)oxy]phenyl}methanamine obtained in Reference Example 32, the title compound was obtained as a white powder (161.3 mg, 65%).

melting point: 220-221° C.

Example 56

5-(2-fluorophenyl)-4-oxo-N-{3-[2-(1H-1,2,4-triazol-3-yloxy)ethoxy]benzyl}-3,4-dihydrothieno[2,3-d]pyrimidine-2-carboxamide

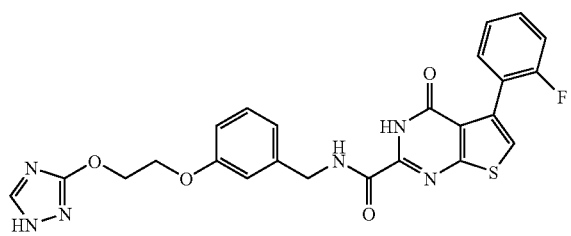

By a method similar to that in Example 22r and using, instead of ethyl 4-oxo-3,4-dihydro-2-quinazolinecarboxylate, ethyl 5-(2-fluorophenyl)-4-oxo-3,4-dihydrothieno[2,3-d]pyrimidine-2-carboxylate obtained in Reference Example 69 and using, instead of 1-[2-({3-[1-(triphenylmethyl)-1H-1,2,4-triazol-3-yl]propyl}oxy)pyridin-4-yl]methaneamine, 1-{3-[(2-{[1-(triphenylmethyl)-1H-1,2,4-triazol-3-yl]oxy}ethyl)oxy]phenyl}methanamine obtained in Reference Example 32, the title compound was obtained as a white powder (59.0 mg, 46%).

melting point: 178-179° C.

Example 57

5-(2-chlorophenyl)-4-oxo-N-{3-[2-(1H-1,2,4-triazol-3-yloxy)ethoxy]benzyl}-3,4-dihydrothieno[2,3-d]pyrimidine-2-carboxamide

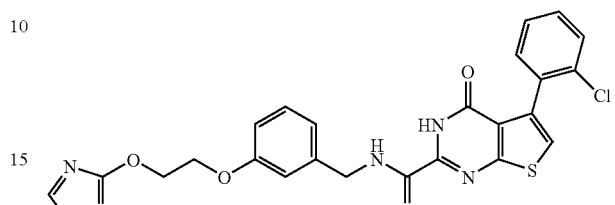

By a method similar to that in Example 22, and using, instead of ethyl 4-oxo-3,4-dihydro-2-quinazolinecarboxylate, ethyl 5-(2-chlorophenyl)-4-oxo-3,4-dihydrothieno[2,3-d]pyrimidine-2-carboxylate obtained in Reference Example 70 and using, instead of 1-[2-({3-[1-(triphenylmethyl)-1H-1,2,4-triazol-3-yl]propyl}oxy)pyridin-4-yl]methaneamine, 1-{3-[(2-{[1-(triphenylmethyl)-1H-1,2,4-triazol-3-yl]oxy}ethyl)oxy]phenyl}methanamine obtained in Reference Example 32, the title compound was obtained as a white powder (68.2 mg, 44%).

melting point: 169-171° C.

Example 58

5-(2-methoxyphenyl)-4-oxo-N-{3-[2-(1H-1,2,4-triazol-3-yloxy)ethoxy]benzyl}-3,4-dihydrothieno[2,3-d]pyrimidine-2-carboxamide

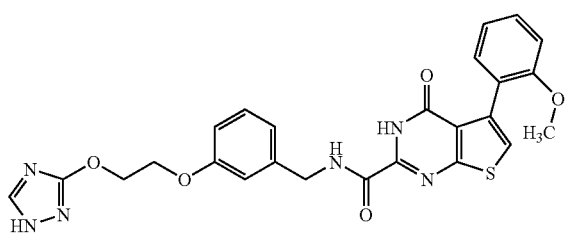

By a method similar to that in Example 22, and using, instead of ethyl 4-oxo-3,4-dihydro-2-quinazolinecarboxylate, ethyl 5-(2-methoxyphenyl)-4-oxo-3,4-dihydrothieno[2,3-d]pyrimidine-2-carboxylate obtained in Reference Example 71 and using, instead of 1-[2-({3-[1-(triphenylmethyl)-1H-1,2,4-triazol-3-yl]propyl}oxy)pyridin-4-yl]methaneamine, 1-{3-[(2-{[1-(triphenylmethyl)-1H-1,2,4-triazol-3-yl]oxy}ethyl)oxy]phenyl}methanamine obtained in Reference Example 32, the title compound was obtained as a white powder (114.4 mg, 49%).

melting point: 211-213° C.

Example 59

5-(3-fluorophenyl)-4-oxo-N-{3-[2-(1H-1,2,4-triazol-3-yloxy)ethoxy]benzyl}-3,4-dihydrothieno[2,3-d]pyrimidine-2-carboxamide

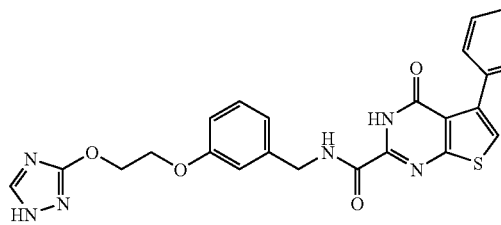

By a method similar to that in Example 22, and using, instead of ethyl 4-oxo-3,4-dihydro-2-quinazolinecarboxylate, ethyl 5-(3-fluorophenyl)-4-oxo-3,4-dihydrothieno[2,3-d]pyrimidine-2-carboxylate obtained in Reference Example 72 and using, instead of 1-[2-({3-[1-(triphenylmethyl)-1H-1,2,4-triazol-3-yl]propyl}oxy)pyridin-4-yl]methaneamine, 1-{3-[(2-{[1-(triphenylmethyl)-1H-1,2,4-triazol-3-yl]oxy}ethyl)oxy]phenyl}methanamine obtained in Reference Example 32, the title compound was obtained as a white powder (131.0 mg, 55%).

melting point: 158-161° C.

Example 60

5-(3-chlorophenyl)-4-oxo-N-{3-[2-(1H-1,2,4-triazol-3-yloxy)ethoxy]benzyl}-3,4-dihydrothieno[2,3-d]pyrimidine-2-carboxamide

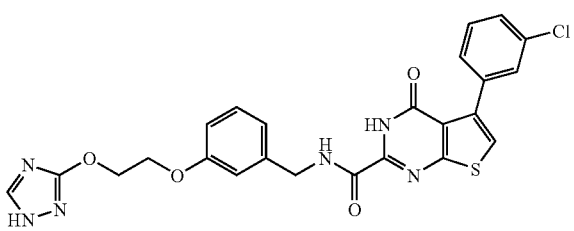

By a method similar to that in Example 22, and using, instead of ethyl 4-oxo-3,4-dihydro-2-quinazolinecarboxylate, ethyl 5-(3-chlorophenyl)-4-oxo-3,4-dihydrothieno[2,3-d]pyrimidine-2-carboxylate obtained in Reference Example 73 and using, instead of 1-[2-({3-[1-(triphenylmethyl)-1H-1,2,4-triazol-3-yl]propyl}oxy)pyridin-4-yl]methaneamine, 1-{3-[(2-{[1-(triphenylmethyl)-1H-1,2,4-triazol-3-yl]oxy}ethyl)oxy]phenyl}methanamine obtained in Reference Example 32, the title compound was obtained as a white powder (100.0 mg, 45%).

melting point: 153-154° C.

Example 61

5-(3-methoxyphenyl)-4-oxo-N-{3-[2-(1H-1,2,4-triazol-3-yloxy)ethoxy]benzyl}-3,4-dihydrothieno[2,3-d]pyrimidine-2-carboxamide

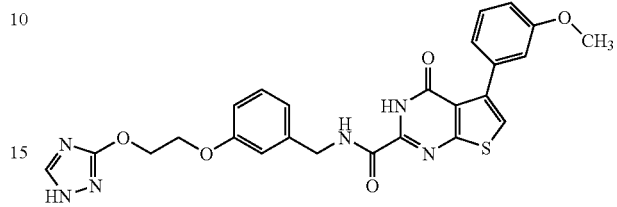

By a method similar to that in Example 22, and using, instead of ethyl 4-oxo-3,4-dihydro-2-quinazolinecarboxylate, ethyl 5-(3-methoxyphenyl)-4-oxo-3,4-dihydrothieno[2,3-d]pyrimidine-2-carboxylate obtained in Reference Example 74 and using, instead of 1-[2-({3-[1-(triphenylmethyl)-1H-1,2,4-triazol-3-yl]propyl}oxy)pyridin-4-yl]methaneamine, 1-{3-[(2-{[1-(triphenylmethyl)-1H-1,2,4-triazol-3-yl]oxy}ethyl)oxy]phenyl}methanamine obtained in Reference Example 32, the title compound was obtained as a white powder (117.5 mg, 50%).

melting point: 163-165° C.

Example 62

5-(3-cyanophenyl)-4-oxo-N-{3-[2-(1H-1,2,4-triazol-3-yloxy)ethoxy]benzyl}-3,4-dihydrothieno[2,3-d]pyrimidine-2-carboxamide

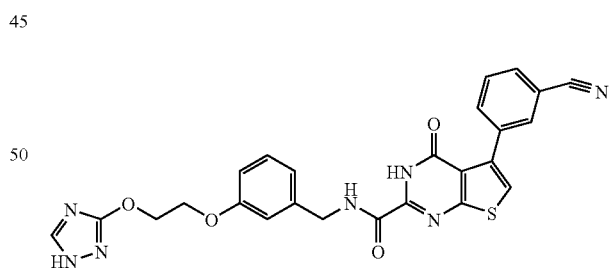

By a method similar to that in Example 22, and using, instead of ethyl 4-oxo-3,4-dihydro-2-quinazolinecarboxylate, ethyl 5-(3-cyanophenyl)-4-oxo-3,4-dihydrothieno[2,3-d]pyrimidine-2-carboxylate obtained in Reference Example 75 and using, instead of 1-[2-({3-[1-(triphenylmethyl)-1H-1,2,4-triazol-3-yl]propyl}oxy)pyridin-4-yl]methaneamine, 1-{3-[(2-{[1-(triphenylmethyl)-1H-1,2,4-triazol-3-yl]oxy}ethyl)oxy]phenyl}methanamine obtained in Reference Example 32, the title compound was obtained as a white powder (124.4 mg, 61%).

melting point: 180-182° C.

Example 63

5-(3-methylphenyl)-4-oxo-N-{3-[2-(1H-1,2,4-triazol-3-yloxy)ethoxy]benzyl}-3,4-dihydrothieno[2,3-d]pyrimidine-2-carboxamide

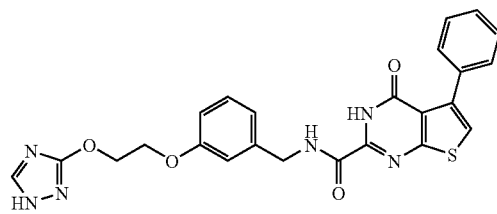

By a method similar to that in Example 22, and using, instead of ethyl 4-oxo-3,4-dihydro-2-quinazolinecarboxylate, ethyl 5-(3-methylphenyl)-4-oxo-3,4-dihydrothieno[2,3-d]pyrimidine-2-carboxylate obtained in Reference Example 76 and using, instead of 1-[2-({3-[1-(triphenylmethyl)-1H-1,2,4-triazol-3-yl]propyl}oxy)pyridin-4-yl]methaneamine, 1-{3-[(2-{[1-(triphenylmethyl)-1H-1,2,4-triazol-3-yl]oxy}ethyl)oxy]phenyl}methanamine obtained in Reference Example 32, the title compound was obtained as a white powder (150.0 mg, 74%).

melting point: 123-125° C.

Example 64

5-(4-fluorophenyl)-4-oxo-N-{3-[2-(1H-1,2,4-triazol-3-yloxy)ethoxy]benzyl}3,4-dihydrothieno[2,3-d]pyrimidine-2-carboxamide

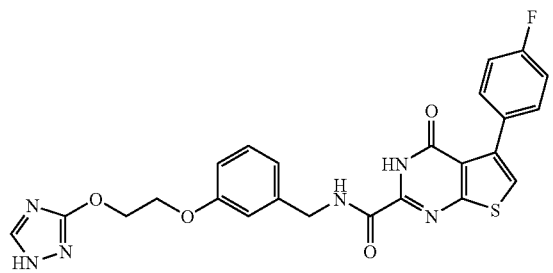

By a method similar to that in Example 22, and using, instead of ethyl 4-oxo-3,4-dihydro-2-quinazolinecarboxylate, ethyl 5-(4-fluorophenyl)-4-oxo-3,4-dihydrothieno[2,3-d]pyrimidine-2-carboxylate obtained in Reference Example 77 and using, instead of 1-[2-({3-[1-(triphenylmethyl)-1H-1,2,4-triazol-3-yl]propyl}oxy)pyridin-4-yl]methaneamine, 1-{3-[(2-{[1-(triphenylmethyl)-1H-1,2,4-triazol-3-yl]oxy}ethyl)oxy]phenyl}methanamine obtained in Reference Example 32, the title compound was obtained as a white powder (187.2 mg, 69%).

melting point: 188-190° C.

Example 65

5-(4-chlorophenyl)-4-oxo-N-{3-[2-(1H-1,2,4-triazol-3-yloxy)ethoxy]benzyl}-3,4-dihydrothieno[2,3-d]pyrimidine-2-carboxamide

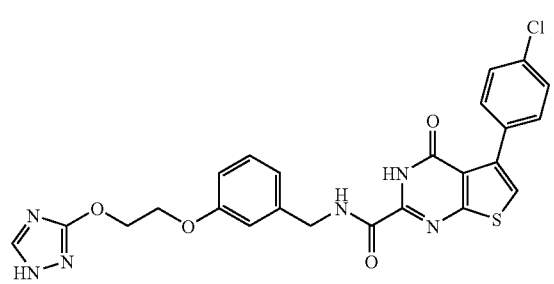

By a method similar to that in Example 22, and using, instead of ethyl 4-oxo-3,4-dihydro-2-quinazolinecarboxylate, ethyl 5-(4-chlorophenyl)-4-oxo-3,4-dihydrothieno[2,3-d]pyrimidine-2-carboxylate obtained in Reference Example 78 and using, instead of 1-[2-({3-[1-(triphenylmethyl)-1H-1,2,4-triazol-3-yl]propyl}oxy)pyridin-4-yl]methaneamine, 1-{3-[(2-{[1-(triphenylmethyl)-1H-1,2,4-triazol-3-yl]oxy}ethyl)oxy]phenyl}methanamine obtained in Reference Example 32, the title compound was obtained as a white powder (180.0 mg, 80%).

melting point: 160-164° C.

Example 66

5-(4-bromophenyl)-4-oxo-N-{3-[2-(1H-1,2,4-triazol-3-yloxy)ethoxy]benzyl}-3,4-dihydrothieno[2,3-d]pyrimidine-2-carboxamide

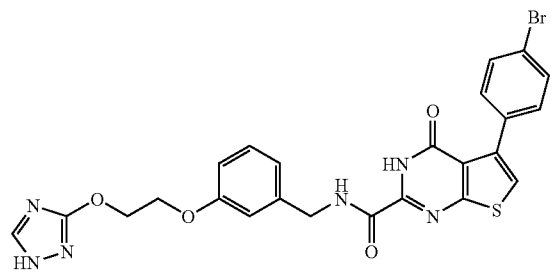

By a method similar to that in Example 22, and using, instead of ethyl 4-oxo-3,4-dihydro-2-quinazolinecarboxylate, ethyl 5-(4-bromophenyl)-4-oxo-3,4-dihydrothieno[2,3-d]pyrimidine-2-carboxylate obtained in Reference Example 79 and using, instead of 1-[2-({3-[1-(triphenylmethyl)-1H-1,2,4-triazol-3-yl]propyl}oxy)pyridin-4-yl]methaneamine, 1-{3-[(2-{[1-(triphenylmethyl)-1H-1,2,4-triazol-3-yl]oxy}ethyl)oxy]phenyl}methanamine obtained in Reference Example 32, the title compound was obtained as a white powder (147.7 mg, 71%).

melting point: 189-192° C.

Example 67

5-(4-methoxyphenyl)-4-oxo-N-{3-[2-(1H-1,2,4-triazol-3-yloxy)ethoxy]benzyl}-3,4-dihydrothieno[2,3-d]pyrimidine-2-carboxamide

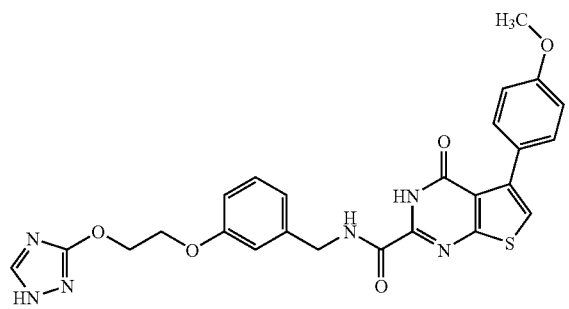

By a method similar to that in Example 22, and using, instead of ethyl 4-oxo-3,4-dihydro-2-quinazolinecarboxylate, ethyl 5-(4-methoxyphenyl)-4-oxo-3,4-dihydrothieno[2,3-d]pyrimidine-2-carboxylate obtained in Reference Example 80 and using, instead of 1-[2-({3-[1-(triphenylmethyl)-1H-1,2,4-triazol-3-yl]propyl}oxy)pyridin-4-yl]methaneamine, 1-{3-[(2-{[1-(triphenylmethyl)-1H-1,2,4-triazol-3-yl]oxy}ethyl)oxy]phenyl}methanamine obtained in Reference Example 32, the title compound was obtained as a white powder (123.6 mg, 50%).

melting point: 93-98° C.

Example 68

5-(4-methylphenyl)-4-oxo-N-{3-[2-(1H-1,2,4-triazol-3-yloxy)ethoxy]benzyl}-3,4-dihydrothieno[2,3-d]pyrimidine-2-carboxamide

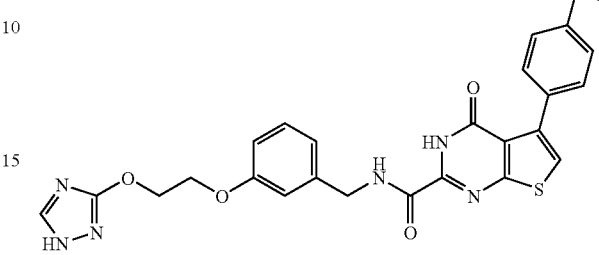

By a method similar to that in Example 22, and using, instead of ethyl 4-oxo-3,4-dihydro-2-quinazolinecarboxylate, ethyl 5-(4-methylphenyl)-4-oxo-3,4-dihydrothieno[2,3-d]pyrimidine-2-carboxylate obtained in Reference Example 81 and using, instead of 1-[2-({3-[1-(triphenylmethyl)-1H-1,2,4-triazol-3-yl]propyl}oxy)pyridin-4-yl]methaneamine, 1-{3-[(2-{[1-(triphenylmethyl)-1H-1,2,4-triazol-3-yl]oxy}ethyl)oxy]phenyl}methanamine obtained in Reference Example 32, the title compound was obtained as a white powder (162.0 mg, 68%).

melting point: 122-125° C.

Example 69 ethyl 3-[4-oxo-2-({3-[2-(1H-1,2,4-triazol-3-yloxy)ethoxy]benzyl}carbamoyl)-3,4-dihydrothieno[2,3-d]pyrimidin-5-yl]benzoate

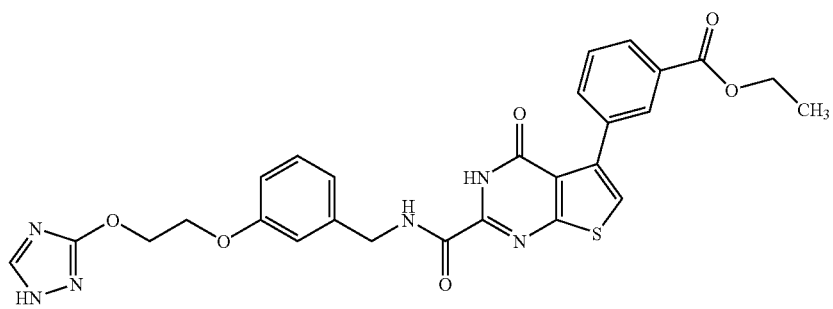

By a method similar to that in Example 22, and using, instead of ethyl 4-oxo-3,4-dihydro-2-quinazolinecarboxylate, ethyl 5-[3-(ethoxycarbonyl)phenyl]-4-oxo-3,4-dihydrothieno[2,3-d]pyrimidine-2-carboxylate obtained in Reference Example 82 and using, instead of 1-[2-({3-[1-(triphenylmethyl)-1H-1,2,4-triazol-3-yl]propyl}oxy)pyridin-4-yl]methaneamine, 1-{3-[(2-{[1-(triphenylmethyl)-1H-1,2,4-triazol-3-yl]oxy}ethyl)oxy]phenyl}methanamine obtained in Reference Example 32, the title compound was obtained as a white powder (132.7 mg, 58%).

melting point: 151-153° C.

Example 70

3-[4-oxo-2-({3-[2-(1H-1,2,4-triazol-3-yloxy)ethoxy]benzyl}carbamoyl)-3,4-dihydrothieno[2,3-d]pyrimidin-5-yl]benzoic acid

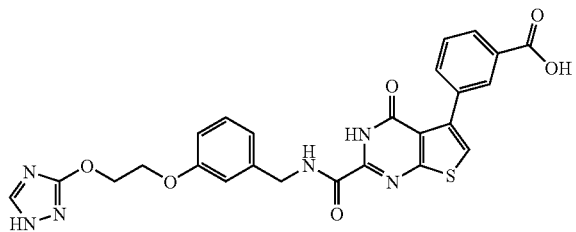

By a method similar to that in Example 42 and using, instead of ethyl 4-[({[4-oxo-2-({[(2-{[3-(1H-1,2,4-triazol-3-yl)propyl]oxy}pyridin-4-yl)methyl]amino}carbonyl)-3,4-dihydrothieno[2,3-d]pyrimidin-5-yl]methyl}oxy)methyl]benzoate, ethyl 3-[4-oxo-2-({3-[2-(1H-1,2,4-triazol-3-yloxy)ethoxy]benzyl}carbamoyl)-3,4-dihydrothieno[2,3-d]pyrimidin-5-yl]benzoate obtained in Example 69, the title compound was obtained as a white powder (80.0 mg, 73%).

melting point: 230-232° C.

Example 71

4-oxo-N-[(3-{[3-(1H-1,2,4-triazol-3-yloxy)propyl]oxy}phenyl)methyl]-3,4-dihydroquinazoline-2-carboxamide

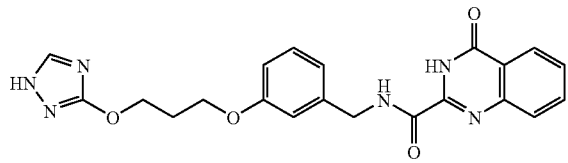

To a suspension of 4-oxo-N-({3-[(3-{[1-(triphenylmethyl)-1H-1,2,4-triazol-3-yl]oxy}propyl)oxy]phenyl}methyl)-3,4-dihydroquinazoline-2-carboxamide obtained in Reference Example 86 (0.285 g, 0.430 mmol) in acetonitrile (6 mL) were added trifluoroacetic acid (1.27 mL) and triethylsilane (0.082 mL, 0.516 mmol) at room temperature, and the mixture was stirred at room temperature for 12 hr. The reaction mixture was concentrated under reduced pressure, and the residue was crystallized from diethyl ether-EtOH to give the title compound as a white powder (0.173 g, 96%).

melting point: 190-192° C.

Example 72

5-(3-chlorophenyl)-4-oxo-N-[(3-{[3-(1H-1,2,4-triazol-3-yloxy)propyl]oxy}phenyl)methyl]-3,4-dihydrothieno[2,3-d]pyrimidine-2-carboxamide

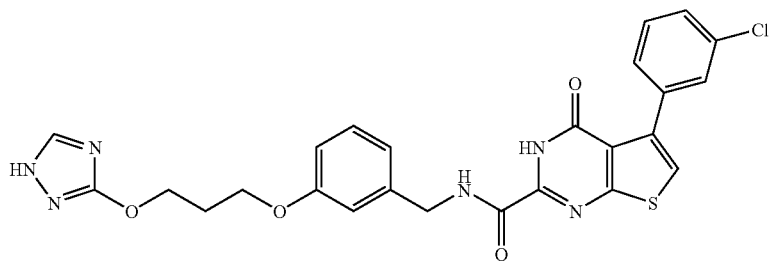

By a method similar to that in Example 71 and using 5-(3-chlorophenyl)-4-oxo-N-({3-[(3-{[1-(triphenylmethyl)-1H-1,2,4-triazol-3-yl]oxy}propyl)oxy]phenyl}methyl)-3,4-dihydrothieno[2,3-d]pyrimidine-2-carboxamide obtained in Reference Example 87, the title compound was obtained as a white powder (0.200 g, 97%).

melting point: 167-169° C.

Example 73

5-(3-fluorophenyl)-4-oxo-N-[(3-{[3-(1H-1,2,4-triazol-3-yloxy)propyl]oxy}phenyl)methyl]-3,4-dihydrothieno[2,3-d]pyrimidine-2-carboxamide

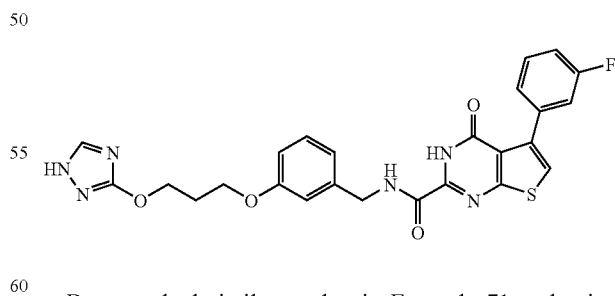

By a method similar to that in Example 71 and using 5-(3-fluorophenyl)-4-oxo-N-({3-[(3-{[1-(triphenylmethyl)-1H-1,2,4-triazol-3-yl]oxy}propyl)oxy]phenyl}methyl)-3,4-dihydrothieno[2,3-d]pyrimidine-2-carboxamide obtained in Reference Example 88, the title compound was obtained as a pale-yellow powder (0.155 g, 95%).

melting point: 130-132° C.

Example 74

5-(2-chlorophenyl)-4-oxo-N-[(3-{[3-(1H-1,2,4-triazol-3-yloxy)propyl]oxy}phenyl)methyl]-3,4-dihydrothieno[2,3-d]pyrimidine-2-carboxamide

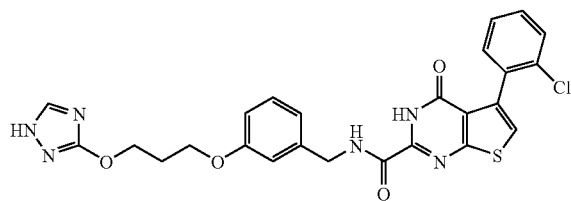

By a method similar to that in Example 71 and using 5-(2-chlorophenyl)-4-oxo-N-({3-[(3-{[1-(triphenylmethyl)-1H-1,2,4-triazol-3-yl]oxy}propyl)oxy]phenyl}methyl)-3,4-dihydrothieno[2,3-d]pyrimidine-2-carboxamide obtained in Reference Example 89, the title compound was obtained as a pale-yellow powder (0.165 g, 96%).

melting point: 165-167° C.

Example 75

5-(2-fluorophenyl)-4-oxo-N-[(3-{[3-(1H-1,2,4-triazol-3-yloxy)propyl]oxy}phenyl)methyl]-3,4-dihydrothieno[2,3-d]pyrimidine-2-carboxamide

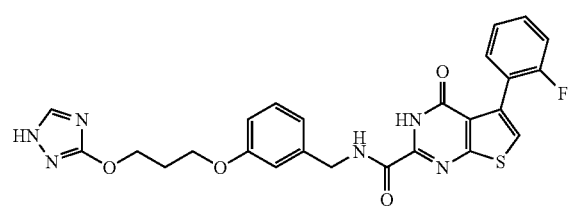

By a method similar to that in Example 71 and using 5-(2-fluorophenyl)-4-oxo-N-({3-[(3-[(1-(triphenylmethyl)-1H-1,2,4-triazol-3-yl]oxy}propyl)oxy]phenyl methyl)-3,4-dihydrothieno[2,3-d]pyrimidine-2-carboxamide obtained in Reference Example 90, the title compound was obtained as a pale-yellow powder (0.145 g, 97%).

melting point: 159-161° C.

Example 76

5-(4-fluorophenyl)-4-oxo-N-[(3-{[3-(1H-1,2,4-triazol-3-yloxy)propyl]oxy}phenyl)methyl]-3,4-dihydrothieno[2,3-d]pyrimidine-2-carboxamide

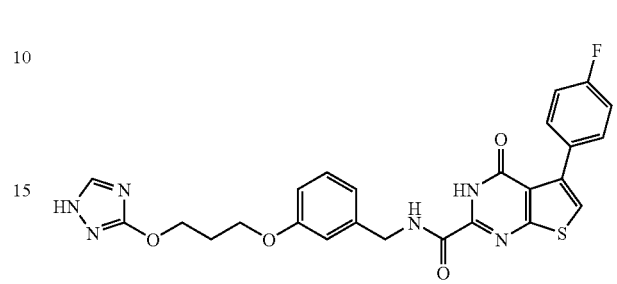

By a method similar to that in Example 71 and using 5-(4-fluorophenyl)-4-oxo-N-({3-[(3-{[1-(triphenylmethyl)-1H-1,2,4-triazol-3-yl]oxy}propyl)oxy]phenyl}methyl)-3,4-dihydrothieno[2,3-d]pyrimidine-2-carboxamide obtained in Reference Example 91, the title compound was obtained as a white powder (0.172 g, 97%).

melting point: 186-188° C.

Example 77

N-{[3'-({[(4-oxo-3,4-dihydroquinazolin-2-yl)carbonyl]amino}methyl)biphenyl-4-yl]sulfonyl}valine

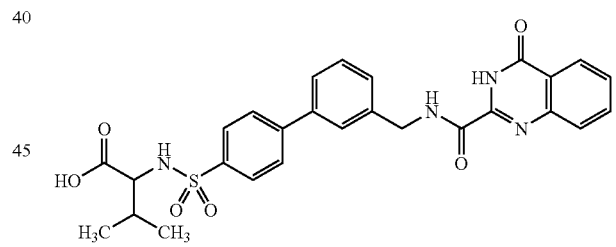

To a suspension of methyl N-{[3'-({[(4-oxo-3,4-dihydroquinazolin-2-yl)carbonyl]amino}methyl)biphenyl-4-yl]sulfonyl}valinate obtained in Reference Example 95 (0.250 g, 0.456 mmol) in THF (3 mL)-methanol (3 mL)-water (3 mL) was added 4N aqueous sodium hydroxide solution (0.399 mL, 1.60 mmol) at room temperature, and the mixture was stirred under heating at 80° C. for 15 hr. The reaction mixture was allowed to cool to room temperature, and concentrated under reduced pressure, and the residue was diluted with water. The mixture was acidified with 1N hydrochloric acid, and partitioned between ethyl acetate and water. The organic layer was washed with saturated brine, and dried over sodium sulfate. The solvent was evaporated under reduced pressure, and the residue was crystallized from methanol to give the title compound as a white powder (0.202 g, 83%).

melting point: 141-143° C.

Example 78

N-({4'-[({1-[(hydroxyamino)carbonyl]-2-methylpropyl}amino)sulfonyl]biphenyl-3-yl}methyl)-4-oxo-3,4-dihydroquinazoline-2-carboxamide

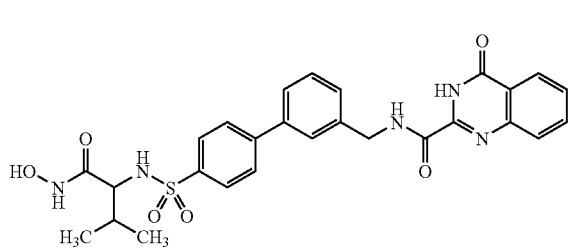

A suspension of N-{[3'-({[(4-oxo-3,4-dihydroquinazolin-2-yl)carbonyl]amino}methyl)biphenyl-4-yl]sulfonyl}valine obtained in Example 77 (0.080 g, 0.150 mmol), O-(trimethylsilyl)hydroxylamine (0.055 mL, 0.449 mmol), 1-[3-(dimethylamino)propyl]-3-ethyl-carbodiimide hydrochloride (0.086 g, 0.449 mmol) and 1-hydroxybenzotriazole (0.061 g, 0.449 mmol) in DMF (5 mL) was stirred at room temperature for 12 hr. The reaction mixture was diluted with ethyl acetate, and washed successively with 0.05N hydrochloric acid, aqueous sodium hydrogencarbonate solution, water and saturated brine, and dried over sodium sulfate. The solvent was evaporated under reduced pressure, and the residue was crystallized from methanol-diethyl ether to give the title compound as a white powder (0.058 g, 71%).

melting point: 153-155° C.

Example 79

N-{[3'-({[(5-methyl-4-oxo-3,4-dihydrothieno[2,3-d]pyrimidin-2-yl)carbonyl]amino}methyl)biphenyl-4-yl]sulfonyl}valine

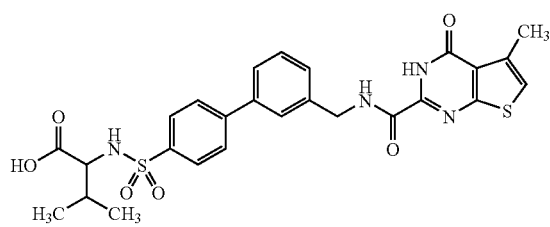

By a method similar to that in Example 77 and using methyl N-{[3'-({[(5-methyl-4-oxo-3,4-dihydrothieno[2,3-d]pyrimidin-2-yl)carbonyl]amino}methyl)biphenyl-4-yl]sulfonyl}valinate obtained in Reference Example 96, the title compound was obtained as a pale-yellow powder (0.133 g, 52%).

melting point: 154-156° C.

Example 80

N-({-4'-[({1-[(hydroxyamino)carbonyl]-2-methylpropyl}amino)sulfonyl]biphenyl-3-yl}methyl)-5-methyl-4-oxo-3,4-dihydrothieno[2,3-d]pyrimidine-2-carboxamide

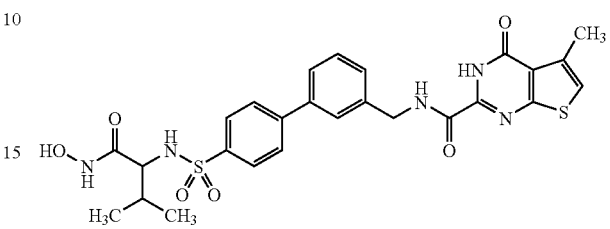

By a method similar to that in Example 78 and using N-{[3'-({[(5-methyl-4-oxo-3,4-dihydrothieno[2,3-d]pyrimidin-2-yl)carbonyl]amino}methyl)biphenyl-4-yl]sulfonyl}valine obtained in Example 79, the title compound was obtained as a pale-yellow powder (0.046 g, 61%).

melting point: 162-164° C.

Example 81

1-[(3-{[3-({[(4-oxo-3,4-dihydroquinazolin-2-yl)carbonyl]amino}methyl)phenyl]oxy}propyl)sulfonyl]piperidine-2-carboxylic acid

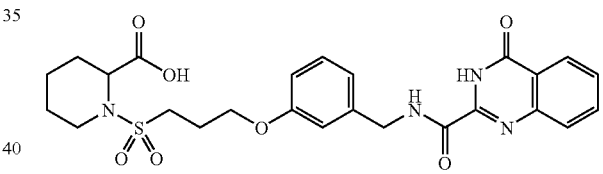

By a method similar to that in Example 77 and using ethyl 1-[(3-{[3-({[(4-oxo-3,4-dihydroquinazolin-2-yl)carbonyl]amino}methyl)phenyl]oxy}propyl)sulfonyl]piperidine-2-carboxylate obtained in Reference Example 100, the title compound was obtained as a white powder (0.332 g, 97%).

melting point: 204-206° C.

Example 82

N-[(3-{[3-({2-[(hydroxyamino)carbonyl]piperidin-1-yl}sulfonyl)propyl]oxy}phenyl)methyl]-4-oxo-3,4-dihydroquinazoline-2-carboxamide

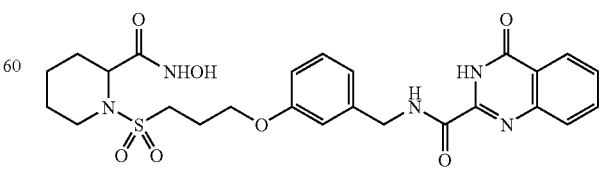

By a method similar to that in Example 78 and using 1-[(3-{[3-({[(4-oxo-3,4-dihydroquinazolin-2-yl)carbonyl]

amino}methyl)phenyl]oxy}propyl)sulfonyl]piperidine-2-carboxylic acid obtained in Example 81, the title compound was obtained as a white powder (0.120 g, 78%).

melting point: 106-108° C.

Example 83

1-[(3-{[3-({[(5-methyl-4-oxo-3,4-dihydrothieno[2,3-d]pyrimidin-2-yl)carbonyl]amino}methyl)phenyl]oxy}propyl)sulfonyl]piperidine-2-carboxylic acid

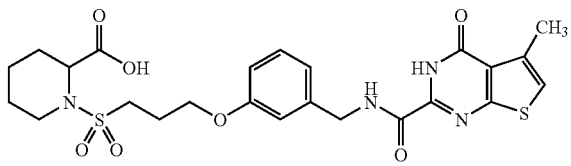

By a method similar to that in Example 77 and using ethyl 1-[(3-{[3-({[(5-methyl-4-oxo-3,4-dihydrothieno[2,3-s d]pyrimidin-2-yl)carbonyl]amino}methyl)phenyl]oxy}propyl)sulfonyl]piperidine-2-carboxylate obtained in Reference Example 101, the title compound was obtained as a yellow powder (0.170 g, 66%).

melting point: 209-211° C.

Example 84

N-{[4'-({2-[formyl(hydroxy)amino]-3-methylbutyl}sulfonyl)biphenyl-3-yl]methyl}-4-oxo-3,4-dihydroquinazoline-2-carboxamide

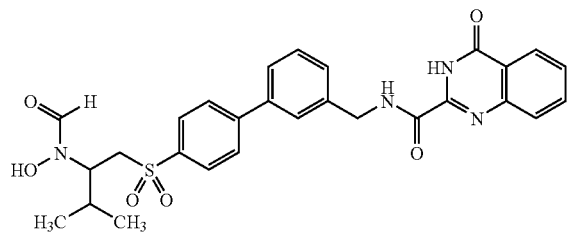

To formic acid (0.217 mL) was added acetic anhydride (0.054 mL, 0.576 mmol) at room temperature, and the mixture was stirred at room temperature for 2 hr. This solution was added to a suspension of N-[(4'-{[2-(hydroxyamino)-3-methylbutyl]sulfonyl}biphenyl-3-yl)methyl]-4-oxo-3,4-dihydroquinazoline-2-carboxamide obtained in Reference Example 107 (0.285 g, 0.430 mmol) and formic acid (2 mL) in THF (20 mL), and the mixture was stirred at room temperature for 4 hr. The reaction mixture was concentrated under reduced pressure, and the residue was purified by preparative HPLC (GILSON 215LIQUD HANDLER, 322PUMP, UV/VIS-156, SHISEIDO CAPCELL PACK C-18 UG120 S-s (20 mmϕ×50 mm), mobile phase: distilled water (containing 0.1% trifluoroacetic acid)/acetonitrile (containing 0.1% trifluoroacetic acid), gradient: distilled water/acetonitrile=90/10→0/100, time: 10 min, flow rate: 25 mL/min, detection wavelength: 220 nm), and crystallized from EtOH-ethyl acetate-diethyl ether to give the title compound as a pale-yellow powder (0.077 g, 37%).

melting point: 153-155° C.

Example 85

N-{[4'-({2-[acetyl(hydroxy)amino]-3-methylbutyl}sulfonyl)biphenyl-3-yl]methyl}-4-oxo-3,4-dihydroquinazoline-2-carboxamide

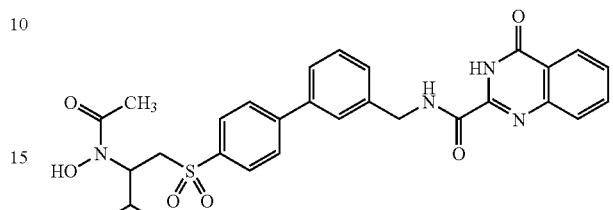

To a suspension of N-[(4'-{[2-(hydroxyamino)-3-methylbutyl]sulfonyl}biphenyl-3-yl)methyl]-4-oxo-3,4-dihydroquinazoline-2-carboxamide obtained in Reference Example 107 (0.100 g, 0.192 mmol) and acetic acid (2 mL) in THF (20 mL) was added acetic anhydride (0.018 mL, 0.192 mmol) at room temperature, and the mixture was stirred at room temperature for 2 hr. The reaction mixture was concentrated under reduced pressure, and the residue was crystallized from EtOH-ethyl acetate-diethyl ether-hexane to give the title compound as a white powder (0.085 g, 79%).

melting point: 167-169° C.

Example 86

N-{[4'-({2-[(aminocarbonyl)(hydroxy)amino]-3-methylbutyl}sulfonyl)biphenyl-3-yl]methyl}-4-oxo-3,4-dihydroquinazoline-2-carboxamide

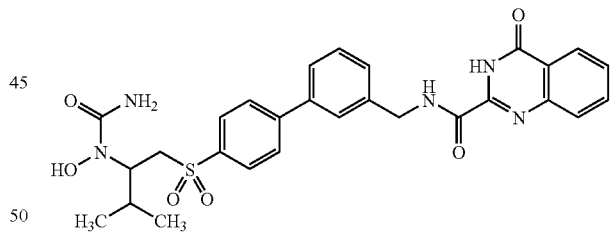

A suspension of N-[(4'-{[2-(hydroxyamino)-3-methylbutyl]sulfonyl}biphenyl-3-yl)methyl]-4-oxo-3,4-dihydroquinazoline-2-carboxamide obtained in Reference Example 107 (0.050 g, 0.096 mmol) and N,N-diisopropylethylamine (0.017 mL, 0.096 mmol) in THF (10 mL) was added dropwise to a suspension of triphosgene (0.0094 g, 0.032 mmol) in THF (2 mL) at 0° C., and the mixture was stirred at room temperature for 2 hr. 28% Aqueous ammonia (0.065 mL, 0.960 mmol) was added thereto, and the mixture was stirred at room temperature for 2 hr. The reaction mixture was concentrated under reduced pressure, and the residue was crystallized from EtOH-water to give the title compound as a white powder (0.045 g, 83%)

melting point: 193-195° C. .

Example 87

4-oxo-N-{[4'-({[(5-oxo-4,5-dihydro-1H-1,2,4-triazol-3-yl)methyl]sulfonyl}methyl)biphenyl-3-yl]methyl}-3,4-dihydroquinazoline-2-carboxamide

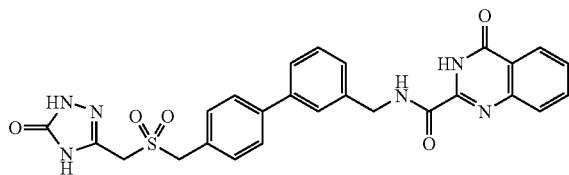

A solution of 5-[({[3'-(aminomethyl)biphenyl-4-yl]methyl}sulfonyl)methyl]-2,4-dihydro-3H-1,2,4-triazol-3-one obtained in Reference Example 111 (0.060 g, 0.167 mmol), ethyl 4-oxo-3,4-dihydro-2-quinazolinecarboxylate obtained according to the methods described in Journal of Organic Chemistry (1978), 43(23), 4485-7 and the like (0.024 g, 0.112 mmol) and triethylamine (0.389 mL, 1.12 mmol) in EtOH (3 mL)-DMA (3 mL) was stirred at 90° C. for 24 hr. The reaction mixture was diluted with ethyl acetate, washed with 0.1N hydrochloric acid and saturated brine, and dried over sodium sulfate. The solvent was evaporated under reduced pressure, and the residue was crystallized from EtOH-diethyl ether to give the title compound as a pale-yellow powder (0.032 g, 55%).

melting point: 245-247° C.

Example 88

5-methyl-4-oxo-N-{[4'-({[(5-oxo-4,5-dihydro-1H-1,2,4-triazol-3-yl)methyl]sulfonyl}methyl)biphenyl-3-yl]methyl}-3,4-dihydrothieno[2,3-d]pyrimidine-2-carboxamide

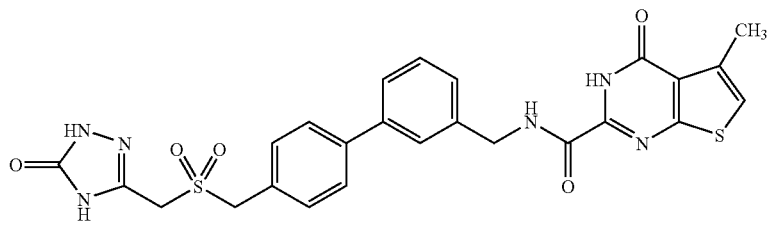

By a method similar to that in Example 87 and using 5-[({[3'-(aminomethyl)biphenyl-4-yl]methyl}sulfonyl)methyl]-2,4-dihydro-3H-1,2,4-triazol-3-one obtained in Reference Example 111 and ethyl 5-methyl-4-oxo-3,4-dihydrothieno[2,3-d]pyrimidine-2-carboxylate obtained according to the methods described in U.S. Pat. No. 4,054,656 and the like, the title compound was obtained as a pale-yellow powder (0.043 g, 34%).

melting point: 273-275° C.

Example 89

5-(3-chlorophenyl)-4-oxo-N-{[4'-({[(5-oxo-4,5-dihydro-1H-1,2,4-triazol-3-yl)methyl]sulfonyl}methyl)biphenyl-3-yl]methyl}-3,4-dihydrothieno[2,3-d]pyrimidine-2-carboxamide

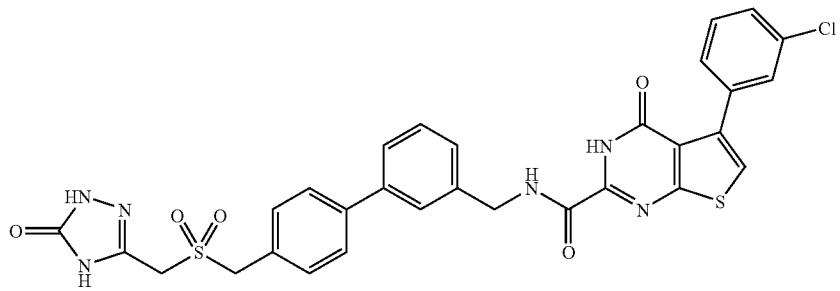

By a method similar to that in Example 87 and using 5-[({[3'-(aminomethyl)biphenyl-4-yl]methyl}sulfonyl)methyl]-2,4-dihydro-3H-1,2,4-triazol-3-one obtained in Refer ence Example 111 and ethyl 5-(3-chlorophenyl)-4-oxo-3,4-dihydrothieno[2,3-d]pyrimidine-2-carboxylate obtained in Reference Example 73, the title compound was obtained as a pale-yellow powder (0.067 g, 45%).

melting point: 276-278° C.

Example 90

N-[(3-{4-[(2,5-dioxoimidazolidin-4-yl)acetyl]piperazin-1-yl}phenyl)methyl]-4-oxo-3,4-dihydroquinazoline-2-carboxamide

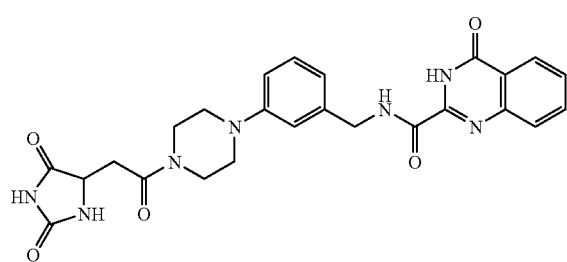

A suspension of 4-oxo-N-[(3-piperazin-1-ylphenyl)methyl]-3,4-dihydroquinazoline-2-carboxamide dihydrochloride obtained in Reference Example 116 (0.109 g, 0.250 mmol), (2,5-dioxoimidazolidin-4-yl)acetic acid (0.047 g, 0.300 mmol), 1-[3-(dimethylamino)propyl]-3-ethyl-carbodiimide hydrochloride (0.096 g, 0.500 mmol) and 1-hydroxybenzotriazole (0.068 g, 0.500 mmol) in DMF (5 mL) was stirred at room temperature for 1 hr. Triethylamine (0.139 mL, 1.00 mmol) was added thereto, and the mixture was stirred at room temperature for 12 hr. The reaction mixture was concentrated under reduced pressure, and the residue was purified by preparative HPLC (GILSON 215LIQUD HANDLER, 322PUMP, UV/VIS-156, SHISEIDO CAPCELL PACK C-18 UG120 S-5 (20 mmφ×50 mm), mobile phase: distilled water (containing 0.1% trifluoroacetic acid)/acetonitrile (containing 0.1% trifluoroacetic acid), gradient: distilled water/acetonitrile=90/100/100, time: 10 min, flow rate: 25 mL/min, detection wavelength: 220 nm), and crystallized from methanol-diethyl ether to give the title compound as a pale-yellow powder (0.078 g, 62%).

melting point: 280-282° C.

Example 91

4-oxo-N-[(3-{4-[(5-oxo-4,5-dihydro-1H-1,2,4-triazol-3-yl)acetyl]piperazin-1-yl}phenyl)methyl]-3,4-dihydroquinazoline-2-carboxamide

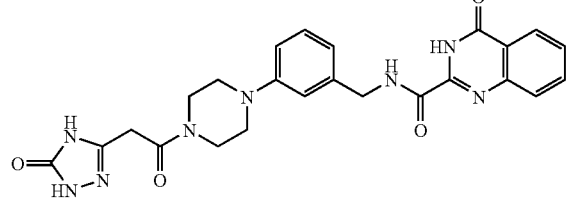

By a method similar to that in Example 90 and using 4-oxo-N-[(3-piperazin-1-ylphenyl)methyl]-3,4-dihydroquinazoline-2-carboxamide dihydrochloride obtained in Reference Example 116 and (5-oxo-4,5-dihydro-1H-1,2,4-triazol-3-yl)acetic acid obtained according to the methods described in Australian Journal of Chemistry, 1979, 32, 161-165 and the like, the title compound was obtained as a pale-yellow powder (0.077 g, 63%).

melting point: 311-313° C.

Example 92

4-oxo-N-[(3-{4-[(5-oxo-2,5-dihydro-1H-pyrazol-3-yl)acetyl]piperazin-1-yl}phenyl)methyl]-3,4-dihydroquinazoline-2-carboxamide

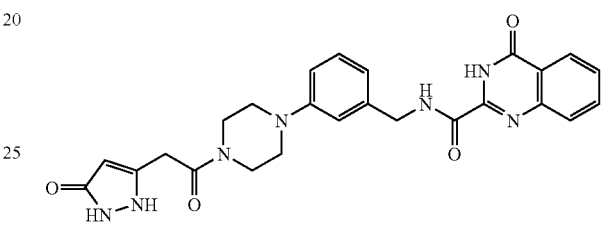

By a method similar to that in Example 90 and using 4-oxo-N-[(3-piperazin-1-ylphenyl)methyl]-3,4-dihydroquinazoline-2-carboxamide dihydrochloride obtained in Reference Example 116 and (5-oxo-2,5-dihydro-1H-pyrazol-3-yl)acetic acid obtained in Reference Example 118, the title compound was obtained as a pale-yellow powder (0.040 g, 33%).

melting point: 183-185° C.

Example 93

N-({3-[4-(1H-imidazol-4-ylacetyl)piperazin-1-yl]phenyl}methyl)-4-oxo-3,4-dihydroquinazoline-2-carboxamide trifluoroacetate

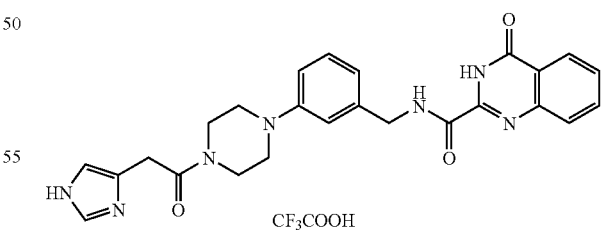

By a method similar to that in Example 90 and using 4-oxo-N-[(3-piperazin-1-ylphenyl)methyl]-3,4-dihydroquinazoline-2-carboxamide dihydrochloride obtained in Reference Example 116 and 1H-imidazol-4-ylacetic acid hydrochloride, the title compound was obtained as a pale-yellow powder (0.093 g, 79%).

melting point: 202-204° C.

Example 94

4-oxo-N-({3-[4-(1H-tetrazol-5-ylacetyl)piperazin-1-yl]phenyl}methyl)-3,4-dihydroquinazoline-2-carboxamide

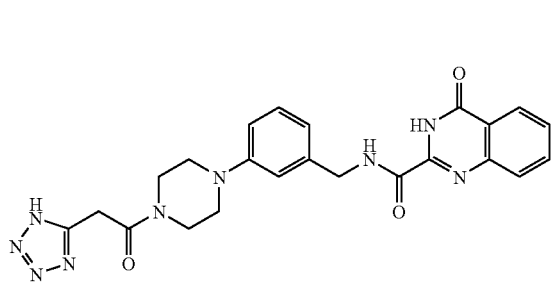

By a method similar to that in Example 90 and using 4-oxo-N-[(3-piperazin-1-ylphenyl)methyl]-3,4-dihydroquinazoline-2-carboxamide dihydrochloride obtained in Reference Example 116 and 1H-tetrazol-5-ylacetic acid, the title compound was obtained as a pale-yellow powder (0.038 g, 32%).

melting point: 163-165° C.

Example 95

4-[3-({[(4-oxo-3,4-dihydroquinazolin-2-yl)carbonyl]amino}methyl)phenyl]piperazine-1-carbothioacid S-(5-amino-1,3,4-thiadiazol-2-yl)

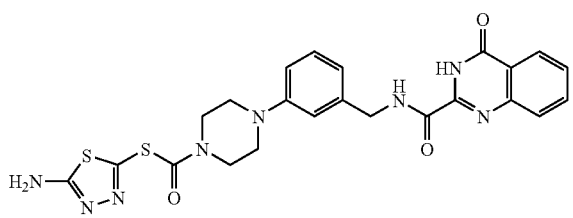

A suspension of 4-oxo-N-[(3-piperazin-1-ylphenyl)methyl]-3,4-dihydroquinazoline-2-carboxamide dihydrochloride obtained in Reference Example 116 (0.100 g, 0.229 mmol) and N,N-diisopropylethylamine (0.120 mL, 0.688 mmol) in nitromethane (10 mL) was added dropwise to a solution of triphosgene (0.024 g, 0.080 mmol) in nitromethane (2 mL) at 0° C., and the mixture was stirred at room temperature for 2 hr. A suspension of 5-amino-1,3,4-thiadiazol-2-thiol (0.061 g, 0.458 mmol) and N,N-diisopropylethylamine (0.040 mL, 0.229 mmol) in nitromethane (5 mL) was added to this mixture at room temperature, and the mixture was stirred at room temperature for 4 hr, and then at 50° C. for 2 hr. The reaction mixture was concentrated under reduced pressure, and water was added to the residue. The precipitated solid was collected by filtration, and washed with water, a mixed solution of dimethyl sulfoxide-methanol (1:1 (v/v)) and methanol to give the title compound as a white powder (0.066 g, 55%).

melting point: 212-214° C.

Example 96

N-{[4'-({5-[2-(ethyloxy)ethyl]-2,4,6-trioxohexahydropyrimidin-5-yl}oxy)biphenyl-3-yl]methyl}-4-oxo-3,4-dihydroquinazoline-2-carboxamide

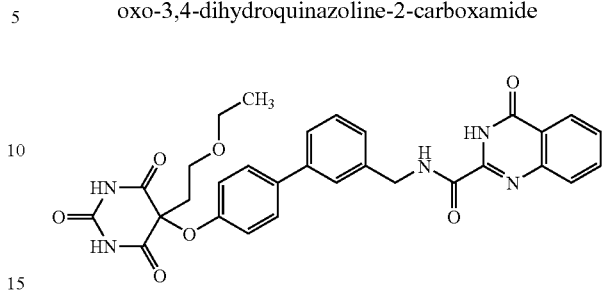

A suspension of N-[(4'-hydroxybiphenyl-3-yl)methyl]-4-oxo-3,4-dihydroquinazoline-2-carboxamide obtained in Reference Example 119 (0.100 g, 0.269 mmol), 5-bromo-5-[2-(ethyloxy)ethyl]pyrimidine-2,4,6(1H,3H,5H)-trione obtained according to the methods described in WO02/34726 and the like (0.075 g, 0.269 mmol) and potassium carbonate (0.186 g, 1.34 mmol) in DMF (5 mL) was stirred at room temperature for 5 hr. The reaction mixture was diluted with ethyl acetate, washed with water and saturated brine, and dried over sodium sulfate. The solvent was evaporated under reduced pressure, and the residue was crystallized from ethyl acetate-IPE to give the title compound as a white powder (0.078 g, 51%).

melting point: 163-165° C.

Example 97

5-methyl-4-oxo-N-[3-(3-{[5-(trifluoromethyl)-1H-1,2,4-triazol-3-yl]thio}propoxy)benzyl]-3,4-dihydrothieno[2,3-d]pyrimidine-2-carboxamide

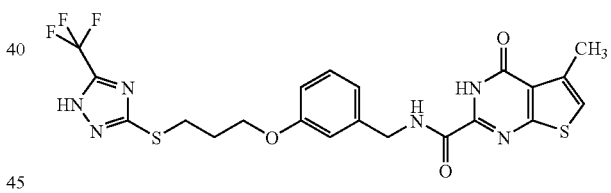

A solution of ethyl 5-methyl-4-oxo-3,4-dihydrothieno[2,3-d]pyrimidine-2-carboxylate obtained according to the method described in U.S. Pat. No. 4,054,656 (150 mg, 0.630 mmol), 1-[3-(3-{[5-(trifluoromethyl)-1H-1,2,4-triazol-3-yl]thio}propoxy)phenyl]methanamine hydrochloride obtained in Reference Example 121 (243.80 mg, 0.661 mmol) and triethylamine (0.263 mL, 1.889 mmol) in a mixed solvent of EtOH (10 mL)-DMA (2 mL) was stirred at 90° C. for 3 days. The solvent was evaporated under reduced pressure, and ethyl acetate-THF and 1N hydrochloric acid were added to the residue. The organic layer was washed with 1N hydrochloric acid and saturated brine, dried over sodium sulfate, and concentrated. The residue was purified by preparative HPLC (GILSON 215LIQUD HANDLER, 322PUMP, UV/VIS-156, SHISEIDO CAPCELL PACK C-18 UG120 S-5 (20 mmφ×50 mm), mobile phase: distilled water (containing 0.1% trifluoroacetic acid)/acetonitrile (containing 0.1% trifluoroacetic acid), gradient: distilled water/acetonitrile=95/5→0/100, time: 10 min, flow rate: 25 mL/min, detection wavelength: 220 nm), and crystallized from EtOH to give the title compound as a white powder (83.8 mg, 25%).

melting point: 170-172° C.

Example 98

4-[3-({[(5-methyl-4-oxo-3,4-dihydrothieno[2,3-d]pyrimidin-2-yl)carbonyl]amino}methyl)phenoxy]butanoic acid

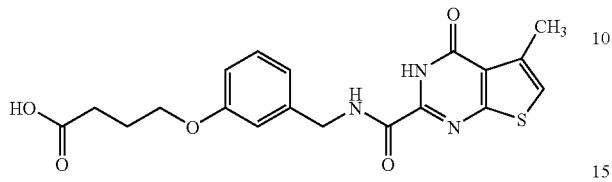

By a method similar to that in Example 42 and using, instead of ethyl 4-[({[4-oxo-2-({[(2-{[3-(1H-1,2,4-triazol-3-yl)propyl]oxy}pyridin-4-yl)methyl]amino}carbonyl)-3,4-dihydrothieno[2,3-d]pyrimidin-5-yl]methyl}oxy)methyl]benzoate, ethyl 4-[3-({[(5-methyl-4-oxo-3,4-dihydrothieno[2,3-d]pyrimidin-2-yl)carbonyl]amino}methyl)phenoxy]butanoate obtained in Reference Example 122, the title compound was obtained as a white powder (465.7 mg, 91%).

melting point: 179-181° C.

Example 99

5-methyl-N-(3-{3-[(5-methyl-1H-1,2,4-triazol-3-yl)thio]propoxy}benzyl)-4-oxo-3,4-dihydrothieno[2,3-d]pyrimidine-2-carboxamide

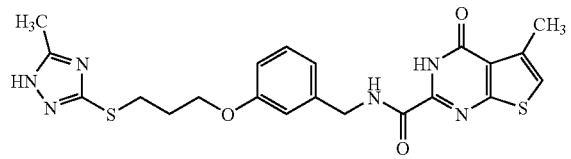

By a method similar to that in Example 97 and using, instead of 1-[3-(3-{[5-(trifluoromethyl)-1H-1,2,4-triazol-3-yl]thio}propoxy)phenyl]methanamine hydrochloride, 1-(3-{3-[(5-methyl-1H-1,2,4-triazol-3-yl)thio]propoxy}phenyl)methanamine hydrochloride obtained in Reference Example 124, the title compound was obtained as a white powder (31.2 mg, 11%)

melting point: 170-171° C.

Example 100

N-{3-[3-(1H-imidazol-1-yl)propoxy]benzyl}-5-methyl-4-oxo-3,4-dihydrothieno[2,3-d]pyrimidine-2-carboxamide

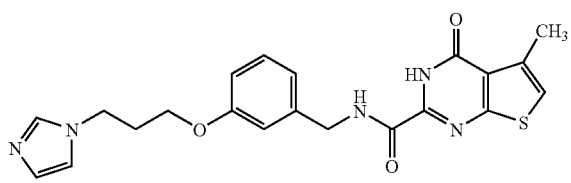

By a method similar to that in Example 97 and using, instead of 1-[3-(3-{[5-(trifluoromethyl)-1H-1,2,4-triazol-3-yl]thio}propoxy)phenyl]methanamine hydrochloride, 1-{3-[3-(1H-imidazol-1-yl)propoxy]phenyl}methanamine hydrochloride obtained in Reference Example 126, the title compound was obtained as a white powder (186.6 mg, 68%).

melting point: 222-225° C.

Example 101

5-methyl-4-oxo-N-{3-[3-(1H-1,2,4-triazol-1-yl)propoxy]benzyl}-3,4-dihydrothieno[2,3-d]pyrimidine-2-carboxamide

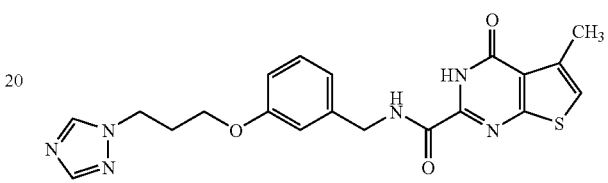

By a method similar to that in Example 97 and using, instead of 1-[3-(3-{[5-(trifluoromethyl)-1H-1,2,4-triazol-3-yl]thio}propoxy)phenyl]methanamine hydrochloride, 1-{3-[3-(1H-1,2,4-triazol-1-yl)propoxy]phenyl}methanamine hydrochloride obtained in Reference Example 128, the title compound was obtained as a white powder (177.7 mg, 59%).

melting point: 180-182° C.

Example 102

5-biphenyl-4-yl-4-oxo-N-{3-[2-(1H-1,2,4-triazol-3-yloxy)ethoxy]benzyl}-3,4-dihydrothieno[2,3-d]pyrimidine-2-carboxamide

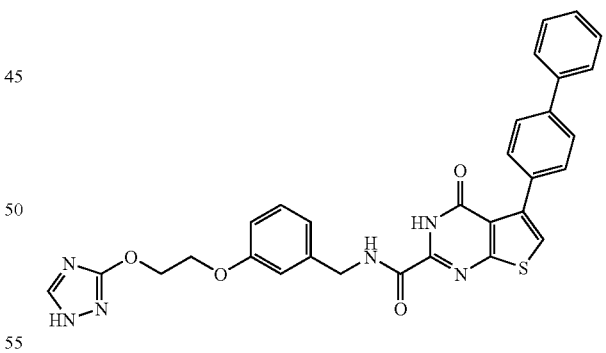

By a method similar to that in Example 22, and using, instead of ethyl 4-oxo-3,4-dihydro-2-quinazolinecarboxylate, ethyl 5-biphenyl-4-yl-4-oxo-3,4-dihydrothieno[2,3-d]pyrimidine-2-carboxylate obtained in Reference Example 136 and using, instead of 1-[2-({3-[1-(triphenylmethyl)-1H-1,2,4-triazol-3-yl]propyl}oxy)pyridin-4-yl]methaneamine, 1-{3-[(2-{[1-(triphenylmethyl)-1H-1,2,4-triazol-3-yl]oxy}ethyl)oxy]phenyl}methanamine obtained in Reference Example 32, the title compound was obtained as a white powder (155.4 mg, 85%).

melting point: 185-187° C.

Example 103

5-methyl-4-oxo-N-{3-[3-(1H-pyrazol-1-yl)propoxy]benzyl}-3,4-dihydrothieno[2,3-d]pyrimidine-2-carboxamide

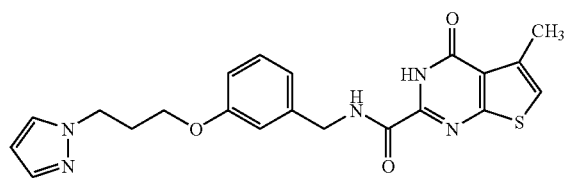

By a method similar to that in Example 97 and using, instead of 1-[3-(3-{[5-(trifluoromethyl)-1H-1,2,4-triazol-3-yl]thio}propoxy)phenyl]methanamine hydrochloride, 1-{3-[3-(1H-pyrazol-1-yl)propoxy]phenyl}methanamine hydrochloride obtained in Reference Example 130, the title compound was obtained as a white powder (163.0 mg, 61%).
melting point: 162-163° C.

Example 104

5-methyl-4-oxo-N-(3-{3-[(5-phenyl-1H-1,2,4-triazol-3-yl)thio]propoxy}benzyl)-3,4-dihydrothieno[2,3-d]pyrimidine-2-carboxamide

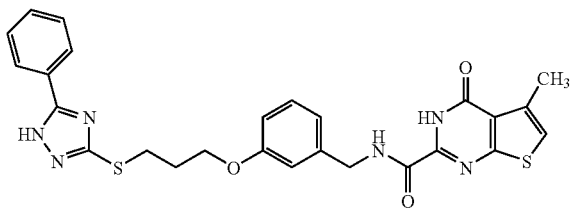

By a method similar to that in Example 97 and using, instead of 1-[3-(3-{[5-(trifluoromethyl)-1H-1,2,4-triazol-3-yl]thio}propoxy)phenyl]methanamine hydrochloride, 1-(3-{3-[(5-phenyl-1H-1,2,4-triazol-3-yl)thio]propoxy}phenyl)methanamine hydrochloride obtained in Reference Example 132, the title compound was obtained as a white powder (42.0 mg, 13%).
melting point: 119-121° C.

Example 105

5-methyl-4-oxo-N-({3'-[(1H-1,2,4-triazol-3-yloxy)methyl]biphenyl-3-yl}methyl)-3,4-dihydrothieno[2,3-d]pyrimidine-2-carboxamide

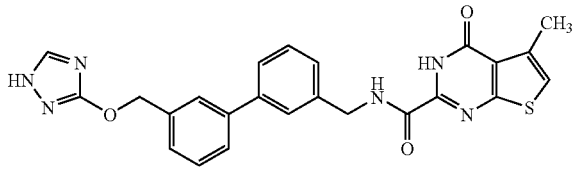

By a method similar to that in Example 22, and using, instead of ethyl 4-oxo-3,4-dihydro-2-quinazolinecarboxylate, ethyl 5-methyl-4-oxo-3,4-dihydrothieno[2,3-d]pyrimidine-2-carboxylate obtained according to the method described in U.S. Pat. No. 4,054,656 and using, instead of 1-[2-({3-[1-(triphenylmethyl)-1H-1,2,4-triazol-3-yl]propyl}oxy)pyridin-4-yl]methaneamine, 1-(3'-{[(1-trityl-1H-1,2,4-triazol-3-yl)oxy]methyl}biphenyl-3-yl)methanamine obtained in Reference Example 135, the title compound was obtained as a white powder (4.7 mg, 2%).
melting point: 152-154° C.

Reference Example 1

3-[(2-chloroethyl)oxy]benzonitrile

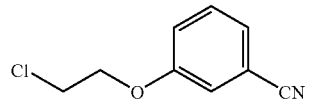

A suspension of 3-hydroxybenzonitrile (5.00 g, 42.0 mmol), 1-bromo-2-chloroethane (9.00 g, 62.8 mmol) and potassium hydroxide (2.5 g, 44.6 mmol) in ethanol (100 mL) was stirred at 90° C. for 24 hr. The reaction mixture was concentrated under reduced pressure, and the residue was extracted with diethyl ether and water. The organic layer was washed with saturated brine, dried over sodium sulfate, and concentrated. The obtained oil was purified by silica gel column chromatography (2%-50% ethyl acetate/hexane) to give the title compound as a colorless oil (1.39 g, 18%).
$^1$H-NMR (300 MHz, CDCl$_3$) δ: 3.83 (2H, t, J=5.7 Hz), 4.25 (2H, t, J=5.7 Hz), 7.14-7.19 (2H, m), 7.29 (1H, dt, J=7.6, 1.3 Hz), 7.37-7.43 (1H, m).

Reference Example 2

3-{[2-(1H-1,2,4-triazol-3-ylthio)ethyl]oxy}benzonitrile

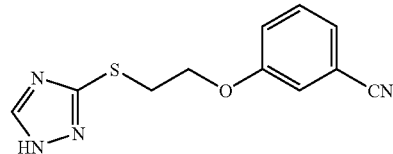

A solution of 3-[(2-chloroethyl)oxy]benzonitrile obtained in Reference Example 1 (11.3 g, 62.3 mmol), 1H-1,2,4-triazole-3-thiol (6.00 g, 59.3 mmol) and triethylamine (8.40 mL, 62.3 mmol) in ethanol (50 mL) was stirred at 80° C. for 15 hr. The reaction mixture was concentrated under reduced pressure, and ethyl acetate and water were added to the residue. The organic layer was washed with saturated brine, dried over sodium sulfate, and concentrated to give the title compound as a white powder (14.4 g, 98%).
$^1$H-NMR (300 MHz, DMSO-d$_6$) δ: 3.48 (2H, t, J=6.7 Hz), 4.32 (2H, t, J=6.6 Hz), 7.29-7.36 (1H, m), 7.38-7.43 (1H, m), 7.44-7.54 (2H, m), 8.46 (1H, s), 14.09 (1H, s).

Reference Example 3

1-(3-{[2-(1H-1,2,4-triazol-3-ylthio)ethyl]oxy}phenyl)methanamine

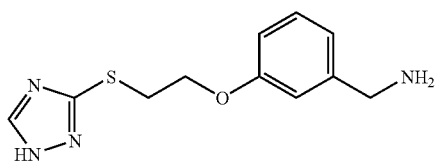

A solution of 3-{[2-(1H-1,2,4-triazol-3-ylthio)ethyl]oxy}benzonitrile obtained in Reference Example 2 (9.00 g, 36.5 mmol) and Raney-nickel (5.00 g) in 5N ammonia/methanol (300 mL) was stirred at room temperature overnight under hydrogen atmosphere (1 atm). The catalyst was filtered off, and the filtrate was concentrate. The obtained residue was crystallized from toluene to give the title compound as a pale-blue powder (6.45 g, 71%).

melting point: not less than 300° C.

Reference Example 4

3-[(3-chloropropyl)oxy]benzonitrile

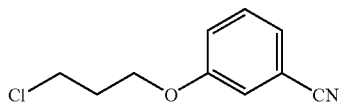

A suspension of 1-bromo-3-chloropropane (13.9 g, 88.1 mmol) and 60% sodium hydride (oil dispersion, 3.02 g, 126 mmol) in ethanol (50 mL) was stirred at room temperature for 30 min. 3-Hydroxybenzonitrile (10.0 g, 83.9 mmol) was added to the reaction mixture at 0° C., and the mixture was stirred at 60° C. for 15 hr. The reaction mixture was concentrated under reduced pressure, and the residue was extracted with ethyl acetate and water. The organic layer was washed with saturated brine, dried over sodium sulfate, and concentrated. The obtained oil was purified by silica gel column chromatography (5%-15% ethyl acetate/hexane) to give the title compound as a colorless oil (14.2 g, 86%).

$^1$H-NMR (300 MHz, CDCl$_3$) δ: 2.26 (2H, tt, J=6.0, 6.0 Hz), 3.75 (2H, t, J=6.2 Hz), 4.14 (2H, t, J=5.8 Hz), 7.11-7.18 (2H, m), 7.23-7.28 (1H, m), 7.34-7.41 (1H, m).

Reference Example 5

3-{[3-(1H-1,2,4-triazol-3-ylthio)propyl]oxy}benzonitrile

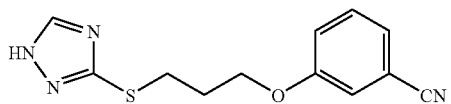

By a method similar to that in Reference Example 2 and using, instead of 3-[(2-chloroethyl)oxy]benzonitrile, 3-[(3-chloropropyl)oxy]benzonitrile obtained in Reference Example 4, the title compound was obtained as a white powder (7.87 g, 100%).

$^1$H-NMR (300 MHz, DMSO-d$_6$) δ: 2.11 (2H, tt, J=6.8, 6.6 Hz), 3.22 (2H, t, J=7.1 Hz), 4.14 (2H, t, J=6.2 Hz), 7.26-7.53 (4H, m), 8.42 (1H, s), 14.03 (1H, s).

Reference Example 6

3-[(3-{[1-(triphenylmethyl)-1H-1,2,4-triazol-3-yl]thio}propyl)oxy]benzonitrile

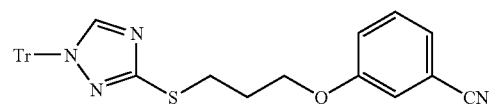

wherein Tr is triphenylmethyl, which is the same as in the other formulas in the present specification.

A solution of 3-{[3-(1H-1,2,4-triazol-3-ylthio)propyl]oxy}benzonitrile obtained in Reference Example 5 (4.00 g, 15.4 mmol), trityl chloride (6.43 g, 23.0 mmol) and triethylamine (2.33 g, 23.0 mmol) in THF (50 mL) was stirred at room temperature for 48 hr. The reaction mixture was concentrated under reduced pressure, and ethyl acetate and water were added to the residue. The organic layer was washed with saturated brine, dried over sodium sulfate, and concentrated. The obtained oil was purified by silica gel column chromatography (5%-40% ethyl acetate/hexane) to give the title compound as a white powder (3.52 g, 46%).

$^1$H-NMR (300 MHz, DMSO-d$_6$) δ: 2.00-2.09 (1H, m), 3.16 (2H, t, J=7.1 Hz), 4.02-4.09 (2H, m), 7.01-7.11 (6H, m), 7.19-7.49 (13H, m), 8.13 (1H, s)

Reference Example 7

1-{3-[(3-{[1-(triphenylmethyl)-1H-1,2,4-triazol-3-yl]thio}propyl)oxy]phenyl}methanamine

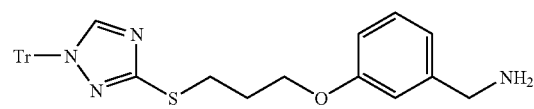

A solution of 3-[(3-{[1-(triphenylmethyl)-1H-1,2,4-triazol-3-yl]thio}propyl)oxy]benzonitrile obtained in Reference Example 6 (2.00 g, 3.98 mmol) in THF (15 mL) was added slowly to a suspension of lithium aluminum hydride (1.51 g, 39.8 mmol) in THF (45 mL) at room temperature, and the mixture was stirred at room temperature for 4 hr. Sodium hydrogensulfate 10 hydrate (5.13 g, 15.9 mmol) was added to the reaction mixture at 0° C., and mixture was stirred at room temperature for 30 min. The insoluble material was filtered off, and the filtrate was concentrated under reduced pressure. Toluene and ethanol were added to the residue, and the mixture was concentrated under reduced pressure to give the title compound as a pale-yellow oil (1.91 g, 95%).

$^1$H-NMR (300 MHz, DMSO-d$_6$) δ: 1.94-2.08 (2H, m), 3.16 (2H, t, J=7.1 Hz), 3.62-3.67 (2H, m), 3.97 (2H, t, J=6.1

Hz), 6.60-6.74 (1H, m), 6.82-6.92 (2H, m), 6.98-7.11 (6H, m), 7.12-7.45 (12H, m), 8.14 (1H, s).

Reference Example 8

3-[(4-chlorobutyl)oxy]benzonitrile

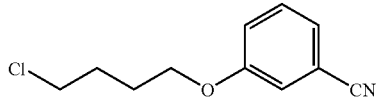

By a method similar to that in Reference Example 4 and using, instead of 1-bromo-3-chloropropane, 1-bromo-4-chlorobutane, the title compound was obtained as a colorless oil (8.33 g, 95%).

$^1$H-NMR (300 MHz, CDCl$_3$) δ: 1.94-2.02 (4H, m), 3.60-3.66 (2H, m), 4.02 (2H, t, J=5.4 Hz), 7.08-7.15 (2H, m), 7.21-7.27 (1H, m), 7.33-7.41 (1H, m).

Reference Example 9

3-{[4-(1H-1,2,4-triazol-3-ylthio)butyl]oxy}benzonitrile

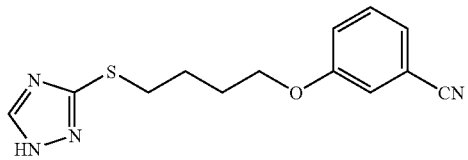

By a method similar to that in Reference Example 2 and using, instead of 3-[(2-chloroethyl)oxy]benzonitrile, 3-[(4-chlorobutyl)oxy]benzonitrile, the title compound was obtained as a white powder (7.25 g, 100%).

$^1$H-NMR (300 MHz, CDCl$_3$) δ: 1.87-2.02 (5H, m), 3.20-3.31 (2H, m), 3.96-4.05 (2H, m), 7.06-7.16 (2H, m), 7.20-7.27 (1H, m), 7.32-7.40 (1H, m), 8.13 (1H, s).

Reference Example 10

3-[(4-{[1-(triphenylmethyl)-1H-1,2,4-triazol-3-yl]thio}butyl)oxy]benzonitrile

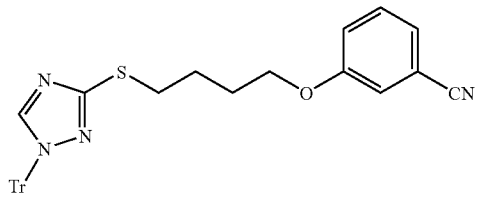

By a method similar to that in Reference Example 6 and using, instead of 3-{[3-(1H-1,2,4-triazol-3-ylthio)propyl]oxy}benzonitrile, 3-{[4-(1H-1,2,4-triazol-3-ylthio)butyl]oxy}benzonitrile obtained in Reference Example 9, the title compound was obtained as a white powder (10.7 g, 78%).

$^1$H-NMR (300 MHz, CDCl$_3$) δ: 1.81-1.89 (4H, m), 3.07-3.16 (2H, m), 3.83-3.90 (2H, m), 7.01-7.06 (2H, m), 7.11-7.17 (6H, m), 7.19-7.24 (1H, m), 7.28-7.36 (10H, m), 7.87 (1H, s).

Reference Example 11

1-{3-[(4-{[1-(triphenylmethyl)-1H-1,2,4-triazol-3-yl]thio}butyl)oxy]phenyl}methanamine

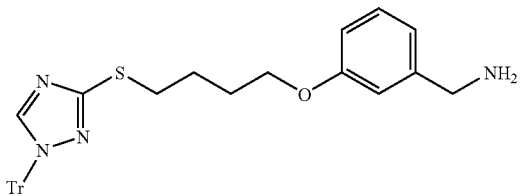

By a method similar to that in Reference Example 7 and using, instead of 3-[(3-{[1-(triphenylmethyl)-1H-1,2,4-triazol-3-yl]thio}propyl)oxy]benzonitrile, 3-[(4-{[1-(triphenylmethyl)-1H-1,2,4-triazol-3-yl]thio}butyl)oxy]benzonitrile obtained in Reference Example 10, the title compound was obtained as a yellow oil (8.65 g, 86%).

$^1$H-NMR (300 MHz, CDCl$_3$) δ: 1.79-1.89 (4H, m), 2.35 (2H, s), 3.09-3.16 (2H, m), 3.81 (2H, s), 3.85-3.93 (2H, m), 6.71 (1H, dd, J=8.1, 2.3 Hz), 6.81 (1H, s), 6.87 (1H, d, J=7.0 Hz), 7.08-7.37 (16H, m), 7.86 (1H, 5).

Reference Example 12 ethyl 3-[2-(aminocarbonothioyl)hydrazino]-3-oxopropanoate

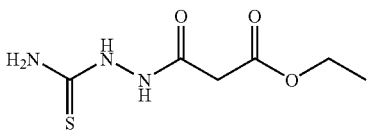

To a suspension of hydrazinecarbothioamide (15.0 g, 165 mmol) in pyridine (100 mL) was added dropwise ethyl 3-chloro-3-oxopropanoate (24.8 g, 165 mmol) over 30 min at 0° C., and the reaction solution was stirred at room temperature for 2 days. The reaction mixture was concentrated under reduced pressure, and methanol was added to the residue. The resulting solid was filtered off, the filtrate was concentrated under reduced pressure, and the residue was extracted with ethyl acetate, THF and saturated aqueous ammonium chloride solution. The organic layer was washed with saturated aqueous ammonium chloride solution, dried over sodium sulfate, and concentrated. The residue was crystallized from ethyl acetate and isopropyl ether, and the obtained crystals were washed with isopropyl ether, and dried to give the title compound (14.2 g, 42%).

$^1$H-NMR (300 MHz, DMSO-d$_6$) δ: 1.10-1.27 (3H, m), 3.28 (2H, s), 4.09 (2H, q, J=7.2 Hz), 7.36 (1H, s), 7.98 (1H, s), 9.38 (1H, s), 10.02 (1H, 5).

Reference Example 13 ethyl (5-mercapto-1H-1,2,4-triazol-3-yl)acetate

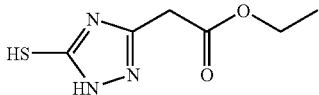

A suspension of ethyl 3-[2-(aminocarbonothioyl)hydrazino]-3-oxopropanoate (14.0 g, 68.2 mmol) and sodium ethoxide (9.52 g, 140 mmol) in ethanol (200 mL) was stirred at 80° C. for 15 hr. The mixture was concentrated under reduced pressure, and the residue was acidified with 1N hydrochloric acid, and extracted with ethyl acetate. The organic layer was washed with saturated brine, dried over sodium sulfate, and concentrated to give the title compound as an orange powder (12.2 g, 96%).

$^1$H-NMR (300 MHz, DMSO-d$_6$) δ: 1.20 (3H, t, J=7.1 Hz), 3.74 (2H, s), 4.12 (2H, q, J=7.0 Hz).

Reference Example 14 ethyl 1H-1,2,4-triazol-3-ylacetate

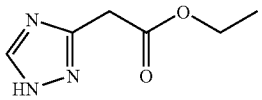

A suspension of ethyl (5-mercapto-1H-1,2,4-triazol-3-yl)acetate obtained in Reference Example 13 (2.00 g, 10.7 mmol) and Raney-nickel (5.00 g) in ethanol (20 mL) was stirred at 80° C. for 15 hr. The catalyst was filtered off, and the filtrate was concentrated under reduced pressure. To a suspension of the residue in ethyl acetate was added activated carbon, and the mixture was filtered. the filtrate was concentrated under reduced pressure to give the title compound as a pale-green powder (900 mg, 54%).

$^1$H-NMR (300 MHz, CDCl$_3$) δ: 1.32 (3H, t, J=6.8 Hz), 3.96 (2H, s), 4.26 (2H, q, J=6.5 Hz), 8.03 (1H, s), 11.53 (1H, brs).

Reference Example 15

1H-1,2,4-triazol-3-ylacetic acid

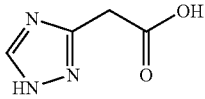

A mixture of ethyl 1H-1,2,4-triazol-3-ylacetate obtained in Reference Example 14 (900 mg, 5.80 mmol), 4N aqueous sodium hydroxide solution (7.25 mL, 29.0 mmol), water (10 mL), methanol (10 mL) and THF (10 mL) was stirred at 100° C. for 2 hr. The reaction mixture was concentrated under reduced pressure, and the residue was acidified with 1N hydrochloric acid, and the mixture was concentrated under reduced pressure. Ethanol was added to the residue, and the insoluble material was filtered off, and the filtrate was concentrated. The residue was crystallized from toluene to give the title compound as a white powder (369 mg, 50%).

$^1$H-NMR (300 MHz, DMSO-d$_6$) δ: 3.49 (2H, s), 7.92 (1H, s).

Reference Example 16

2-(1H-1,2,4-triazol-3-ylthio)ethanol

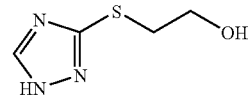

A solution of 1H-1,2,4-triazole-3-thiol (14.7 g, 145 mmol), 2-iodoethanol (25.0 g, 145 mmol) and triethylamine (14.7 g, 145 mmol) in ethanol (400 mL) was stirred at 80° C. for 15 hr. The reaction mixture was concentrated under reduced pressure, and the residue was acidified with water and 1N hydrochloric acid, and extracted with ethyl acetate. The organic layer was washed with saturated brine, dried over sodium sulfate, and concentrated. The obtained oil was purified by silica gel column chromatography (10%-100% ethyl acetate/hexane) to give the title compound as a colorless oil (7.30 g, 35%).

$^1$H-NMR (300 MHz, DMSO-d$_6$) δ: 3.08-3.26 (2H, m), 3.62 (2H, t, J=6.7 Hz), 8.38 (1H, s)

Reference Example 17

2-{[2-(1H-1,2,4-triazol-3-ylthio)ethyl]oxy}pyridine-4-carbonitrile

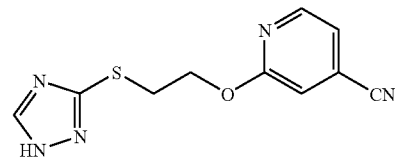

A solution of 2-(1H-1,2,4-triazol-3-ylthio)ethanol obtained in Reference Example 16 (7.34 g, 50.6 mmol) in DMF (50 mL) was added to a solution of 60% sodium hydride (oil dispersion, 4.91 g, 123 mmol) in DMF (50 mL) at 0° C. The mixture was stirred at 0° C. for 15 min, and then at room temperature for 30 min. A solution of 2-chloropyridine-4-carbonitrile (6.80 g, 49.1 mmol) in DMF (50 mL) was added at 0° C., and the mixture was stirred at 0° C. for 15 min, and then at room temperature for 2 hr. The mixture was neutralized with 1N hydrochloric acid, and extracted with ethyl acetate. The organic layer was washed with saturated brine, dried over sodium sulfate, and concentrated. The residue was purified by silica gel column chromatography (10%-80% ethyl acetate/hexane) to give the title compound as a white powder (4.01 g, 33%).

$^1$H-NMR (300 MHz, DMSO-d$_6$) δ: 3.48 (2H, t, J=6.5 Hz), 4.56 (2H, t, J=6.5 Hz), 7.38 (1H, s), 7.42 (1H, dd, J=5.3, 1.3 Hz), 8.38 (1H, dd, J=5.3, 0.8 Hz), 8.46 (1H, brs), 14.08 (1H, brs).

Reference Example 18

1-(2-{[2-(1H-1,2,4-triazol-3-ylthio)ethyl]oxy}pyridin-4-yl)methanamine hydrochloride

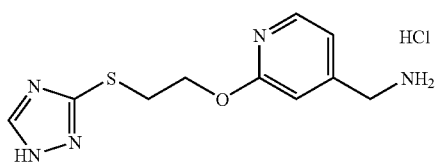

A suspension of 2-{[2-(1H-1,2,4-triazol-3-ylthio)ethyl]oxy}pyridine-4-carbonitrile obtained in Reference Example 17 (3.80 g, 15.4 mmol) and Raney-nickel (19.0 g) in 7N ammonia/methanol (100 mL) was stirred at room temperature for 5 hr under hydrogen atmosphere (1 atm). The catalyst was filtered off, and the filtrate was concentrated under reduced pressure. 2N Hydrogen chloride/ethanol solution (20 mL) was added to the residue, and the mixture was stirred at room temperature for 2 hr, and concentrated under reduced pressure. The obtained solid was stirred under heating in ethanol at 90° C. for 2 hr to give the title compound as a white powder (1.27 g, 33%).

$^1$H-NMR (300 MHz, DMSO-$d_6$) δ: 3.51 (2H, t, J=6.3 Hz), 4.03 (2H, g, J=5.7 Hz), 4.52 (2H, t, J=6.4 Hz), 7.00 (1H, s), 7.15 (1H, dd, J=5.3, 1.1 Hz), 8.16 (1H, d, J=5.3 Hz), 8.61 (1H, s), 8.75 (3H, s).

Reference Example 19

2-[(2-{[1-(triphenylmethyl)-1H-1,2,4-triazol-3-yl]thio}ethyl)oxy]pyridine-4-carbonitrile

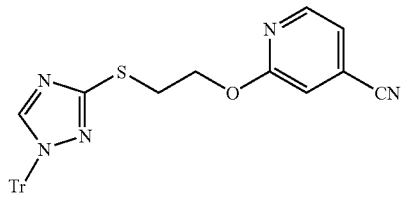

A solution of 2-{[2-(1H-1,2,4-triazol-3-ylthio)ethyl]oxy}pyridine-4-carbonitrile obtained in Reference Example 17 (3.40 g, 13.7 mmol), trityl chloride (5.73 g, 20.6 mmol) and triethylamine (2.87 mL, 20.6 mmol) in THF (30 mL) was stirred at room temperature for 15 hr. The mixture was concentrated under reduced pressure, and the residue was extracted with ethyl acetate and water. The organic layer was washed with saturated brine, dried over sodium sulfate, and concentrated. The obtained oil was purified by silica gel column chromatography (20%-40% ethyl acetate/hexane) to give the title compound as a white powder (5.37 g, 80%).

$^1$H-NMR (300 MHz, DMSO-$d_6$) δ: 3.22-3.31 (1H, m), 3.42 (1H, t, J=6.5 Hz), 4.18 (1H, t, J=6.4 Hz), 4.48 (1H, t, J=6.4 Hz), 7.06 (7H, dd, J=6.6, 2.8 Hz), 7.25-7.45 (11H, m), 8.15 (1H, s).

Reference Example 20

1-{2-[(2-{[1-(triphenylmethyl)-1H-1,2,4-triazol-3-yl]thio}ethyl)oxy]pyridin-4-yl}methanamine

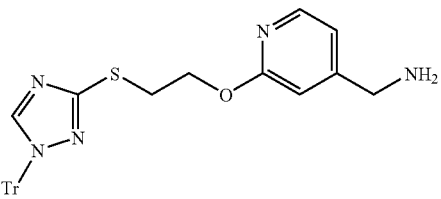

A solution of 2-[(2-{[1-(triphenylmethyl)-1H-1,2,4-triazol-3-yl]thio}ethyl)oxy]pyridine-4-carbonitrile obtained in Reference Example 19 (5.00 g, 10.2 mmol) in THF (40 mL) was added to a suspension of lithium aluminum hydride (0.775 g, 20.4 mmol) in THF (60 mL) at 0° C., and the mixture was stirred at room temperature for 7 hr. The mixture was cooled to 0° C., water and 1N aqueous sodium hydroxide solution were added, and the insoluble material was filtered off. The filtrate was dried over sodium sulfate, and concentrated. The obtained oil was purified by silica gel column chromatography (0-20% methanol/ethyl acetate) to give the title compound as a yellow oil (2.06 g, 41%).

$^1$H-NMR (300 MHz, DMSO-$d_6$) δ: 3.10 (2H, t, J=6.6 Hz), 3.51-3.64 (2H, m), 4.94 (2H, t, J=5.6 Hz), 6.95-7.48 (20H, m), 8.12 (1H, s).

Reference Example 21 ethyl 3-(5-mercapto-1H-1,2,4-triazol-3-yl)propanoate

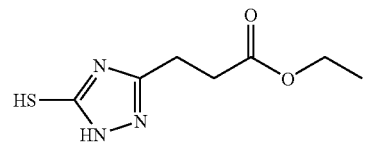

Step 1

By a method similar to that in Reference Example 12 and using, instead of ethyl 3-chloro-3-oxopropanoate, ethyl 4-chloro-4-oxobutanoate, ethyl 4-[2-(aminocarbonothioyl)hydrazino]-4-oxobutanoate was obtained as a white powder (16.8 g, 35%).

Step 2

A suspension of ethyl 4-[2-(aminocarbonothioyl)hydrazino]-4-oxobutanoate (16.8 g, 76.7 mmol) and sodium ethoxide (10.4 g, 153 mmol) in ethanol (200 mL) was stirred at 80° C. for 15 hr. The mixture was concentrated under reduced pressure, and the residue was acidified with 1N hydrochloric acid, and extracted with ethyl acetate. The organic layer was washed with saturated brine, dried over sodium sulfate, and concentrated to give the title compound as a white powder (14.0 g, 91%).

$^1$H-NMR (300 MHz, DMSO-$d_6$) δ: 1.01-1.28 (3H, m), 2.64-2.83 (4H, m), 4.05 (2H, q, J=7.2 Hz), 13.10 (1H, brs), 13.21 (1H, brs).

Reference Example 22

3-(1H-1,2,4-triazol-3-yl)propanoic acid

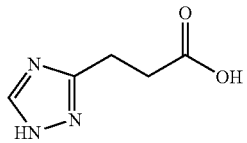

ethyl 3-(5-mercapto-1H-1,2,4-triazol-3-yl)propanoate obtained in Reference Example 21 (650 mg, 3.23 mmol) was added slowly to a mixed solution of sodium nitrite (8.91 mg, 0.129 mmol), nitric acid (3 mL) and water (6 mL) while keeping 45° C. or less. The solution was stirred at room temperature for 15 hr, and neutralized with saturated aqueous sodium carbonate solution. The mixture was concentrated under reduced pressure, and the residue was crystallized from THF, and washed with THF. Ethanol was added thereto, and the insoluble material was filtered off. The filtrate was concentrated under reduced pressure to give the title compound as a pale-yellow powder (454 mg, 99%).

$^1$H-NMR (300 MHz, DMSO-$d_6$) δ: 2.24 (2H, t, J=7.5 Hz), 2.80 (2H, t, J=7.5 Hz), 7.82 (1H, s).

Reference Example 23 ethyl 3-(1H-1,2,4-triazol-3-yl)propanoate

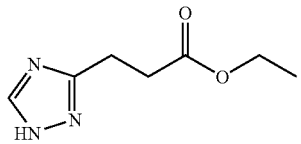

A suspension of 3-(1H-1,2,4-triazol-3-yl)propanoic acid obtained in Reference Example 22 (11.6 g, 3.54 mmol) and 2N hydrogen chloride/ethanol (100 mL) in ethanol (100 mL) was stirred at 90° C. for 15 hr. The insoluble material was filtered off, and the filtrate was concentrated under reduced pressure. The residue was extracted with ethyl acetate and water. The aqueous layer was neutralized with saturated aqueous sodium carbonate solution, and the organic layer was washed with saturated brine, dried over sodium sulfate, and concentrated to give the title compound as a yellow powder (4.36 g, 33%).

$^1$H-NMR (300 MHz, DMSO-$d_6$) δ: 1.11-1.20 (3H, m), 2.72 (2H, d, J=1.7 Hz), 2.92 (2H, s), 4.00-4.08 (2H, m), 7.79 (1H, s), 13.59 (1H, brs).

Reference Example 24 ethyl 3-[1-(triphenylmethyl)-1H-1,2,4-triazol-3-yl]propanoate

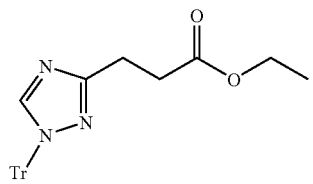

By a method similar to that in Reference Example 6 and using, instead of 3-{[3-(TH-1,2,4-triazol-3-ylthio)propyl]oxy}benzonitrile, ethyl 3-(1H-1,2,4-triazol-3-yl)propanoate obtained in Reference Example 23, the title compound was obtained as a white powder (773 mg, 32%).

$^1$H-NMR (300 MHz, DMSO-$d_6$) δ: 1.10 (3 Hr t, J=7.2 Hz), 2.67 (2H, t, J=7.1 Hz), 2.90 (2H, t, J=7.0 Hz), 3.98 (2H, q, J=6.9 Hz), 6.99-7.08 (6H, m), 7.34-7.40 (9H, m), 7.95 (1H, s).

Reference Example 25

3-[1-(triphenylmethyl)-1H-1,2,4-triazol-3-yl]propanoic acid

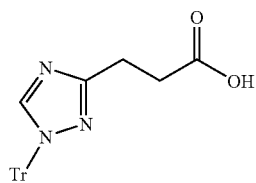

By a method similar to that in Reference Example 15 and using, instead of ethyl 1H-1,2,4-triazol-3-ylacetate, ethyl 3-[1-(triphenylmethyl)-1H-1,2,4-triazol-3-yl]propanoate obtained in Reference Example 24, the title compound was obtained as a white powder (175 mg, 85%).

$^1$H-NMR (300 MHz, DMSO-$d_6$) δ: 2.59 (2H, t, J=7.3 Hz), 2.86 (2H, t, J=7.3 Hz), 7.04 (6H, dd, J=6.7, 2.9 Hz), 7.33-7.45 (9H, m), 7.93 (1H, s), 12.17 (1H, brs).

Reference Example 26

3-[1-(triphenylmethyl)-1H-1,2,4-triazol-3-yl]propan-1-ol

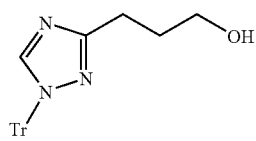

A solution of ethyl 3-[1-(triphenylmethyl)-1H-1,2,4-triazol-3-yl]propanoate obtained in Reference Example 24 (700 mg, 1.70 mmol) in THF (5 mL) was added to a suspension of lithium aluminum hydride (84.0 mg, 2.21 mmol) in THF (5 mL) at 0° C., and the mixture was stirred at 0° C. for 5 hr, and then at room temperature for 15 hr. Water and 1N aqueous sodium hydroxide solution were added to the mixture, and the insoluble material was filtered off. The filtrate was concentrated under reduced pressure, and the residue was purified by silica gel column chromatography (0-80% ethyl acetate/hexane) to give the title compound as a white powder (289 mg, 46%).

$^1$H-NMR (300 MHz, DMSO-$d_6$) δ: 1.70-1.83 (2H, m), 2.65 (2H, t, J=7.5 Hz), 3.36-3.45 (2H, m), 4.44 (1H, t, J=5.2 Hz), 7.00-7.09 (6H, m), 7.33-7.41 (9H, m), 7.95 (1H, s).

Reference Example 27

2-({3-[1-(triphenylmethyl)-1H-1,2,4-triazol-3-yl]propyl}oxy)pyridine-4-carbonitrile

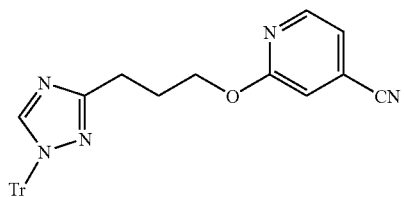

By a method similar to that in Reference Example 17 and using, instead of 2-(1H-1,2,4-triazol-3-ylthio)ethanol, 3-[1-(triphenylmethyl)-1H-1,2,4-triazol-3-yl]propan-1-ol obtained in Reference Example 26, the title compound was obtained as a white powder (314 mg, 88%).

$^1$H-NMR (300 MHz, DMSO-$d_6$) δ: 2.03-2.14 (2H, m), 2.79 (2H, t, J=7.3 Hz), 4.30 (2H, t, J=6.4 Hz), 7.04 (6H, dd, J=6.4, 3.2 Hz), 7.31-7.41 (11H, m), 7.99 (1H, s), 8.38 (1H, d, J=5.1 Hz).

Reference Example 28

1-[2-({3-[1-(triphenylmethyl)-1H-1,2,4-triazol-3-yl]propyl}oxy)pyridin-4-yl]methanamine

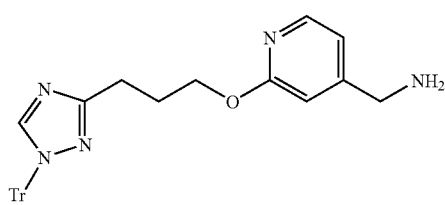

By a method similar to that in Reference Example 20 and using, instead of 2-[(2-{[1-(triphenylmethyl)-1H-1,2,4-triazol-3-yl]thio}ethyl)oxy]pyridine-4-carbonitrile, 2-({3-[1-(triphenylmethyl)-1H-1,2,4-triazol-3-yl]propyl}oxy)pyridine-4-carbonitrile obtained in Reference Example 27, the title compound was obtained as a yellow oil (67 mg, 27%).

$^1$H-NMR (300 MHz, DMSO-$d_6$) δ: 2.00-2.12 (2H, m), 2.77 (2H, t, J=7.3 Hz), 3.67 (2H, s), 4.23 (2H, t, J=6.5 Hz), 6.75 (1H, s), 6.91 (1H, dd, J=5.2, 1.0 Hz), 6.99-7.08 (6H, m), 7.29-7.40 (9H, m), 7.97 (1H, s), 8.02 (1H, d, J=5.3 Hz).

Reference Example 29 ethyl [(3-cyanophenyl)oxy]acetate

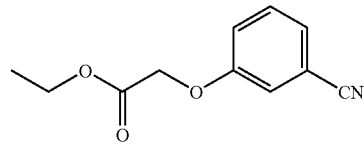

Ethyl bromoacetate (14.7 g, 88.1 mmol) was added dropwise to a suspension of potassium carbonate (12.8 g, 92.3 mmol) and 3-hydroxybenzonitrile (10.0 g, 83.9 mmol) in THF (50 mL) at room temperature, and the mixture was stirred at 50° C. for 24 hr. The mixture was extracted with ethyl acetate and saturated aqueous ammonium chloride solution, and the organic layer was washed with saturated brine, dried over sodium sulfate, and concentrated to give the title compound as a pale-yellow powder (17.5 g, 99%).

$^1$H-NMR (300 MHz, CDCl$_3$) δ: 1.31 (3H, t, J=7.2 Hz), 4.29 (2H, q, J=7.1 Hz), 4.65 (2H, s), 7.13-7.18 (2H, m), 7.28-7.32 (1H, m), 7.36-7.44 (1H, m).

Reference Example 30

3-[(2-hydroxyethyl)oxy]benzonitrile

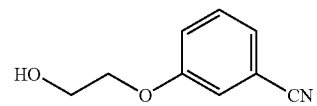

A suspension of ethyl [(3-cyanophenyl)oxy]acetate obtained in Reference Example 29 (8.00 g, 39.0 mmol) and sodium borohydride (1.47 g, 39.0 mmol) in ethanol (120 mL) was stirred at 50° C. for 15 hr, and the mixture was concentrated under reduced pressure. The residue was extracted with ethyl acetate and water, and the organic layer was washed with saturated brine, dried over sodium sulfate, and concentrated to give the title compound as a white powder (5.85 g, 92%).

$^1$H-NMR (300 MHz, CDCl$_3$) δ: 1.67 (1H, brs), 3.97-4.02 (2H, m) 4.08-4.13 (2H, m), 7.13-7.20 (2H, m), 7.24-7.30 (1H, m), 7.35-7.43 (1H, m).

Reference Example 31

3-[(2-{[1-(triphenylmethyl)-1H-1,2,4-triazol-3-yl]oxy}ethyl)oxy]benzonitrile

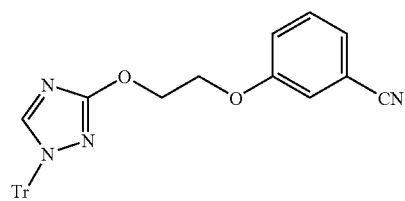

A solution of 3-[(2-hydroxyethyl)oxy]benzonitrile obtained in Reference Example 30 (19.2 g, 118 mmol) in THF (100 mL) was added dropwise to a suspension of 3-nitro-1-(triphenylmethyl)-1H-1,2,4-triazole obtained in Reference Example 33 (40.0 g, 112 mmol) and 60% sodium hydride (oil dispersion, 6.06 g, 151.52 mmol) in THF (300 mL), and the mixture was stirred at room temperature for 12 hr. The mixture was cooled to 0° C., and extracted with water and ethyl acetate. The organic layer was washed with saturated brine, dried over sodium sulfate, and concentrated. The residue was purified by silica gel column chromatography (0-30% ethyl acetate/hexane) to give the title compound as a white powder (25.0 g, 46%).

$^1$H-NMR (300 MHz, CDCl$_3$) δ: 4.23-4.29 (2H, m), 4.56-4.63 (2H, m), 7.07-7.41 (19H, m), 7.67 (1H, s).

Reference Example 32

1-{3-[(2-([1-(triphenylmethyl)-1H-1,2,4-triazol-3-yl]oxy)ethyl)oxy}phenyl]methanamine

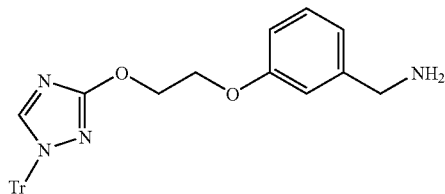

By a method similar to that in Reference Example 20 and using, instead of 2-[(2-{[1-(triphenylmethyl)-1H-1,2,4-triazol-3-yl]thio}ethyl)oxy]pyridine-4-carbonitrile, 3-[(2-{[1-(triphenylmethyl)-1H-1,2,4-triazol-3-yl]oxy}ethyl)oxy]benzonitrile obtained in Reference Example 31, the title compound was obtained as a colorless oil (504 mg, 99%).

$^1$H-NMR (300 MHz, DMSO-d$_6$) δ: 1.58-2.00 (2H, m), 3.66 (2H, s), 4.20-4.27 (2H, m), 4.45 (2H, dd, J=5.5, 3.4 Hz), 6.75 (1H, dd, J=8.1, 2.1 Hz), 6.86-6.96 (2H, m), 7.06-7.14 (6H, m), 7.19 (1H, t, J=7.8 Hz), 7.34-7.44 (9H, m), 7.86 (1H, s).

Reference Example 33

3-nitro-1-(triphenylmethyl)-1H-1,2,4-triazole

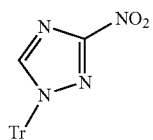

A solution of 3-nitro-1H-1,2,4-triazole (1.00 g, 8.77 mmol), trityl chloride (4.89 g, 17.5 mmol) and diisopropylethylamine (3.05 mL, 17.5 mmol) in THF (50 mL) was stirred at room temperature for 15 hr. The mixture was concentrated under reduced pressure, and the residue was extracted with ethyl acetate and water. The organic layer was washed with saturated brine, dried over sodium sulfate, and concentrated. The residue was purified by silica gel column chromatography (15-30% ethyl acetate/hexane) to give the title compound as a white powder (2.90 g, 93%).

$^1$H-NMR (300 MHz, CDCl$_3$) δ: 7.08-7.17 (6H, m), 7.33-7.47 (9H, m), 8.04 (1H, s).

Reference Example 34 methyl 1-(triphenylmethyl)-1H-1,2,4-triazole-3-carboxylate

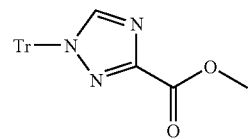

By a method similar to that in Reference Example 33 and using, instead of 3-nitro-1H-1,2,4-triazole, methyl 1H-1,2,4-triazole-3-carboxylate, the title compound was obtained as a white powder (17.0 g, 59%).

$^1$H-NMR (300 MHz, DMSO-d$_6$) δ: 3.84 (3H, s), 7.07 (6H, dd, J=6.8, 2.8 Hz), 7.34-7.46 (9H, m), 8.39 (1H, s).

Reference Example 35

1-(triphenylmethyl)-1H-1,2,4-triazole-3-carboxylic acid

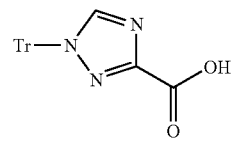

By a method similar to that in Reference Example 15 and using, instead of ethyl 1H-1,2,4-triazol-3-ylacetate, methyl 1-(triphenylmethyl)-1H-1,2,4-triazole-3-carboxylate obtained in Reference Example 34, the title compound was obtained as a white powder (2.82 g, 98%).

$^1$H-NMR (300 MHz, DMSO-d$_6$) δ: 7.07 (6H, dd, J=6.9, 2.9 Hz), 7.30-7.56 (9H, m), 8.31 (1H, s), 13.49 (1H, s).

Reference Example 36

[1-(triphenylmethyl)-1H-1,2,4-triazol-3-yl]methanol

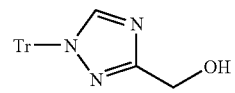

By a method similar to that in Reference Example 26 and using, instead of ethyl 3-[1-(triphenylmethyl)-1H-1,2,4-triazol-3-yl]propanoate, methyl 1-(triphenylmethyl)-1H-1,2,4-triazole-3-carboxylate obtained in Reference Example 34, the title compound was obtained as a white powder (5.35 g, 58%).

$^1$H-NMR (300 MHz, DMSO-d$_6$) δ: 4.44 (2H, d, J=6.0 Hz), 5.29-5.35 (1H, m), 7.03-7.10 (6H, m), 7.36-7.42 (9H, m), 8.04 (1H, s).

Reference Example 37

3-[({[1-(triphenylmethyl)-1H-1,2,4-triazol-3-yl]methyl}oxy)methyl]benzonitrile

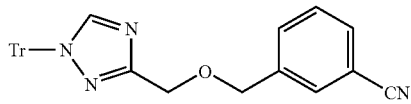

A suspension of [1-(triphenylmethyl)-1H-1,2,4-triazol-3-yl]methanol obtained in Reference Example 36 (3.00 g, 8.79 mmol), 3-(bromomethyl)benzonitrile (1.89 g, 9.67 mmol) and 60% sodium hydride (oil dispersion, 0.316 g, 13.2 mmol) in THF (100 mL) was stirred at 70° C. for 15 hr. The reaction mixture was cooled to room temperature, and extracted with water and ethyl acetate. The organic layer was washed with saturated brine, dried over sodium sulfate, and concentrated. The residue was purified by silica gel column chromatography (10-30% ethyl acetate/hexane) to give the title compound as a colorless oil (3.50 g, 87%).

$^1$H-NMR (300 MHz, DMSO-$d_6$) δ: 4.54 (2H, s), 4.57 (2H, s), 7.04-7.11 (6H, m), 7.35-7.43 (9H, m), 7.51-7.64 (2H, m), 7.68 (1H, s), 7.76 (1H, d, J=7.3 Hz), 8.16 (1H, s).

Reference Example 38

1-{3-[({[1-(triphenylmethyl)-1H-1,2,4-triazol-3-yl]methyl}oxy)methyl]phenyl}methanamine

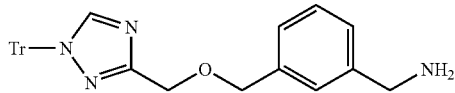

By a method similar to that in Reference Example 20 and using, instead of 2-[(2-{([1-(triphenylmethyl)-1H-1,2,4-triazol-3-yl]thio}ethyl)oxy]pyridine-4-carbonitrile, 3-[({[1-(triphenylmethyl)-1H-1,2,4-triazol-3-yl]methyl}oxy)methyl]benzonitrile obtained in Reference Example 37, the title compound was obtained as a pale-yellow oil (1.96 g, 67%).

$^1$H-NMR (300 MHz, DMSO-$d_6$) δ: 1.96 (2H, brs), 3.68 (2H, s), 4.46 (2H, s), 4.52 (2H, s), 6.97-7.17 (7H, m), 7.16-7.31 (3H, m), 7.33-7.47 (9H, m), 8.14 (1H, 5).

Reference Example 39 ethyl 4-oxo-5-(2-thienyl)-3,4-dihydrothieno[2,3-d]pyrimidine-2-carboxylate

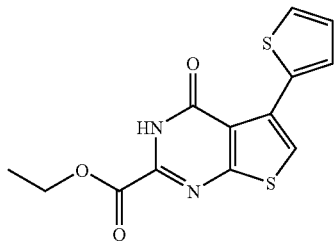

Ethyl 5'-amino-2,3'-bithiophene-4'-carboxylate (3.00 g, 11.842 mmol) was suspended in 1N hydrogen chloride-acetic acid solution (30 mL), ethyl cyanoformate (1.29 g, 13.026 mmol) was added, and the mixture was stirred under heating at 90° C. for 2 hr. The reaction mixture was allowed to cool to room temperature, and concentrated under reduced pressure. The residue was suspended in diethyl ether, and the insoluble material was collected by filtration, washed with water to give the title compound as a brown powder (3.21 g, 88%).

$^1$H-NMR (300 MHz, DMSO-$d_6$) δ: 1.36 (3H, t, J=7.1 Hz), 4.39 (2H, q, J=7.2 Hz), 7.12 (1H, dd, J=5.1, 3.6 Hz), 7.57 (1H, dd, J=5.1, 1.3 Hz), 7.65 (1H, dd, J=3.6, 1.3 Hz), 7.87 (1H, s), 12.89 (1H, brs).

Reference Example 40 ethyl 5-furan-2-yl-4-oxo-3,4-dihydrothieno[2,3-d]pyrimidine-2-carboxylate

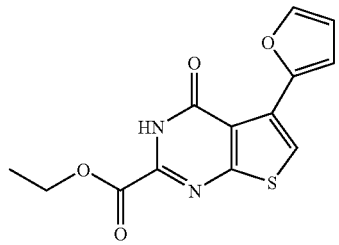

By a method similar to that in Reference Example 39 and using, instead of ethyl 5'-amino-2,3'-bithiophene-4'-carboxylate, ethyl 2-amino-4-furan-2-ylthiophene-3-carboxylate, the title compound was obtained as a brown powder (2.85 g, 47%).

$^1$H-NMR (300 MHz, DMSO-$d_6$) δ: 1.36 (3H, t, J=7.1 Hz), 4.38 (2H, q, J=7.1 Hz), 6.60 (1H, dd, J=3.4, 1.9 Hz), 7.57 (1H, d, J=3.2 Hz), 7.76 (1H, d, J=1.1 Hz), 7.95 (1H, s), 12.93 (1H, brs).

Reference Example 41 ethyl 4-[(3-cyanophenyl)oxy]butanoate

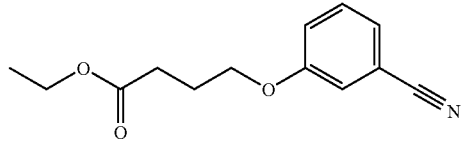

Step 1

A solution of 4-bromobutanoic acid (25.0 g, 150 mmol), DMF (5 drops) and oxalyl chloride (17.0 mL, 195.0 mmol) in dichloromethane (250 mL) was stirred at room temperature for 5 hr. The reaction mixture was concentrated under reduced pressure, dichloromethane (200 mL) and ethanol (9.0 mL, 170 mmol) were added to the residue, and the mixture was stirred at room temperature for 15 hr. The reaction mixture was washed with saturated aqueous sodium hydrogencarbonate and saturated brine, and the organic layer was dried over sodium sulfate, and concentrated. The residue was purified by silica gel column chromatography (0-5% ethyl acetate/hexane) to give ethyl 4-bromobutanoate as a colorless oil (24.5 g, 84%).

Step 2

A suspension of 3-hydroxybenzonitrile (5.00 g, 42.0 mmol) and 60% sodium hydride (oil dispersion, 2.01 g, 50.3 mmol) in DMF (200 mL) was stirred at room temperature for 30 min, ethyl 4-bromobutanoate (9.82 g, 50.3 mmol) was added thereto, and the mixture was stirred at room temperature for 15 hr. The mixture was allowed to cool to room temperature, and concentrated under reduced pressure. The residue was extracted with ethyl acetate and saturated aqueous ammonium chloride solution. The organic layer was washed with saturated aqueous ammonium chloride solution and saturated brine, dried over sodium sulfate, and concentrated. The obtained residue was purified by silica gel column chromatography (0-10% ethyl acetate/hexane) to give the title compound as a colorless oil (10.2 g, 100%).

$^1$H-NMR (300 MHz, CDCl$_3$) δ: 1.27 (3H, t, J=7.2 Hz), 2.13 (2H, tt, J=6.7, 6.7 Hz), 2.52 (2H, t, J=7.2 Hz), 4.03 (2H, t, J=6.1 Hz), 4.16 (2H, q, J=7.2 Hz), 7.08-7.16 (2H, m), 7.21-7.26 (1H, m), 7.32-7.40 (1H, m).

Reference Example 42 ethyl 4-{[3-(aminomethyl)phenyl]oxy}butanoate hydrochloride

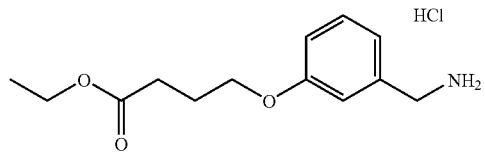

A mixture of ethyl 4-[(3-cyanophenyl)oxy]butanoate obtained in Reference Example 41 (8.50 g, 36.4 mmol), 10% palladium carbon (containing 50% water)(12.8 g), formic acid (98 mL) and methanol (80 mL) was stirred at room temperature for 5 hr under hydrogen atmosphere (1 atm). The precipitate was filtered off, and the filtrate was concentrated under reduced pressure. 4N Hydrogen chloride/ethyl acetate solution (15.0 mL, 60.0 mmol) was added to the obtained residue, and the mixture was stirred, and concentrated under reduced pressure. The residue was crystallized from toluene, and the crude crystals were recrystallized from diethyl ether to give the title compound as a white powder (7.79 g, 78%).

$^1$H-NMR (300 MHz, DMSO-d$_6$) δ: 1.18 (3H, t, J=7.2 Hz), 1.98 (2H, tt, J=6.8, 6.8 Hz), 2.46 (2H, t, J=7.3 Hz), 3.95-4.03 (4H, m), 4.07 (2H, q, J=7.1 Hz), 6.92 (1H, dd, J=8.2, 2.2 Hz), 7.04 (1H, d, J=7.3 Hz), 7.12 (1H, s), 7.31 (1H, t, J=7.9 Hz), 8.26 (3H, s).

Reference Example 43 ethyl 4-{[3-({[(4-oxo-3,4-dihydroquinazolin-2-yl)carbonyl]amino}methyl)phenyl]oxy}butanoate

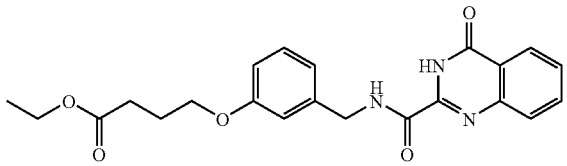

By a method similar to that in Example 1 and using, instead of 1-(3-{[2-(1H-1,2,4-triazol-3-ylthio)ethyl]oxy}phenyl)methaneamine, ethyl 4-{[3-(aminomethyl)phenyl]oxy}butanoate hydrochloride obtained in Reference Example 42, the title compound was obtained as a white powder (807 mg, 86%).

$^1$H-NMR (300 MHz, DMSO-d$_6$) δ: 1.15 (3H, t, J=7.1 Hz), 1.89-2.01 (2H, m), 2.44 (2H, t, J=7.3 Hz), 3.96 (2H, t, J=6.3 Hz), 4.04 (2H, q, J=7.0 Hz), 4.45 (2H, d, J=6.2 Hz), 6.77-6.84 (1H, m), 6.88-6.94 (2H, m), 7.19-7.27 (1H, m), 7.57-7.65 (1H, m), 7.75-7.81 (1H, m), 7.84-7.94 (1H, m), 8.17 (1H, dd, J=7.9, 1.1 Hz), 9.54 (1H, t, J=6.3 Hz), 12.29 (1H, brs).

Reference Example 44

4-{[3-({[(4-oxo-3,4-dihydroquinazolin-2-yl)carbonyl]amino}methyl)phenyl]oxy}butanoic acid

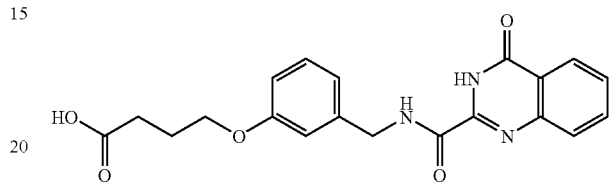

A mixture of ethyl 4-{[3-({[(4-oxo-3,4-dihydroquinazolin-2-yl)carbonyl]amino}methyl)phenyl]oxy}butanoate obtained in Reference Example 43 (525 mg, 1.28 mmol), 4N aqueous sodium hydroxide solution (1.6 mL), THF (10 mL), methanol (10 mL) and water (10 mL) was stirred at 100° C. for 2 hr. The mixture was allowed to cool to room temperature, and the solvent was evaporated under reduced pressure. Water and 1N hydrochloric acid (6.41 mL) were added to the residue, and the resulting precipitate was collected by filtration, washed with water, and dried. The obtained crude crystals were recrystallized from ethanol to give the title compound as a white powder (339 mg, 69%).

$^1$H-NMR (300 MHz, DMSO-d$_6$) δ: 1.85-1.99 (2H, m), 2.37 (2H, t, J=7.3 Hz), 3.96 (2H, t, J=6.4 Hz), 4.45 (2H, d, J=6.4 Hz), 6.76-6.86 (1H, m), 6.88-6.96 (2H, m), 7.23 (1H, t, J=8.1 Hz), 7.56-7.67 (1H, m), 7.75-7.82 (1H, m), 7.83-7.93 (1H, m), 8.18 (1H, dd, J=7.9, 1.1 Hz), 9.55 (1H, t, J=6.3 Hz), 12.21 (2H, s).

Reference Example 45

N-[(3-aminophenyl)methyl]-6-cyano-4-oxo-3,4-dihydroquinazoline-2-carboxamide

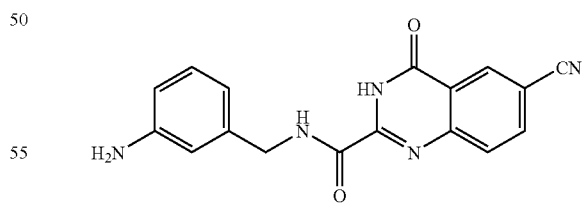

A suspension of ethyl 6-cyano-4-oxo-3,4-dihydroquinazoline-2-carboxylate obtained in Reference Example 51 (1.00 g, 4.11 mmol) and 3-(aminomethyl)aniline (0.753 g, 6.17 mmol) in THF (15 mL) was stirred at 80° C. for 15 hr. The reaction mixture was cooled to room temperature, IPE was added, and the insoluble material was filtered off. The filtrate was concentrated under reduced pressure, and the obtained crude crystals were recrystallized from ethyl acetate-IPE to give the title compound as a white powder (899 mg, 69%).

¹H-NMR (300 MHz, DMSO-d₆) δ: 4.34 (2H, d, J=6.2 Hz), 5.11 (2H, s), 6.40-6.56 (3H, m), 6.95 (1H, t, J=7.6 Hz), 7.88 (1H, d, J=8.5 Hz), 8.23 (1H, dd, J=8.5, 1.9 Hz), 8.55 (1H, d, J=1.5 Hz), 9.50 (1H, t, J=6.2 Hz), 12.48 (1H, s).

Reference Example 46

1,1-dimethylethyl {[3-({[(6-cyano-4-oxo-3,4-dihydroquinazolin-2-yl) carbonyl]amino}methyl)phenyl]methyl}carbamate

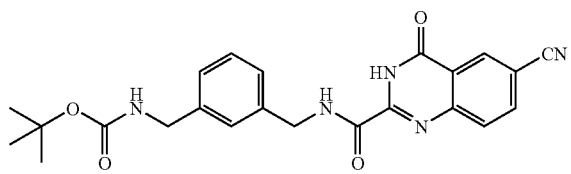

By a method similar to that in Reference Example 45 and using, instead of 3-(aminomethyl)aniline, 1,1-dimethylethyl {[3-(aminomethyl)phenyl]methyl}carbamate, the title compound was obtained as a white powder (2.36 g, 88%).

¹H-NMR (300 MHz, DMSO-d₆) δ: 1.34 (9H, s), 4.10 (2H, d, J=6.0 Hz), 4.47 (2H, d, J=5.8 Hz), 7.07-7.42 (5H, m), 7.88 (1H, d, J=8.9 Hz), 8.22 (1H, d, J=9.4 Hz), 8.54 (1H, s), 9.65 (1H, s), 12.65 (1H, s).

Reference Example 47

N-{[3-(aminomethyl)phenyl]methyl}-6-cyano-4-oxo-3,4-dihydroquinazoline-2-carboxamide hydrochloride

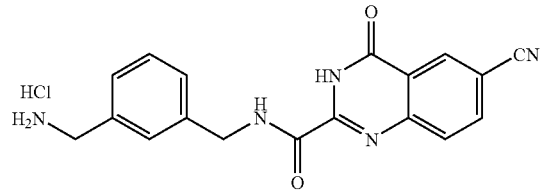

To a suspension of 1,1-dimethylethyl {[3-({[(6-cyano-4-oxo-3,4-dihydroquinazolin-2-yl)carbonyl]amino}methyl)phenyl]methyl}carbamate obtained in Reference Example 46 (2.14 g, 4.94 mmol) in ethyl acetate (5 mL) was added 4N hydrogen chloride/ethyl acetate (60 mL), and the mixture was stirred at room temperature for 15 hr. The reaction mixture was concentrated under reduced pressure, and the residue was crystallized from toluene. The obtained crude crystals were suspended in ethyl acetate, and the suspension was stirred under heating for 3 hr to give the title compound as a white powder (1.86 g, 99%).

¹H-NMR (300 MHz, DMSO-d₆) δ: 3.91-4.09 (2H, m), 4.51 (2H, d, J=6.4 Hz), 7.31-7.46 (4H, m), 7.90 (1H, d, J=8.7 Hz), 8.25 (1H, dd, J=8.5, 2.1 Hz), 8.36 (3H, brs), 8.54-8.58 (1H, m), 9.63-9.75 (1H, m), 12.73 (1H, brs).

Reference Example 48

N-[(3-aminophenyl)methyl]-5-methyl-4-oxo-3,4-dihydrothieno[2,3-d]pyrimidine-2-carboxamide

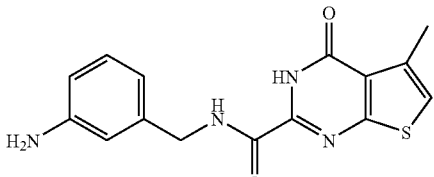

By a method similar to that in Reference Example 45 and using, instead of ethyl 6-cyano-4-oxo-3,4-dihydroquinazoline-2-carboxylate, ethyl 5-methyl-4-oxo-3,4-dihydrothieno[2,3-d]pyrimidine-2-carboxylate obtained according to the method described in U.S. Pat. No. 4,054,656, the title compound was obtained as a yellow powder (1.92 g, 97%).

¹H-NMR (300 MHz, DMSO-d₆) δ: 3.33 (3H, s), 4.30 (2H, d, J=6.2 Hz), 5.03 (2H, s), 6.40-6.52 (3H, m), 6.94 (1H, t, J=7.7 Hz), 7.31 (1H, d, J=1.3 Hz), 9.48 (1H, t, J=6.3 Hz), 12.20 (1H, s).

Reference Example 49

1,1-dimethylethyl {[3-({[(5-methyl-4-oxo-3,4-dihydrothieno[2,3-d]pyrimidin-2-yl)carbonyl]amino}methyl)phenyl]methyl}carbamate

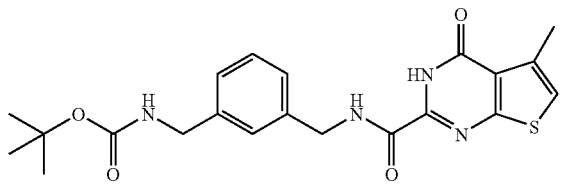

By a method similar to that in Reference Example 45, and using, instead of ethyl 6-cyano-4-oxo-3,4-dihydroquinazoline-2-carboxylate, ethyl 5-methyl-4-oxo-3,4-dihydrothieno[2,3-d]pyrimidine-2-carboxylate obtained according to the method described in U.S. Pat. No. 4,054,656 and using, instead of 3-(aminomethyl)aniline, 1,1-dimethylethyl {[3-(aminomethyl)phenyl]methyl}carbamate, the title compound was obtained as a white powder (2.11 g, 82%).

¹H-NMR (300 MHz, DMSO-d₆) δ: 1.35 (9H, s), 2.47-2.53 (3H, m), 4.10 (2H, d, J=6.2 Hz), 4.43 (2H, d, J=6.4 Hz), 7.08-7.41 (6H, m), 9.62 (1H, t, J=6.3 Hz), 12.25 (1H, s).

Reference Example 50

N-{[3-(aminomethyl)phenyl]methyl}-5-methyl-4-oxo-3,4-dihydrothieno[2,3-d]pyrimidine-2-carboxamide hydrochloride

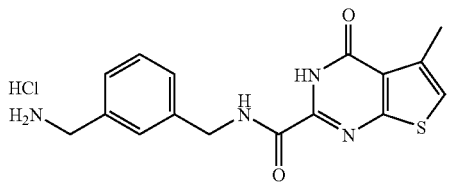

By a method similar to that in Reference Example 47 and using, instead of 1,1-dimethylethyl {[3-({[(6-cyano-4-oxo-3,4-dihydroquinazolin-2-yl)carbonyl]amino}methyl)phenyl]methyl}carbamate, 1,1-dimethylethyl {[3-({[(5-methyl-4-oxo-3,4-dihydrothieno[2,3-d]pyrimidin-2-yl)carbonyl]amino}methyl)phenyl]methyl}carbamate obtained in Reference Example 49, the title compound was obtained as a white powder (1.39 g, 3.80 mmol).

$^1$H-NMR (300 MHz, DMSO-d$_6$) δ: 2.47-2.53 (3H, m), 3.99 (2H, s), 4.46 (2H, d, J=6.4 Hz), 7.25-7.52 (5H, m), 9.58 (3H, brs), 9.67 (1H, t, J=6.4 Hz).

Reference Example 51 ethyl 6-cyano-4-oxo-3,4-dihydroquinazoline-2-carboxylate

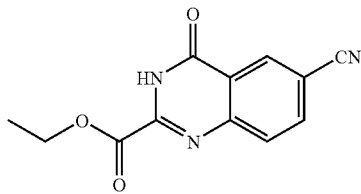

Step 1

To a solution of 5-iodoanthranilic acid (25.0 g, 95.0 mmol) in THF (400 mL) was added bis(trichloromethyl) carbonate (9.40 g, 31.7 mmol), and the mixture was stirred under heating at 60° C. for 15 hr. The reaction mixture was concentrated under reduced pressure, and 2N aqueous ammonia (235 mL) was added thereto. The mixture was stirred under heating at 60° C. for 2 hr, and extracted with ethyl acetate. The organic layer was washed with saturated brine, dried over sodium sulfate, and concentrated under reduced pressure. The residue was suspended in diisopropyl ether, and the insoluble material was collected by filtration to give 2-amino-5-iodobenzamide as a white powder (15.9 g, 64%).

Step 2

To a solution of 2-amino-5-iodobenzamide (15.8 g, 60.3 mmol) and triethylamine (7.32 g, 72.4 mmol) in THF (300 mL) was added dropwise ethyl chloroglyoxylate (9.05 g, 66.3 mmol) under ice-cooling, and the mixture was stirred at room temperature for 2 hr. Water was added to the reaction mixture, and the precipitated insoluble material was collected by filtration. The solid was washed with water to give ethyl ((2-(aminocarbonyl)-4-iodophenyl)amino)(oxo)acetate as a white powder (20.9 g, 96%).

Step 3

To a suspension of ethyl ((2-(aminocarbonyl)-4-iodophenyl)amino)(oxo)acetate (20.9 g, 57.7 mmol) in ethanol (300 mL) was added dropwise sodium ethylate (20% ethanol solution, 21.6 g, 63.5 mmol) under ice-cooling, and the mixture was stirred at room temperature for 1 hr. The reaction mixture was poured into 0.3N hydrochloric acid (600 mL) under ice-cooling, and the precipitated insoluble material was collected by filtration. The filtered cake was washed with water and ethanol to give ethyl 6-iodo-4-oxo-3,4-dihydroquinazoline-2-carboxylate as a pale-pink powder (17.0 g, 86%).

$^1$H-NMR (200 MHz, DMSO-d$_6$) δ: 1.35 (3H, t, J=7.0 Hz), 4.38 (2H, q, J=7.0 Hz), 7.61 (1H, d, J=8.5 Hz), 8.18 (1H, dd, J=8.5, 2.0 Hz), 8.44 (1H, d, J=2.0 Hz).

Step 4

A suspension of ethyl 6-iodo-4-oxo-3,4-dihydroquinazoline-2-carboxylate (2.00 g, 5.81 mmol), zinc cyanide (375 mg, 3.19 mmol) and tetrakis(triphenylphosphine)palladium (336 mg, 0.29 mmol) in DMF (10 mL) was stirred at 80° C. for 5 hr under argon atmosphere. After cooling to room temperature, ethyl acetate was added to the reaction mixture. The precipitated solid was collected by filtration, washed with ethyl acetate, diisopropyl ether and water, dried over diphosphorus pentaoxide under reduced pressure to give the title compound as a pale-yellow powder (965 mg, 68%).

$^1$H-NMR (200 MHz, DMSO-d$_6$) δ: 1.35 (3H, t, J=6.8 Hz), 4.39 (2H, q, J=6.8 Hz), 7.96 (1H, d, J=8.4 Hz), 8.23 (1H, dd, J=8.4, 1.8 Hz), 8.55 (1H, d, J=1.8 Hz).

Reference Example 52 ethyl 6-fluoro-4-oxo-3,4-dihydroquinazoline-2-carboxylate

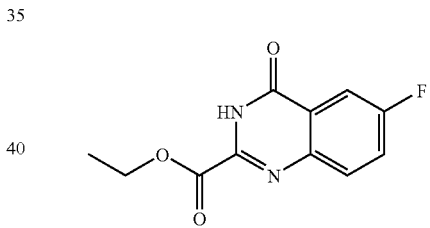

Step 1

To a solution of 2-amino-5-fluorobenzamide (2.00 g, 13.0 mmol) and triethylamine (1.45 g, 14.3 mmol) in THF (40 mL) was added dropwise ethyl chloroglyoxylate (1.95 g, 14.3 mmol) under ice-cooling, and the mixture was stirred at room temperature for 2 hr. The reaction mixture was diluted with ethyl acetate, washed with water and saturated brine, dried over sodium sulfate, and concentrated under reduced pressure. The residue was washed with ethanol to give ethyl ((2-(aminocarbonyl)-4-fluorophenyl)amino)(oxo)acetate as a white powder (2.88 g, 87%).

Step 2

To a suspension of ethyl ((2-(aminocarbonyl)-4-fluorophenyl)amino)(oxo)acetate (1.50 g, 5.90 mmol) in ethanol (30 mL) was added dropwise sodium ethylate (20% ethanol solution, 2.40 g, 7.08 mmol) under ice-cooling, and the mixture was stirred for 2 hr. The reaction mixture was adjusted to pH 3-4 with 1N hydrochloric acid, and the precipitated insoluble material was collected by filtration. The filtered cake was washed with water and ethanol to give the title compound as a white powder (1.05 g, 75%).

$^1$H-NMR (200 MHz, DMSO-d$_6$) δ: 1.36 (3H, t, J=7.2 Hz), 4.39 (2H, q, J=7.2 Hz), 7.77-7.97 (3H, m).

Reference Example 53 ethyl 6-(methyloxy)-4-oxo-3,4-dihydroquinazoline-2-carboxylate

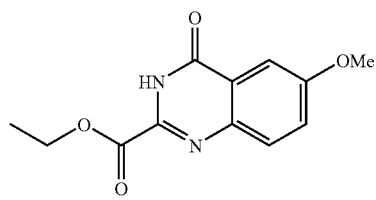

wherein Me is methyl, which is the same as in the other formulas in the present specification.

Step 1

To a solution of 5-methoxy-2-nitrobenzoic acid (18.0 g, 91.3 mmol) and DMF (0.1 mL) in THF (150 mL) was added dropwise oxalyl chloride (12.7 g, 100 mmol) under ice-cooling, and the mixture was stirred at 0° C. for 1 hr, and then at room temperature for 3 hr. This solution was added dropwise to aqueous ammonia (7% aqueous solution, 200 mL) under ice-cooling. The reaction solution was concentrated under reduced pressure to evaporated THF, and the precipitated insoluble material was collected by filtration. The filtered cake was washed with water to give 5-methoxy-2-nitrobenzamide as a pale-yellow powder (10.0 g, 56%).

Step 2

To a solution of 5-methoxy-2-nitrobenzamide (9.70 g, 49.4 mmol) in methanol (250 mL) was added 10% palladium carbon (2.00 g), and the mixture was stirred under hydrogen atmosphere (1 atm) at room temperature for 6 hr. The insoluble material was filtered off, and the filtrate was concentrated to give 2-amino-5-methoxybenzamide as a pale-yellow powder (8.20 g, 99%).

Step 3

To a solution of 2-amino-5-methoxybenzamide (1.50 g, 9.03 mmol) and triethylamine (1.00 g, 9.93 mmol) in THF (40 mL) was added dropwise ethyl chloroglyoxylate (1.36 g, 9.93 mmol) under ice-cooling, and the mixture was stirred at room temperature for 2 hr. Water was added to the reaction mixture, and the precipitated insoluble material was collected by filtration. The filtered cake was washed with water and ethanol to give ethyl ((2-(aminocarbonyl)-4-methoxyphenyl)amino)(oxo)acetate as a pale-yellow powder (2.42 g, 100%).

Step 4

To a suspension of ethyl ((2-(aminocarbonyl)-4-methoxyphenyl)amino)(oxo)acetate (1.50 g, 5.63 mmol) in ethanol (30 mL) was added dropwise sodium ethylate (20% ethanol solution, 2.30 g, 6.76 mmol) under ice-cooling, and the mixture was stirred for 2 hr. The reaction mixture was adjusted to pH 3-4 with 1N hydrochloric acid, and the precipitated insoluble material was collected by filtration. The filtered cake was washed with water and ethanol to give the title compound as a white powder (1.04 g, 74%).

$^1$H-NMR (2001 MHz, DMSO-$d_6$) δ: 1.35 (3H, t, J=7.2 Hz), 3.91 (3H, s), 4.38 (2H, q, J=7.2 Hz), 7.49 (1H, dd, J=8.8, 3.0 Hz), 7.57 (1H, d, J=3.0 Hz), 7.79 (1H, d, J=8.8 Hz).

Reference Example 54 ethyl 6-chloro-4-oxo-3,4-dihydro-2-quinazolinecarboxylate

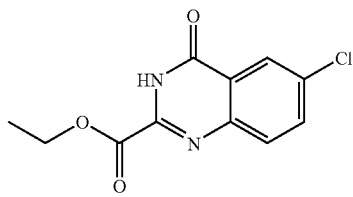

2-Amino-5-chlorobenzamide (2.387 g) and diethyl oxalate were stirred at 175° C. for 6 hr. The mixture was allowed to cool, and the obtained crude crystals were washed with hot ethanol to give the title compound (2.051 g, 58%).

melting point: 249-251° C.

Reference Example 55 ethyl 6-methyl-4-oxo-3,4-dihydroquinazoline-2-carboxylate

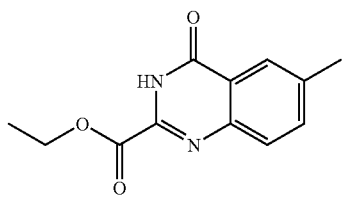

Step 1

To a solution of 5-methyl-2-nitrobenzoic acid (17.0 g, 93.8 mmol) and DMF (0.1 mL) in THF (150 mL) was added dropwise oxalyl chloride (13.1 g, 103 mmol) under ice-cooling, and the mixture was stirred at room temperature for 3 hr. This solution was added dropwise to aqueous ammonia (8% aqueous solution, 210 mL) under ice-cooling. The reaction solution was concentrated under reduced pressure to evaporated THF, and the precipitated insoluble material was collected by filtration. The filtered cake was washed with water to give 5-methyl-2-nitrobenzamide as a pale-yellow powder (15.3 g, 90%).

Step 2

To a solution of 5-methyl-2-nitrobenzamide (15.0 g, 83.3 mmol) in methanol (300 mL) was added 10% palladium carbon (2.50 g), and the mixture was stirred at room temperature for 12 hr under hydrogen atmosphere (1 atm). The insoluble material was filtered off, and the filtrate was concentrated to give 2-amino-5-methylbenzamide as a white powder (12.4 g, 99%).

Step 3

To a solution of 2-amino-5-methylbenzamide (5.80 g, 38.6 mmol) and triethylamine (4.69 g, 46.3 mmol) in THF (200 mL) was added dropwise ethyl chloroglyoxylate (5.80 g, 42.5 mmol) under ice-cooling, and the mixture was stirred at room temperature for 3 hr. The reaction mixture was diluted with ethyl acetate, washed with water and saturated brine, dried over sodium sulfate, and concentrated under reduced pressure. The residue was washed with ethanol to give ethyl ((2-(aminocarbonyl)-4-methylphenyl)amino)(oxo)acetate as a white powder (9.83 g, 100%).

Step 4

To a suspension of ethyl ((2-(aminocarbonyl)-4-methylphenyl)amino)(oxo)acetate (4.90 g, 19.6 mmol) in ethanol (100 mL) was added dropwise sodium ethylate (20% ethanol solution, 7.33 g, 21.5 mmol) under ice-cooling, and the mixture was stirred at room temperature for 2 hr. The reaction mixture was poured into 0.25N hydrochloric acid (200 mL) under ice-cooling, and the precipitated insoluble material was collected by filtration. The filtered cake was washed with water and ethanol to give the title compound as a pale-orange powder (2.90 g, 64%).

$^1$H-NMR (200 MHz, DMSO-$d_6$) δ: 1.36 (3H, t, J=7.2 Hz), 2.48 (3H, s), 4.39 (2H, g, J=7.2 Hz), 7.69-7.79 (2H, m), 7.98 (1H, s).

Reference Example 56 ethyl 6-amino-4-oxo-3,4-dihydro-2-quinazolinecarboxylate

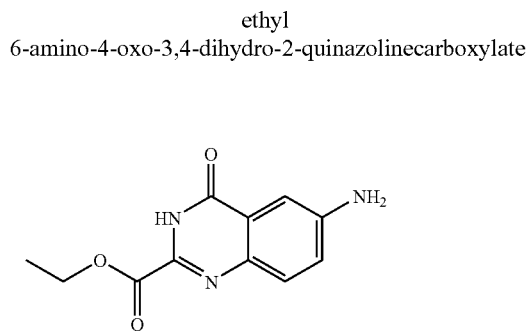

Step 1

A mixture of 2-amino-5-nitrobenzonitrile (25.4 g) and sulfuric acid (70 mL) was stirred at 130° C. for 40 min. The reaction mixture was added slowly to ice water, and the precipitate was collected by filtration, washed with water, ethanol and diethyl ether to give 2-amino-5-nitrobenzamide (24.6 g).

Step 2

To a solution of 2-amino-5-nitrobenzamide (18.1 g) and triethylamine (15 mL) in THF (100 mL) was added dropwise a solution of ethyl chloroglyoxylate (14.4 g) in THF (20 mL) under ice-cooling, and the mixture was stirred at 0° C. for 1 hr. 1N Hydrochloric acid was added to the reaction mixture, and the mixture was extracted with ethyl acetate. The organic layer was washed with water, saturated aqueous sodium hydrogencarbonate and saturated brine, dried, and concentrated. The obtained crude crystals were washed with diisopropyl ether to give ethyl {[2-(aminocarbonyl)-4-nitrophenyl]amino}(oxo)acetate (8.1 g).

$^1$H-NMR (300 MHz, DMSO-$d_6$) δ: 1.37 (3H, t, J=7.1 Hz), 3.33 (3H, s), 4.41 (2H, q, J=7.1 Hz), 8.03 (1H, d, J=8.8 Hz), 8.59 (1H, dd, J=8.8, 2.7 Hz), 8.83 (1H, d, J=2.2 Hz).

Step 3

To a solution of ethyl {[2-(aminocarbonyl)-4-nitrophenyl]amino}(oxo)acetate (2.292 g) in a mixed solvent of THF (100 mL)-ethanol (50 mL) was added 10% palladium carbon (405 mg), and the mixture was subjected to catalytic reduction under hydrogen atmosphere at room temperature for 8 hr. The catalyst was filtered off, and the filtrate was concentrated. The obtained crude crystals were washed with diisopropyl ether to give ethyl {[4-amino-2-(aminocarbonyl)phenyl]amino}(oxo)acetate (1.96 g, 96%).

Step 4

To a solution of ethyl {[4-amino-2-(aminocarbonyl)phenyl]amino}(oxo)acetate (1.96 g) in a mixed solvent of THF (60 ml)-ethanol (30 mL) was added dropwise sodium ethylate (20% ethanol solution, 2.82 g), and the mixture was stirred at room temperature for 12 hr. 10% Aqueous citric acid solution was added to the reaction mixture, and the mixture was extracted with ethyl acetate. The organic layer was dried and concentrated, and the obtained crude crystals were washed with diisopropyl ether to give the title compound (738 mg).

melting point: 233-235° C.

Reference Example 57 ethyl 5,6-difluoro-4-oxo-3,4-dihydroquinazoline-2-carboxylate

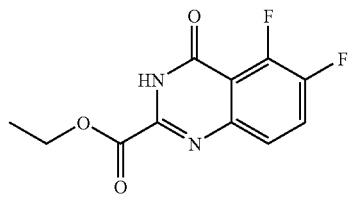

Step 1

To a solution of tert-butyl (3,4-difluorophenyl)carbamate synthesized according to the method described in document (Tetrahedron, 1992, 48, 7373) (5.00 g, 21.3 mmol) in THF (50 mL) was added dropwise n-butyllithium (1.6M hexane solution, 30 mL, 48.0 mmol) at −78° C., and the mixture was stirred at −78° C. for 3 hr. A solution of ethyl chlorocarbonate (2.60 g, 24.0 mmol) in THF (15 mL) was added to the reaction mixture, and the mixture was stirred at −78° C. for 1 hr. Saturated aqueous ammonium chloride solution (50 mL) was added, and the mixture was partitioned between ethyl acetate and water. The organic layer was washed with saturated brine, dried over sodium sulfate, and concentrated under reduced pressure to give a yellow oil (7.14 g). The obtained oil was dissolved in ethyl acetate (10 mL), 4N hydrogen chloride-ethyl acetate solution (40 mL) was added thereto, and the mixture was stirred at room temperature for 3 hr. Diethyl ether (20 mL) was added to the reaction mixture, and the insoluble material was collected by filtration. The solid was washed with ethanol and ether to give ethyl 5,6-difluoroanthranilate hydrochloride as a white powder (2.91 g, 70% in two steps).

Step 2

Ethyl 5,6-difluoroanthranilate hydrochloride (2.50 g, 10.5 mmol) was suspended in 1N hydrogen chloride-acetic acid solution (50 mL), ethyl cyanoformate (1.14 g, 11.6 mmol) was added thereto, and the mixture was stirred under heating at 80° C. for 3 hr. The reaction mixture allowed to cool to room temperature, and concentrated under reduced pressure. The residue was suspended in ethanol, and the insoluble material was collected by filtration to give the title compound as a white powder (2.18 g, 82%).

$^1$H-NMR (300 MHz, DMSO-$d_6$) δ: 1.35 (3H, t, J=7.2 Hz), 4.38 (2H, q, J=7.2 Hz), 7.70 (1H, ddd, J=9.0, 7.5, 2.1 Hz), 7.92-8.02 (1H, m), 12.78 (1H, brs).

Reference Example 58 ethyl 5-methyl-4-oxo-3,4-dihydroquinazoline-2-carboxylate

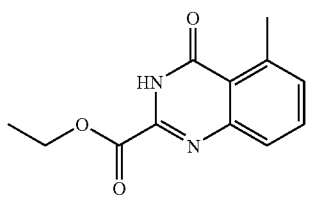

Step 1

To a solution of 6-methylanthranilic acid (10.2 g, 67.5 mmol) in THF (100 mL) was added bis(trichloromethyl) carbonate (6.67 g, 22.5 mmol), and the mixture was stirred under heating at 50° C. for 15 hr, and the reaction mixture was concentrated under reduced pressure. 6N Aqueous ammonia (100 mL) was added thereto, and the mixture was stirred under heating at 60° C. for 3 hr, and extracted with ethyl acetate. The organic layer was washed with saturated brine, dried over sodium sulfate, and concentrated under reduced pressure. The residue was suspended in disopropyl ether, and the insoluble material was collected by filtration to give 2-amino-6-methylbenzamide as a pale-yellow powder (1.35 g, 13%).

Step 2

To a solution of 2-amino-6-methylbenzamide (1.28 g, 8.52 mmol) and triethylamine (1.03 g, 10.2 mmol) in THF (30 mL) was added dropwise ethyl chloroglyoxylate (1.28 g, 9.38 mmol) under ice-cooling, and the mixture was stirred at room temperature for 3 hr, and extracted with ethyl acetate. The organic layer was washed with saturated brine, dried over sodium sulfate, and concentrated under reduced pressure. The residue was suspended in diisopropyl ether-ethanol, and the insoluble material was collected by filtration to give ethyl ((2-(aminocarbonyl)-3-methylphenyl)amino)(oxo)acetate as a white powder (1.85 g, 87%).

Step 3

To a suspension of ethyl ((2-(aminocarbonyl)-3-methylphenyl)amino)(oxo)acetate (760 mg, 3.04 mmol) in ethanol (15 mL) was added dropwise sodium ethylate (20% ethanol solution, 1.14 g, 3.34 mmol) under ice-cooling, and the mixture was stirred at room temperature for 2 hr. 1N Hydrochloric acid (5 mL) was added to the reaction mixture, and the mixture was extracted with ethyl acetate. The organic layer was washed with saturated brine, dried over sodium sulfate, and concentrated under reduced pressure. The residue was suspended in diisopropyl ether-ethanol, and the insoluble material was collected by filtration to give the title compound as a white powder (450 mg, 64%).

$^1$H-NMR (200 MHz, DMSO-$d_6$) δ: 1.36 (3H, t, J=7.2 Hz), 2.79 (3H, s), 4.37 (2H, q, J=7.2 Hz), 7.37 (1H, d, J=7.5 Hz), 7.61 (1H, d, J=7.5 Hz), 7.70 (1H, t, J=7.5 Hz), 12.35 (1H, brs).

Reference Example 59 ethyl 5-fluoro-4-oxo-3,4-dihydroquinazoline-2-carboxylate

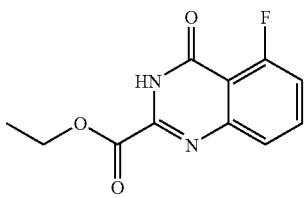

Step 1

To a solution of 2-amino-6-fluorobenzamide (3.80 g, 24.7 mmol) and triethylamine (2.99 g, 29.6 mmol) in THF (50 mL) was added dropwise ethyl chloroglyoxylate (3.70 g, 27.1 mmol) under ice-cooling, and the mixture was stirred at room temperature for 3 hr. The mixture was partitioned between ethyl acetate and water, and the organic layer was washed with saturated brine, dried over sodium sulfate, and concentrated under reduced pressure. The residue was suspended in ethanol, and the insoluble material was collected by filtration to give ethyl ((2-(aminocarbonyl)-3-fluorophenyl)amino)(oxo)acetate as a white powder (4.95 g, 79%).

Step 2

To a suspension of ethyl ((2-(aminocarbonyl)-3-fluorophenyl)amino)(oxo)acetate (2.45 g, 9.64 mmol) in ethanol (50 mL) was added dropwise sodium ethylate (20% ethanol solution, 3.61 g, 10.6 mmol) under ice-cooling, and the mixture was stirred at room temperature for 1 hr. 1N Hydrochloric acid (20 mL) was added to the reaction mixture, and the insoluble material was collected by filtration. The solid was washed with water and diethyl ether to give the title compound as a pale-yellow powder (1.29 g, 57%).

$^1$H-NMR (200 MHz, DMSO-$d_6$) δ: 1.35 (3H, t, J=7.2 Hz), 4.37 (2H, q, J=7.2 Hz), 7.34-7.41 (1H, m), 7.62 (1H, d, J=8.1 Hz), 7.81-7.89 (1H, m), 12.64 (1H, brs).

Reference Example 60 ethyl 4-oxo-3,4-dihydrothieno[2,3-d]pyrimidine-2-carboxylate

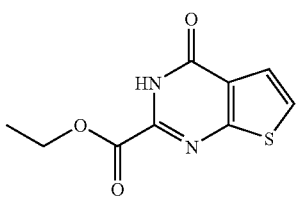

Step 1

A solution of 2,5-dihydroxy-1,4-dithiane (11.8 g, 155 mmol), cyanoacetamide (17.0 g, 202 mmol) and triethylamine (20 ml) in ethanol (100 mL) was stirred under heating at 70° C. for 4 hr. The reaction mixture was cooled to room temperature, and concentrated under reduced pressure to an about half volume. Water was added to the residue, the precipitated insoluble material was collected by filtration, and the solid was washed with water to give 2-amino-3-thiophenecarboxamide as a brown powder (15.3 g, 69%).

¹H-NMR (200 MHz, DMSO-d₆) δ: 6.22 (1H, d, J=6.0 Hz), 7.04 (1H, d, J=6.0 Hz), 7.21 (2H, brs).

Step 2

To a solution of 2-amino-3-thiophenecarboxamide (5.00 g, 35.2 mmol) and triethylamine (5.39 mL, 38.7 mmol) in THF (200 mL) was added dropwise ethyl chloroglyoxylate (4.81 g, 35.2 mmol) under ice-cooling, and the mixture was stirred at room temperature for 1 hr. The mixture was partitioned between ethyl acetate and water, and the organic layer was washed with saturated brine, dried over sodium sulfate, and concentrated under reduced pressure. The residue was suspended in ethanol, and the insoluble material was collected by filtration to give ethyl (3-(aminocarbonyl)-2-thiopheneamino)(oxo)acetate as a pale-yellow powder (8.32 g, 97%).

¹H-NMR (200 MHz, DMSO-d₆) δ: 1.32 (3H, t, J=7.0 Hz), 4.33 (2H, q, J=7.0 Hz), 7.15 (1H, d, J=6.0 Hz), 7.50 (1H, d, J=6.0 Hz), 7.67 (1H, bs), 8.03 (1H, brs).

Step 3

To a suspension of ethyl (3-(aminocarbonyl)-2-thiopheneamino)(oxo)acetate (2.00 g, 8.26 mmol) in xylene (50 mL) was added p-toluenesulfonic acid monohydrate (314 mg, 1.65 mmol), and the mixture was heated under reflux for 3 hr. p-Toluenesulfonic acid monohydrate (200 mg, 1.05 mmol) was added again, and the mixture was heated under reflux for 8 hr. The reaction mixture was diluted with ethyl acetate, washed with water and saturated brine, dried over sodium sulfate, and concentrated under reduced pressure. The residue was purified by silica gel column chromatography (67% ethyl acetate/hexane) to give the title compound as a pale-yellow powder (531 mg, 29%).

¹H-NMR (200 MHz, DMSO-d₆) δ: 1.35 (3H, t, J=7.2 Hz), 4.38 (2H, q, J=7.2 Hz), 7.49 (1H, d, J=5.6 Hz), 7.81 (1H, d, J=5.6 Hz).

Reference Example 61 ethyl 5-(cyanomethyl)-4-oxo-3,4-dihydrothieno[2,3-d]pyrimidine-2-carboxylate

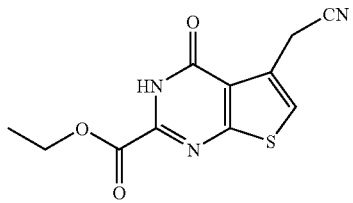

Step 1

A mixture of ethyl 5-methyl-4-oxo-3,4-dihydrothieno[2,3-d]pyrimidine-2-carboxylate obtained according to the method described in U.S. Pat. No. 4,054,656 (1.00 g, 4.20 mmol), N-bromosuccinimide (784 mg, 4.41 mmol), 2,2'-azobis-isobutyronitrile (68.9 mg, 0.420 mmol) and carbon tetrachloride (30 mL) was heated under reflux for 3 hr. The solvent was evaporated under reduced pressure, and the obtained residue was extracted with ethyl acetate. The organic layer was washed with water (×3) and saturated brine, and dried over anhydrous sodium sulfate. The solvent was evaporated, and the obtained crude crystals were recrystallized from ethyl acetate to give ethyl 5-(bromomethyl)-4-oxo-3,4-dihydrothieno[2,3-d]pyrimidine-2-carboxylate (662 mg, 50%) as a pale-yellow powder.

melting point: 176° C.

Step 2

To a mixture of ethyl 5-(bromomethyl)-4-oxo-3,4-dihydrothieno[2,3-d]pyrimidine-2-carboxylate (2000 mg, 6.31 mmol) in DMF (10 mL) was added sodium cyanide (649 mg, 13.2 mmol) at room temperature, and the mixture was stirred for 12 hr. The reaction mixture was acidified with 1N hydrochloric acid, and extracted with ethyl acetate. The organic layer was washed with water and saturated brine, dried over anhydrous sodium sulfate, and concentrated under reduced pressure. The residue was crystallized from ethyl acetate to give the title compound as a pale-brown powder (300 mg, 18%).

melting point: 183° C.

¹H-NMR (300 MHz, DMSO-d₆) δ: 1.35 (3H, t, J=7.2 Hz), 4.27 (2H, d, J=1.1 Hz), 4.37 (2H, q, J=7.0 Hz), 7.75 (1H, s), 13.00 (1H, s).

Reference Example 62 ethyl 5-{[([4-[(ethyloxy)carbonyl]phenyl}methyl)oxy]methyl]-4-oxo-3,4-dihydrothieno[2,3-d]pyrimidine-2-carboxylate

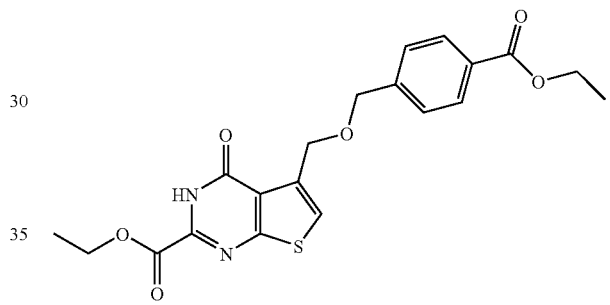

Step 1

To a mixture of 60% sodium hydride (oil dispersion, 1.39 g, 36.4 mmol) and THF (43 mL) was added dropwise a solution of ethyl 5-(bromomethyl)-4-oxo-3,4-dihydrothieno[2,3-d]pyrimidine-2-carboxylate obtained in Step 1 of Reference Example 61 (5.49 g, 17.3 mmol) and ethyl 4-(hydroxymethyl)benzoate (3.27 g, 18.2 mmol) obtained according to the methods described in J. Am. Chem. Soc. (2004), 126(23), 7186-7187 and the like in THF (72 mL) at 0° C. The reaction mixture was stirred for 1 hr, and added dropwise to a mixture of 2N hydrochloric acid (210 mL), ethyl acetate (70 mL) and dry ice. After adding dropwise, the mixture was added to ethyl acetate (700 mL), washed with saturated brine, dried over anhydrous sodium sulfates and concentrated under reduced pressure. Diethyl ether was added to the residue, and the precipitated solid was collected by filtration. To a solution of the obtained solid in THF (58 mL) were added oxalyl chloride (1.51 mL, 17.3 mmol) and DMF (one drop), and the mixture was stirred at room temperature for 20 min, and concentrated under reduced pressure. THE (30 mL), ethanol (30 mL) and pyridine (3.50 mL, 43.3 mmol) were added to the residue, and the mixture was stirred at room temperature for 30 min, and concentrated under reduced pressure. Diethyl ether and 1N hydrochloric acid were added to the residue, and the precipitated solid was collected by filtration, washed with 1N hydrochloric acid (×3), water (×4) and diethyl ether (×3), and dried to give a pale-yellow powder (5.17 g). The obtained solid (3.52 g) and 4N aqueous sodium hydroxide solution (10.6 mL, 42.3 mmol) were suspended in water (45 mL), methanol (45 mL) and THF (45 mL), and the mixture was stirred at 90° C. for 1 hr, and concentrated under reduced pressure. The residue was acidified with 1N hydrochloric acid (10.6 mL), and extracted with THF (1000 mL). The organic layer was washed with 1N hydrochloric acid and saturated brine, dried over anhydrous sodium sulfate, and concentrated under reduced pressure. The residue was crystallized from a mixed solvent of methanol-THF to give 5-({[(4-carboxyphenyl)methyl]oxy}methyl)-4-oxo-3,4-dihydrothieno[2,3-d]pyrimidine-2-carboxylic acid as a pale-yellow powder (2.88 g, 46%).

melting point: 248° C.

$^1$H-NMR (300 MHz, DMSO-d$_6$) δ: 4.74 (2H, s), 4.89 (2H, d, J=0.9 Hz), 7.51 (2H, d, J=8.3 Hz), 7.67 (1H, s), 7.94 (2H, d, J=8.1 Hz), 12.61 (1H, s), 12.94 (1H, s).

Step 2

To a mixture of 5-({[(4-carboxyphenyl)methyl]oxy}methyl)-4-oxo-3,4-dihydrothieno[2,3-d]pyrimidine-2-carboxylic acid (2.88 g, 7.99 mmol) and THF (30 mL) were added oxalyl chloride (4.60 mL, 52.7 mmol) and DMF (one drop), and the mixture was stirred at room temperature for 1 hr, and concentrated. THF (15 mL) and ethanol (15 mL) were added to the residue. Pyridine (5.69 mL, 70.3 mmol) was added to the mixture, and the mixture was stirred at room temperature for 12 hr, and concentrated under reduced pressure. Ethyl acetate and 1N hydrochloric acid were added to the residue, and the precipitated solid was collected by filtration, and washed with 1N hydrochloric acid (×2), water (×4) and diethyl ether (×1). The obtained crude crystals were recrystallized from THF-ethyl acetate to give the title compound as a white powder (1.87 g, 56%).

melting point: 181° C.

$^1$H-NMR (300 MHz, DMSO-d$_6$) δ: 1.29-1.36 (3H, m), 1.35 (3H, t, J=6.7 Hz), 4.25-4.44 (4H, m), 4.76 (2H, s), 4.90 (2H, s), 7.54 (2H, d, J=8.1 Hz), 7.70 (1H, s), 7.89-8.01 (2H, m), 12.87 (1H, s).

Reference Example 63 ethyl 1-[2-({4-[(methyloxy)carbonyl]phenyl}oxy)ethyl]7-oxo-6,7-dihydro-1H-pyrazolo[4,3-d]pyrimidine-5-carboxylate

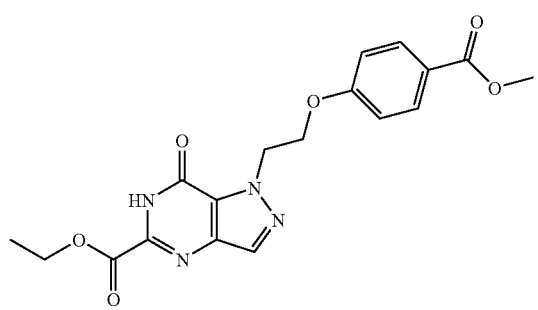

Step 1

Thionyl chloride (9.2 mL) was added dropwise to a solution of 4-nitro-1H-pyrazole-3-carboxylic acid (19.77 g, 125.9 mmol) in methanol (200 mL) at 0° C. The reaction mixture was stirred at room temperature overnight, and the solvent was evaporated under reduced pressure. Water was added to the residue, and the mixture was extracted with ethyl acetate. The organic layer was washed with saturated aqueous sodium hydrogencarbonate solution and saturated brine, dried and concentrated. The obtained crude crystals were washed with diisopropyl ether to give methyl 4-nitro-1H-pyrazole-5-carboxylate (17.8 g, 82%).

$^1$H-NMR (300 MHz, CDCl$_3$) δ: 4.06 (3H, s), 8.50 (1H, s).

Step 2

Methyl 4-nitro-1H-pyrazole-5-carboxylate (5.37 g, 31.4 mmol), methyl 4-[(2-bromoethyl)oxy]benzoate (8.15 g, 31.5 mmol) and potassium carbonate (4.37 g, 31.6 mmol) were added to acetone (150 mL), and the reaction mixture was heated under reflux for 4 hr. After the mixture was allowed to cool, a mixed solution of water and ethyl acetate/THF, and the organic layer was separated. The organic layer was washed with saturated brine, dried, and concentrated under reduced pressure. The obtained solid was washed with hexane to give a mixture of methyl 1-[2-({4-[(methyloxy)carbonyl]phenyl}oxy)ethyl]-4-nitro-1H-pyrazole-5-carboxylate and methyl 1-[2-({4-[(methyloxy)carbonyl]phenyl}oxy)ethyl]-4-nitro-1H-pyrazole-3-carboxylate (7.42 g).

Step 3

To a solution of a mixture of methyl 1-[2-({4-[(methyloxy)carbonyl]phenyl}oxy)ethyl]-4-nitro-1H-pyrazole-5-carboxylate and methyl 1-[2-({4-[(methyloxy)carbonyl]phenyl}oxy)ethyl]-4-nitro-1H-pyrazole-3-carboxylate (7.42 g) in a mixed solvent of THF (200 mL)-methanol (100 mL) was added 10% palladium carbon (1.17 g), and the mixture was subjected to catalytic reduction under hydrogen atmosphere (1 atm) at room temperature overnight. The catalyst was filtered off, and the filtrate was concentrated. The precipitated methyl 4-amino-1-[2-({4-[(methyloxy)carbonyl]phenyl}oxy)ethyl]-1H-pyrazole-3-carboxylate (3.62 g) was filtered off, and the filtrate was concentrated. The residue was purified by silica gel column chromatography to give methyl 4-amino-1-[2-({4-[(methyloxy)carbonyl]phenyl}oxy)ethyl]-1H-pyrazole-5-carboxylate (2.18 g).

$^1$H-NMR (300 MHz, CDCl$_3$) δ: 3.88 (3H, s), 3.93 (3H, s), 4.33-4.40 (2H, m), 4.44-4.51 (2H, m), 6.85-6.91 (2H, m), 7.15 (1H, s), 7.95-8.01 (2H, m).

Step 4

Methyl 4-amino-1-[2-({4-[(methyloxy)carbonyl]phenyl}oxy)ethyl]-1H-pyrazole-5-carboxylate (2.18 g, 6.83 mmol) and ethyl cyanoformate (811 mg, 8.18 mmol) were added to 1N hydrogen chloride-acetic acid (40 mL), and the mixture was stirred under heating at 90° C. for 4 hr. After the mixture was allowed to cool, diethyl ether was added, and the precipitated crude crystals were collected by filtration, and washed with diethyl ether to give the title compound (1.79 g).

melting point: 194-196° C.

$^1$H-NMR (300 MHz, CDCl$_3$) δ: 1.48 (3H, t, J=7.1 Hz), 3.87 (3H, s), 4.49-4.59 (4H, m), 5.09 (2H, t, J=5.5 Hz), 6.85 (2H, d, J=9.0 Hz), 7.94 (2H, 4, J=9.0 Hz), 8.13 (1H, s), 9.99 (1H, s)

Reference Example 64 ethyl 4-oxo-5-phenyl-3,4-dihydrothieno[2,3-d]pyrimidine-2-carboxylate

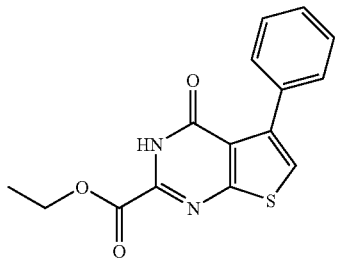

By a method similar to that in Reference Example 39 and using, instead of ethyl 5'-amino-2,3'-bithiophene-4'-carboxylate, methyl 2-amino-4-phenylthiophene-3-carboxylate, the title compound was obtained as a brown powder (5.73 g, 80%).

$^1$H-NMR (300 MHz, DMSO-$d_6$) δ: 1.36 (3H, t, J=7.2 Hz), 4.39 (2H, q, J=7.2 Hz), 7.32-7.45 (3H, m), 7.51-7.57 (2H, m), 7.74 (1H, s), 12.80 (1H, br).

Reference Example 65 ethyl 4-oxo-5-(3-thienyl)-3,4-dihydrothieno[2,3-d]pyrimidine-2-carboxylate

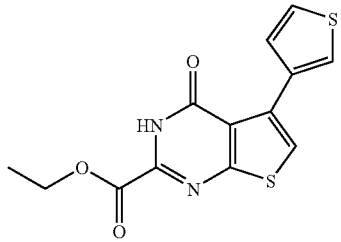

Step 1

By a method similar to that in Step 1 of Reference Example 69 and using, instead of 2-fluoroacetophenone, 3-acetylthiophene, ethyl 5-amino-3,3'-bithiophene-4-carboxylate was obtained as a yellow powder (3.30 g, 33%).

Step 2

By a method similar to that in Reference Example 39 and using, instead of ethyl 5'-amino-2,3'-bithiophene-4'-carboxylate, ethyl 5-amino-3,3'-bithiophene-4-carboxylate obtained in Step 1 of Reference Example 65, the title compound was obtained as a green powder (2.02 g, 56%).

$^1$H-NMR (300 MHz, DMSO-$d_6$) δ: 1.35 (3H, t, J=7.0 Hz), 4.38 (2H, q, J=6.9 Hz), 7.46-7.50 (1H, m), 7.56 (1H, dd, J=3.0, 4.9 Hz), 7.86 (1H, s), 8.01 (1H, d, J=1.9 Hz), 12.86 (1H, br).

Reference Example 66 ethyl 4-oxo-5-pyridin-4-yl-3,4-dihydrothieno[2,3-d]pyrimidine-2-carboxylate

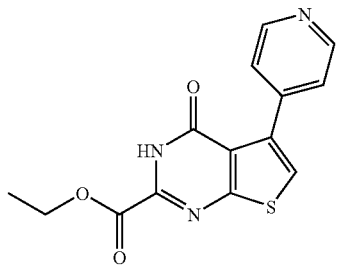

Step 1

A solution of 4-acetylpyridine (5.00 g, 41.275 mmol), ethyl cyanoacetate (4.67 mg, 41.275 mmol), morpholine (3.60 g, 41.275 mmol) and sulfur (1.32 g, 41.275 mmol) in toluene (40 mL) was stirred at 120° C. for 10 hr. The reaction mixture was concentrated under reduced pressure, and ethyl acetate was added to the residue. The insoluble material was filtered off, and the filtrate was purified by silica gel column chromatography (hexane/ethyl acetate=10/1→4/1) to give an orange powder. The obtained solids were combined, and recrystallized from ethyl acetate to give ethyl 2-amino-4-pyridin-4-ylthiophene-3-carboxylate as a yellow powder (4.00 g, 39%).

$^1$H-NMR (300 MHz, DMSO-$d_6$) δ: 0.93 (3H, t, J=7.1 Hz), 3.98 (2H, q, J=7.0 Hz), 6.37 (1H, s), 7.22-7.28 (2H, m), 7.46 (2H, br), 8.45-8.52 (2H, m).

Step 2

By a method similar to that in Reference Example 39 and using, instead of ethyl 5'-amino-2,3'-bithiophene-4'-carboxylate, ethyl 2-amino-4-pyridin-4-ylthiophene-3-carboxylate obtained in Step 1 of Reference Example 66, the title compound was obtained as an orange powder (3.08 g, 67%).

$^1$H-NMR (300 MHz, DMSO-$d_6$) δ: 1.36 (3 Hr, t, J=7.0 Hz), 4.40 (2H, q, J=7.1 Hz), 7.94 (2H, d, J=5.3 Hz), 8.19 (1H, 5), 8.80 (2H, d, J=5.3 Hz), 13.11 (1H, br).

Reference Example 67 ethyl 4-oxo-5-pyridin-3-yl-3,4-dihydrothieno[2,3-d]pyrimidine-2-carboxylate

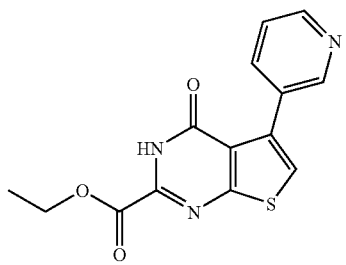

Step 1

By a method similar to that in Step 1 of Reference Example 66 and using, instead of 4-acetylpyridine, 3-acetylpyridine, ethyl 2-amino-4-pyridin-3-ylthiophene-3-carboxylate was obtained as a yellow powder (1.95 g, 19%).

$^1$H-NMR (300 MHz, DMSO-$d_6$) δ: 0.90 (3H, t, J=7.0 Hz), 3.96 (2H, q, J=7.1 Hz), 6.31 (1H, s), 7.33 (1H, dd, J=4.9, 8.0 Hz), 7.47 (2H, br), 7.66 (1H, d, J=7.6 Hz), 8.42-8.49 (2H, m).

Step 2

By a method similar to that in Reference Example 39 and using, instead of ethyl 5'-amino-2,3'-bithiophene-4'-carboxylate, ethyl 2-amino-4-pyridin-3-ylthiophene-3-carboxylate obtained in Step 1 of Reference Example 67, the title compound was obtained as a yellow powder (1.09 g, 47%).

$^1$H-NMR (300 MHz, DMSO-d$_6$) δ: 1.36 (3H, t, J=7.2 Hz), 4.39 (2H, q, J=7.2 Hz), 7.63 (1H, dd, J=5.1, 7.7 Hz), 7.99 (1H, s), 8.17 (1H, d, J=7.9 Hz), 8.66 (1H, d, J=4.1 Hz), 8.85 (1H, s), 13.00 (1H, br).

Reference Example 68 ethyl 5-isopropyl-4-oxo-3,4-dihydrothieno[2,3-d]pyrimidine-2-carboxylate

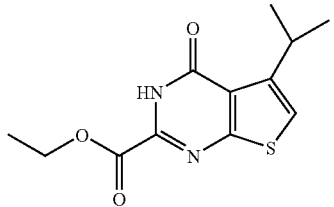

By a method similar to that in Reference Example 39 and using, instead of ethyl 5'-amino-2,3'-bithiophene-4'-carboxylate, ethyl 2-amino-4-isopropylthiophene-3-carboxylate, the title compound was obtained as a pale-yellow powder (301.0 mg, 24%).

$^1$H-NMR (300 MHz, DMSO-d$_6$) δ: 1.23 (3H, s), 1.25 (3H, s), 1.34 (3H, t, J=7.0 Hz), 3.59-3.70 (1H, m), 4.36 (2H, q, J=7.2 Hz), 7.41 (1H, s), 12.72 (1H, br).

Reference Example 69 ethyl 5-(2-fluorophenyl)-4-oxo-3,4-dihydrothieno[2,3-d]pyrimidine-2-carboxylate

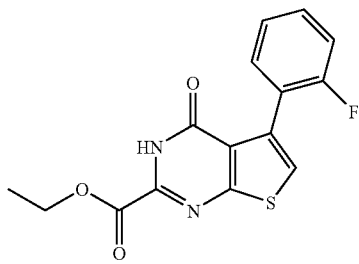

Step 1

A solution of 2-fluoroacetophenone (5.00 g, 36.195 mmol), ethyl cyanoacetate (4.09 mg, 36.195 mmol) and morpholine (3.15 g, 36.195 mmol) in toluene (40 mL) was stirred at 120° C. for 10 hr. Sulfur (1.16 g, 36.195 mmol) and EtOH (40 mL) were added to the reaction mixture, and the mixture was stirred at 70° C. for 10 hr, and concentrated under reduced pressure. The residue was purified by silica gel column chromatography (hexane/ethyl acetate=10/1→4/1) to give ethyl 2-amino-4-(2-fluorophenyl)thiophene-3-carboxylate as a yellow powder (2.52 g, 26%).

Step 2

By a method similar to that in Reference Example 39 and using, instead of ethyl 5'-amino-2,3'-bithiophene-4'-carboxylate, ethyl-2-amino-4-(2-fluorophenyl)thiophene-3-carboxylate obtained in Step 1 of Reference Example 69, the title compound was obtained as a pale-yellow powder (1.43 g, 60%).

$^1$H-NMR (300 MHz, DMSO-d$_6$) δ: 1.35 (3H, t, J=7.2 Hz), 4.38 (2H, q, J=7.0 Hz), 7.19-7.30 (2H, m), 7.38-7.50 (2H, m), 7.79 (1H, s), 12.83 (1H, br).

Reference Example 70 ethyl 5-(2-chlorophenyl)-4-oxo-3,4-dihydrothieno[2,3-d]pyrimidine-2-carboxylate

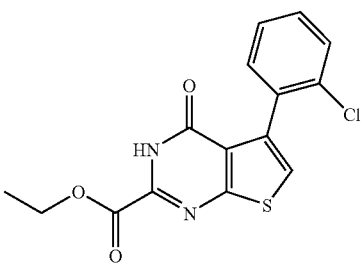

Step 1

By a method similar to that in Step 1 of Reference Example 66 and using, instead of 4-acetylpyridine, 2-chloroacetophenone, ethyl 2-amino-4-(2-chlorophenyl)thiophene-3-carboxylate was obtained as a brown powder (2.5 g, 27%).

Step 2

By a method similar to that in Reference Example 39 and using, instead of ethyl 5-amino-2,3'-bithiophene-4'-carboxylate, ethyl 2-amino-4-(2-chlorophenyl)thiophene-3-carboxylate obtained in Step 1 of Reference Example 70, the title compound was obtained as a pale-yellow powder (141.0 mg, 5%).

$^1$H-NMR (300 MHz, DMSO-d$_6$) δ: 1.35 (3H, t, J=7.1 Hz), 4.37 (2H, q, J=7.0 Hz), 7.33-7.55 (4H, m), 7.70 (1H, s), 12.82 (1H, s).

Reference Example 71 ethyl 5-(2-methoxyphenyl)-4-oxo-3,4-dihydrothieno[2,3-d]pyrimidine-2-carboxylate

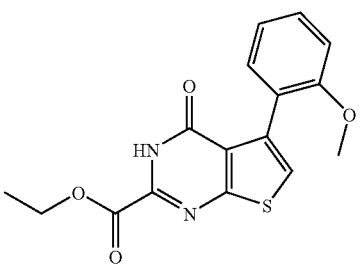

Step 1

By a method similar to that in Step 1 of Reference Example 66 and using, instead of 4-acetylpyridine, 2-methoxyacetophenone, ethyl 2-amino-4-(2-methoxyphenyl)thiophene-3-carboxylate was obtained as a yellow oil (3.28 g, 36%).

Step 2

By a method similar to that in Reference Example 39 and using, instead of ethyl 5'-amino-2,3'-bithiophene-4'-carboxylate, ethyl 2-amino-4-(2-methoxyphenyl)thiophene-3-carboxylate obtained in Step 1 of Reference Example 71, the title compound was obtained as a brown powder (180.3 mg, 5%).

$^1$H-NMR (300 MHz, DMSO-$d_6$) δ: 1.36 (3H, t, J=7.2 Hz), 3.97 (3H, s), 4.38 (2H, q, J=7.1 Hz), 7.08 (1H, t, J=7.4 Hz), 7.22 (1H, d, J=8.0 Hz), 7.37-7.45 (1H, m), 7.89-7.97 (2H, m), 12.87 (1H, br)

Reference Example 72 ethyl 5-(3-fluorophenyl)-4-oxo-3,4-dihydrothieno[2,3-d]pyrimidine-2-carboxylate

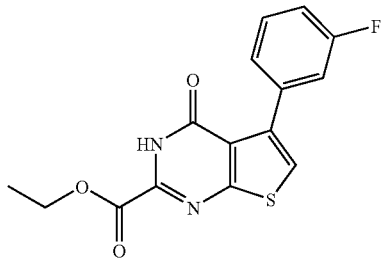

Step 1

By a method similar to that in Step 1 of Reference Example 66 and using, instead of 4-acetylpyridine, 3-fluoroacetophenone, ethyl 2-amino-4-(3-fluorophenyl)thiophene-3-carboxylate was obtained as a brown oil (1.77 g, 18%).

Step 2

By a method similar to that in Reference Example 39 and using, instead of ethyl 5'-amino-2,3'-bithiophene-4'-carboxylate, ethyl 2-amino-4-(3-fluorophenyl)thiophene-3-carboxylate obtained in Step 1 of Reference Example 72, the title compound was obtained as a brown powder (180.3 mg, 5%).

$^1$H-NMR (300 MHz, DMSO-$d_6$) δ: 1.36 (3H, t, J=7.2 Hz), 4.38 (2H, q, J=7.1 Hz), 7.16-7.27 (1H, m), 7.36-751 (3H, m), 7.84 (1H, s), 12.91 (1H, br).

Reference Example 73 ethyl 5-(3-chlorophenyl)-4-oxo-3,4-dihydrothieno[2,3-d]pyrimidine-2-carboxylate

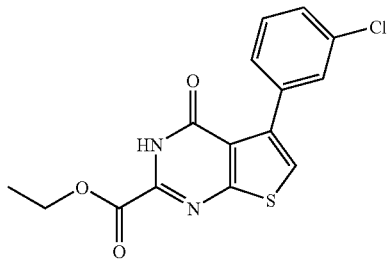

Step 1

By a method similar to that in Step 1 of Reference Example 66 and using, instead of 4-acetylpyridine, 3-chloroacetophenone, ethyl 2-amino-4-(3-chlorophenyl)thiophene-3-carboxylate was obtained as a brown oil (4.12 g, 51%).

Step 2

By a method similar to that in Reference Example 39 and using, instead of ethyl 5'-amino-2,3'-bithiophene-4-f carboxylate, ethyl 2-amino-4-(3-chlorophenyl)thiophene-3-carboxylate obtained in Step 1 of Reference Example 73, the title compound was obtained as a pale-yellow powder (1.74 g, 36%).

$^1$H-NMR (300 MHz, DMSO-$d_6$) δ: 1.36 (3H, t, J=7.2 Hz), 4.39 (2H, q, J=7.2 Hz), 7.41 17.47 (2H, m), 7.48-7.54 (1H, m), 7.62 (1H, d, J=0.8 Hz), 7.85 (1H, s), 12.88 (1H, s).

Reference Example 74 ethyl 5-(3-methoxyphenyl)-4-oxo-3,4-dihydrothieno[2,3-d]pyrimidine-2-carboxylate

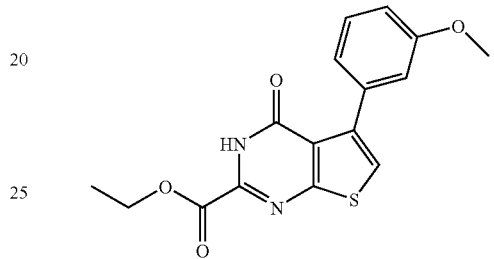

Step 1

By a method similar to that in Step 1 of Reference Example 66 and using, instead of 4-acetylpyridine, 3-methoxyacetophenone, ethyl 2-amino-4-(3-methoxyphenyl)thiophene-3-carboxylate was obtained as a brown oil (10.0 g, 77%).

Step 2

By a method similar to that in Reference Example 39 and using, instead of ethyl 5'-amino-2,3'-bithiophene-4'-carboxylate, ethyl 2-amino-4-(3-methoxyphenyl)thiophene-3-carboxylate obtained in Step 1 of Reference Example 74, the title compound was obtained as a brown powder (4.99 g, 32%).

$^1$H-NMR (300 MHz, DMSO-$d_6$) δ: 1.36 (3H, t, J=7.2 Hz), 3.78 (3H, s), 4.38 (2H, q, J=7.2 Hz), 6.94 (1H, dd, J=2.1, 7.8 Hz), 7.08-7.16 (2H, m), 7.31 (1H, t, J=7.8 Hz), 7.76 (1H, s), 12.82 (1H, br).

Reference Example 75 ethyl 5-(3-cyanophenyl)-4-oxo-3,4-dihydrothieno[2,3-d]pyrimidine-2-carboxylate

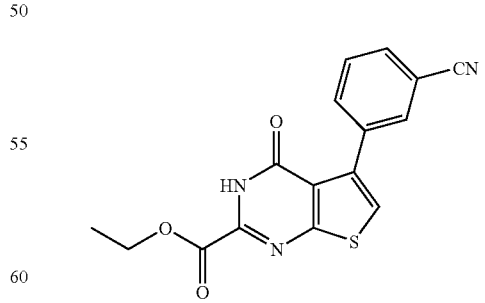

Step 1

By a method similar to that in Step 1 of Reference Example 66 and using, instead of 4-acetylpyridine, 3-cyanoacetophenone, ethyl 2-amino-4-(3-cyanophenyl)thiophene-3-carboxylate was obtained as a yellow powder (9.37 g, 59%).

Step 2

By a method similar to that in Reference Example 39 and using, instead of ethyl 5'-amino-2,3'-bithiophene-4'-carboxylate, ethyl 2-amino-4-(3-cyanophenyl)thiophene-3-carboxylate obtained in Step 1 of Reference Example 75, the title compound was obtained as a brown powder (6.33 g, 57%).

¹H-NMR (300 MHz, DMSO-d₆) δ: 1.36 (3H, t, J=7.2 Hz), 4.39 (2H, g, J=7.0 Hz), 7.63 (1H, t, J=7.8 Hz), 7.82-7.94 (3H, m), 8.02 (1H, t, J=1.5 Hz), 12.94 (1H, br).

Reference Example 76 ethyl 5-(3-methylphenyl)-4-oxo-3,4-dihydrothieno[2,3-d]pyrimidine-2-carboxylate

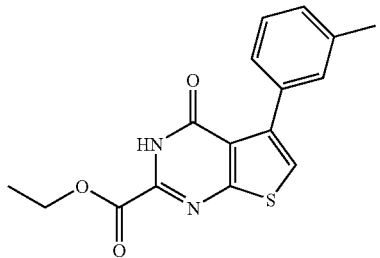

Step 1

By a method similar to that in Step 1 of Reference Example 66 and using, instead of 4-acetylpyridine, 3-methylacetophenone, ethyl 2-amino-4-(3-methylphenyl)thiophene-3-carboxylate was obtained as a yellow powder (18.9 g, 64%)

Step 2

By a method similar to that in Reference Example 39 and using, instead of ethyl 5'-amino-2,3'-bithiophene-4'-carboxylate, ethyl 2-amino-4-(3-methylphenyl)thiophene-3-carboxylate obtained in Step 1 of Reference Example 76, the title compound was obtained as a brown powder (7.90 g, 35%).

¹H-NMR (300 MHz, DMSO-d₆) δ: 1.36 (3H, t, J=7.1 Hz), 2.35 (3H, s), 4.39 (2H, q, J=7.0 Hz), 7.15-7.21 (1H, m), 7.23-7.39 (3H, m), 7.72 (1H, s), 12.79 (1H, br).

Reference Example 77 ethyl 5-(4-fluorophenyl)-4-oxo-3,4-dihydrothieno[2,3-d]pyrimidine-2-carboxylate

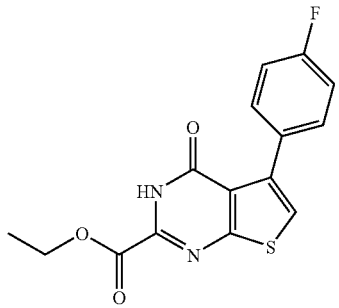

By a method similar to that in Reference Example 39 and using, instead of ethyl 5'-amino-2,3'-bithiophene-4'-carboxylate, ethyl 2-amino-4-(4-fluorophenyl)thiophene-3-carboxylate, the title compound was obtained as a brown powder (1.77 g, 78%).

¹H-NMR (300 MHz, DMSO-d₆) δ: 1.36 (3H, t, J=7.2 Hz), 4.39 (2H, q, J=7.1 Hz), 7.18-7.28 (2H, m), 7.52-7.63 (2H, m), 7.72-7.77 (1H, m), 12.81 (1H, br).

Reference Example 78 ethyl 5-(4-chlorophenyl)-4-oxo-3,4-dihydrothieno[2,3-s d]pyrimidine-2-carboxylate

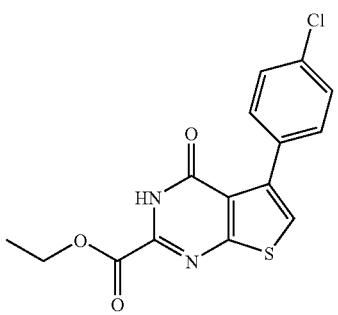

By a method similar to that in Reference Example 39 and using, instead of ethyl 5'-amino-2,3'-bithiophene-4'-carboxylate, ethyl 2-amino-4-(4-chlorophenyl)thiophene-3-carboxylate, the title compound was obtained as a pale-yellow powder (2.04 g, 86%).

¹H-NMR (300 MHz, DMSO-d₆) δ: 1.35 (3H, t, J=7.2 Hz), 4.38 (2H, q, J=7.0 Hz), 7.42-7.51 (2H, m), 7.53-7.60 (2H, m), 7.78 (1H, s), 12.89 (1H, br).

Reference Example 79 ethyl 5-(4-bromophenyl)-4-oxo-3,4-dihydrothieno[2,3-d]pyrimidine-2-carboxylate

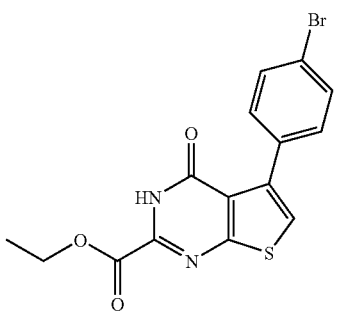

By a method similar to that in Reference Example 39 and using, instead of ethyl 5'-amino-2,3'-bithiophene-4'-carboxylate, ethyl 2-amino-4-(4-bromophenyl)thiophene-3-carboxylate, the title compound was obtained as a pale-yellow powder (1.77 g, 76%).

¹H-NMR (300 MHz, DMSO-d₆) δ: 1.35 (3H, t, J=7.0 Hz), 4.37 (2H, q, J=7.1 Hz), 7.45-7.55 (2H, m), 7.57-7.63 (2H, m), 7.77 (1H, s), 12.89 (1H, br).

Reference Example 80 ethyl 5-(4-methoxyphenyl)-4-oxo-3,4-dihydrothieno[2,3-d]pyrimidine-2-carboxylate

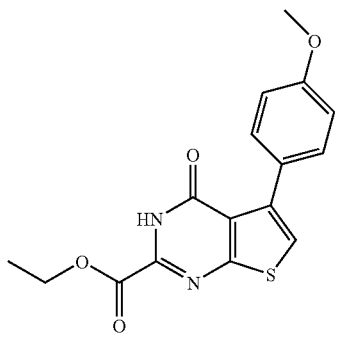

By a method similar to that in Reference Example 39 and using, instead of ethyl 5'-amino-2,3'-bithiophene-41-carboxylate, ethyl 2-amino-4-(4-methoxyphenyl)thiophene-3-carboxylate, the title compound was obtained as a pale-yellow powder (1.88 g, 79%).

$^1$H-NMR (300 MHz, DMSO-$d_6$) δ: 1.35 (3H, t, J=7.1 Hz), 3.80 (3H, s), 4.38 (2H, q, J=7.0 Hz), 6.96 (2H, d, J=8.7 Hz), 7.49 (2H, d, J=8.5 Hz), 7.65 (1H, s), 12.79 (1H, br).

Reference Example 81 ethyl 5-(4-methylphenyl)-4-oxo-3,4-dihydrothieno[2,3-d]pyrimidine-2-carboxylate

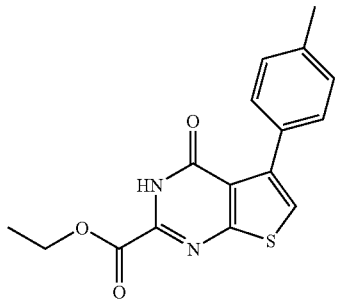

Step 1

By a method similar to that in Step 1 of Reference Example 66 and using, instead of 4-acetylpyridine, 4-methylacetophenone, ethyl 2-amino-4-(4-methylphenyl)thiophene-3-carboxylate was obtained as an orange powder (3.52 g, 30%).

Step 2

By a method similar to that in Reference Example 39 and using, instead of ethyl 5'-amino-2,3'-bithiophene-4'-carboxylate, ethyl 2-amino-4-(4-methylphenyl)thiophene-3-carboxylate obtained in Step 1 of Reference Example 81, the title compound was obtained as a yellow powder (3.40 g, 80%).

$^1$H-NMR (300 MHz, DMSO-$d_6$) δ: 1.35 (3H, t, J=7.2 Hz), 2.35 (3H, s), 4.38 (2H, q, J=7.0 Hz), 7.21 (2H, d, J=7.9 Hz), 7.43 (2H, d, U=8.1 Hz), 7.68 (1H, s), 12.82 (1H, br).

Reference Example 82 ethyl 5-[3-(ethoxycarbonyl)phenyl]-4-oxo-3,4-dihydrothieno[2,3-d]pyrimidine-2-carboxylate

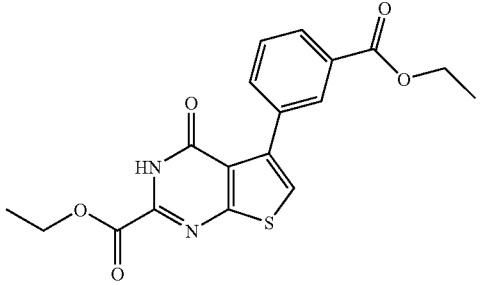

Step 1

A solution of 3-acetylbenzoic acid (4.00 g, 24.366 mmol) and concentrated sulfuric acid (0.078 mL, 1.462 mmol) in ethanol (100 mL) was stirred at 80° C. for 3 days. The reaction mixture was concentrated under reduced pressure, and ethyl acetate was added to the residue. The organic layer was washed with saturated brine, dried over sodium sulfate, and concentrated to give ethyl 3-acetylbenzoate as a brown powder (4.59 g, 98%).

$^1$H-NMR (300 MHz, CDCl$_3$)) δ: 1.43 (3H, t, J=7.2 Hz), 4.42 (2H, q, J=7.2 Hz), 7.56 (1H, dd, J=7.7, 7.7 Hz), 8.13-8.18 (1H, m), 8.22-8.27 (1H, m), 8.60 (1H, dd, J=1.6, 1.6 Hz).

Step 2

By a method similar to that in Step 1 of Reference Example 66 and using, instead of 4-acetylpyridine, ethyl 3-acetylbenzoate obtained in Step 1 of Reference Example 82, ethyl 2-amino-4-[3-(ethoxycarbonyl)phenyl]thiophene-3-carboxylate was obtained as an orange powder (3.51 g, 53%).

Step 3

By a method similar to that in Reference Example 39 and using, instead of ethyl 5'-amino-2,3'-bithiophene-4'-carboxylate, ethyl 2-amino-4-[3-(ethoxycarbonyl)phenyl]thiophene-3-carboxylate obtained in Step 2 of Reference Example 82, the title compound was obtained as an orange powder (1.55 g, 38%).

$^1$H-NMR (300 MHz, DMSO-$d_6$) δ: 1.28-1.40 (6H, m), 4.28-4.45 (4H, m), 7.57 (1H, t, J=7.8 Hz), 7.80-7.84 (1H, m), 7.87 (1H, s), 7.94-8.00 (1H, m), 8.12 (1H, t, J=1.5 Hz), 12.87 (1H, br).

Reference Example 84

3-[(3-{[1-(triphenylmethyl)-1H-1,2,4-triazol-3-yl]oxy}propyl)oxy]benzonitrile

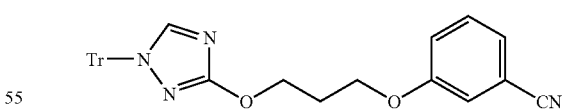

By a method similar to that in Reference Example 31 and using 3-[(3-hydroxypropyl)oxy]benzonitrile obtained according to the methods described in Bioorganic & Medicinal Chemistry Letters (2001), 11, 2279 and the like and 3-nitro-1-(triphenylmethyl)-1H-1,2,4-triazole obtained in Reference Example 33, the title compound was obtained as a pale-yellow solid (14.0 g, 100%).

$^1$H-NMR (300 MHz, DMSO-$d_6$) δ 2.08-2.19 (2H, m), 4.14 (2H, t, J=6.2 Hz), 4.30 (2H, t, J=6.2 Hz), 7.04-7.12 (6H, m), 7.24-7.30 (1H, m), 7.34-7.43 (11H, m), 7.47 (1H, t, J=7.9 Hz), 7.82 (1H, s)

Reference Example 85

1-{3-[(3-{[1-(triphenylmethyl)-1H-1,2,4-triazol-3-yl]oxy}propyl)oxy]phenyl}methanamine

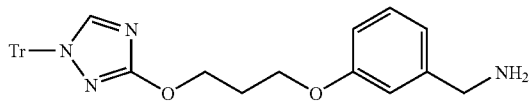

By a method similar to that in Reference Example 20 and using 3-[(3-{[1-(triphenylmethyl)-1H-1,2,4-triazol-3-yl]oxy}propyl)oxy]benzonitrile obtained in Reference Example 84, the title compound was obtained as a yellow oil (1.74 g, 91%).

$^1$H-NMR (300 MHz, DMSO-$d_6$) δ: 2.06-2.17 (2H, m), 3.65 (2H, s), 3.99-4.09 (2H, m), 4.29 (2H, t, J=6.3 Hz), 6.70-6.76 (1H, m), 6.84-6.89 (1H, m), 6.90-6.93 (1H, m), 7.05-7.11 (6H, m), 7.12-7.32 (1H, m), 7.34-7.41 (9H, m), 7.82 (1H, s), 2H hidden.

Reference Example 86

4-oxo-N-({3-[(3-{[1-(triphenylmethyl)-1H-1,2,4-triazol-3-yl]oxy}propyl)oxy]phenyl}methyl)-3,4-dihydroquinazoline-2-carboxamide

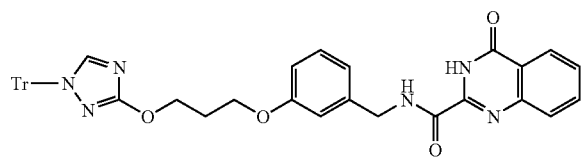

A suspension of 1-{3-[(3-{[1-(triphenylmethyl)-1H-1,2,4-triazol-3-yl]oxy}propyl)oxy]phenyl}methanamine obtained in Reference Example 85 (0.300 g, 0.611 mmol), ethyl 4-oxo-3,4-dihydro-2-quinazolinecarboxylate obtained according to the methods described in Journal of Organic Chemistry (1978), 43(23), 4485-7 and the like (0.133 g, 0.611 mmol) and N,N-diisopropylethylamine (0.213 mL, 1.22 mmol) in EtOH (4.5 mL) was stirred under microwave irradiation at 100° C. for 1.5 hr (Discover (trademark; CEM Corp), 50 W, run time: 5 min, hold time: 1.5 hr). After the reaction mixture was allowed to cool to room temperature, the precipitated solid was collected by filtration, and washed with EtOH to give the title compound as a white powder (0.315 g, 78%).

$^1$H-NMR (300 MHz, DMSO-$d_6$) δ: 2.05-2.17 (2H, m), 4.06 (2H, t, J=6.1 Hz), 4.29 (2H, t, J=6.1 Hz), 4.44 (2H, d, J=6.4 Hz), 6.78-6.85 (1H, m), 6.88-6.96 (2H, m), 7.02-7.11 (6H, m), 7.23 (1H, t, J=8.0 Hz), 7.30-7.42 (9H, m), 7.60 (1H, t, J=7.6 Hz), 7.74-7.82 (2H, m), 7.87 (1H, t, J=7.6 Hz), 8.17 (1H, d, J=7.2 Hz), 9.51 (1H, t, J=6.2 Hz), 11.86 (1H, br).

Reference Example 87

5-(3-chlorophenyl)-4-oxo-N-({3-[(3-{[1-(triphenylmethyl)-1H-1,2,4-triazol-3-yl]oxy}propyl)oxy]phenyl}methyl)-3,4-dihydrothieno[2,3-d]pyrimidine-2-carboxamide

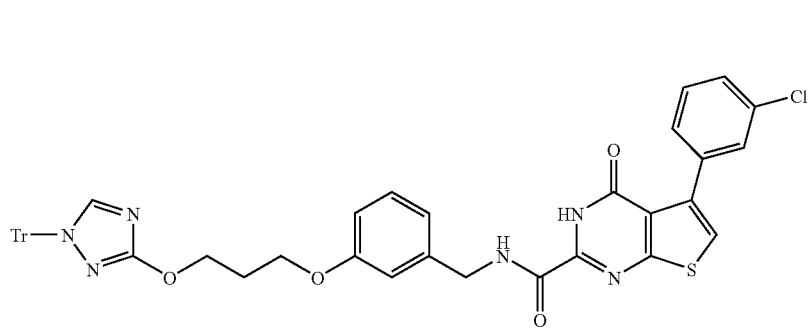

By a method similar to that in Reference Example 86 and using T-{3-[(3-{[1-(triphenylmethyl)-1H-1,2,4-triazol-3-yl]oxy}propyl)oxy]phenyl}methanamine obtained in Reference Example 85 and ethyl 5-(3-chlorophenyl)-4-oxo-3,4-dihydrothieno[2,3-d]pyrimidine-2-carboxylate obtained in Reference Example 73, the title compound was obtained as a white powder (0.320 g, 69%).

$^1$H-NMR (300 MHz, DMSO-$d_6$) δ: 2.06-2.17 (2H, m), 4.03-4.10 (2H, m), 4.29 (2H, t, J=6.3 Hz), 4.42 (2H, d, J=6.4 Hz), 6.79-6.84 (1H, m), 6.89-6.94 (2H, m), 7.04-7.11 (6H, m), 7.23 (TH, t, J=8.0 Hz), 7.34-7.40 (9H, m), 7.40-7.45 (2H, m), 7.47-7.54 (TH, m), 7.59-7.63 (1H, m), 7.79 (1H, s), 7.81 (1H, s), 9.67 (1H, t, J=6.7 Hz), 12.45 (1H, br).

Reference Example 88

5-(3-fluorophenyl)-4-oxo-N-({3-[(3-{[1-(triphenyl-methyl)-1H-1,2,4-triazol-3-yl]oxy}propyl)oxy]phenyl}methyl)-3,4-dihydrothieno[2,3-d]pyrimidine-2-carboxamide

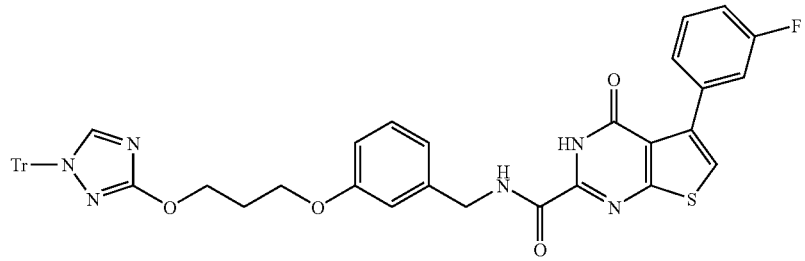

By a method similar to that in Reference Example 86 and using 1-{3-[(3-{[1-(triphenylmethyl)-1H-1,2,4-triazol-3-yl]oxy}propyl)oxy]phenyl}methanamine obtained in Reference Example 85 and ethyl 5-(3-fluorophenyl)-4-oxo-3,4-dihydrothieno[2,3-d]pyrimidine-2-carboxylate obtained in Reference Example 72, the title compound was obtained as a white powder (0.275 g, 62%).

$^1$H-NMR (300 MHz, DMSO-$d_6$) δ: 2.07-2.18 (2H, m), 4.02-4.10 (2H, m), 4.29 (2H, t, J=6.2 Hz), 4.42 (2H, d, J=6.2 Hz), 6.78-6.84 (1H, m), 6.88-6.94 (2H, m), 7.03-7.12 (6H, m), 7.16-7.26 (2H, m), 7.32-7.49 (12H, m), 7.77 (1H, s), 7.81 (1H, s), 9.66 (1H, t, J=6.7 Hz), 12.44 (1H, br).

Reference Example 89

5-(2-chlorophenyl)-4-oxo-N-({3-[(3-{[1-(triphenyl-methyl)-1H-1,2,4-triazol-3-yl]oxy}propyl)oxy]phenyl}methyl)-3,4-dihydrothieno[2,3-d]pyrimidine-2-carboxamide

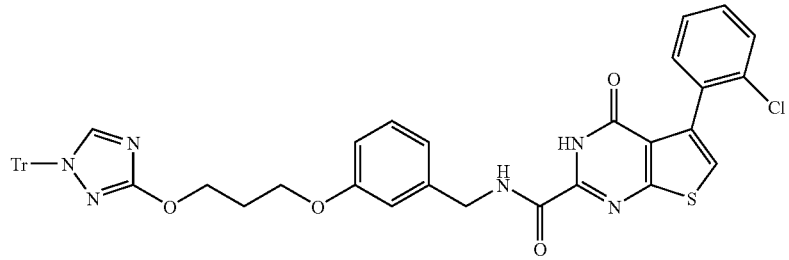

By a method similar to that in Reference Example 86 and using 1-{3-[(3-{[1-(triphenylmethyl)-1H-1,2,4-triazol-3-yl]oxy}propyl)oxy]phenyl}methanamine obtained in Reference Example 85 and ethyl 5-(2-chlorophenyl)-4-oxo-3,4-dihydrothieno[2,3-d]pyrimidine-2-carboxylate obtained in Reference Example 70, the title compound was obtained as a white powder (0.156 g, 66%).

$^1$H-NMR (300 MHz, DMSO-$d_6$) δ: 2.05-2.18 (2H, m), 4.06 (2H, t, J=6.2 Hz), 4.29 (2H, t, J=6.3 Hz), 4.42 (2H, d, J=6.2 Hz), 6.78-6.83 (1H, m), 6.88-6.94 (2H, m), 7.03-7.12 (6H, m), 7.22 (1H, t, J=7.9 Hz), 7.32-7.45 (12H, m), 7.47-7.54 (1H, m), 7.63 (1H, s), 7.81 (1H, s), 9.63 (1H, t, J=6.2 Hz), 12.03 (1H, br).

Reference Example 90

5-(2-fluorophenyl)-4-oxo-N-([3-[(3-{[1-(triphenylmethyl)-1H-1,2,4-triazol-3-yl]oxy}propyl)oxy]phenyl]methyl)-3,4-dihydrothieno[2,3-d]pyrimidine-2-carboxamide

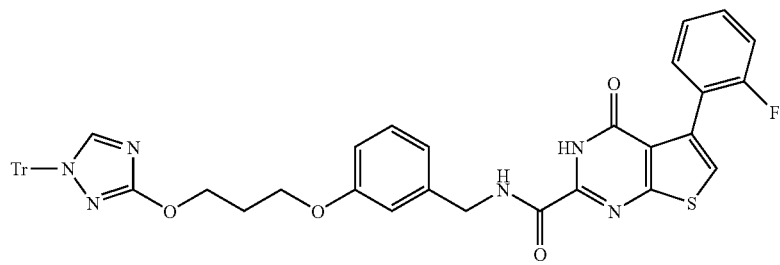

By a method similar to that in Reference Example 86 and using 1-{3-[(3-{[1-(triphenylmethyl)-1H-1,2,4-triazol-3-yl]oxy}propyl)oxy]phenyl}methanamine obtained in Reference Example 85 and ethyl 5-(2-fluorophenyl)-4-oxo-3,4-dihydrothieno[2,3-d]pyrimidine-2-carboxylate obtained in Reference Example 69, the title compound was obtained as a white powder (0.245 g, 57%).

$^1$H-NMR (300 MHz, DMSO-$d_6$) δ: 2.07-2.17 (2H, m), 4.03-4.09 (2H, m), 4.29 (2H, t, J=6.2 Hz), 4.42 (2H, d, J=6.2 Hz), 6.78-6.84 (1H, m), 6.88-6.95 (2H, m), 7.04-7.12 (6H, m), 7.19-7.28 (3H, m), 7.33-7.48 (11H, m), 7.71 (1H, s), 7.81 (1H, s), 9.65 (1H, t, J=5.9 Hz), 12.39 (1H, br).

Reference Example 91

5-(4-fluorophenyl)-4-oxo-N-({3-[(3-{([1-(triphenylmethyl)-1H-1,2,4-triazol-3-yl]oxy}propyl)oxy]phenyl}methyl)-3,4-dihydrothieno[2,3-d]pyrimidine-2-carboxamide

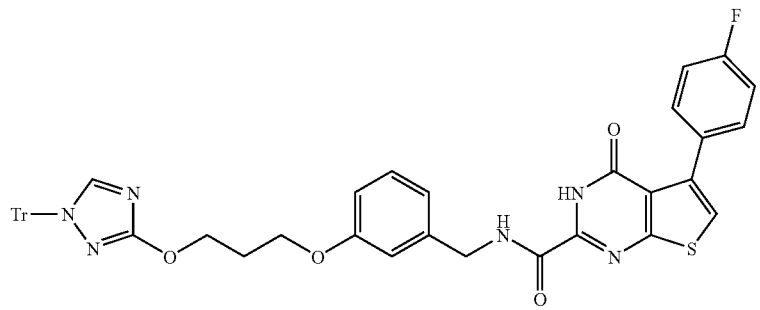

By a method similar to that in Reference Example 86 and using 1-{3-[(3-{[1-(triphenylmethyl)-1H-1,2,4-triazol-3-yl]oxy}propyl)oxy]phenyl}methanamine obtained in Reference Example 85 and ethyl 5-(4-fluorophenyl)-4-oxo-3,4-dihydrothieno[2,3-d]pyrimidine-2-carboxylate obtained in Reference Example 77, the title compound was obtained as a white powder (0.274 g, 62%).

$^1$H-NMR (300 MHz, DMSO-$d_6$) δ: 2.07-2.18 (2H, m), 4.06 (2H, t, J=6.3 Hz), 4.29 (2H, t, J=6.3 Hz), 4.42 (2H, d, J=6.4 Hz), 6.81 (1H, dd, J=8.9, 1.8 Hz), 6.88-6.95 (2H, m), 7.04-7.11 (6H, m), 7.18-7.27 (3H, m), 7.33-7.42 (9H, m), 7.54-7.62 (2H, m), 7.68 (1H, s), 7.81 (1H, s), 9.65 (1H, t, J=6.5 Hz), 12.39 (1H, br).

Reference Example 92 methyl N-[(4-bromophenyl)sulfonyl]valinate

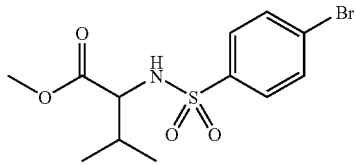

To a suspension of methyl valinate hydrochloride (10.0 g, 59.7 mmol) and sodium carbonate (15.8 g, 149 mmol) in acetone (200 ml)-water (100 mL) was added 4-bromobenzenesulfonyl chloride (12.7 g, 49.7 mmol) at 0° C., and the mixture was stirred at room temperature for 12 hr after addition. The reaction mixture was concentrated under reduced pressure, and the residue was diluted with ethyl acetate, washed with 0.1N hydrochloric acid, water and saturated brine, and dried over sodium sulfate. The solvent was evaporated under reduced pressure, and the residue was crystallized from hexane-ethyl acetate to give the title compound as a white powder (14.7 g, 84%).

$^1$H-NMR (300 MHz, DMSO-$d_6$) δ: 0.76-0.85 (6H, m), 1.84-1.98 (1H, m), 3.37 (3H, s), 3.57 (1H, d, J=7.2 Hz), 7.63-7.71 (2H, m), 7.76-7.83 (2H, m), 8.39 (1H, s).

Reference Example 93 methyl N-[(3'-cyanobiphenyl-4-yl)sulfonyl]valinate

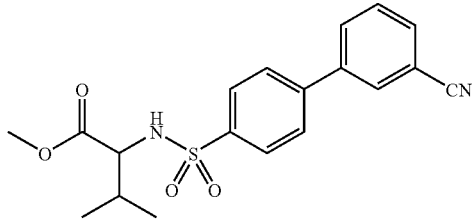

A suspension of methyl N-[(4-bromophenyl)sulfonyl]valinate obtained in Reference Example 92 (5.00 g, 14.3 mmol), (3-cyanophenyl)boronic acid (2.52 g, 17.1 mmol), tetrakis(triphenylphosphine)palladium (0.330 g, 0.286 mmol) and 2N aqueous sodium carbonate solution (8.57 mL, 17.1 mmol) in EtOH (15 mL)-toluene (50 mL) was heated under reflux for 8 hr under nitrogen atmosphere. The reaction mixture was diluted with ethyl acetate, washed with water and saturated brine, and dried over sodium sulfate. The solvent was evaporated under reduced pressure, and the residue was crystallized from hexane-ethyl acetate to give the title compound as a yellow powder (5.18 g, 97%).

$^1$H-NMR (300 MHz, DMSO-$d_6$) δ: 0.81 (3H, d, J=6.8 Hz), 0.84 (3H, d, J=6.8 Hz), 1.86-1.98 (1H, m), 3.34 (3H, s), 3.55-3.64 (1H, m), 7.72 (1H, t, J=7.8 Hz), 7.81-7.86 (2H, m), 7.91 (1H, d, J=7.6 Hz), 7.94-8.00 (2H, m), 8.10 (1H, d, J=8.0 Hz), 8.27 (1H, s), 8.32-8.40 (1H, m, J=3.0 Hz).

Reference Example 94 methyl N-{[3'-(aminomethyl)biphenyl-4-yl]sulfonyl}valinate

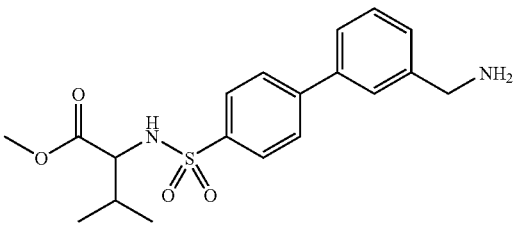

A suspension of methyl N-[(3'-cyanobiphenyl-4-yl)sulfonyl]valinate obtained in Reference Example 93 (5.00 g, 13.4 mmol), Raney-nickel (5.00 g) and 28% aqueous ammonia (50 mL) in THF (50 ml)-methanol (50 mL) was stirred at room temperature for 15 hr under hydrogen atmosphere (1 atm). The catalyst was filtered off, and the filtrate was concentrated under reduced pressure. A mixed solvent of ethyl acetate-hexane was added to the residue, and the precipitated insoluble material was filtered off. The filtrate was washed with saturated brine, and dried over sodium sulfate. The solvent was evaporated under reduced pressure, and diethyl ether was added to the residue. The precipitated solid was collected by filtration to give the title compound as a white powder (3.84 g, 76%).

$^1$H-NMR (300 MHz, DMSO-$d_6$) δ: 0.80 (3H, d, J=6.8 Hz), 0.84 (3H, d, J=6.8 Hz), 1.85-1.98 (1H, m), 3.34 (3H, s), 3.58 (1H, d, J=7.2 Hz), 3.80 (2H, s), 7.35-7.48 (2H, m), 7.56 (1H, d, J=7.2 Hz), 7.71 (1H, s), 7.78-7.84 (2H, m), 7.84-7.91 (2H, m), 3H hidden.

Reference Example 95 methyl N-{[3'-({[(4-oxo-3,4-dihydroquinazolin-2-yl)carbonyl]amino}methyl)biphenyl-4-yl]sulfonyl}valinate

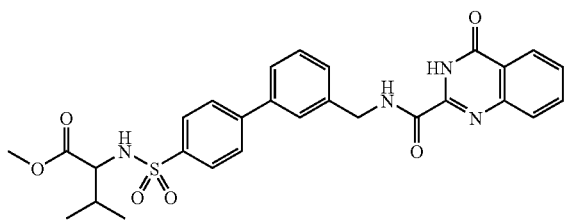

A suspension of methyl N-{[3'-(aminomethyl)biphenyl-4-yl]sulfonyl}valinate obtained in Reference Example 94 (0.300 g, 0.797 mmol) and ethyl 4-oxo-3,4-dihydro-2-quinazolinecarboxylate obtained according to the methods described in Journal of Organic Chemistry (1978), 43(23), 4485-7 and the like (0.145 g, 0.664 mmol) in EtOH (9 mL) was stirred at 90° C. for 5 hr. The reaction mixture was concentrated under reduced pressure, and the residue was diluted with ethyl acetate, washed with 0.1N hydrochloric acid and saturated brine, and dried over sodium sulfate. The solvent was evaporated under reduced pressure to give the title compound as a colorless oil (0.375 g, 86%).

¹H-NMR (300 MHz, DMSO-d₆) δ: 0.76-0.86 (6H, m, J=6.8, 10.8 Hz), 1.84-1.97 (1H, m), 3.33 (3H, s), 3.57 (1H, d, J=7.0 Hz), 4.58 (2H, d, J=6.2 Hz), 7.38-7.52 (2H, m), 7.57-7.67 (2H, m, J=7.5, 7.5 Hz), 7.71-7.94 (7H, m), 8.13-8.21 (1H, m), 8.32 (1H, s), 9.65 (1H, t, J=6.2 Hz), 11.95 (1H, s).

Reference Example 96 methyl N-{[3'-({[(5-methyl-4-oxo-3,4-dihydrothieno[2,3-d]pyrimidin-2-yl)carbonyl]amino}methyl)biphenyl-4-yl]sulfonyl}valinate

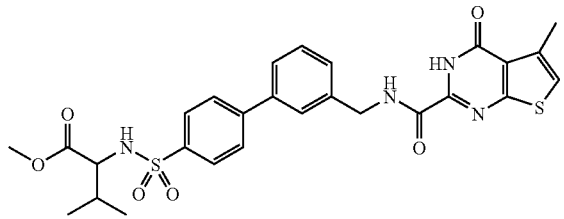

By a method similar to that in Reference Example 95 and using methyl N-{([3'-(aminomethyl)biphenyl-4-yl]sulfonyl}valinate obtained in Reference Example 94 (0.300 g, 0.797 mmol) and ethyl 5-methyl-4-oxo-3,4-dihydrothieno[2,3-d]pyrimidine-2-carboxylate obtained according to the methods described in U.S. Pat. No. 4,054,656 and the like, the title compound was obtained as a pale-yellow powder (0.255 g, 56%).

¹H-NMR (300 MHz, DMSO-d₆) δ: 0.75-0.87 (6H, m, J=6.6, 10.5 Hz), 1.83-1.98 (1H, m), 2.44-2.55 (3H, m, J=2.1 Hz), 3.33 (3H, s), 3.52-3.63 (1H, m), 4.53 (2H, d, J=6.2 Hz), 7.31 (1H, s), 7.37-7.52 (2H, m), 7.63 (1H, d, J=7.5 Hz), 7.72 (1H, s), 7.78-7.89 (4H, m), 8.25-8.37 (1H, m), 9.70 (1H, t, J=6.3 Hz), 12.21 (1H, s).

Reference Example 97 ethyl 1-[(3-chloropropyl)sulfonyl]piperidine-2-carboxylate

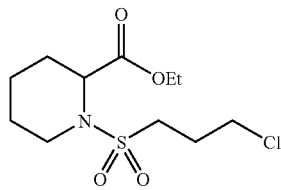

wherein Et is ethyl, which is the same as in the other formulas in the present specification.

To a solution of 3-chloropropane-1-sulfonyl chloride (4.72 g, 26.7 mmol) in THF (100 mL) were added successively ethyl piperidine-2-carboxylate (4.19 g, 26.7 mmol) and triethylamine (3.72 mL, 26.7 mmol) at 0° C., and the mixture was stirred at room temperature for 12 hr after addition. The reaction mixture was concentrated under reduced pressure, and the residue was diluted with ethyl acetate, washed with water, 0.1N hydrochloric acid and saturated brine, and dried over sodium sulfate. The solvent was evaporated under reduced pressure to give the title compound as a yellow oil (6.44 g, 81%).

¹H-NMR (300 MHz, DMSO-d₆) δ: 1.13-1.27 (1H, m), 1.22 (3H, t, J=7.0 Hz), 1.33-1.50 (1H, m), 1.59-1.72 (3H, m), 2.05-2.17 (3H, m), 3.06-3.27 (3H, m), 3.54-3.63 (1H, m), 3.70-3.77 (2H, m), 4.12-4.22 (2H, m), 4.52-4.59 (1H, m).

Reference Example 98 ethyl 1-({3-[(3-cyanophenyl)oxy]propyl}sulfonyl)piperidine-2-carboxylate

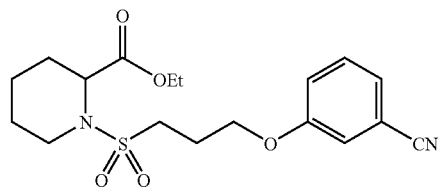

A suspension of ethyl 1-[(3-chloropropyl)sulfonyl]piperidine-2-carboxylate obtained in Reference Example 97 (2.00 g, 6.72 mmol), 3-hydroxybenzonitrile (0.800 g, 6.72 mmol), potassium carbonate (0.928 g, 6.72 mmol) and sodium iodide (0.101 g, 0.672 mmol) in DMF (20 mL) was stirred at 100° C. for 51 hr. The reaction mixture was diluted with ethyl acetate, washed with water, 0.5N aqueous sodium hydroxide solution, 0.1N aqueous sodium hydroxide solution and saturated brine, and dried over sodium sulfate. The solvent was evaporated under reduced pressure, and the residue was crystallized from methanol to give the title compound as a pale-yellow powder (1.34 g, 52%).

¹H-NMR (300 MHz, DMSO-d₆) δ: 1.13-1.27 (1H, m), 1.21 (3H, t, J=7.2 Hz), 1.30-1.47 (1H, m), 1.59-1.73 (3H, m), 2.04-2.16 (3H, m), 3.08-3.20 (1H, m), 3.21-3.31 (2H, m), 3.56-3.66 (1H, m), 4.10-4.21 (4H, m), 4.53-4.59 (1H, m), 7.27-7.33 (1H, m), 7.38-7.46 (2H, m), 7.50 (1H, t, J=8.0 Hz).

Reference Example 99 ethyl 1-[(3-{[3-(aminomethyl)phenyl]oxy}propyl)sulfonyl]piperidine-2-carboxylate

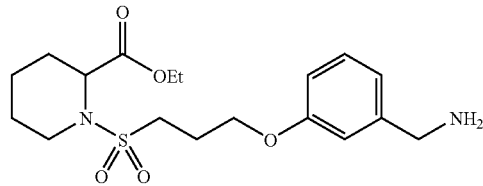

By a method similar to that in Reference Example 94 and using ethyl 1-({3-[(3-cyanophenyl)oxy]propyl}sulfonyl)piperidine-2-carboxylate obtained in Reference Example 98, the title compound was obtained as a pale-green oil (1.21 g, 100%).

¹H-NMR (300 MHz, DMSO-d₆) δ: 1.13-1.28 (4H, m), 1.31-1.48 (1H, m), 1.59-1.75 (3H, m), 2.03-2.15 (3H, m), 3.07-3.38 (5H, m), 3.61 (1H, d, J=13.0 Hz), 3.98-4.09 (2H, m), 4.11-4.22 (2H, m), 4.51-4.63 (1H, m), 6.69-6.79 (1H, m), 6.80-6.96 (2H, m), 7.22 (1H, br), 2H hidden.

Reference Example 100 ethyl 1-[(3-{[3-({[(4-oxo-3,4-dihydroquinazolin-2-yl)carbonyl]amino}methyl)phenyl]oxy}propyl)sulfonyl]piperidine-2-carboxylate

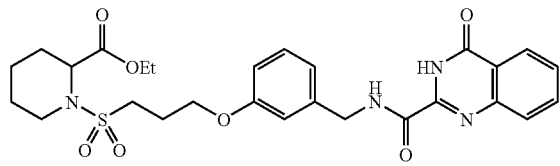

By a method similar to that in Example 87 and using ethyl 1-[(3-{[3-(aminomethyl)phenyl]oxy}propyl)sulfonyl]piperidine-2-carboxylate obtained in Reference Example 99 and ethyl 4-oxo-3,4-dihydro-2-quinazolinecarboxylate obtained according to the methods described in Journal of Organic Chemistry (1978), 43(23), 4485-7 and the like, the title compound was obtained as a white powder (0.464 g, 59%).

$^1$H-NMR (300 MHz, DMSO-$d_6$) δ: 1.08-1.25 (1H, m), 1.19 (3H, t, J=7.2 Hz), 1.27-1.45 (1H, m), 1.55-1.71 (3H, m), 2.00-2.15 (3H, m), 3.05-3.18 (1H, m), 3.19-3.29 (2H, m), 3.54-3.63 (1H, m), 4.05 (2H, t, J=6.2 Hz), 4.09-4.18 (2H, m), 4.45 (2H, d, J=6.4 Hz), 4.51-4.60 (1H, m), 6.83 (1H, d, J=8.3 Hz), 6.90-6.97 (2H, m), 7.25 (1H, t, J=8.0 Hz), 7.61 (1H, t, J=7.6 Hz), 7.74-7.82 (1H, m), 7.84-7.93 (1H, m), 8.17 (1H, d, J=8.0 Hz), 9.54 (1H, t, J=6.2 Hz), 12.25 (1H, br)

Reference Example 101 ethyl 1-[(3-{[3-({[(5-methyl-4-oxo-3,4-dihydrothieno[2,3-d]pyrimidin-2-yl)carbonyl]amino}methyl)phenyl]oxy}propyl)sulfonyl]piperidine-2-carboxylate

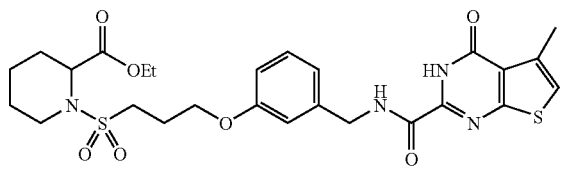

By a method similar to that in Example 87 and using ethyl 1-[(3-{[3-(aminomethyl)phenyl]oxy}propyl)sulfonyl]piperidine-2-carboxylate obtained in Reference Example 99 and ethyl 5-methyl-4-oxo-3,4-dihydrothieno[2,3-d]pyrimidine-2-carboxylate obtained according to the methods described in U.S. Pat. No. 4,054,656 and the like, the title compound was obtained as a yellow powder (0.270 g, 99%).

$^1$H-NMR (300 MHz, DMSO-$d_6$) δ: 1.14-1.25 (4H, m), 1.30-1.43 (1H, m), 1.55-1.73 (3H, m), 2.02-2.15 (3H, m), 2.48-2.52 (3H, m), 3.06-3.29 (3H, m), 3.54-3.64 (1H, m), 3.97-4.21 (4H, m), 4.41 (2H, d, J=6.8 Hz), 4.52-4.60 (1H, m), 6.79-6.86 (1H, m), 6.87-6.95 (2H, m), 7.24 (1H, t, J=8.0 Hz), 7.32 (1H, d, J=1.1 Hz), 9.62 (1H, t, J=6.3 Hz), 12.20 (1H, br).

Reference Example 102

4'-(methylsulfonyl)biphenyl-3-carbonitrile

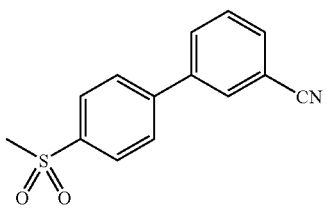

By a method similar to that in Example 81 and using 1-bromo-4-(methylsulfonyl)benzene and (3-cyanophenyl)boronic acid, the title compound was obtained as a pale-yellow powder (10.4 g, 95%).

$^1$H-NMR (300 MHz, DMSO-$d_6$) δ: 3.28 (3H, s), 7.73 (1H, t, J=8.0 Hz), 7.89-7.95 (1H, m), 7.99-8.06 (4H, m), 8.09-8.15 (1H, m), 8.29 (1H, t).

Reference Example 103

4'-[(2-hydroxy-3-methylbutyl)sulfonyl]biphenyl-3-carbonitrile

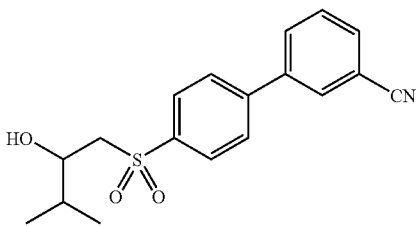

To a solution of 4'-(methylsulfonyl)biphenyl-3-carbonitrile obtained in Reference Example 102 (2.00 g, 7.77 mmol) in THF (40 mL) was added dropwise n-butyllithium (1.6M hexane solution, 5.34 mL, 8.55 mmol) at −78° C., and the mixture was stirred at −78° C. for 1 hr. Isobutyraldehyde (1.06 mL, 11.7 mmol) was added to this solution at −78° C., and the mixture was further stirred at −78° C. for 3 hr. Saturated aqueous ammonium chloride solution was added to the reaction mixture, and the mixture was extracted with ethyl acetate, and washed with saturated sodium chloride aqueous solution. The organic layer was dried over sodium sulfate, and the solvent was evaporated under reduced pressure. The residue was purified by silica gel chromatography (25%-50% ethyl acetate/hexane) to give the title compound as a pale-yellow oil (1.66 g, 65%).

$^1$H-NMR (300 MHz, DMSO-$d_6$) δ: 0.78 (3H, d, J=6.8 Hz), 0.82 (3H, d, J=6.8 Hz), 1.57-1.70 (1H, m), 3.39 (2H, d, J=6.1 Hz), 3.74-3.82 (1H, m), 4.84 (1H, d, J=5.7 Hz), 7.73 (1H, t, J=8.0 Hz), 7.90-7.95 (1H, m), 7.98-8.05 (4H, m), 8.10-8.15 (1H, m), 8.29 (1H, t, J=1.5 Hz).

Reference Example 104

1-{[3'-(aminomethyl)biphenyl-4-yl]sulfonyl}-3-methylbutan-2-ol hydrochloride

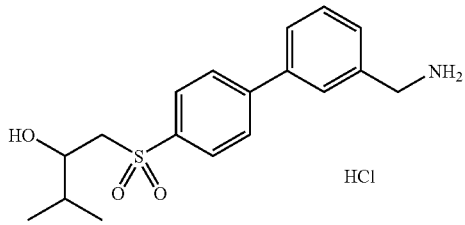

A suspension of 4'-[(2-hydroxy-3-methylbutyl)sulfonyl]biphenyl-3-carbonitrile obtained in Reference Example 103 (1.60 g, 4.86 mmol), Raney-nickel (1.60 g) and 28% aqueous ammonia (16 mL) in THF (32 mL)-methanol (16 mL) was stirred at room temperature for 12 hr under hydrogen atmosphere (1 atm). The insoluble material was filtered off, and the filtrate was concentrated under reduced pressure. The residue was dissolved in a mixed solvent of ethyl acetate-diethyl ether-methanol, and 4N hydrogen chloride-ethyl acetate (1.82 mL) was added thereto. The precipitated solid was collected by filtration, and the solid was washed with diethyl ether to give the title compound as a white powder (1.44 g, 80%).

$^1$H-NMR (300 MHz, DMSO-$d_6$) δ: 0.77 (3H, d, J=6.8 Hz), 0.81 (3H, d, J=6.8 Hz), 1.58-1.71 (1H, m), 3.35-3.40 (2H, m), 3.73-3.82 (1H, m), 4.12 (2H, br), 4.84 (m, d, J=5.7 Hz), 7.53-7.60 (2H, m), 7.76-7.81 (1H, m), 7.92-8.04 (5H, m), 8.47 (3H, br).

Reference Example 105

N-({4'-[(2-hydroxy-3-methylbutyl)sulfonyl]biphenyl-3-yl}methyl)-4-oxo-3,4-dihydroquinazoline-2-carboxamide

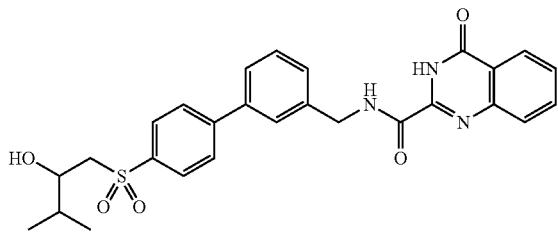

By a method similar to that in Example 87 and using 1-{[3'-(aminomethyl)biphenyl-4-yl]sulfonyl}-3-methylbutan-2-ol hydrochloride obtained in Reference Example 104 and ethyl 4-oxo-3,4-dihydro-2-quinazolinecarboxylate obtained according to the methods described in Journal of Organic Chemistry (1978), 43(23), 4485-7 and the like, the title compound was obtained as a white powder (0.774 g, 78%)

$^1$H-NMR (300 MHz, DMSO-$d_6$) δ: 0.76 (3H, d, J=6.8 Hz), 0.81 (3H, d, J=6.8 Hz), 1.56-1.69 (1H, m), 3.34-3.38 (2H, m) 3.72-3.81 (1H, m), 4.58 (2H, d, J=6.4 Hz), 4.81 (1H, d, J=5.8 Hz), 7.42-7.53 (2H, m), 7.57-7.68 (2H, m), 7.74-7.81 (2H, m), 7.85-7.92 (3H, m), 7.95-8.01 (2H, m), 8.17 (1H, dd, J=1.3, 7.9 Hz), 9.65 (1H, t, J=6.4 Hz), 12.03 (1H, br).

Reference Example 106

N-[(4'-{[(1E)-3-methylbut-1-en-1-yl]sulfonyl}biphenyl-3-yl)methyl]-4-oxo-3,4-dihydroquinazoline-2-carboxamide

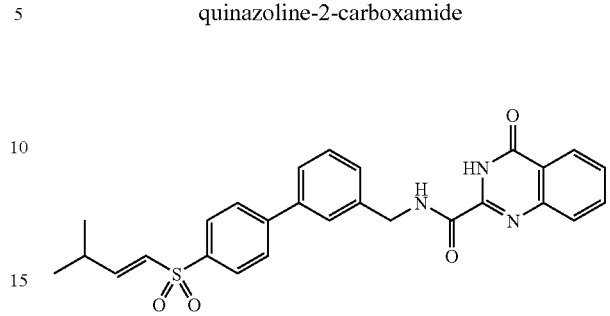

To a suspension of N-([4'-[(2-hydroxy-3-methylbutyl)sulfonyl]biphenyl-3-yl]methyl)-4-oxo-3,4-dihydroquinazoline-2-carboxamide obtained in Reference Example 105 (0.300 g, 0.593 mmol) and triethylamine (0.579 mL, 4.15 mmol) in THF (6 mL) was added dropwise methanesulfonyl chloride (0.083 mL, 1.07 mmol) at 0° C., and the reaction mixture was stirred at room temperature for 12 hr. The reaction mixture was diluted with ethyl acetate, washed with 0.1N hydrochloric acid and saturated brine, and dried over sodium sulfate. The solvent was evaporated under reduced pressure, and the residue was crystallized from ethyl acetate-diethyl ether to give the title compound as a pale-yellow powder (0.220 g, 76%).

$^1$H-NMR (300 MHz, DMSO-$d_6$) δ: 1.02 (6H, d, J=6.8 Hz), 2.44-2.59 (1H, m), 4.58 (2H, d, J=6.1 Hz), 6.71-6.80 (1H, m), 6.86-6.96 (1H, m), 7.37-7.54 (2H, m), 7.55-7.68 (2H, m), 7.70-7.83 (2H, m), 7.82-7.98 (5H, m), 8.17 (1H, d, J=7.6 Hz), 9.65 (1H, t, J=5.9 Hz), 12.29 (1H, br).

Reference Example 107

N-[(4'-{[2-(hydroxyamino)-3-methylbutyl]sulfonyl}biphenyl-3-yl)methyl]-4-oxo-3,4-dihydroquinazoline-2-carboxamide

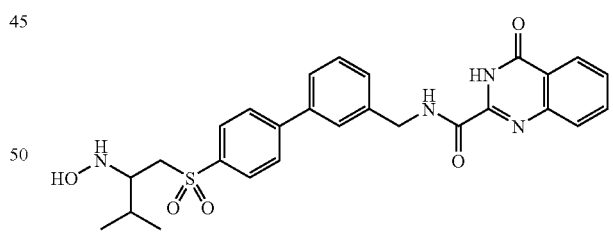

To a solution of N-[(4'-{[(1E)-3-methylbut-1-en-1-yl]sulfonyl}biphenyl-3-yl)methyl]-4-oxo-3,4-dihydroquinazoline-2-carboxamide obtained in Reference Example 106 (0.180 g, 0.369 mmol) in THF (4 mL) was added O-(trimethylsilyl)hydroxylamine (0.271 mL, 2.22 mmol) at room temperature, and the mixture was stirred at room temperature for 12 hr. The reaction mixture was concentrated under reduced pressure, and the residue was crystallized from ethyl acetate-diethyl ether to give the title compound as a white powder (0.125 g, 65%).

$^1$H-NMR (300 MHz, DMSO-$d_6$) δ: 0.76 (3H, d, J=6.8 Hz), 0.80 (3H, d, J=6.8 Hz), 1.87-2.03 (1H, m), 2.86-2.96 (1H, m), 3.25-3.43 (2H, m), 4.58 (2H, dr J=6.2 Hz), 5.52 (1H, br), 7.31

(1H, s), 7.41-7.55 (2H, m), 7.57-7.70 (2H, m), 7.74-7.83 (2H, m), 7.84-8.05 (5H, m), 8.14-8.21 (1H, m), 9.66 (1H, t, J=6.4 Hz), 12.26 (1H, br).

Reference Example 108

5-({[(4-bromophenyl)methyl]thio}methyl)-2,4-dihydro-3H-1,2,4-triazol-3-one

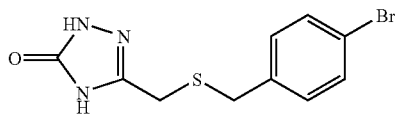

To a solution of 5-(chloromethyl)-2,4-dihydro-3H-1,2,4-triazol-3-one obtained according to the methods described in Tetrahedron Letter, 2000, 41, 8661 and the like (2.00 g, 15.0 mmol), (4-bromophenyl)methanethiol (3.04 g, 15.0 mmol) and potassium carbonate (2.48 g, 0.369 mmol) in THF (4 mL) was added a suspension of O-(trimethylsilyl)hydroxylamine (0.271 mL, 18.0 mmol) in DMF (40 mL) at room temperature, and the mixture was stirred at room temperature for 12 hr. Water was added to the reaction mixture, and the precipitated solid was collected by filtration. The solid was washed with water and diethyl ether to give the title compound as a white powder (3.97 g, 88%).

$^1$H-NMR (300 MHz, DMSO-$d_6$) δ: 3.36 (2H, s), 3.70 (2H, s), 7.28 (2H, d, J=8.3 Hz), 7.52 (2H, d, J=8.3 Hz), 11.29 (1H, br), 11.39 (1H, br).

Reference Example 109

5-({[(4-bromophenyl)methyl]sulfonyl}methyl)-2,4-dihydro-3H-1,2,4-triazol-3-one

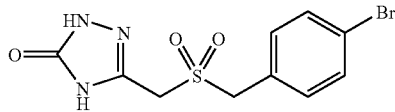

To a solution of 5-({[(4-bromophenyl)methyl]thio}methyl)-2,4-dihydro-3H-1,2,4-triazol-3-one obtained in Reference Example 108 (0.500 g, 1.67 mmol) in DMF (5 mL) was added m-chloroperbenzoic acid (0.903 g, 3.67 mmol) at room temperature, and the mixture was stirred for 12 hr. Water and saturated aqueous sodium hydrogencarbonate solution were added to the reaction mixture, and the precipitated solid was collected by filtration. The solid was washed with water and diethyl ether to give the title compound as a white powder (0.508 g, 92%).

$^1$H-NMR (300 MHz, DMSO-$d_6$) δ: 4.32 (2H, s), 4.60 (2H, s), 7.38 (2H, d, J=8.3 Hz), 7.63 (2H, d, J=8.3 Hz), 11.62 (1H, br), 11.68 (1H, br).

Reference Example 110

4'-({[(5-oxo-4,5-dihydro-1H-1,2,4-triazol-3-yl)methyl]sulfonyl}methyl)biphenyl-3-carbonitrile

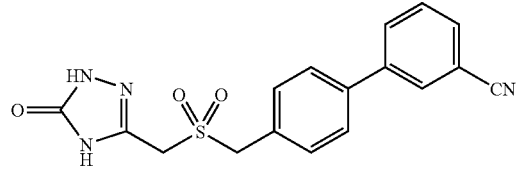

By a method similar to that in Reference Example 93 and using 5-({[(4-bromophenyl)methyl]sulfonyl}methyl)-2,4-dihydro-3H-1,2,4-triazol-3-one obtained in Reference Example 109, the title compound was obtained as a pale-yellow powder (0.308 g, 60%).

$^1$H-NMR (300 MHz, DMSO-$d_6$) δ: 4.36 (2H, s), 4.67 (2H, s), 7.56 (2H, d, J=8.3 Hz), 7.69 (1H, t, J=7.8 Hz), 7.79-7.89 (3H, m), 8.06 (1H, d, J=8.0 Hz), 8.20 (1H, s), 11.65 (1H, br), 11.70 (1H, br).

Reference Example 111

5-[({[3'-(aminomethyl)biphenyl-4-yl]methyl}sulfonyl)methyl]-2,4-dihydro-3H-1,2,4-triazol-3-one

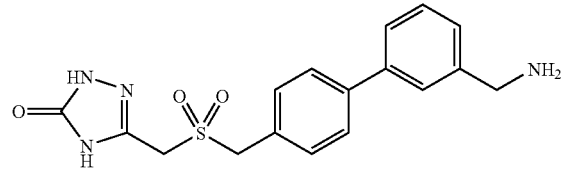

A suspension of 4'-({[(5-oxo-4,5-dihydro-1H-1,2,4-triazol-3-yl)methyl]sulfonyl}methyl)biphenyl-3-carbonitrile obtained in Reference Example 110 (0.250 g, 0.705 mmol), Raney-nickel (0.250 g) and 28% aqueous ammonia (5 mL) in THF (5 mL)-methanol (5 mL) was stirred at room temperature for 4 hr under hydrogen atmosphere (1 atm). The insoluble material was filtered off, and the filtrate was concentrated under reduced pressure. Diethyl ether was added to the residue, and the precipitated solid was collected by filtration to give the title compound as a pale-blue powder (0.250 g, 99%).

ESI-MS: m/z 359.1 [M+H]$^+$

Reference Example 112

1,1-dimethylethyl 4-(3-bromophenyl)piperazine-1-carboxylate

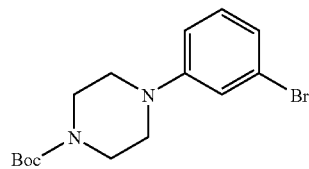

wherein Boc is tert-butoxycarbonyl, which is the same as in the other formulas in the present specification.

To a solution of 1-(3-bromophenyl)piperazine (6.97 g, 27.4 mmol) and triethylamine (3.82 mL, 27.4 mmol) in THF (60 mL) was added bis(1,1-dimethylethyl) dicarbonate (5.97 g, 27.4 mmol) at room temperature, and the mixture was stirred for 3 hr. The reaction mixture was concentrated under reduced pressure, and the residue was diluted with ethyl acetate and water, and neutralized with 1N hydrochloric acid. The organic layer was separated, washed with saturated brine, and dried over sodium sulfate. The solvent was evaporated under reduced pressure, and the residue was crystallized from hexane to give the title compound as a white powder (5.39 g, 64%).

$^1$H-NMR (300 MHz, DMSO-$d_6$) δ: 1.42 (9H, s), 3.09-3.17 (4H, m), 3.39-3.47 (4H, m), 6.91-6.97 (2H, m), 7.09 (1H, t, J=2.1 Hz), 7.12-7.19 (1H, m).

Reference Example 113

1,1-dimethylethyl 4-(3-cyanophenyl)piperazine-1-carboxylate

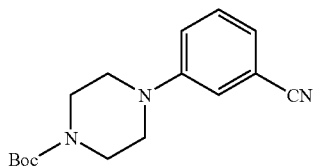

A suspension of 1,1-dimethylethyl 4-(3-bromophenyl)piperazine-1-carboxylate obtained in Reference Example 112 (3.10 g, 9.09 mmol), zinc cyanide (0.587 g, 5.00 mmol) and tetrakis(triphenylphosphine)palladium (0.525 g, 0.454 mmol) in DMF (30 mL) was stirred at 80° C. for 12 hr under nitrogen atmosphere. The reaction mixture was diluted with ethyl acetate, washed with water and saturated brine, and dried over sodium sulfate. The solvent was evaporated under reduced pressure, and the residue was purified by silica gel chromatography (25%-40% ethyl acetate/hexane), and crystallized from hexane to give the title compound as a white powder (2.10 g, 80%).

$^1$H-NMR (300 MHz, DMSO-$d_6$) δ: 1.42 (9H, s), 3.16-3.24 (4H, m), 3.40-3.48 (4H, m), 7.16-7.21 (1H, m), 7.25-7.31 (1H, m), 7.33-7.36 (1H, m), 7.36-7.43 (1H, m).

Reference Example 114

1,1-dimethylethyl 4-[3-(aminomethyl)phenyl]piperazine-1-carboxylate

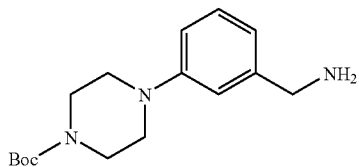

By a method similar to that in Reference Example 94 and using 1,1-dimethylethyl 4-(3-cyanophenyl)piperazine-1-carboxylate obtained in Reference Example 113, the title compound was obtained as a pale-blue oil (2.03 g, 100%).

$^1$H-NMR (300 MHz, DMSO-$d_6$) δ: 1.42 (9H, s), 3.04-3.13 (4H, m), 3.17-3.51 (6H, m), 3.50-3.82 (2H, m), 6.71-6.80 (2H, m), 6.92 (1H, br), 7.16 (1H, t, J=7.2 Hz).

Reference Example 115

1,1-dimethylethyl 4-[3-({[(4-oxo-3,4-dihydroquinazolin-2-yl)carbonyl]amino}methyl)phenyl]piperazine-1-carboxylate

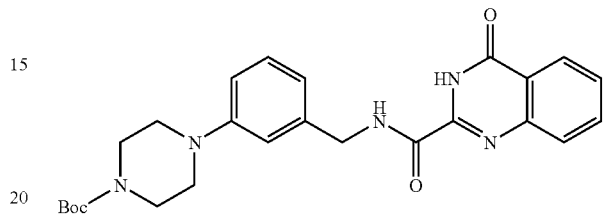

By a method similar to that in Example 87 and using 1,1-dimethylethyl 4-[3-(aminomethyl)phenyl]piperazine-1-carboxylate obtained in Reference Example 114 and ethyl 4-oxo-3,4-dihydro-2-quinazolinecarboxylate obtained according to the methods described in Journal of Organic Chemistry (1978), 43(23), 4485-7 and the like, the title compound was obtained as a white powder (2.44 g, 92%).

$^1$H-NMR (300 MHz, DMSO-$d_6$) δ: 1.41 (9H, s), 3.03-3.14 (4H, m), 3.39-3.50 (4H, m), 4.43 (2H, d, J=6.4 Hz), 6.76-6.88 (2H, m), 6.97 (1H, s), 7.18 (1H, t, J=7.8 Hz), 7.56-7.66 (1H, m), 7.74-7.82 (1H, m), 7.84-7.94 (1H, m), 8.17 (1H, dd, J=1.1, 7.9 Hz), 9.48 (1H, t, J=6.4 Hz), 12.27 (1H, br).

Reference Example 116

4-oxo-N-[(3-piperazin-1-ylphenyl)methyl]-3,4-dihydroquinazoline-2-carboxamide dihydrochloride

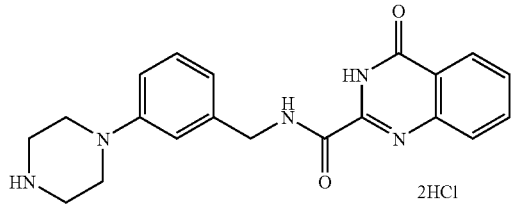

To a suspension of 1,1-dimethylethyl 4-[3-({[(4-oxo-3,4-dihydroquinazolin-2-yl)carbonyl]amino}methyl)phenyl]piperazine-1-carboxylate obtained in Reference Example 115 (2.40 g, 6.86 mmol) in ethyl acetate (10 mL)-THF (50 ml)-methanol (40 mL) was added 4N hydrogen chloride-ethyl acetate (10.4 mL), and the mixture was stirred at room temperature for 4 hr, and then at 50° C. for 2 hr. Diethyl ether (about 100 mL) was added to the reaction mixture, and the precipitated solid was collected by filtration to give the title compound as a white powder (2.18 g, 97%).

$^1$H-NMR (300 MHz, DMSO-$d_6$) δ: 3.14-3.26 (4H, m), 3.31-3.42 (4H, m), 4.45 (2H, d, J=6.4 Hz), 6.83-6.93 (2H, m), 7.00 (1H, br), 7.22 (1H, t, J=7.8 Hz), 7.62 (1H, t, J=7.6 Hz), 7.75-7.83 (1H, m), 7.90 (1H, t, J=7.6 Hz), 8.18 (1H, d, J=8.0 Hz), 9.25-9.40 (2H, m), 9.52 (1H, t, J=6.4 Hz), 2H hidden.

Reference Example 117 ethyl (5-oxo-2,5-dihydro-1H-pyrazol-3-yl)acetate

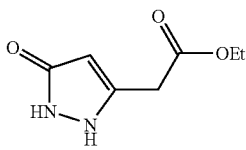

To a solution of diethyl 3-oxopentanedioate (26.0 g, 129 mmol) in EtOH (250 mL) was added hydrazine (4.38 g, 129 mmol) at room temperature, and the mixture was stirred at 80° C. for 3 hr. The reaction mixture was concentrated under reduced pressure, and the residue was crystallized from diethyl ether-hexane to give the title compound as a white powder (9.79 g, 45%).

$^1$H-NMR (300 MHz, DMSO-$d_6$) δ: 1.19 (3H, t, J=7.0 Hz), 3.53 (2H, s), 4.08 (2H, q, J=6.9 Hz), 5.34 (1H, s), 9.53 (1H, br), 11.39 (1H, br).

Reference Example 118

(5-oxo-2,5-dihydro-1H-pyrazol-3-yl)acetic acid

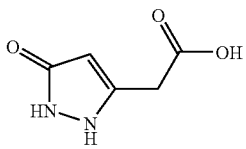

To a suspension of ethyl (5-oxo-2,5-dihydro-1H-pyrazol-3-yl)acetate obtained in Reference Example 117 (5.00 g, 29.4 mmol) in THF (20 mL)-methanol (20 mL)-water (20 mL) was added 5N aqueous sodium hydroxide solution (11.0 mL, 88.0 mmol) at room temperature, and the mixture was stirred under heating at 80° C. for 3 hr. The reaction mixture allowed to cool to room temperature, and concentrated under reduced pressure, and the residue was diluted with water, and acidified with 6N hydrochloric acid. The precipitated solid was collected by filtration, and washed with water, and dried under nitrogen stream to give the title compound as a white powder (3.43 g, 82%).

$^1$H-NMR (300 MHz, DMSO-$d_6$) δ: 3.45 (2H, s), 5.33 (1H, s), 10.52-12.13 (3H, m).

Reference Example 119

N-[(4'-hydroxybiphenyl-3-yl)methyl]-4-oxo-3,4-dihydroquinazoline-2-carboxamide

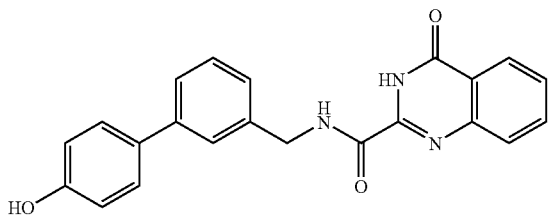

A suspension of 4'-hydroxybiphenyl-3-carbonitrile obtained according to the methods described in Bioorganic & Medicinal Chemistry, 2003, 11, 3457 and the like (1.40 g, 7.17 mmol), 5-bromo-5-[2-(ethyloxy)ethyl]pyrimidine-2,4,6 (1H,3H,5H)-trione obtained according to the methods described in WO02/34726 and the like (2.00 g, 7.17 mmol) and potassium carbonate (3.47 g, 25.1 mmol) in DMF (40 mL) was stirred at room temperature for 4 hr. The reaction mixture was diluted with ethyl acetate, washed with water and saturated brine, and dried over sodium sulfate. The solvent was evaporated under reduced pressure, and the residue was crystallized from methanol-diethyl ether to give 4'-({5-[2-(ethyloxy)ethyl]-2,4,6-trioxohexahydropyrimidin-5-yl}oxy)biphenyl-3-carbonitrile as a white powder (1.95 g). A suspension of the obtained white powder (1.50 g, 3.81 mmol), Raney-nickel (1.50 g) and 28% aqueous ammonia (15 mL) in THF (30 mL)-methanol (15 mL) was stirred at room temperature for 12 hr under hydrogen atmosphere (1 atm). The catalyst was filtered off, and the filtrate was concentrated under reduced pressure. The residue was diluted with water, and acidified with 1N hydrochloric acid, and the precipitated insoluble material was filtered off. The filtrate was basified with 1N aqueous sodium hydroxide solution, and the precipitated solid was collected by filtration; and washed with water and EtOH to give sodium 31-(aminomethyl)biphenyl-4-olate as a pale-green powder (0.800 g). A suspension of the obtained pale-green powder (0.200 g, 0.904 mmol), ethyl 4-oxo-3,4-dihydro-2-quinazolinecarboxylate obtained according to the methods described in Journal of Organic Chemistry (1978), 43(23), 4485-7 and the like (0.132 g, 0.603 mmol) and triethylamine (0.336 mL, 2.41 mmol) in EtOH (10 mL) was stirred at 90° C. for 12 hr. After the reaction mixture was allowed to cool to room temperature, 2N hydrogen chloride-so EtOH (2 mL) was added, and the precipitated solid was collected by filtration. The solid was washed with EtOH to give the title compound as a white powder (0.149 g, 67%).

$^1$H-NMR (300 MHz, DMSO-$d_6$) δ: 4.53 (2H, d, J=6.1 Hz), 6.84 (2H, d, J=8.3 Hz), 7.23-7.30 (1H, m), 7.37 (1H, t, J=7.6 Hz), 7.42-7.50 (3H, m), 7.55-7.64 (2H, m), 7.73-7.80 (1H, m), 7.87 (1H, t, J=7.6 Hz), 8.16 (1H, d, J=8.0 Hz), 9.51-9.64 (2H, m), 12.01 (1H, br).

Reference Example 120

3-(3-{[5-(trifluoromethyl)-1H-1,2,4-triazol-3-yl]thio}propoxy)benzonitrile

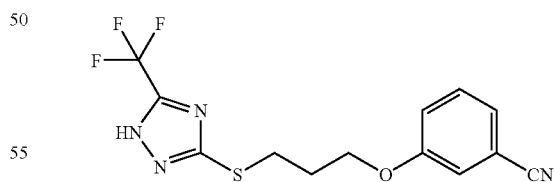

By a method similar to that in Reference Example 2, and using, instead of 3-[(2-chloroethyl)oxy]benzonitrile, 3-[(3-chloropropyl)oxy]benzonitrile obtained in Reference Example 4 and using, instead of 1H-1,2,4-triazole-3-thiol, 5-(trifluoromethyl)-1H-1,2,4-triazole-3-thiol, the title compound was obtained as a yellow oil (1.25 g, 64%).

$^1$H-NMR (300 MHz, DMSO-$d_6$) δ: 2.07-2.19 (2H, m), 3.31-3.43 (2H, m), 4.14 (2H, tt J=6.0 Hz), 7.25-7.30 (1H, m), 7.37-7.42 (2H, m), 7.48 (1H, t, J=8.1 Hz), 14.94 (1H, br).

Reference Example 121

1-[3-(3-{[5-(trifluoromethyl)-1H-1,2,4-triazol-3-yl]thio}propoxy)phenyl]methanamine hydrochloride

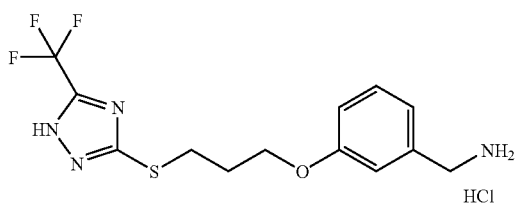

A solution of 3-(3-{[5-(trifluoromethyl)-1H-1,2,4-triazol-3-yl]thio}propoxy)benzonitrile obtained in Reference Example 120 (1.10 g, 3.350 mmol) and Raney-nickel (1.0 g) in 7N ammonia/methanol (50 mL) was stirred at room temperature for 5 hr under hydrogen atmosphere (1 atm). The catalyst was filtered off, and a 2N hydrogen chloride/methanol solution was added to the filtrate. The mixture was concentrated, and the obtained residue was crystallized from EtOH/toluene to give the title compound as a red powder (1.39 g, quant).

$^1$H-NMR (300 MHz, DMSO-$d_6$) δ: 2.08-2.19 (2H, m), 3.38 (2H, t, J=7.0 Hz), 3.89-4.05 (2H, m), 4.11 (2H, t, J=5.9 Hz), 6.89-6.97 (1H, m), 7.00-7.09 (1H, m), 7.17 (1H, s), 7.30 (1H, t, J=7.8 Hz), 8.57 (3H, br), 15.31 (1H, br).

Reference Example 122 ethyl 4-[3-({[(5-methyl-4-oxo-3,4-dihydrothieno[2,3-d]pyrimidin-2-yl)carbonyl]amino}methyl)phenoxy]butanoate

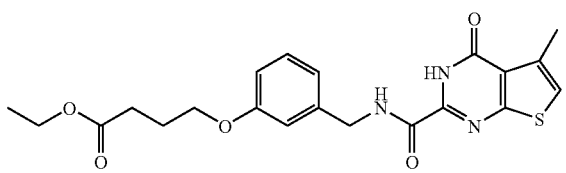

By a method similar to that in Example 97 and using, instead of 1-[3-(3-{[5-(trifluoromethyl)-1H-1,2,4-triazol-3-yl]thio}propoxy)phenyl]methanamine hydrochloride, ethyl 4-{[3-(aminomethyl)phenyl]oxy}butanoate hydrochloride obtained in Reference Example 42, the title compound was obtained as a pale-yellow powder (580.0 mg, 64%).

$^1$H-NMR (300 MHz, DMSO-$d_6$) δ: 1.15 (3H, t, J=7.2 Hz), 1.89-2.01 (2H, m), 2.44 (2H, t, J=7.3 Hz), 3.96 (2H, t, J=6.3 Hz), 4.05 (2H, q, J=7.2 Hz), 4.40 (2H, d, J=6.4 Hz), 6.76-6.83 (1H, m), 6.85-6.94 (2H, m), 7.22 (1H, t, J=8.1 Hz), 7.31 (1H, dr J=1.1 Hz), 9.60 (1H, t, J=6.3 Hz), 12.06 (1H, s), 3H hidden.

Reference Example 123

3-{3-[(5-methyl-1H-1,2,4-triazol-3-yl)thio]propoxy}benzonitrile

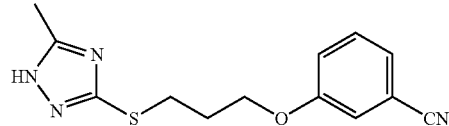

By a method similar to that in Reference Example 2, and using, instead of 3-[(2-chloroethyl)oxy]benzonitrile, 3-[(3-chloropropyl)oxy]benzonitrile obtained in Reference Example 4 and using, instead of 1H-1,2,4-triazole-3-thiol, 5-methyl-1H-1,2,4-triazole-3-thiol, the title compound was obtained as a yellow oil (643.0 mg, 46%).

$^1$H-NMR (300 MHz, CDCl$_3$) δ: 2.17-2.29 (2H, m), 2.45 (3H, s), 3.30 (2H, t, J=6.8 Hz), 4.12 (2H, t, J=6.1 Hz), 7.08-7.17 (2H, m), 7.21-7.29 (1H, m), 7.36 (1H, t, J=8.1 Hz), 1H hidden.

Reference Example 124

1-(3-{3-[(5-methyl-1H-1,2,4-triazol-3-yl)thio]propoxy}phenyl)methanamine hydrochloride

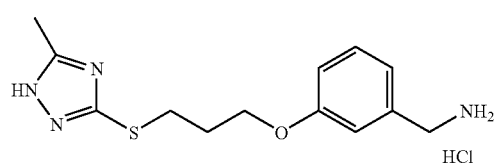

By a method similar to that in Reference Example 121 and using, instead of 3-(3-{[5-(trifluoromethyl)-1H-1,2,4-triazol-3-yl]thio}propoxy)benzonitrile, 3-{3-[(5-methyl-1H-1,2,4-triazol-3-yl)thio]propoxy}benzonitrile obtained in Reference Example 123, the title compound was obtained as a blue powder (366.4 mg, 68%).

$^1$H-NMR (300 MHz, DMSO-$d_6$) δ: 2.04-2.15 (2H, m), 2.30 (3H, s), 3.13-3.21 (2H, m), 3.99 (2H, q, J=6.0 Hz), 4.08 (2H, t, J=6.3 Hz), 6.92-6.97 (1H, m), 7.00-7.05 (1H, m, J=7.5 Hz), 7.08-7.11 (1H, m, J=1.5 Hz), 7.28-7.36 (1H, m), 8.24 (3H, br), 1H hidden.

Reference Example 125

3-[3-(1H-imidazol-1-yl)propoxy]benzonitrile

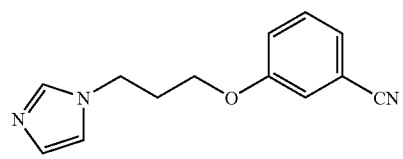

By a method similar to that in Reference Example 2, and using, instead of 3-[(2-chloroethyl)oxy]benzonitrile, 3-[(3-chloropropyl)oxy]benzonitrile obtained in Reference Example 4 and using, instead of 1H-1,2,4-triazole-3-thiol, 1H-imidazole, the title compound was obtained as a colorless oil (1.65 g, 71%).

¹H-NMR (300 MHz, CDCl₃) δ: 2.21-2.31 (2H, m), 3.92 (2H, t, J=5.7 Hz), 4.20 (2H, t, J=6.8 Hz), 6.90-6.93 (1H, m), 7.07-7.14 (3H, m), 7.25-7.29 (1H, m), 7.39 (1H, t, J=7.8 Hz), 7.47 (1H, s).

Reference Example 126

1-{3-[3-(1H-imidazol-1-yl)propoxy]phenyl}methanamine hydrochloride

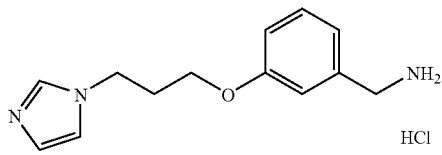

By a method similar to that in Reference Example 121 and using, instead of 3-(3-{[5-(trifluoromethyl)-1H-1,2,4-triazol-3-yl]thio}propoxy)benzonitrile, 3-[3-(1H-imidazol-1-yl)propoxy]benzonitrile obtained in Reference Example 125, the title compound was obtained as a white powder (1.25 g, 66%).

¹H-NMR (300 MHz, DMSO-d₆) δ: 2.19-2.30 (2H, m), 3.89-4.05 (4H, m), 4.26 (2H, t, J=6.7 Hz), 6.92 (1H, d, J=10.0 Hz), 7.04 (1H, d, J=7.2 Hz), 7.11 (1H, br), 7.27-7.36 (2H, m), 7.53 (5H, s), 8.25-8.61 (4H, m).

Reference Example 127

3-[3-(1H-1,2,4-triazol-1-yl)propoxy]benzonitrile

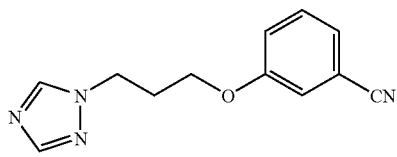

By a method similar to that in Reference Example 2, and using, instead of 3-[(2-chloroethyl)oxy]benzonitrile, 3-[(3-chloropropyl)oxy]benzonitrile obtained in Reference Example 4 and using, instead of 1H-1,2,4-triazole-3-thiol, 1H-1,2,4-triazole, the title compound was obtained as a colorless oil (750.0 mg, 32%).

¹H-NMR (300 MHz, CDCl₃) δ: 2.35-2.45 (2H, m), 3.96 (2H, t, J=5.7 Hz), 4.42 (2H, t, J=6.7 Hz), 7.07-7.14 (2H, m), 7.24-7.29 (1H, m), 7.34-7.42 (1H, m), 7.97 (1H, s), 8.06 (1H, s).

Reference Example 128

1-{3-[3-(1H-1,2,4-triazol-1-yl)propoxy]phenyl}methanamine hydrochloride

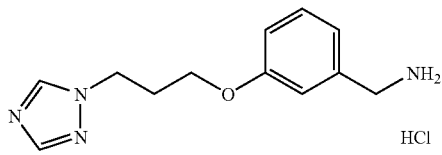

By a method similar to that in Reference Example 121 and using, instead of 3-(3-{[5-(trifluoromethyl)-1H-1,2,4-triazol-3-yl]thio}propoxy)benzonitrile, 3-[3-(1H-1,2,4-triazol-1-yl)propoxy]benzonitrile obtained in Reference Example 127, the title compound was obtained as a white powder (545.0 mg, 73%).

¹H-NMR (300 MHz, DMSO-d₆) δ: 2.20-2.31 (2H, m), 3.93-4.03 (4H, m), 4.38 (2H, t, J=6.9 Hz), 6.92 (1H, dd, J=1.9, 8.3 Hz), 7.04 (1H, d, J=7.5 Hz), 7.10 (1H, s), 7.32 (1H, t, J=7.8 Hz), 8.07 (1H, s), 8.36 (3H, br), 8.66 (1H, s).

Reference Example 129

3-[3-(1H-pyrazol-1-yl)propoxy]benzonitrile

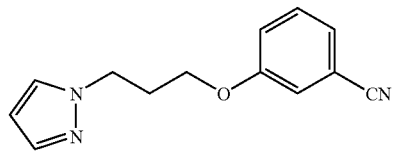

By a method similar to that in Reference Example 2, and using, instead of instead of 3-[(2-chloroethyl)oxy]benzonitrile, 3-[(3-chloropropyl)oxy]benzonitrile obtained in Reference Example 4 and using, instead of 1H-1,2,4-triazole-3-thiol, 1H-pyrazole, the title compound was obtained as a colorless oil (2.05 g, 88%).

¹H-NMR (300 MHz, CDCl₃) δ: 2.31-2.42 (2H, m), 3.92 (2H, t, J=5.9 Hz), 4.36 (2H, t, J=6.6 Hz), 6.24 (1H, t, J=2.1 Hz), 7.07-7.13 (2H, m), 7.20-7.29 (1H, m), 7.32-7.41 (2H, m), 7.53 (1H, d, J=1.5 Hz).

Reference Example 130

1-{3-[3-(1H-pyrazol-1-yl)propoxy]phenyl}methanamine hydrochloride

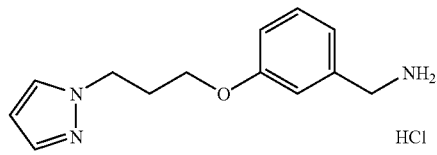

By a method similar to that in Reference Example 121 and using, instead of 3-(3-{[5-(trifluoromethyl)-1H-1,2,4-triazol-3-yl]thio}propoxy)benzonitrile, 3-[3-(1H-pyrazol-1-yl)propoxy]benzonitrile obtained in Reference Example 129, the title compound was obtained as a white powder (1.88 g, 80%).

¹H-NMR (300 MHz, DMSO-d₆) δ: 2.22 (2H, tt, J=6.5, 6.5 Hz), 3.90-4.02 (4H, m), 4.28 (2H, t, J=6.9 Hz), 6.23 (1H, t, J=2.1 Hz), 6.92 (1H, dd, J=1.9, 8.1 Hz), 7.04 (1H, d, J=7.7 Hz), 7.11 (1H, s), 7.31 (1H, t, J=7.9 Hz), 7.44 (1H, d, J=1.3 Hz), 7.73 (1H, d, J=1.9 Hz), 8.39 (3H, br).

Reference Example 131

3-{3-[(5-phenyl-1H-1,2,4-triazol-3-yl)thio]propoxy}benzonitrile

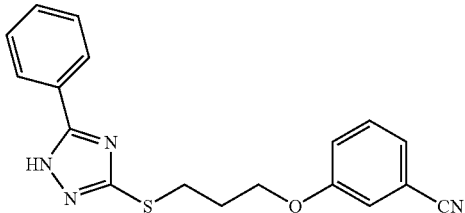

By a method similar to that in Reference Example 2, and using, instead of 3-[(2-chloroethyl)oxy]benzonitrile, 3-[(3-chloropropyl)oxy]benzonitrile obtained in Reference Example 4 and using, instead of 1H-1,2,4-triazole-3-thiol, 5-phenyl-1H-1,2,4-triazole-3-thiol, the title compound was obtained as a white powder (1.01 g, 59%).

$^1$H-NMR (300 MHz, DMSO-$d_6$) δ: 2.12-2.22 (2H, m), 3.30 (2H, t, J=7.1 Hz), 4.17 (2H, t, J=6.1 Hz), 7.26-7.32 (1H, m), 7.36-7.54 (6H, m), 7.88-7.97 (2H, m), 14.32 (1H, br).

Reference Example 132

1-(3-{3-[(5-phenyl-1H-1,2,4-triazol-3-yl)thio]propoxy}phenyl)methanamine hydrochloride

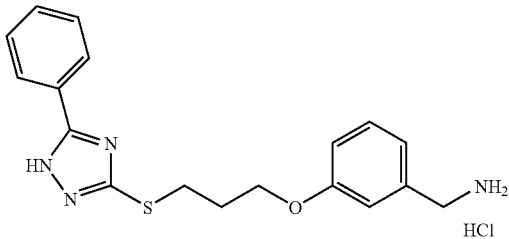

By a method similar to that in Reference Example 121 and using, instead of 3-(3-{[5-(trifluoromethyl)-1H-1,2,4-triazol-3-yl]thio}propoxy)benzonitrile, 3-{3-[(5-phenyl-1H-1,2,4-triazol-3-yl)thio]propoxy}benzonitrile obtained in Reference Example 131, the title compound was obtained as a green powder (859.7 mg, 77%).

$^1$H-NMR (300 MHz, DMSO-$d_6$) δ: 2.11-2.23 (2H, m), 3.31 (2H, t, J=7.0 Hz), 3.96 (2H, d, J=5.1 Hz), 4.13 (2H, t, J=6.0 Hz), 6.95 (1H, dd, J=2.0, 8.2 Hz), 7.05 (1H, d, J=7.3 Hz), 7.16 (1H, s), 7.30 (1H, t, J=7.8 Hz), 7.44-7.57 (3H, m), 7.99 (2H, dd, J=1.6, 7.6 Hz), 8.50 (3H, br).

Reference Example 133

3'-(hydroxymethyl)biphenyl-3-carbonitrile

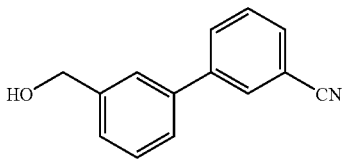

To a solution of 3-bromobenzonitrile (1.20 g, 6.58 mmol) in toluene (40 mL) was added a solution of tetrakistriphenylphosphinepalladium (0.38 g, 0.33 mmol), 2N aqueous sodium carbonate solution (21 mL) and [3-(hydroxymethyl)phenyl]boronic acid (1.00 g, 6.58 mmol) in EtOH (19 mL), and the mixture was heated under reflux for 10 hr under nitrogen atmosphere. The reaction mixture was cooled to room temperature, water was added, and the mixture was extracted with ethyl acetate. The organic layer was dried over sodium sulfate, and concentrated. The residue was purified by silica gel column chromatography (hexane/ethyl acetate=1/9→1/1) to give the title compound as a yellow oil (1.28 g, 93%).

$^1$H-NMR (300 MHz, CDCl$_3$) δ: 4.79 (2H, d, J=5.3 Hz), 7.39-7.67 (6H, m), 7.82 (1H, d, J=7.6 Hz), 7.87 (1H, s), 1H hidden.

Reference Example 134

3'-{[(1-trityl-1H-1,2,4-triazol-3-yl)oxy]methyl}biphenyl-3-carbonitrile

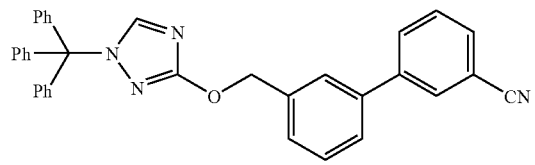

wherein Ph is phenyl, which is the same as in the other formulas in the present specification.

By a method similar to that in Reference Example 31 and using, instead of 3-[(2-hydroxyethyl)oxy]benzonitrile, 3'-(hydroxymethyl)biphenyl-3-carbonitrile obtained in Reference Example 133, the title compound was obtained as a colorless oil (1.62 g, 69%).

$^1$H-NMR (300 MHz, DMSO-$d_6$) δ: 5.30 (2H, s), 7.03-7.11 (6H, m), 7.32-7.40 (9H, m), 7.42-7.53 (2H, m), 7.63-7.70 (1H, m), 7.70-7.75 (1H, m), 7.78 (1H, br), 7.81-7.87 (2H, m), 7.97-8.02 (1H, m), 8.12-8.14 (1H, m).

Reference Example 135

1-(3'-{[(1-trityl-1H-1,2,4-triazol-3-yl)oxy]methyl}biphenyl-3-yl)methanamine

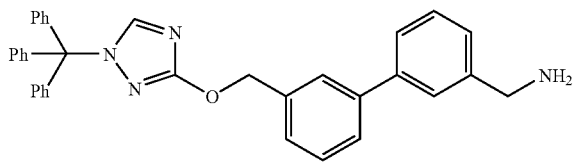

By a method similar to that in Reference Example 20 and using, instead of 2-[(2-{[1-(triphenylmethyl)-1H-1,2,4-triazol-3-yl]thio}ethyl)oxy]pyridine-4-carbonitrile, 3'-{[(1-trityl-1H-1,2,4-triazol-3-yl)oxy]methyl}biphenyl-3-carbonitrile obtained in Reference Example 134, the title compound was obtained as a colorless oil (1.12 mg, 74%).

$^1$H-NMR (300 MHz, DMSO-$d_6$) δ: 2.30 (2H, s), 3.73-3.79 (2H, m), 5.30 (2H, s), 6.95-7.55 (20H, m), 7.62 (2H, s), 7.70 (1H, s), 7.84 (1H, s).

Reference Example 136 ethyl 5-biphenyl-4-yl-oxo-3,4-dihydrothieno[2,3-d]pyrimidine-2-carboxylate

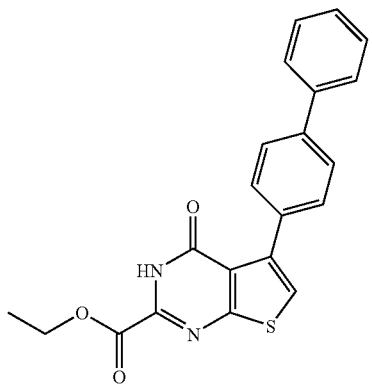

By a method similar to that in Reference Example 39 and using, instead of ethyl 5'-amino-2,3'-bithiophene-4'-carboxylate, ethyl 2-amino-4-biphenyl-4-ylthiophene-3-carboxylate, the title compound was obtained as a pale-yellow powder (1.97 g, 85%).

$^1$H-NMR (300 MHz, DMSO-d$_6$) δ: 1.36 (3H, t, J=7.1 Hz)/ 4.38 (2H, q, J=7.2 Hz), 7.40 (1H, d, J=7.3 Hz), 7.50 (2H, t, J=7.5 Hz), 7.61-7.78 (7H, m), 12.86 (1H, br).

Formulation Example 1

| | |
|---|---:|
| (1) Compound of Example 1 | 50 mg |
| (2) Lactose | 34 mg |
| (3) Cornstarch | 10.6 mg |
| (4) Cornstarch (paste) | 5 mg |
| (5) Magnesium stearate | 0.4 mg |
| (6) Carboxymethylcellulose calcium | 20 mg |
| total | 120 mg |

The above-mentioned (1)-(6) are mixed by a conventional method and compressed by a tableting machine to give tablets.

Formulation Example 2

| | |
|---|---:|
| (1) Compound of Example 2 | 10.0 mg |
| (2) Lactose | 60.0 mg |
| (3) Cornstarch | 35.0 mg |
| (4) Gelatin | 5 mg |
| (5) Magnesium stearate | 2.0 mg |

A mixture of the compound of Example 2 (10.0 mg), lactose (60.0 mg) and cornstarch (35.0 mg) is granulated using 10% aqueous gelatin solution (0.03 ml, 3.0 mg as gelatin) and passing through a 1 mm mesh sieve, dried at 40° C. and passed through a sieve again. The granules thus obtained are mixed with magnesium stearate (2.0 mg) and compressed. The obtained core tablet is sugar-coated with an aqueous suspension of sucrose, titanium dioxide, talc and gum arabic. The coated tablet is polished with bee wax to give a coated tablet.

Formulation Example 3

| | |
|---|---:|
| (1) Compound of Example 3 | 10.0 mg |
| (2) Lactose | 70.0 mg |
| (3) Cornstarch | 50.0 mg |
| (4) Soluble starch | 7.0 mg |
| (5) Magnesium stearate | 3.0 mg |

The compound of Example 3 (10.0 mg) and magnesium stearate (3.0 mg) are granulated with an aqueous solution (0.07 ml) of soluble starch (7.0 mg as soluble starch), dried and mixed with lactose (70.0 mg) and cornstarch (50.0 mg). The mixture is compressed to give tablets.

Experimental Example 1

MMP-13 Inhibitory Activity

[Method]

To 10 µg of MMP-13 precursor (GenzymeTechne) was added 1 ml of assay buffer (50 mM Tris-HCl (pH 7.5), 10 mM CaCl$_2$, 150 mM NaCl, 0.05% Brij-35), and 4-aminophenylmercuric acid (Sigma) was added to the final concentration of 1 mM. The MMP-13 precursor was activated by incubating at 37° C. for 2 hr.

In a 96 well black plate (Corning), to 6.3 ng/ml of MMP-13 solution (49 µl) diluted with assay buffer was added the test compound (1 µl) diluted with dimethyl sulfoxide (DMSO) and 620 nM Cy3-PLGLK(Cy5Q)AR-NH$_2$ (50 µl, synthesized by Amersham Biosciences) in assay buffer was added to start the enzyme reaction. After incubation at 37° C. for 40 min, 500 mM EDTA solution (6 µl) was added to stop the reaction. For measurement, Farcyte (Amersham Biosciences) was used to measure at excitation wavelength 535 nm and measurement wavelength 595 nm. The enzyme inhibitory activity was calculated in inhibitory rate (% inhibition) by the following formula:

% inhibition=$100-(X-C)/(T-C)\times 100$

T: value of well with addition of DMSO instead of test compound

C: value of well with addition of DMSO instead of test compound and addition of EDTA solution before addition of substrate solution X: value of well with addition of test compound

[Results]

The MMP-13 activity inhibitory rates of the compound (1 µM) are described below.

TABLE 1

| Example No. | MMP-13 inhibitory rate (%) at 1 µM |
|---|---|
| 1 | 91 |
| 2 | 97 |
| 3 | 98 |
| 4 | 99 |
| 5 | 97 |
| 6 | 97 |
| 7 | 97 |
| 8 | 99 |

TABLE 1-continued

| Example No. | MMP-13 inhibitory rate (%) at 1 μM |
|---|---|
| 9 | 98 |
| 10 | 98 |
| 11 | 97 |
| 12 | 99 |
| 13 | 97 |
| 14 | 98 |
| 15 | 98 |
| 16 | 98 |
| 17 | 97 |
| 18 | 94 |
| 19 | 93 |
| 20 | 89 |
| 21 | 100 |
| 22 | 95 |
| 23 | 96 |
| 24 | 93 |
| 25 | 97 |
| 26 | 95 |
| 27 | 98 |
| 28 | 96 |
| 29 | 98 |
| 30 | 96 |
| 31 | 97 |
| 32 | 98 |
| 33 | 98 |
| 34 | 90 |
| 35 | 89 |
| 36 | 97 |
| 37 | 96 |
| 38 | 85 |
| 39 | 81 |
| 40 | 94 |
| 41 | 96 |
| 42 | 98 |
| 43 | 99 |
| 44 | 98 |
| 45 | 97 |
| 46 | 100 |
| 47 | 98 |
| 48 | 99 |

INDUSTRIAL APPLICABILITY

Since compound (I), a salt thereof and a prodrug thereof of the present invention have a superior MMP inhibitory action, particularly an MMP-13 inhibitory action, they are useful as safe drugs for the prophylaxis or treatment of all MMP associated diseases, such as joint disease (e.g., osteoarthritis, rheumatoid arthritis and the like), osteoporosis, cancer, periodontal disease, cornea ulcer, chronic ulcer, pathologic bone resorption (Paget's disease and the like), nephritis, angiogenesis, aneurysm, arteriosclerosis, emphysema, chronic obstructive pulmonary disease (COPD), liver cirrhosis, autoimmune disease (Crohn's disease, Sjogren's disease and the like), infiltration or metastasis of cancer and the like, or as contraceptives.

While some of the embodiments of the present invention have been described in detail in the above, it will, however, be evident for those of ordinary skill in the art that various modifications and changes may be made to the particular embodiments shown without substantially departing from the novel teaching and advantages of the present invention. Such modifications and changes are encompassed in the spirit and scope of the present invention as set forth in the appended claims.

This application is based on patent application No. 2005-315267 filed in Japan, the contents of which are hereby incorporated by reference.

The invention claimed is:

1. A compound represented by the formula

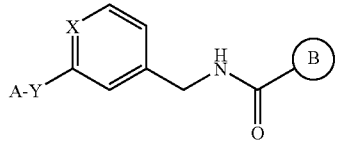

wherein
A is a triazolyl group optionally having substituent(s);
X is CZ wherein Z is a hydrogen atom or a halogen atom;
Y is a spacer having 2 to 10 atoms and optionally having substituent(s); and
a group represented by the formula

is a group represented by the formula

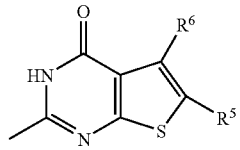

wherein
$R^5$ and $R^6$ are each
(i) a hydrogen atom,
(ii) a halogen atom,
(iii) a cyano group,
(iv) a hydroxy group,
(v) a nitro group,
(vi) a carboxyl group,
(vii) an alkoxycarbonyl group optionally having substituent(s),
(viii) an amino group optionally having substituent(s),
(ix) an alkyl group optionally having substituent(s),
(x) an alkenyl group optionally having substituent(s),
(xi) an alkynyl group optionally having substituent(s),
(xii) an aryl group optionally having substituent(s),
(xiii) an alkoxy group optionally having substituent(s),
(xiv) an aralkyloxy group optionally having substituent(s),
(xv) an aryloxy group optionally having substituent(s),
(xvi) a thiol group,
(xvii) an alkylthio group optionally having substituent(s),
(xviii) an aralkylthio group optionally having substituent(s),
(xix) a 5- to 8-membered aromatic heterocyclyl-thio group containing, besides carbon atoms, 1 to 4 heteroatoms selected from a nitrogen atom, an oxygen atom and a sulfur atom,
(xx) a mono- or di-alkylcarbamoyl-thio group,
(xxi) an alkylsulfonyl group optionally having substituent(s),
(xxii) an arylsulfonyl group optionally having substituent(s),
(xxiii) an aralkylsulfonyl group optionally having substituent(s),
(xxiv) a carbamoyl group optionally having substituent(s), (xxv) a mono- or di-alkylamino-thiocarbonyloxy group,
(xxvi) a 5- to 8-membered non-aromatic heterocyclic group containing, besides carbon atoms, 1 to 4 heteroatoms selected from a nitrogen atom, a sulfur atom and an oxygen atom, or
(xxvii) a 5- to 8-membered aromatic heterocyclic group containing, besides carbon atoms, 1 to 4 heteroatoms selected from a nitrogen atom, a sulfur atom and an oxygen atom, or a pharmaceutically acceptable salt thereof.

2. The compound of claim 1, wherein Y is a spacer having 2 to 7 atoms and optionally having substituent(s), or a pharmaceutically acceptable salt thereof.

3. The compound of claim 1, wherein the group represented by the formula

is a group represented by the formula

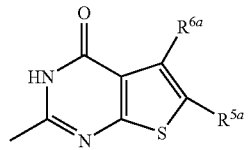

wherein
$R^{5a}$ and $R^{6a}$ are each
(i) a hydrogen atom,
(ii) an alkyl group optionally having substituent(s),
(iii) a cyano group,
(iv) a halogen atom,
(v) an aryl group optionally having substituent(s), or
(vi) a 5- to 8-membered aromatic heterocyclic group containing, besides carbon atoms, 1 to 4 heteroatoms selected from a nitrogen atom, a sulfur atom and an oxygen atom or a pharmaceutically acceptable salt thereof.

4. A compound which is selected from the group consisting of the following, or a pharmaceutically acceptable salt thereof:
   4-oxo-5-phenyl-N-{3-[2-(1H-1,2,4-triazol-3-yloxy)ethoxy]benzyl}-3,4-dihydrothieno[2,3-d]pyrimidine-2-carboxamide,
   5-(2-fluorophenyl)-4-oxo-N-{3-[2-(1H-1,2,4-triazol-3-yloxy)ethoxy]benzyl}-3,4-dihydrothieno[2,3-d]pyrimidine-2-carboxamide,
   5-(2-chlorophenyl)-4-oxo-N-{3-[2-(1H-1,2,4-triazol-3-yloxy)ethoxy]benzyl}-3,4-dihydrothieno[2,3-d]pyrimidine-2-carboxamide,
   5-(3-fluorophenyl)-4-oxo-N-{3-[2-(1H-1,2,4-triazol-3-yloxy)ethoxy]benzyl}-3,4-dihydrothieno[2,3-d]pyrimidine-2-carboxamide,
   5-(3-methylphenyl)-4-oxo-N-{3-[2-(1H-1,2,4-triazol-3-yloxy)ethoxy]benzyl}-3,4-dihydrothieno[2,3-d]pyrimidine-2-carboxamide,
   5-(3-fluorophenyl)-4-oxo-N-[(3-{[3-(1H-1,2,4-triazol-3-yloxy)propyl]oxy}phenyl)methyl]-3,4-dihydrothieno[2,3-d]pyrimidine-2-carboxamide, and
   5-(2-fluorophenyl)-4-oxo-N-[(3-{[3-(1H-1,2,4-triazol-3-yloxy)propyl]oxy}phenyl)methyl]-3,4-dihydrothieno[2,3-d]pyrimidine-2-carboxamide.

5. A pharmaceutical composition comprising the compound of claim 1 or a pharmaceutically acceptable salt thereof, and pharmaceutically acceptable carrier.

* * * * *